United States Patent [19]

Webber et al.

[11] Patent Number: 5,856,530
[45] Date of Patent: Jan. 5, 1999

[54] ANTIPICORNAVIRAL COMPOUNDS AND METHODS FOR THEIR USE AND PREPARATION

[75] Inventors: Stephen E. Webber, San Diego; Peter S. Dragovich, Encinitas; Thomas J. Prins, Cardiff; Siegfried H. Reich, San Diego, all of Calif.; Thomas L. Little, Jr., Redmond, Wash.; Ethel S. Littlefield, San Diego, Calif.; Joseph T. Marakovits, Encinitas, Calif.; Robert E. Babine, Carlsbad, Calif.; Ted M. Bleckman, La Jolla, Calif.

[73] Assignee: Agouron Pharmaceuticals, Inc., La Jolla, Calif.

[21] Appl. No.: 850,398

[22] Filed: May 2, 1997

[51] Int. Cl.$^6$ ............... C07D 307/12; C07D 307/10; C07C 69/74; C07C 69/757
[52] U.S. Cl. ............... 549/478; 549/483; 549/488; 560/122; 560/128; 560/27
[58] Field of Search ............... 549/475, 478, 549/483, 488; 514/2, 7; 560/122, 27

[56] References Cited

FOREIGN PATENT DOCUMENTS

| | | |
|---|---|---|
| 632051 | 1/1995 | European Pat. Off. . |
| WO92/22570 | 12/1992 | WIPO . |
| WO95/23222 | 8/1995 | WIPO . |
| WO95/314133 | 11/1995 | WIPO . |

OTHER PUBLICATIONS

Vaillancourt, et al., "Synthesis of Novel Inhibitors of the HIV–Protease: Difunctional Enols of Simple N–Protected Amino Acids," *bioorganic & Medicinal Chemistry*, vol. 2, No. 5 (1994), pp. 343–354.

Vaillancourt, et al., "Difunctional Enols of N–Protected Amino Acids as Low Molecular Weight and Novel Inhibitors of HIV–1 Protease," *Bioorganic & Medicinal Chemistry Letters*, vol. 3, No. 6 (1993), pp. 1169–1174.

Carpino, "1–Hydroxy–7–azabenzotriazole. An Efficient Peptide Coupling Additive," *Journal of the American Chemical Society*, vol. 115, No. 10 (1993), pp. 4397–4398.

Mosmann, "Rapid Colorimetric Assay for Cellular Growth and Survival: Application to Proliferation and Cytotoxicity Assays," *Journal of Immunological Methods*, vol. 65, Nos. 1–2 (1983), pp. 55–63.

Hanzlik et al., "Vinylogous Amino Acid Esters: A New Class of Inactivators for the Thiol Proteases," *J. Med. Chem.*, vol. 27, No. 6, Jun. 1984, pp. 711–712.

Thompson et al., "Carboxyl–Modified Amino Acids and Peptides as Protease Inhibitors," *J. Med. Chem.*, vol. 29, No. 1, 1986, pp. 104–111.

Liu et al., "Structure–Activity Relationships for Inhibition of Papain by Peptide Michael Acceptors," *J. Med. Chem.*, vol. 35, 1992, pp. 1067–1075.

White et al., *Principles of Biochemistry*, 6th Ed., McGraw Hill, 1978, pp. 893–895.

Callahan et al., "Molecular cloning and complete sequence determination of RNA genome of human rhinovirus type 14," *Proc. Natl. Acad. Sci. USA*, vol. 82, Feb. 1985, pp. 732–736.

Olson et al., "Structure of a human rhinovirus complexed with its receptor molecule," *Proc. Natl. Acad. Sci. USA*, vol. 90, Jan. 1993, pp. 507–511.

Hammler et al., "Site–directed Mutagenesis of the Putative Catalytic Triad of Poliovirus 3C Proteinase," *J. Biol. Chem.*, vol. 266, No. 9, 1991, pp. 5412–5416.

Orr et al., "Hydrolysis of a Series of Synthetic Peptide Substrates by the Human Rhinovirus 14 3C Proteinase, Cloned and Expressed in *Escherichia coli*," *J. gen. Virol*, vol. 70, 1989, pp. 2931–2942.

Leong et al., "Human Rhinovirus–14 Protease 3C ($3C^{pro}$) Binds Specifically to the 5'–Noncoding Region of the Viral RNA," *J. Biol. Chem.*, vol. 268, 1993, pp. 25735–25739.

*Comprehensive Medicinal Chem.*, vol. 2, C. Hansch, Eds., Pergamon Press, Oxford, 1990, pp. 431–433, 440–441.

Shaw, "Cysteinyl Proteinases and Their Selective Inactivation," *Advance Enz*, vol. 63, 1990, pp. 271–347.

Matthews et al., "Structure of Human Rhinovirus 3C Protease Reveals a Trypsin–like Polypeptide Fold, RNA–Binding Site, and Means for Cleaving Precursor Polyprotein," *Cell*, vol. 77, Jun. 1994, pp. 761–771.

Allaire et al., "Picornaviral 3C cysteine proteinases having a fold similar to chymotrypsin–like serine proteinases," *Nature*, vol. 369, May 1994, pp. 72–76.

Bazan et al., "Viral cysteine proteases are homologous to the trypsin–like family of serine proteases: Structural and functional implications," *Poc. Natl. Acad. Sci. USA*, vol. 85, Nov. 1988, pp. 7872–7876.

Cordingley et al., "Cleavage of Small Peptides In Vitro by Human Rhinovirus 14 3C Protease Expressed in *Escherichia coli*," *Journal of Virology*, vol. 63, No. 12, Dec. 1989, pp. 5037–5045.

Kaldor et al., "Glutamine–Derived Aldehydes for the Inhibition of Human Rhinovirus 3C Protease," *Bioorganic & Medicinal Chemistry Letters*, vol. 5, No. 17, 1995, pp. 2021–2026.

Malcolm et al., "Peptide Aldehyde Inhibitors of Hepatitis A Virus 3C Proteinase," *Biochemistry*, vol. 34, 1995, pp. 8172–8179.

(List continued on next page.)

*Primary Examiner*—Johann Richter
*Assistant Examiner*—Dominic Keating
*Attorney, Agent, or Firm*—Finnegan, Henderson, Farabow, Garrett, and Dunner

[57] ABSTRACT

Picornaviral 3C protease inhibitors, obtainable by chemical synthesis, inhibit or block the biological activity of picornaviral 3C proteases. These compounds, as well as pharmaceutical compositions that contain these compounds, are suitable for treating patients or hosts infected with one or more picornaviruses. Several novel methods and intermediates can be used to prepare the novel picornaviral 3C protease inhibitors of the present invention.

29 Claims, No Drawings

OTHER PUBLICATIONS

Skiles et al., "Spiro Indolinone Beta–Lactams, Inhibitors of Poliovirus and Rhinovirus 3C–Proteinases," *Tetrahedron Letters,* vol. 31, No. 50, 1990, pp. 7277–7280.

Singh et al., "Structure and Stereochemistry of Thysanone: A Novel Human Rhinovirus 3C–Protease Inhibitor from *Thysanophora penicilloides,*" *Tetrahedron Letters,* vol. 32, No. 39, 1991, pp. 5279–5282.

Kadam et al., "Citrinin Hydrate and Radicinin: Human Rhinovirus 3C–Protease Inhibitors Discovered in a Target–Directed Microbial Screen," *The Journal of Antibiotics,* vol. 47, No. 7, Jul. 1994, pp. 836–839.

Palmer et al., "Vinyl Sulfones as Mechanism–Based Cysteine Protease Inhibitors," *J. Med. Chem.,* vol. 38, 1995, pp. 3193–3196.

Maryanoff et al., "Molecular basis for the inhibition of human α–thrombin by the macrycylic peptide cyclotheonamide A," *Proc. Natl. Acad. Sci. USA,* vol. 90, Sep. 1993, pp. 8048–8052.

Rich et al., "Synthesis of Analogues of the Carboxyl Protease Inhibitor Pepatatin. Effect of Structure on Inhibition of Pepsin and Renin," *J. Med. Chem.,* vol. 23, 1980, pp. 27–33.

Hagihara et al., "Reassignment of Streeochemistry and Total Synthesis of the Thrombin Inhibitor Cyclotheonamide B," *J. Am. Chem. Soc.,* vol. 114, 1992, pp. 6570–6571.

Barton et al., "Synthesis of Novel α–Amino–Acids and Derivatives Using Radical Chemistry: Synthesis of L–and D–α–Amino–Adipic Acids, L–α–Aminopimelic Acid and Appropriate Unsaturated Derivatives," *Tetrahedron,* vol. 43, No. 19, 1987, pp. 4297–4308.

Smith et al., "Synthesis and Renin Inhibitory Activity of Angiotensinogen Analogues Having Dehydrostatine, LeuΨ[CH$_2$S]Val, or LeuΨ[CH$_2$SO]Val at the P$_1$–P$_1$' Cleavage Site," *J. Med. Chem.,* vol. 31, 1988, pp. 1377–1382.

Meng et al., "Synthetic Approaches toward Glidobamine, the Core Structure of the Glidobactin Antibiotics," *Tetrahedron,* vol. 47, No. 32, 1991, pp. 6251–6264.

Kolter et al., "Configuratively Stable Dipeptide Aldehydes from D–Glucosamine Hydrochloride," *Angew. Chem. Int. Ed. Engl.,* vol. 31, No. 10, 1992, pp. 1391–1392.

Reetz et al., "Steroselective Nucleophilic Addition Reactions of Reactive Pseudopeptides," *Angew. Chem. Int. Ed. Engl.,* vol. 31, No. 12, 1992, pp. 1626–1629.

Aogyagi et al., "Structures and Activities of Protease Inhibitors of Microbial Origin," Institute of Microbial Chemistry, Tokyo, Japan, 1975, pp. 429–454.

Rich, "Inhibitors of cysteine proteinases," *Proteinase Inhibitors,* Barrett and Salvesen (eds.), Elsvier Science Publishers BV, 1986, pp. 154–178.

Haberson, et al., "Inhibitons of Aminopeptidases by Peptides Containing Ketomethylene and Hydroxyethylene Amide Bond Replacements," *J. Med. Chem.,* vol. 32 (1989), pp. 1378–1392.

Herold, et al., "A Versatile and Stereocontrolled Synthesis of Hydroxyehtylene Dipeptide Isosteres," *J. Org. Chem.,* vol. 54 (1989), pp. 1178–1185.

Bradbury et al., "An Efficient Synthesis of the γ–Lactone Corresponding to a Hydroxyehtylene Dipeptide Isostere Using Stereoselective Bromolactonisation of a Chiral Acyloxasolidinone," *Tetrahedron Letters,* vol. 30, No. 29 (1989), pp. 3845–3848.

Bradbury, et al., "1,2,4–Triazolo[4,3–α]pyrazine Derivatives with Human Renin Inhibitory Activity. 2. Synthesis, Biological Properties and Molecular Modeling of Hydroxyehtylene Isostere Derivatives," *J. Med. Chem.,* vol. 33 (1990), pp. 2335–2342.

Wuts, et al., "Synthesis of the Hydroxyethylene Isostere of Leu–Val," *J. Org. Chem.,* vol. 57 (1992), pp. 6696–6700.

Jones, et al., "A Short Stereocontrolled Synthesis of Hydroxyehtylene Dipeptide Isosteres," *J. Org. Chem.,* vol. 58 (1993), pp. 2286–2290.

Pégorier, et al., "A General Stereocontrolled Synthesis of Hydroxyethylene Dipeptide Isosteres," *Tetrahedron Letters,* vol. 36, No. 16 (1995), pp. 2753–2756.

Dondoni, et al., "Thiazole–Based Stereoselective Routes of Leucine and Phenylalanine Hydroxyethylene Dipeptide Isostere Inhibitors of Renin and HIV–1 Aspartic Protease," *J. Org. Chem.,* vol. 60 (1995), pp. 7927–7933.

Weislow, et al., "New Soluble–Formazan Assay for HIV–1 Cytopathic Effects: Application to High–Flux Screening of Synthetic and Natural Products for AIDS–Antiviral Activity," *Journal of the National Cancer Institute,* vol. 81, No. 8 (1989), pp. 577–586.

ANTIPICORNAVIRAL COMPOUNDS AND METHODS FOR THEIR USE AND PREPARATION

The invention pertains to the discovery and use of new compounds that inhibit the enzymatic activity of picornaviral 3C proteases, specifically rhinovirus proteases (RVPs), as well as retard viral growth in cell culture.

The picornaviruses are a family of tiny non-enveloped positive stranded RNA containing viruses that infect humans and other animals. These viruses include the human rhinoviruses, human polioviruses, human coxsackieviruses, human echoviruses, human and bovine enteroviruses, encephalomyocarditis viruses, menigovirus, foot and mouth viruses, hepatitis A virus and others. The human rhinoviruses are a major cause of the common cold. To date, there are no effective therapies to cure the common cold, only treatments that relieve the symptoms.

One strategy that may be useful to treat picornaviral infections is by inhibiting the proteolytic 3C enzymes. These enzymes are required for the natural maturation of the picornaviruses. They are responsible for the autocatalytic cleavage of the genomic, large polyprotein into the essential viral proteins. Members of the 3C protease family are cysteine proteases, where the sulfhydryl group most often cleaves the glutamine-glycine amide bond. In theory, inhibition of 3C proteases can block proteolytic cleavage of the polyprotein, which in turn can retard the maturation and replication of the viruses by interfering with viral particle production. Therefore, inhibiting the processing of this cysteine protease with selective, small molecules that are specifically recognized, may represent an important and useful approach to treat and cure viral infections of this nature and, in particular, the common cold.

SUMMARY OF THE INVENTION

The present invention is directed to compounds that functions as picornaviral 3C protease inhibitors, particularly those that have antiviral activity. It is further directed to the preparation and use of such 3C protease inhibitors. The Inventors demonstrate that the compounds of the present invention bind to rhinovirus 3C proteases and preferably have antiviral cell culture activity. The enzymatic inhibition assays used reveal that these compounds can bind irreversibly, and the cell culture assays demonstrate that these compounds can possess antiviral activity.

The present invention is directed to compounds of the formula (a):

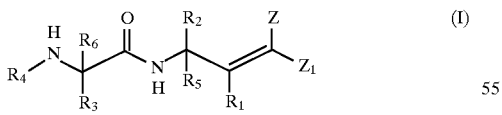

wherein $R_1$ is H, F, an alkyl group, OH, SH, an O-alkyl group, or an S-alkyl group;

$R_2$ and $R_5$ are independently selected from H,

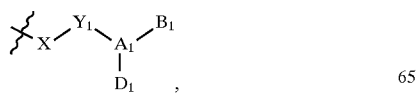

-continued

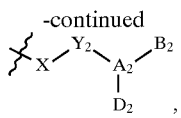

or an alkyl group, wherein said alkyl group is different from

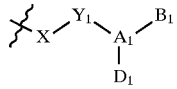

and

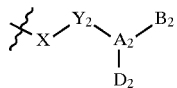

with the proviso that at least one of $R_2$ or $R_5$ must be

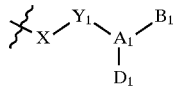

or

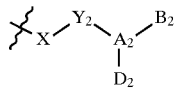

and wherein, when $R_2$ or $R_5$ is

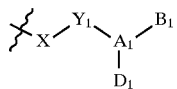

X is =CH or =CF and $Y_1$ is =CH or =CF
or X and $Y_1$ together with Q' form a three-membered ring in which Q' is —C($R_{10}$)($R_{11}$)— or —O—, X is —CH— or —CF—, and $Y_1$ is —CH—, —CF—, or —C(alkyl)—, where $R_{10}$ and $R_{11}$ independently are H, a halogen, or an alkyl group, or, together with the carbon atom to which they are attached, form a cycloalkyl group or a heterocycloalkyl group,
or X is —CH$_2$—, —CF$_2$—, —CHF—, or —S—,
and $Y_1$ is —O—, —S—, —NR$_{12}$—, —C(R$_{13}$)(R$_{14}$)—, —C(O)—, —C(S)—, or —C(CR$_{13}$R$_{14}$)—
wherein $R_{12}$ is H or alkyl, and $R_{13}$ and $R_{14}$ independently are H, F, or an alkyl group, or, together with the atoms to which they are bonded, form a cycloalkyl group or a heterocycloalkyl group;
and $A_1$ is C, CH, CF, S, P, Se, N, NR$_{15}$, S(O), Se(O), P-OR$_1$5, or P—NR$_{15}$R$_{16}$
wherein $R_1$ and $R_{16}$ independently are an alkyl group, a cycloalkyl group, a heterocycloalkyl group, an aryl group, or a heteroaryl group, or, together with the atom to which they are bonded, form a heterocycloalkyl group;
and $D_1$ is a moiety with a lone pair of electrons capable of forming a hydrogen bond;
and B is H, F, an alkyl group, a cycloalkyl group, a heterocycloalkyl group, an aryl group, a heteroaryl group, —OR$_{17}$, —SR$_{17}$, —NR$_{17}$R$_{18}$, —NR$_{19}$NR$_{17}$R$_{18}$, or —NR$_{17}$OR$_{18}$
wherein $R_{17}$, $R_{18}$, and $R_{19}$ independently are H, an alkyl group, a cycloalkyl group, a heterocycloalkyl group, an aryl group, a heteroaryl group, or an acyl group, or, wherein any two of $R_{17}$, $R_{18}$, and $R_{19}$, together with the atom(s) to which they are bonded, form a heterocycloalkyl group;

and with the provisos that when $D_1$ is the moiety ≡N with a lone pair of electrons capable of forming a hydrogen bond, $B_1$ does not exist; and when $A_1$ is an sp$^3$ carbon, $B_1$ is not —$NR_{17}R_{18}$ when $D_1$ is the moiety —$NR_{25}R_{26}$ with a lone pair of electrons capable of forming a hydrogen bond, wherein $R_{25}$ and $R_{26}$ are independently H, an alkyl group, a cycloalkyl group, a heterocycloalkyl group, an aryl group, or a heteroaryl group;

and wherein $D_1$—$A_1$—$B_1$ optionally forms a nitro group where Al is N;

and wherein, when $R_2$ or $R_5$ is

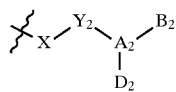

X is =CH or =CF and $Y_2$ is =C, =CH or =CF, or X and $Y_2$ together with Q' form a three-membered ring in which Q' is —C($R_{10}$)($R_{11}$)— or —O—, X is —CH— or —CF—, and $Y_2$ is —CH—, —CF—, or —C(alkyl)—, where $R_{10}$ and $R_{11}$ independently are H, a halogen, or an alkyl group, or, together with the carbon atom to which they are attached, form a cycloalkyl group or a heterocycloalkyl group, or X is —$CH_2$—, —$CF_2$—, —CHF—, or —S—, and $Y_2$ is —O—, —S—, —N(R'$_{12}$)—, —C(R'$_{13}$)(R'$_{14}$)—, —C(O)—, —C(S)—, or —C(CR'$_{13}$R'$_{14}$)— wherein R'$_{12}$ is H, an alkyl group, a cycloalkyl group, a heterocycloalkyl group, an aryl group, a heteroaryl group, —OR'$_{13}$, —NR'$_{13}$R'$_{14}$, —C(O)—R'$_{13}$, —SO$_2$R'$_{13}$, or —C(S)R'$_{13}$, and R'$_{13}$ and R'$_{14}$, independently are H, F, or an alkyl group, a cycloalkyl group, a heterocycloalkyl group, an aryl group, or a heteroaryl group or, together with the atom to which they are attached, form a cycloalkyl group or a heterocycloalkyl group;

and wherein any combination of Y2, $A_2$, $B_2$, and $D_2$ forms a cycloalkyl group, a heterocycloalkyl group, an aryl group, or a heteroaryl group;

and $A_2$ is C, CH, CF, S, P, Se, N, $NR_{15}$, S(O), Se(O), P—$OR_{15}$, or P—$NR_{15}R_{16}$ wherein $R_{15}$ and $R_{16}$ independently are an alkyl group, a cycloalkyl group, a heterocycloalkyl group, an aryl group, or a heteroaryl group or, together with the atom to which they are bonded, form a heterocycloalkyl group;

and $D_2$ is a moiety with a lone pair of electrons capable of forming a hydrogen bond;

and $B_2$ is H, F, an alkyl group, a cycloalkyl group, a heterocycloalkyl group, an aryl group, a heteroaryl group, —$OR_{17}$, —$SR_{17}$, —$NR_{17}R_{18}$, —$NR_{19}NR_{17}R_{18}$, or —$NR_{17}OR_{18}$ wherein $R_{17}$, $R_{18}$, and $R_{19}$ independently are H, an alkyl group, a cycloalkyl group, a heterocycloalkyl group, an aryl group, a heteroaryl group, or an acyl group, or, wherein any two of $R_{17}$, $R_{18}$, and $R_{19}$, together with the atom(s) to which they are bonded, form a heterocycloalkyl group;

$R_3$ and $R_6$ are independently H, F, or an alkyl group;
$R_4$ is H, OH, or a suitable organic moiety;

Z and $Z_1$ are independently H, F, an alkyl group, a cycloalkyl group, a heterocycloalkyl group, an aryl group, a heteroaryl group, —C(O)$R_{21}$, —$CO_2R_{21}$, —CN, —C(O)$NR_2$, $R_{22}$, —C(O)$NR_{21}OR_{22}$, —C(S)$R_{21}$, —C(S)$NR_{21}R_{22}$, —$NO_2$, —$SOR_{21}$, —$SO_2R_{21}$, —$SO_2NR_{21}R_{22}$, —SO($NR_{21}$)($OR_{22}$), —$SONR_{21}$, —$SO_3R_{21}$, —PO($OR_{21}$)$_2$, —PO($R_{21}$)($R_{22}$), —PO($NR_{21}R_{22}$)($OR_{23}$), —PO($NR_{21}R_{22}$)($NR_{23}R_{24}$), —C(O)$NR_{21}NR_{22}R_{23}$, or —C(S)$NR_{21}NR_{22}R_{23}$, wherein $R_{21}$, $R_{22}$, $R_{23}$, and $R_{24}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, $R_{23}$, and $R_{24}$, together with the atom(s) to which they are bonded, form a heterocycloalkyl group;

or $Z_1$, as defined above, together with $R_1$, as defined above, and the atoms to which $Z_1$ and $R_1$ are bonded, form a cycloalkyl or heterocycloalkyl group, or Z and $Z_1$, both as defined above, together with the atoms to which they are bonded, form a cycloalkyl or heterocycloalkyl group;

and pharmaceutically acceptable prodrugs, salts, and solvates thereof;

and wherein these compounds, pharmaceutically acceptable prodrugs, salts, and solvates preferably have antipicornaviral activity with an $EC_{50}$ less than or equal to 100 μM in the HI-HeLa cell culture assay, and more preferably antirhinoviral activity with an $EC_{50}$ less than or equal to 100 μM in the HI-HeLa cell culture assay and/or anticoxsachieviral activity with an $EC_{50}$ less than or equal to 100 μM in the HI-HeLa cell culture assay.

The present invention is also directed to several methods of preparing compounds of formula (I), defined above. One method according to the invention involves converting a compound of formula Q

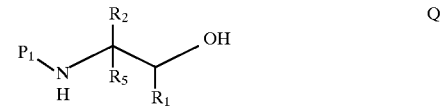

wherein $R_1$, $R_2$ and $R_5$ are as defined above, and $P_1$ is a protective group, preferably benzyloxy carbonyl or t-butoxycarbonyl, or a salt or solvate thereof, to a compound of formula I, as defined above, or a pharmaceutically acceptable prodrug, salt or solvate thereof.

Another method according to the invention involves converting a compound of the formula B:

wherein $R_1$, $R_2$ and $R_5$ are as defined above, or a salt or solvate thereof, to a compound of formula I, as defined above, or a pharmaceutically acceptable prodrug, salt or solvate thereof.

Another method according to the invention involves converting a compound of formula O:

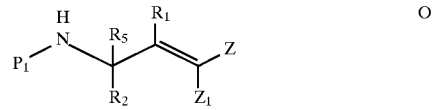

wherein $R_1$, $R_2$, $R_5$, Z and $Z_1$ are as defined above and $P_1$ is a protective group, preferably benzyloxy carbonyl or t-butoxycarbonyl, or a salt or solvate thereof, to a compound of formula I, as defined above, or a pharmaceutically acceptable prodrug, salt or solvate thereof.

Another method according to the present invention involves converting a compound of formula P:

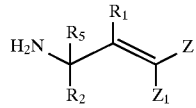

wherein $R_1$, $R_2$, $R_5$, Z and $Z_1$ are as defined above, or a salt or solvate thereof, to a compound of formula I, as defined above, or a pharmaceutically acceptable prodrug, salt or solvate thereof.

DETAILED DESCRIPTION OF THE INVENTION

The present invention relates to compounds of the formula I

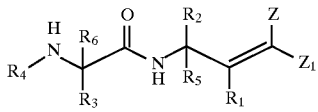

wherein $R_1$, $R_2$, $R_3$, $R_4$, $R_5$, $R_6$, Z and $Z_1$ are as defined above, and to the pharmaceutically acceptable prodrugs, salts, and solvates thereof, where these compounds, pharmaceutically acceptable prodrugs, salts, and solvates preferably have antipicornaviral activity with an $EC_{50}$ less than or equal to 100 FM in the HI-HeLa cell culture assay, and more preferably antirhinoviral activity with an $EC_{50}$ less than or equal to 100 µM in the HI-HeLa cell culture assay and/or anticoxsachieviral activity with an $EC_{50}$ less than or equal to 100 µM in the HI-HeLa cell culture assay.

The present invention preferably relates to compounds of the formula II:

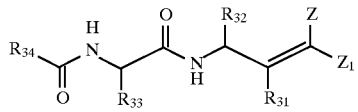

wherein $R_{31}$ is H, F or an alkyl group;

$R_{32}$ is selected from one of the following moieties:

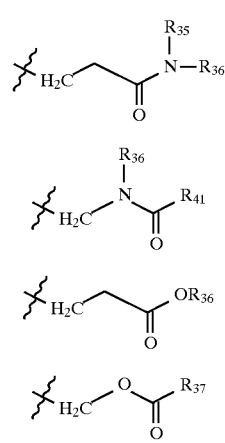

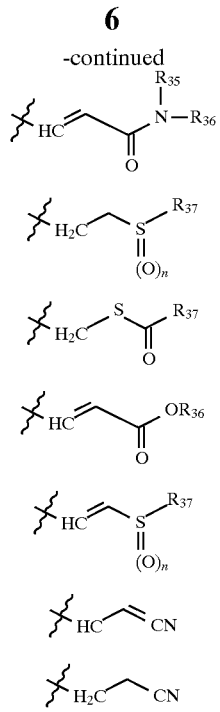

wherein $R_{35}$ is H, an alkyl group, an aryl group, —$OR_{38}$, or —$NR_{38}R_{39}$, and $R_{36}$ is H or an alkyl group, or $R_{35}$ and $R_{36}$, together with the atom(s) to which they are attached, form a heterocycloalkyl group or a heteroaryl group;

$R_{41}$ is H, an alkyl group, an aryl group, —$OR_{38}$, —$SR_{39}$, —$NR_{38}R_{39}$, —$NR_{40}NR_{38}R_{39}$, or —$NR_{38}OR_{39}$, or $R_{41}$ and $R_{36}$, together with the atom(s) to which they are attached, form a heterocycloalkyl group;

$R_{37}$ is an alkyl group, an aryl group, or —$NR_{38}R_{39}$;

wherein $R_{38}$, $R_{39}$, and $R_{40}$ independently are H, an alkyl group, a cycloalkyl group, a heterocycloalkyl group, an aryl group, a heteroaryl group, or an acyl group, or, wherein any two of $R_{38}$, $R_{39}$, and $R_{40}$, together with the atom(s) to which they are bonded, form a heterocycloalkyl group;

n is 0, 1 or 2;

$R_{33}$ is H or an alkyl group;

$R_{34}$ is an alkyl group, a cycloalkyl group, a heterocycloalkyl group, an aryl group, a heteroaryl group, an O-alkyl an O-cycloalkyl group, an O-heterocycloalkyl group, an O-aryl group, an O-heteroaryl group, an S-alkyl group, an NH-alkyl group, an NH-aryl group, an N,N-dialkyl group, or an N,N-diaryl group; and Z and $Z_1$ are independently H, F, an alkyl group, a cycloalkyl group, a heterocycloalkyl group, an aryl group, a heteroaryl group, —$C(O)R_{21}$, —$CO_2R_{21}$, —CN, —$C(O)NR_{21}R_{22}$, —$C(O)NR_{21}OR_{22}$, —C(S) $R_{21}$, —$C(S)NR_{21}R_{22}$, —$NO_2$, —$SOR_{21}$, —$SO_2R_{21}$, —$SO_2NR_{21}R_{22}$, —$SO(NR_{21})(OR_{22})$, —$SONR_{21}$, —$SO_3R_{21}$, —$PO(OR_{21})_{21}$, —$PO(R_{21})(R_{22})$, —PO $(NR_{21}R_{22})(OR_{23})$, —$PO(R_{21}R_{22})(NR_{23}R_{24})$, —C(O) $NR_{21}NR_{22}R_{23}$, or —$C(S)NR_{21}NR_{22}R_{23}$, wherein $R_{21}$, $R_{22}$, $R_{23}$, and $R_{24}$ are independently H, an alkyl group, a cycloalkyl group, a heterocycloalkyl group, an aryl group, a heteroaryl group, an acyl group, or a thioacyl group, or wherein any two of $R_{21}$, $R_{22}$, $R_{23}$, and $R_{24}$, together with the atom(s) to which they are bonded, form a heterocycloalkyl group, or Z and $Z_1$, both as defined above, together with the atoms to which they are bonded, form a heterocyclo alkyl group;

and pharmaceutically acceptable prodrugs, salts, and solvates thereof.

As used in the present application, the following definitions apply:

An "alkyl group" is intended to mean a straight or branched chain monovalent radical of saturated and/or unsaturated carbon atoms and hydrogen atoms, such as methyl, ethyl, propyl, isopropyl, butyl, isobutyl, t-butyl, ethenyl, pentenyl, butenyl, propenyl, ethynyl, butynyl, propynyl, pentynl, hexynyl, and the like, which may be unsubstituted (i.e., containing only carbon and hydrogen) or substituted by one or more suitable substituents as defined below.

A "cycloalkyl group" is intended to mean a non-aromatic, monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more suitable substituents. Illustrative examples of cycloalkyl groups include, but are not limited to, the following moieties:

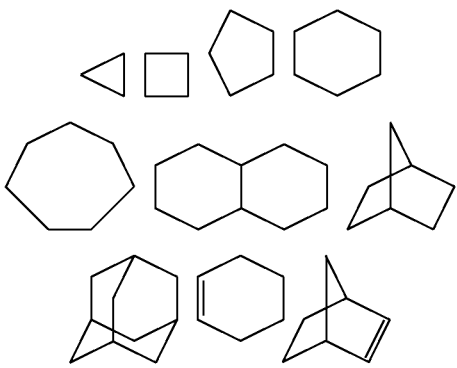

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen and sulfur, wherein the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include, but are not limited to the following moieties:

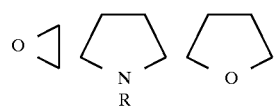

-continued

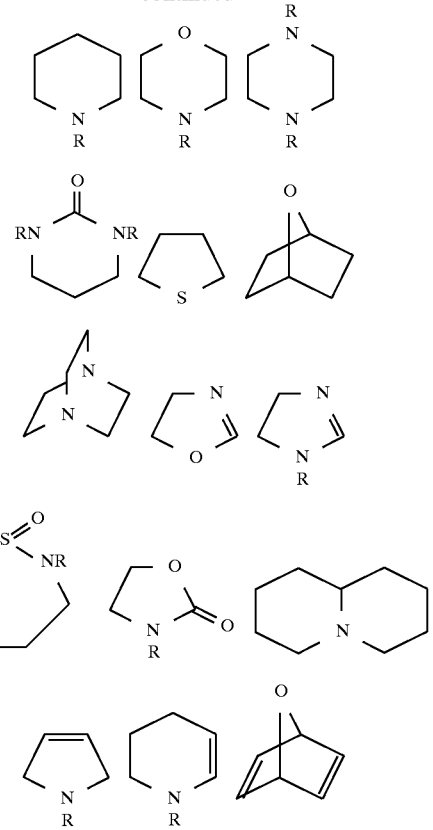

An "aryl group" is intended to mean an aromatic, monovalent monocyclic, bicyclic, or tricyclic radical containing 6, 10, 14, 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, the following moieties:

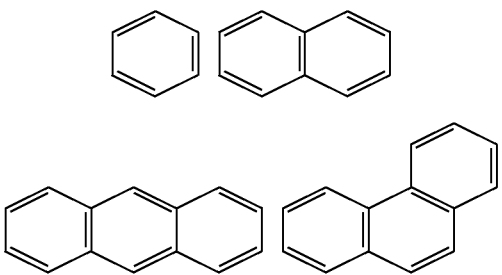

A "heteroaryl group" is intended to mean an aromatic monovalent monocyclic, bicyclic, or tricyclic radical containing 4, 5, 6, 7, 8, 9, 10, 11, 12, 13, 14, 15, 16, 17, or 18 ring atoms, including 1, 2, 3, 4, or 5 heteroatoms selected from nitrogen, oxygen and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include, but are not limited to, the following moieties:

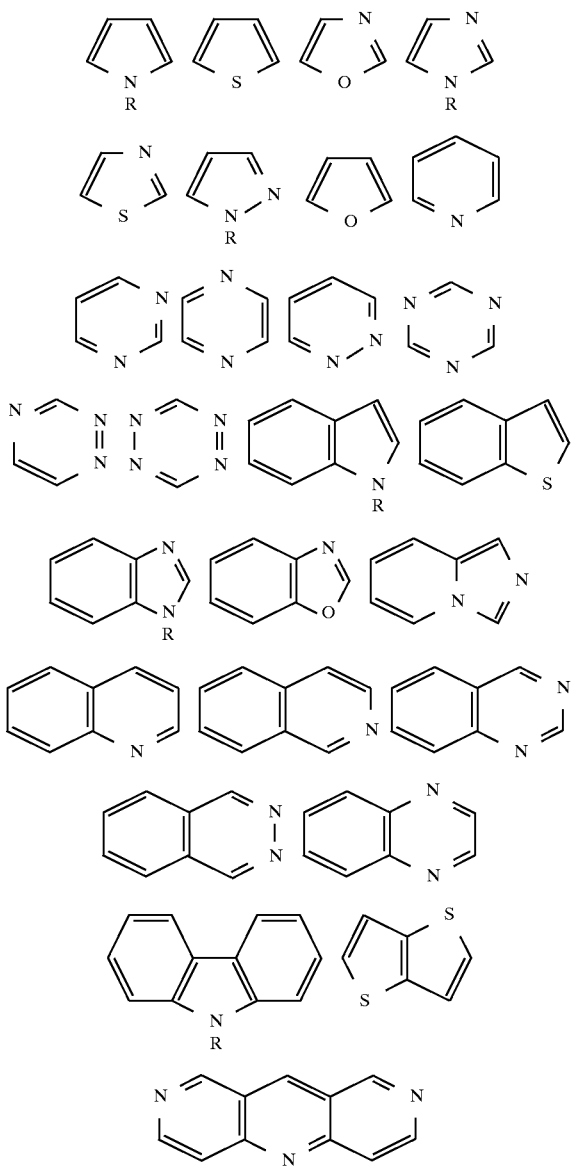

An "acyl group" is intended to mean a —C(O)—R radical, wherein R is any suitable substituent as defined below.

A "thioacyl group" is intended to mean a —C(S)—R radical, wherein R is any suitable substituent as defined below.

A "sulfonyl group" is intended to mean a —SO$_2$R radical, wherein R is any suitable substituent as defined below.

The term "suitable substituent" is intended to mean any of the substituents recognizable, such as by routine testing, to those skilled in the art as not adversely affecting the inhibitory activity of the inventive compounds. Illustrative examples of suitable substituents include, but are not limited to, hydroxy groups, oxo groups, alkyl groups, acyl groups, sulfonyl groups, mercapto groups, alkylthio groups, alkoxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroarlyoxy groups, arylthio groups, heteroarylthio groups, and the like.

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxy groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

A "hydroxy group" is intended to mean the radical —OH.

An "amino group" is intended to mean the radical —NH$_2$.

An "alkylamino group" is intended to mean the radical —NHR where R is an alkyl group as defined above.

A "dialkylamino group" is intended to mean the radical —NR$_a$R$_b$ where R$_a$ and R$_b$ are each independently an alkyl group as defined above.

An "alkoxy group" is intended to mean the radical —OR where R is an alkyl group as defined above, for example, methoxy, ethoxy, propoxy and the like.

An "alkoxycarbonyl group" is intended to mean the radical —C(O)OR where R is an alkyl group as defined above.

An "alkylsulfonyl group" is intended to mean the radical —SO$_2$R where R is an alkyl group as defined above.

An "alkylaminocarbonyl group" is intended to mean the radical —C(O)NHR where R is an alkyl group as defined above.

A "dialkylaminocarbonyl group" is intended to mean the radical —C(O)NR$_a$R$_b$ where R$_a$ and R$_b$ are each independently an alkyl group as defined above.

A "mercapto group" is intended to mean the radical —SH.

An "alkylthio group" is intended to mean the radical —SR where R is an alkyl group as defined above.

A "carboxy group" is intended to mean the radical —C(O)OH.

A "carbamoyl group" is intended to mean the radical —C(O)NH$_2$.

An "aryloxy group" is intended to mean the radical —OR$_c$ where R$_c$ is an aryl group as defined above.

A "heteroarlyoxy group" is intended to mean the radical —OR$_d$ where R$_d$ is a heteroaryl group as defined above.

An "arylthio group" is intended to mean the radical —SR$_d$ where R$_c$ is an aryl group as defined above.

A "heteroarylthio group" is intended to mean the radical —SR$_d$ where R$_d$ is a heteroaryl group as defined above.

A "pharmaceutically acceptable prodrug" is intended to mean a compound that may be converted under physiological conditions or by solvolysis to a compound of formula I or formula II.

A "pharmaceutically acceptable solvate" is intended to mean a solvate that retains the biological effectiveness and properties of the biologically active components of compounds of formulas I and II.

Examples of pharmaceutically acceptable solvates include, but are not limited to, water, isopropanol, ethanol, methanol, DMSO, ethyl acetate, acetic acid, and ethanolamine.

A "pharmaceutically acceptable salt" is intended to a mean a salt that retains the biological effectiveness and properties of the free acids and bases of compounds of formulas I and II and that is not biologically or otherwise undesirable.

Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If the inventive compound is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

In the case of compounds, salts, or solvates that are solids, it is understood by those skilled in the art that the inventive compounds, salts, and solvates may exist in different crystal forms, all of which are intended to be within the scope of the present invention.

The inventive compounds may exist as single stereoisomers, racemates and/or mixtures of enantiomers and/or diastereomers. All such single stereoisomers, racemates and mixtures thereof are intended to be within the scope of the present invention. Preferably, the inventive compounds are used in optically pure form.

As generally understood by those skilled in the art, an optically pure compound is one that is enantiomerically pure. As used herein, the term "optically pure" is intended to mean a compound which comprises at least a sufficient amount of a single enantiomer to yield a compound having the desired pharmacological activity. Preferably, "optically pure" is intended to mean a compound that comprises at least 90% of a single isomer (80% enantiomeric excess), preferably at least 95% (90% e.e.), more preferably at least 97.5% (95% e.e.), and most preferably at least 99% (98% e.e.).

Preferably in the above formulas I and II, $R_1$ and $R_{31}$ are H or F. Preferably in formula I, $R_4$ is an acyl group or a sulfonyl group. Preferably in formulas I and II, $D_1$ and $D_2$ are —$OR_{25}$, =O, =S, =N, =$NR_{25}$, or —$NR_{25}R_{26}$, wherein $R_{25}$ and $R_{26}$ are independently H, an alkyl group, a cycloalkyl group, a heterocycloalkyl group, an aryl group, or a heteroaryl group, or, together with the nitrogen atom to which they are bonded, form a heterocycloalkyl group, and more preferably $D_1$ and $D_2$ are =O. Preferably $A_1$ and $A_2$ are C, CH, S, or S(O), and more preferably $A_1$ and $A_2$ are C.

Preferably $B_1$ and $B_2$ are $NR_{17}R_{18}$, wherein $R_{17}$ and $R_{18}$ are independently H, an alkyl group, a cycloalkyl group, a heterocycloalkyl group, an aryl group, a heteroaryl group, an acyl group, or wherein $R_{17}$ and $R_{18}$, together with the atom(s) to which they are bonded, form a heterocycloalkyl group.

Preferably Z and $Z_1$ are independently H, an aryl group, or a heteroaryl group, —$C(O)R_{21}$, —$CO_2R_{21}$, —CN, —$C(O)NR_{21}R_{22}$, —$C(O)NR_{21}OR_{22}$, —$C(S)R_{21}$, —$C(S)NR_{21}R_{22}$, —$NO_2$, —$SOR_{21}$, —$SO_2R_{21}$, —$SO_2NR_{21}R_{22}$, —$S(NR_{21})(OR_{22})$, —$SONR_{21}$, —$SO_3R_{21}$, —$C(O)NR_{21}NR_{22}R_{23}$, or —$C(S)NR_{21}NR_{22}R_{23}$; wherein $R_{21}$, $R_{22}$, and $R_{23}$ are independently H, an alkyl group, a cycloalkyl group, a heterocycloalkyl group, an aryl group, a heteroaryl group, or an acyl group, or wherein any two of $R_{21}$, $R_{22}$, and $R_{23}$, together with the atom(s) to which they are bonded, form a heterocycloalkyl group, or Z and $Z_1$, together with the atoms to which they are attached, form a heterocycloalkyl group.

Preferably $R_{32}$ is one of the following moieties:

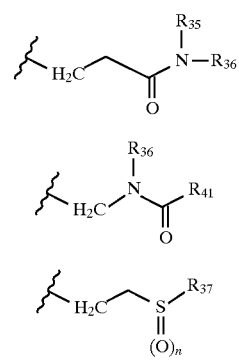

wherein $R_{35}$, $R_{36}$, $R_{37}$, $R_{41}$ and n are as defined above.

Compounds according to formula I include the following, where * indicates point of attachment: Compounds 2, 3, 4, 5, 7, 11, 12, 13, 14, 16, 17, 18, 19, 21, 22, 24, 25, 41–43, 74, and 75 having the formula III:

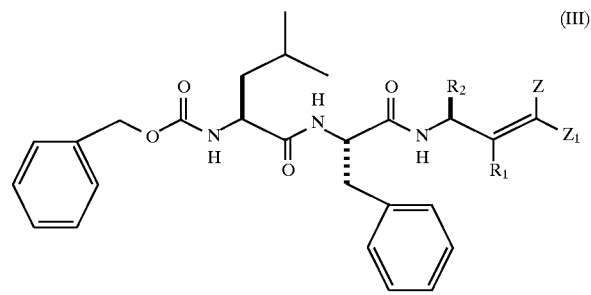

2. $R_2$ is $CH_2CH_2C(O)NHCPh_3$, $R_1$ is H, Z is H, and $Z_1$ is $CO_2CH_2CH_3$ 3. $R_2$ is $CH_2CH_2C(O)NH_2$, $R_1$ is H, Z is H, and $Z_1$ is $CO_2CH_2CH_3$ 4. $R_2$ is $CH_2NHC(O)CH_3$; $R_1$ is H, Z is H, and $Z_1$ is $CO_2CH_2CH_3$ 5. $R_2$ is

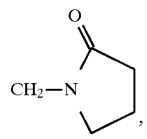

$R_1$ is H, Z is H, and $Z_1$ is $CO_2CH_2CH_3$

7. $R_2$ is $CH_2CH_2C(O)NH_2$, $R_1$ is H, Z is $CO_2CH_3$, and $Z_1$ is H

11. $R_2$ is $CH_2CH_2C(O)NH_2$, $R_1$ is H, Z is H, and $Z_1$ is $CO_2CH_3$

12. $R_2$ is $CH_2CH_2S(O)CH_3$, $R_1$ is H, Z is H, and $Z_1$ is $CO_2CH_2CH_3$ 13. $R_2$ is $CH_2CH_2C(O)NH_2$, $R_1$ is H, Z is H, and $Z_1$ is $C(O)CH_3$ 14. $R_2$ is $CH_2CH_2C(O)NH_2$, $R_1$ is H, Z is H, and $Z_1$ is CN 16. $R_2$ is $CH_2NHC(O)NH_2$, $R_1$ is H, Z is H, and $Z_1$ is $CO_2CH_2CH_3$ 17. $R_2$ is $CH_2CH_2C(O)NH_2$, $R_1$ is H, Z is H, and $Z_1$ is $CO_2CH(CH_3)_2$ 18. $R_2$ is $CH_2CH_2C(O)NH_2$, $R_1$ is H, Z is H, and $Z_1$ is

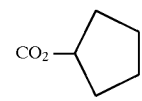

19. $R_2$ is $CH_2CH_2C(C)NH_2$, $R_1$ is H, Z is H, and $Z_1$ is

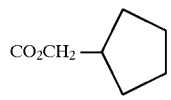

21. $R_2$ is $CH_2CH_2C(O)NH_2$, $R_1$ is H, Z is H, and $Z_1$ is

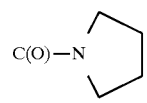

22. $R_2$ is $CH_2CH_2C(O)NH_2$, $R_1$ is H, Z is H, and $Z_1$ is $C(O)N(CH_3)_2$ 24. $R_2$ is $CH_2CH_2C(O)NH_2$; $R_1$ is H, Z is H, and $Z_1$ is $C(O)Ph$ 25. $R_2$ is $CH_2CH_2C(O)NH_2$; $R_1$ is H, Z is H, and $Z_1$ is

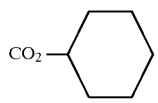

41. $R_1$ is H; $R_2$ is $CH_2CH_2C(O)NH_2$; Z is H; and

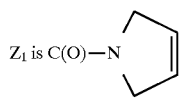

42. $R_2$ is $CH_2CH_2C(O)NH_2$, $R_1$ is H, Z is H, and $Z_1$ is

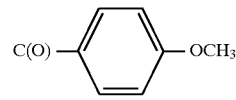

43. $R_1$ is H; $R_2$ is $CH_2CH_2C(O)NH_2$; Z is H; and

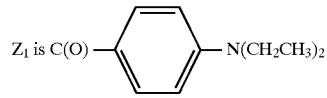

74. $R_1$ is H; $R_2$ is $CH_2CH_2C(O)NH_2$; Z is H; and $Z_1$ is $CH_2Cl$

75. $R_1$ is H; $R_2$ is $CH_2CH_2C(O)NH_2$; Z is H; and $Z_1$ is

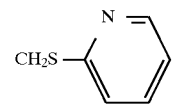

Compounds (26, 27, and 28) having the formula IV:

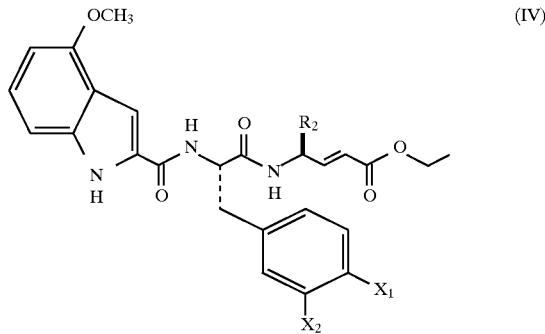

where $X_1$ and $X_2$ independently are H, F, or Cl,

26. $R_2$ is $CH_2CH_2C(O)NH_2$, $X_1$ is Cl and $X_2$ is H
27. $_2$ is $CH_2CH_2C(O)NH_2$, $X_1$ is F and $X_2$ is H
28. $R_2$ is $CH_2CH_2C(O)NH_2$, $X_1$ is H and $X_2$ is F Compounds (30–34) having the formula V:

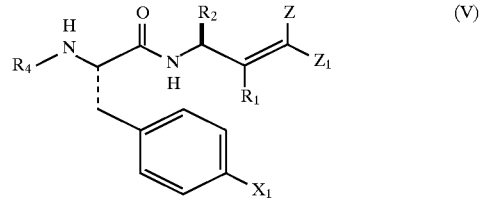

30. $R_4$ is $PhCH_2OC(O)$, $X_1$ is H, $R_2$ is $CH_2CH_2C(O)NH_2$, $R_1$ is H, Z is H, and $Z_1$ is $CO_2CH_2CH_3$ 31. $R_4$ is $CH_3CH_2CH_2SO_2$, $X_1$ is H, $R_2$ is $CH_2CH_2C(O)NH_2$, $R_1$ is H, Z is H, and $Z_1$ is $CO_2CH_2CH_3$ 32. $R_4$ is $PhCH_2SO_2$, $X_1$ is H, $R_2$ is $CH_2CH_2C(O)NH_2$, $R_1$ is H, Z is H, and $Z_1$ is $CO_2CH_2CH_3$ 33. $R_4$ is $CH_3CH_2SO_2$, $X_1$ is H, $R_2$ is $CH_2CH_2C(O)NH_2$, $R_1$ is H, Z is H, and $Z_1$ is $CO_2CH_2CH_3$ 34. $R_4$ is $PhSO_2$, $X_1$ is H, $R_2$ is $CH_2CH_2C(O)NH_2$, $R_1$ is H, Z is H, and $Z_1$ is $CO_2CH_2CH_3$ Compound 29 having the formula VI:

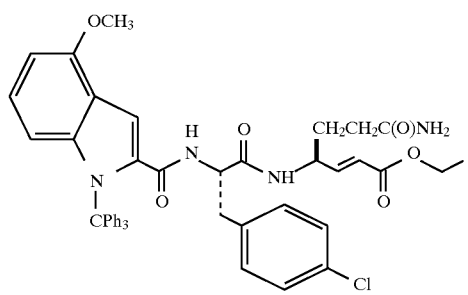

Compound 44 having the formula VII:

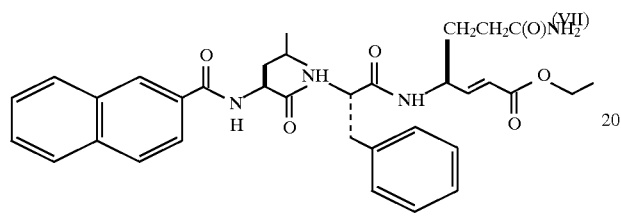

Compounds (35–37) having the formula VIII:

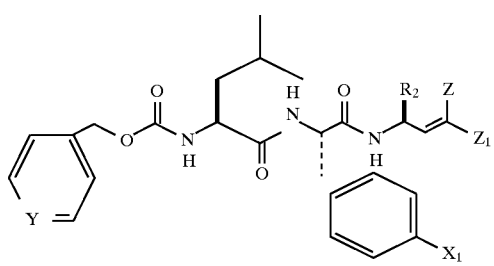

35. $X_1$ is F, $R_2$ is $CH_2CH_2C(O)NH_2$, Y is CH, Z is H, and $Z_1$ is $CO_2CH_2CH_3$
36. $X_1$ is H, $R_2$ is $CH_2CH_2C(O)NH_2$, Y is N, Z is H, and $Z_1$ is $CO_2CH_2CH_3$
37. $X_1$ is H, $R_2$ is $CH_2CH_2C(O)NH_2$, Y is CH, Z is H, and $Z_1$ is $C(O)N(CH_3)OCH_3$ Compounds 46–66 and 78 having the formula IX:

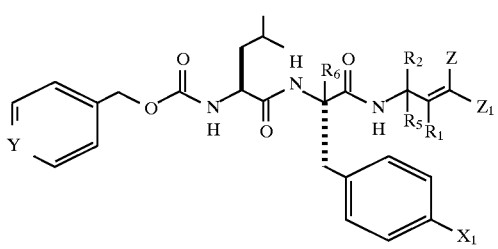

46. $R_1$ is H; $R_2$ is $CH_2CH_2C(O)N_2$; $R_5$, $R_6$, and $X_1$ are H; Y is CH; Z is H; and

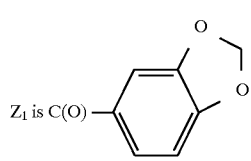

47. $R_1$ is H; $R_2$ is $CH_2CH_2C(O)NH_2$; $R_5$, $R_6$ and $X_1$ are H; Y is CH; Z is H; and

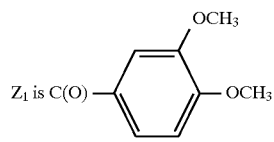

48. $R_1$ is H; $R_2$ is $CH_2CH_2C(O)NH_2$; $R_5$, $R_6$ and $X_1$ are H; Y is CH; Z is H; and

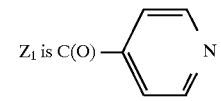

49. $R_1$ is H; $R_2$ is $CH_2CH_2C(O)NH_2$; $R_5$, $R_6$, and $X_1$ are H; Y is CH; Z is H; and

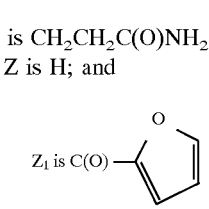

50. $R_1$ is H; $R_2$ is $CH_2CH_2C(O)NH_2$; $R_5$, $R_6$, and $X_1$ are H; Y is CH; Z is H; and

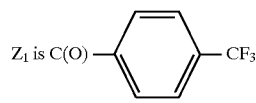

51. $R_1$ is H; $R_2$ is $CH_2CH_2C(O)NH_2$; $R_5$, $R_6$, and $X_1$ are H; Y is CH; Z is H; and

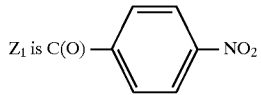

52. $R_1$ is H; $R_2$ is $CH_2CH_2C(O)NH_2$; $R_5$, $R_6$, and $X_1$ are H; Y is CH; Z is H; and $Z_1$ is $C(O)tBu$
53. $R_1$ is H; $R_2$ is $CH_2CH_2C(O)NH_2$; $R_5$, $R_6$ are H; $X_1$ is OH; Y is CH; Z is H; and $Z_1$ is $CO_2CH_2CH_3$
54. $R_1$ is H; $R_2$ is $CH_2CH_2C(O)NH_2$; $R_5$, $R_6$, and $X_1$ are H; Y is CH; Z is H; and $Z_1$ is $C(O)C(O)CH_3$
55. $R_1$ is H; $R_2$ is $CH_2CH_2C(O)NH_2$; $R_5$, $R_6$, and $X_1$ are H; Y is CH; Z is H; and $Z_1$ is $C(O)C(O)N(CH_3)_2$
56. $R_1$ is H; $R_2$ is $CH_2OC(O)NH_2$; $R_5$, $R_6$, and $X_1$ are H; Y is CH; Z is H; and $Z_1$ is $CO_2CH_2CH_3$
57. $R_1$ is H; $R_2$ is $CH_2CH_2C(O)NH_2$; $R_5$, $R_6$, and $X_1$ are H; Y is CH; Z is H; and Z and $Z_1$ together form

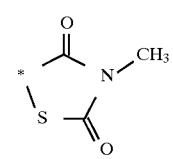

where the S is preferably trans to the $R_1$ group
58. $R_1$ is H; $R_2$ is $CH_2CH_2C(O)NH_2$; $R_5$, $R_6$, and $X_1$ are H; Y is CH; and Z and $Z_1$ together form

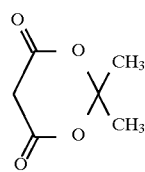

59. $R_1$ is H; $R_2$ is $CH_2CH_2C(O)NH_2$; $R_5$, $R_6$, and $X_1$ are H; Y is CH; Z is H; and $Z_1$ is C(O)NHPh
60. $R_1$ is H; $R_2$ is $CH_2CH_2C(O)NH_2$; $R_5$, $R_6$, and $X_1$ are H; Y is CH; Z is H; and $Z_1$ is $C(O)N(CH_2)Ph$
61. $R_1$ is H; $R_2$ is $CH_2CH_2C(O)NH_2$; $R_5$, $R_6$, and $X_1$ are H; Y is CH; Z is H; and $Z_1$ is

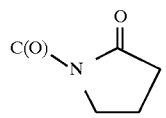

62. $R_1$ is H; $R_2$ is $CH_2CH_2C(O)NH_2$; $R_5$, $R_6$, and $X_1$ are H; Y is CH; Z is H; $Z_1$ is

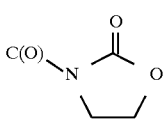

63. $R_1$, $R_5$, $R_6$, $X_1$, and Z are H; Y is CH; $R_2$ is $CH_2CH_2C(O)NH_2$; and $Z_1$ is

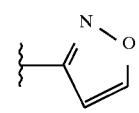

64. $R_1$, $R_5$, $R_6$, $X_1$, and Z are H; Y is CH; $R_2$ is $CH_2CH_2C(O)NH_2$; and $Z_1$ is

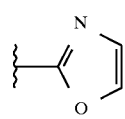

65. $R_1$, $R_5$, $X_1$, and Z are H; Y is CH; $R_2$ is $CH_2CH_2C(O)NH_2$; and $Z_1$ is

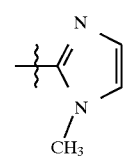

66. $R_1$, $R_5$, $R_6$, $X_1$, and Z are H; Y is CH; $R_2$ is $CH_2CH_2C(O)NH_2$; and $Z_1$ is

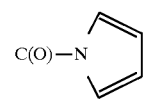

78. $R_1$, $R_5$, $R_6$ and $X_1$ are H; Y is CH; $R_2$ is $CH_2CH_2C(O)NH_2$; Z is $CH_2Cl$; and $Z_1$ is H Compounds 67–69 having the formula X:

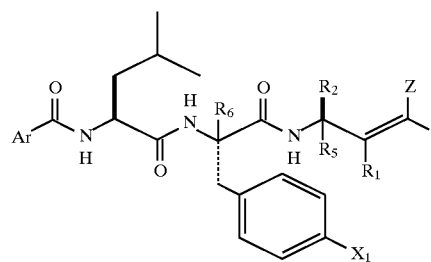

67. $R_1$, $R_6$, $X_1$, and Z are H; $R_2$ is $CH_2CH_2C(O)NH_2$; $Z_1$ is $CO_2CH_2CH_3$; and Ar is Ph
68. $R_1$, $R_5$, $R_6$, $X_1$, and Z are H; $R_2$ is $CH_2CH_2C(O)NH_2$; and Ar is

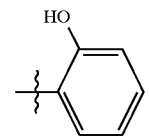

69. $R_1$, $R_5$, $R_6$, $X_1$, and Z are H; $R_2$ is $CH_2CH_2C(O)NH_2$; $Z_1$ is $CO_2CH_2CH_3$; and Ar is

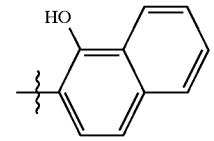

Compounds 70–73 having the formula XI:

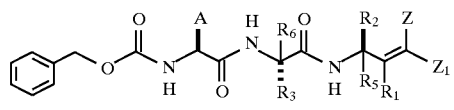

70. $R_1$, $R_5$, $R_6$, and Z are H; $R_2$ is $CH_2CH_2C(O)NH_2$; $R_3$ is $CH_2Ph$; $Z_1$ is $CO_2CH_2CH_3$; and A is

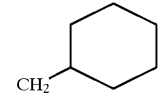

71. $R_1$, $R_5$, $R_6$, and Z are H; $R_2$ is $CH_2CH_2C(O)NH_2$; $R_3$ is $CH_2Ph$; $Z_1$ is $CO_2CH_2CH_3$; and A is Ph
72. $R_1$, $R_5$, $R_6$, and Z are H; $R_2$ is $CH_2CH_2C(O)NH_2$; A is $CH_2CH(CH_3)_2$; $Z_1$ is $CO_2CH_2CH_3$; and $R_3$ is

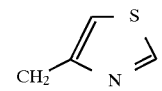

73. $R_1$, $R_5$, $R_6$, and Z are H; $R_2$ is $CH_2CH_2C(O)NH_2$; A is $CH_2CH(CH_3)_2$; $Z_1$ is $CO_2CH_2CH_3$; and $R_3$ is

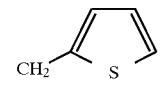

Compounds 1, 6, 8–10, 15, 20, 23, 38–40, 76, and 77 having the formula XII:

(XII)

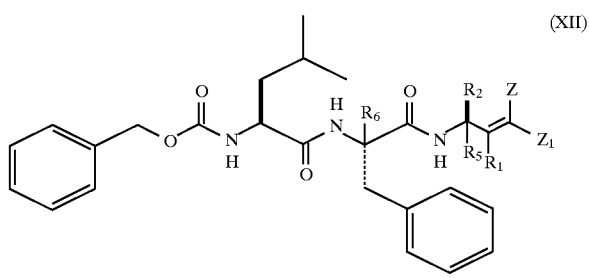

1. $R_1$ is H; $R_2$ is $CH_2CH_2CN$; $R_5$ is H; $R_6$ is H; Z is F; and $Z_1$ is $CO_2CH_2CH_3$
6. $R_1$ is H; $R_2$ is $CH_2CH_2C(O)NH_2$; $R_5$ is H; $R_6$ is H; Z is H; and $Z_1$ is $C(O)NHCH_2CH_3$
8. $R_1$ is H; $R_2$ is $CH_2CH_2C(O)NH_2$; $R_5$ is H; $R_6$ is H; Z is F; and $Z_1$ is $CO_2CH_2CH_3$
9. $R_1$ is H; $R_2$ is $CH_2CH_2C(O)NH_2$; $R_5$ is H; $R_6$ is H; Z is H; and $Z_1$ is $SO_2Ph$
10. $R_1$ is H; $R_2$ is $CH_2CH_2C(O)NH_2$; $R_5$ is H; $R_6$ is H; Z is H; and $Z_1$ is $SO_2Ph$
15. $R_1$ is H; $R_2$ is $CH_2CH_2C(O)NH_2$; $R_5$ is H; $R_6$ is H; Z is H; and $Z_1$ is $CO_2H$
20. $R_1$ is H; $R_2$ is $CH_2CH_2C(O)NH_2$; $R_5$ is H; $R_6$ is H; Z is H; and $Z_1$ is $PO(OCH_2CH_3)_2$
23. $R_1$ is H; $R_2$ is $CH_2CH_2C(O)NH_2$; $R_5$ is H; $R_6$ is H; Z is H; and $Z_1$ is

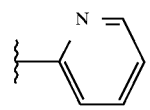

38. $R_1$ is H; $R_2$ is $CH_2CH_2C(O)NH_2$; $R_5$ is H; $R_6$ is H; Z is H; and $Z_1$ is

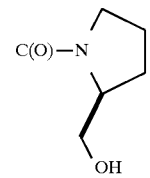

39. $R_1$ is H; $R_2$ is $CH_2CH_2C(O)NH_2$; $R_5$ is H; $R_6$ is H; Z is H; and $Z_1$ is

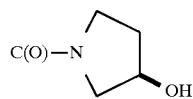

40. $R_1$ is H; $R_2$ is $CH_2CH_2C(O)NH_2$; $R_5$ is H; $R_6$ is H; Z is H; and $Z_1$ is

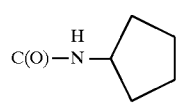

76. $R_1$ is H; $R_2$ is $CH_2CH_2C(O)NH_2$; $R_5$ is H; $R_6$ is H; Z is H; and $Z_1$ is $CH_2OAc$
77. $R_1$ is H; $R_2$ is $CH_2CH_2C(O)NH_2$; $R_5$ is H; $R_6$ is H; Z is H; and $Z_1$ is

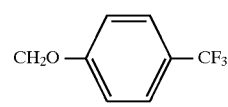

Compound 45 having the formula XIII:

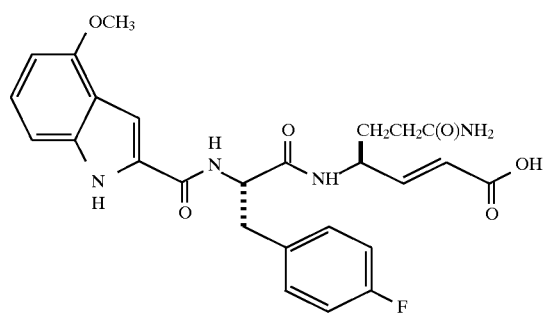

(XIII)

Compounds 79–97, also having the formula III:

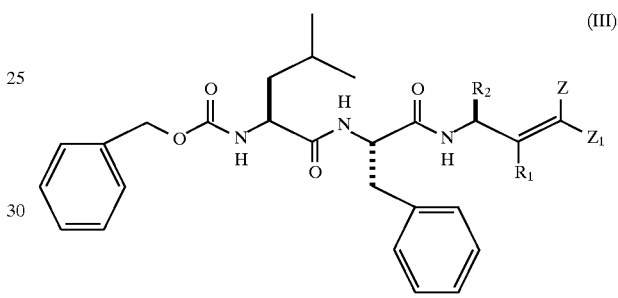

(III)

82. $R_2$ is $CH_2CH_2C(O)NH_2$, $R_1$ is H, Z is $CH_3$ and $Z_1$ is $CO_2CH_2CH_3$,
90. $R_2$ is $CH_2CH_2C(O)NH_2$, $R_1$ is H, and Z and $Z_1$ together form

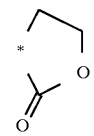

where C=O is preferably cis to the $R_1$ group or wherein $R_2$ is $CH_2CH_2C(O)NH_2$, $R_1$ is H, Z is H, and $Z_1$ is selected from:

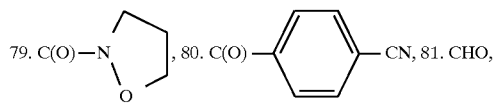

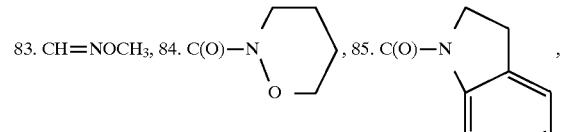

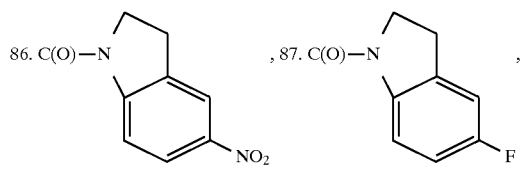

88. 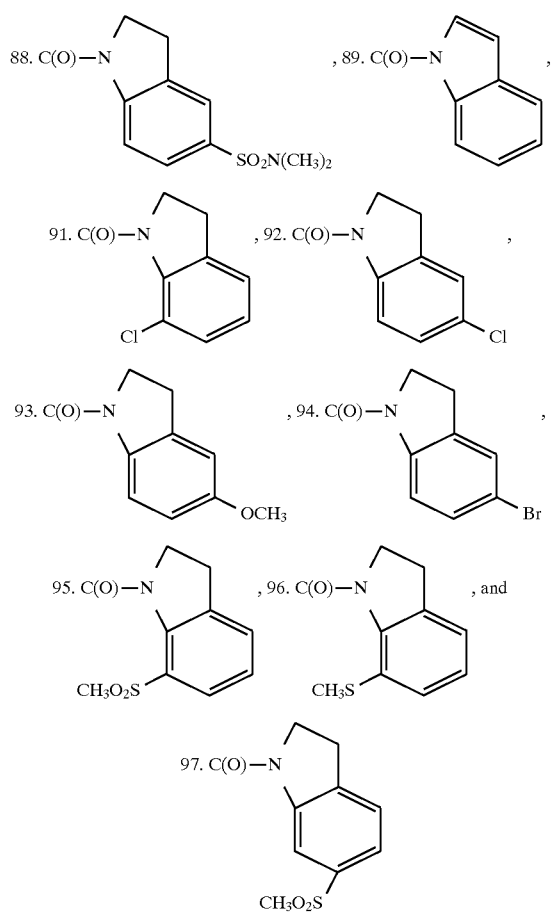
89. 
91.
92.
93.
94.
95.
96. , and
97.
Compounds 98–121 having formula XIV:
(XIV)
wherein $R_6$ is H, $R_1$ is H, $R_2$ is $CH_2CH_2C(O)NH_2$, Z is H, $Z_1$ is $CO_2CH_2CH_3$, and
98. $R_3$ is $CH_2Ph$ and $R_4$ is
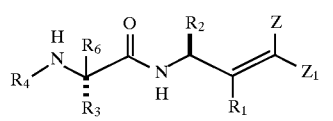
99. $R_3$ is H and $R_4$ is
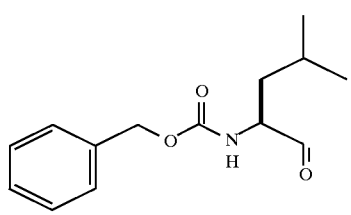
100. $R_3$ is
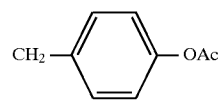
and $R_4$ is
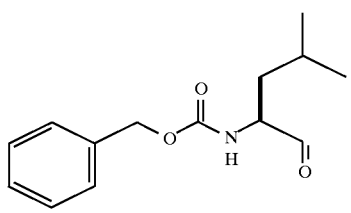
101. $R_3$ is $CH_2Ph$ and $R_4$ is
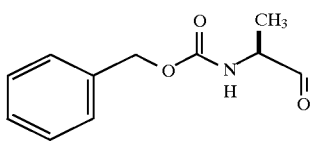
102. $R_3$ is $CH_2Ph$ and $R_4$ is
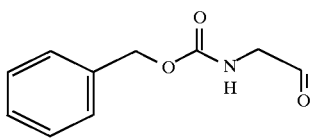
103. $R_3$ is
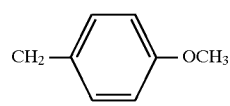
and $R_4$ is
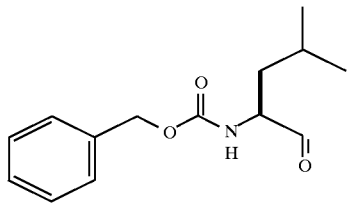
104. $R_3$ is $CH_2Ph$ and $R_4$ is
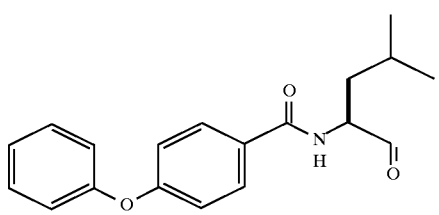

105. $R_3$ is
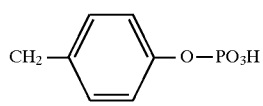
and $R_4$ is
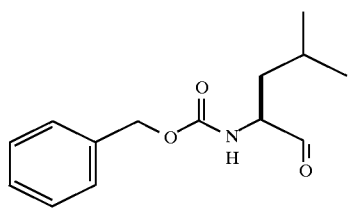
106. $R_3$ is $CH_2Ph$ and $R_4$ is
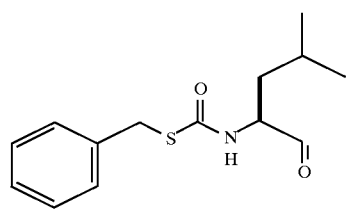
107. $R_3$ is $CH_2Ph$ and $R_4$ is
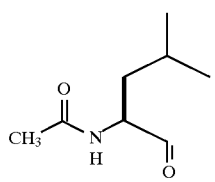
108. $R_3$ is $CH_2CH_3$ and $R_4$ is
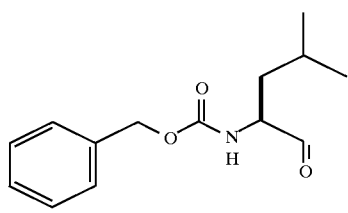
109. $R_3$ is $CH_3$ and $R_4$ is
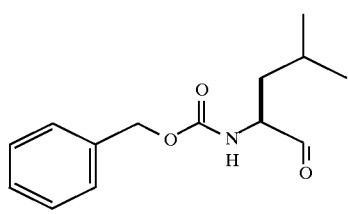
110. $R_3$ is $CH_2Ph$ and $R_4$ is
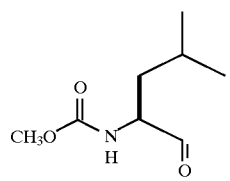
111. $R_3$ is $CH_2Ph$ and $R_4$ is
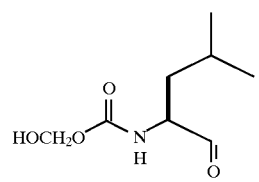
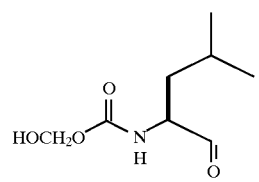
112. $R_3$ is
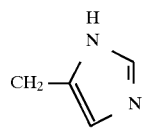
and $R_4$ is
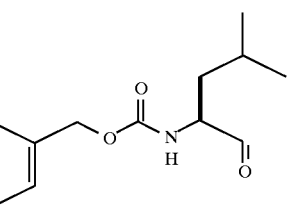
113. $R_3$ is
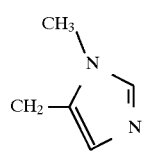
and $R_4$ is
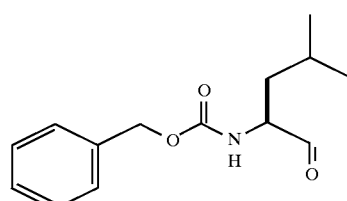
114. $R_3$ is
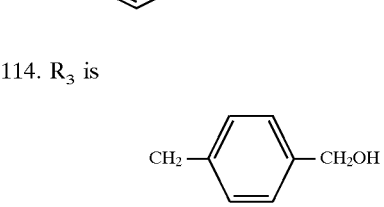
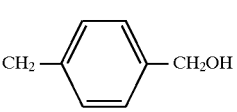

and $R_4$ is

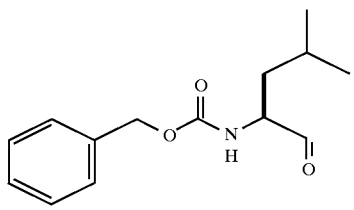

115. $R_3$ is $CH_2Ph$ and $R_4$ is

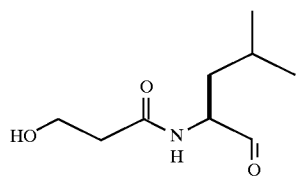

116. $R_3$ is $CH_2Ph$ and $R_4$ is

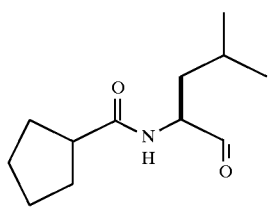

117. $R_3$ is $CH_2Ph$ and $R_4$ is

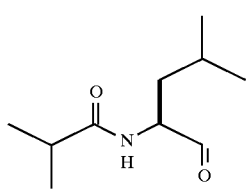

118. $R_3$ is $CH_2Ph$ and $R_4$ is

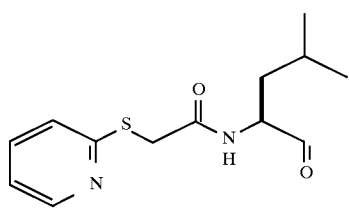

119. $R_3$ is $CH_2Ph$ and $R_4$ is

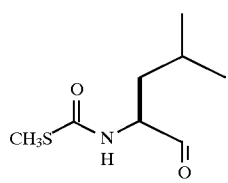

120. $R_3$ is $CH_2Ph$ and $R_4$ is

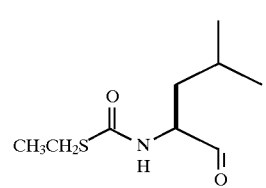

121. $R_3$ is $CH_2CH_2CO_2H$ and $R_4$ is

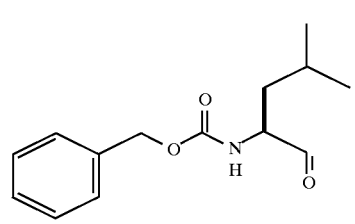

Compounds 122–130, also having the formula XIV:

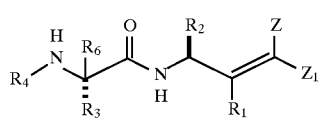

(XIV)

wherein $R_6$ is H, $R_1$ is H, $R_3$ is $CH_2Ph$ and

122. $R_2$ is $CH_2OC(O)NHC(O)CH_2Cl$, Z is H, $Z_1$ is $CO_2CH_2CH_3$ and $R_4$ is

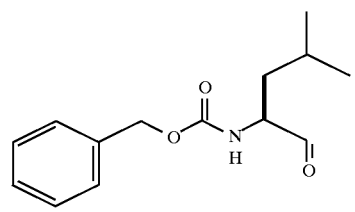

123. $R_2$ is $CH_2CH_2C(O)NH_2$, Z is H, $Z_1$ is $CO_2CH_2CH_3$ and $R_4$ is

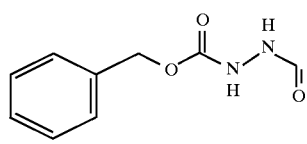

122. $R_2$ is $CH_2CHOC(O)NHC$, Z is H, $Z_1$ is

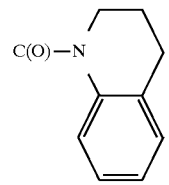

and $R_4$ is
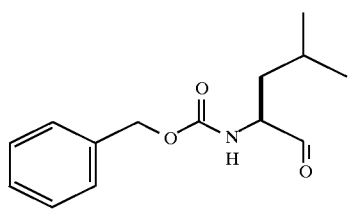
125. $R_2$ is $CH_2CH_2C(O)NH_2$, Z is H, $Z_1$ is $NO_2$, and $R_4$ is
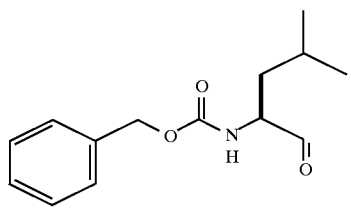
126. $R_2$ is $CH_2CH_2C(O)NH_2$, Z is H, $Z_1$ is
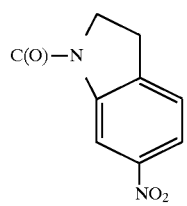
and $R_4$ is
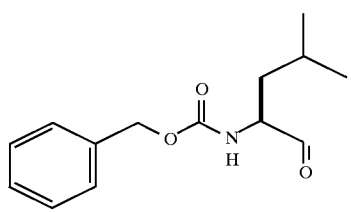
127. $R_2$ is $CH_2CH_2C(O)NH_2$, Z is H, $Z_1$ is
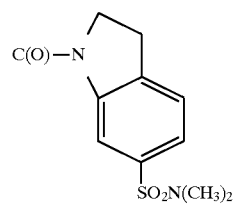
and $R_4$ is
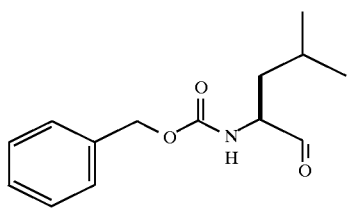
128. $R_2$ is $CH_2CH_2C(O)NH_2$, Z is H, $Z_1$ is
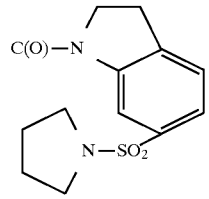
and $R_4$ is
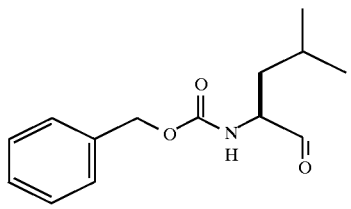
129. $R_2$ is $CH_2CH_2C(O)NH_2$, Z is H, $Z_1$ is $CO_2CH_2CH_3$ and $R_4$ is
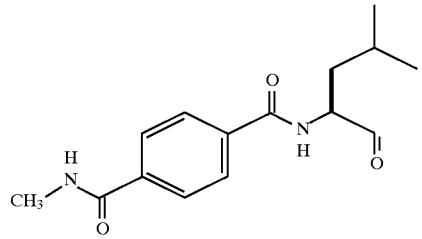
130. $R_2$ is $CH_2CH_2C(O)NH_2$, Z and $Z_1$ together form
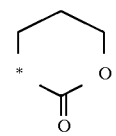
and $R_4$ is
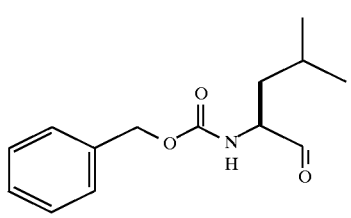
where C=O is preferably cis to the $R_1$ group.

Compounds 131–145, also having the formula XIV:

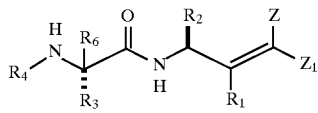

wherein $R_6$ is H, $R_1$ is H, $R_2$ is $CH_2CH_2C(O)NH_2$, $R_4$ is

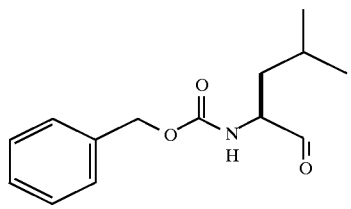

and

131. $R_3$ is $CH_2Ph$, Z is H and $Z_1$ is

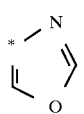

132. $R_3$ is

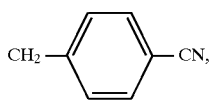

Z is H and $Z_1$ is $CO_2CH_2CH_3$

133. $R_3$ is

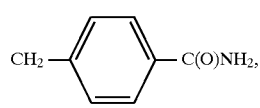

Z is H and $Z_1$ is $CO_2CH_2CH_3$

134. $R_3$ is $CH(OH)CH_3$, Z is H and $Z_1$ is $CO_2CH_2CH_3$

135. $R_3$ is

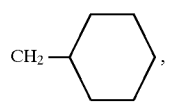

Z is H and $Z_1$ is $CO_2CH_2CH_3$

136. $R_3$ is

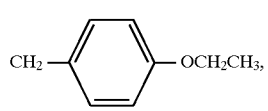

Z is H and $Z_1$ is $CO_2CH_2CH_3$

137. $R_3$ is $CH_2CH_2CH_3$, Z is H and $Z_1$ is $CO_2CH_2CH_3$

138. $R_3$ is $CH_2Ph$, Z is H and $Z_1$ is $C(O)N(OH)CH_3$

139. $R_3$ is

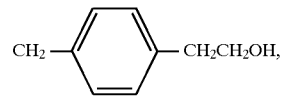

Z is H and $Z_1$ is $CO_2CH_2CH_3$

140. $R_3$ is

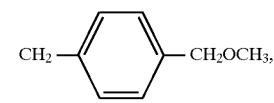

Z is H and $Z_1$ is $CO_2CH_2CH_3$

141. $R_3$ is $CH_2CH(CH_3)_2$, Z is H and $Z_1$ is $CO_2CH_2CH_3$
142. $R_3$ is $CH_2SCH_3$, Z is H and $Z_1$ is $CO_2CH_2CH_3$
143. $R_3$ is $CH_2SCH_2CH_3$, Z is H, and $Z_1$ is $CO_2CH_2CH_3$
144. $R_3$ is $CH_2Ph$, Z is $CH_3$, and $Z_1$ is $CO_2H$,
145. $R_3$ is $CH_2Ph$, Z is H, and $Z_1$ is

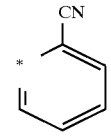

Compounds 146–155, also having the formula XIV:

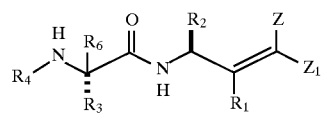

wherein $R_6$ is H, $R_1$ is H, $R_2$ is $CH_2CH_2C(O)NH_2$, Z is H, and

146. $Z_1$ is $CO_2CH_2CH_3$, $R_3$ is $CH_2Ph$, and $R_4$ is

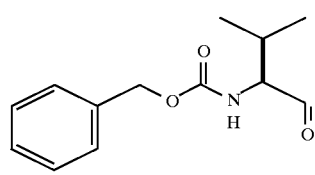

147. $Z_1$ is $CO_2CH_2CH_3$, $R_3$ is $CH_2Ph$, and $R_4$ is

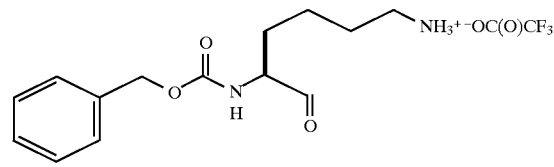

148. $Z_1$ is $CO_2CH_2CH_3$, $R_3$ is $CH_2Ph$, and $R_4$ is

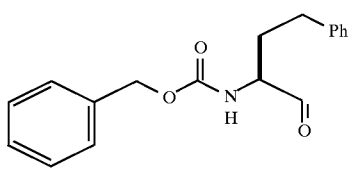

149. $Z_1$ is $CO_2CH_2CH_3$, $R_3$ is $CH_2Ph$, and $R_4$ is

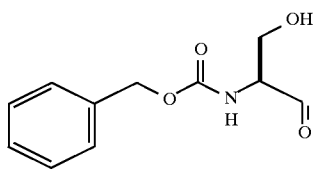

150. $Z_1$ is

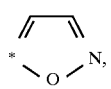

$R_3$ is $CH_2Ph$, and $R_4$ is

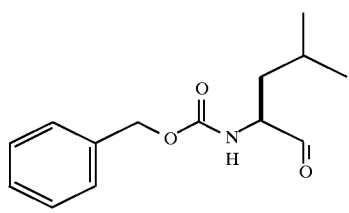

151. $Z_1$ is $CO_2CH_2CH_3$, $R_3$ is $CH_2Ph$, and $R_4$ is

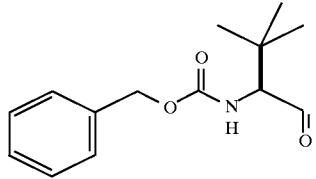

152. $Z_1$ is $CO_2CH_2CH_3$, $R_3$ is $CH_2Ph$, and $R_4$ is

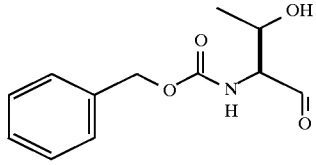

153. $Z_1$ is $CO_2CH_2CH_3$, $R_3$ is $CH_2Ph$, and $R_4$ is

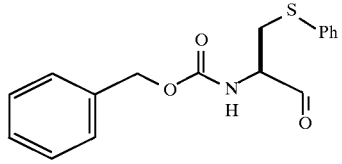

154. $Z_1$ is $CO_2CH_2CH_3$, $R_3$ is $CH_2Ph$, and $R_4$ is

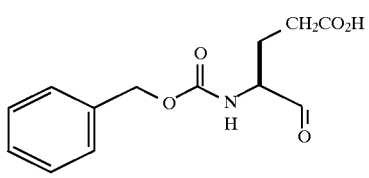

155. $Z_1$ is $CO_2CH_2CH_3$, $R_3$ is

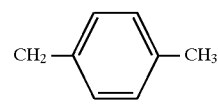

and $R_4$ is

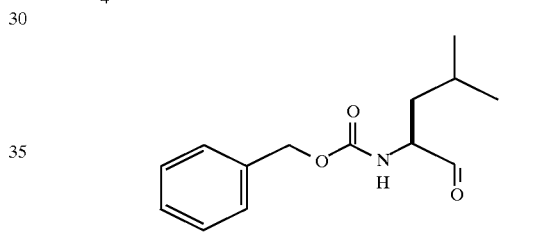

Compounds 156–173, also having formula XIV:

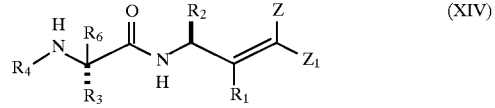

wherein $R_6$ is H, $R_3$ is $CH_2Ph$, $R_2$ is $CH_2CH_2C(O)NH_2$, and

156. $R_1$ is OH, Z is H, $Z_1$ is $CO_2CH_2CH_3$, and $R_4$ is

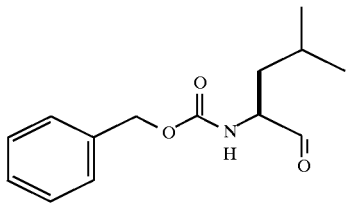

157. $R_1$ is H, Z is H, $Z_1$ is $CO_2CH_2CH_3$, and $R_4$ is

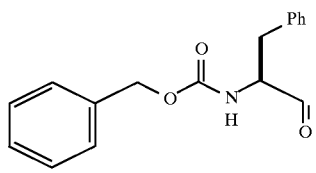

158. $R_1$ is H, Z is H, $Z_1$ is $CO_2CH_2CH_3$, and $R_4$ is

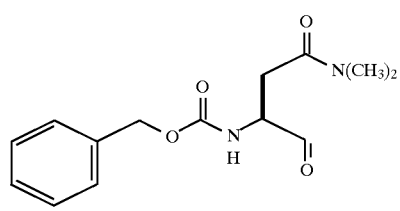

159. $R_1$ is H, Z is H, $Z_1$ is $CO_2CH_2CH_3$, and $R_4$ is

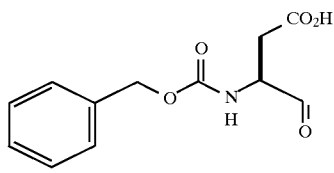

160. $R_1$ is H, Z is H, $Z_1$ is

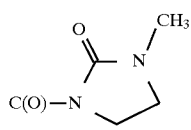

and $R_4$ is

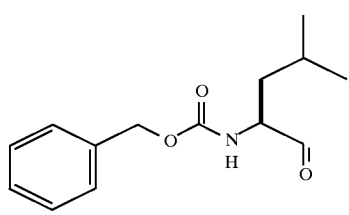

161. $R_1$ is H, Z is H, $Z_1$ is $CO_2CH_2CH_3$, and $R_4$ is

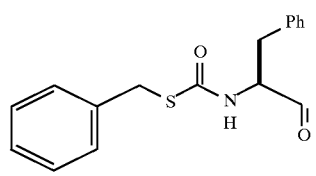

162. $R_1$ is H, Z is H, $Z_1$ is $CO_2CH_2CH_3$, and $R_4$ is

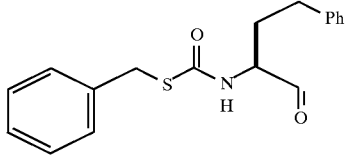

163. $R_1$ is H, Z is H, $Z_1$ is $CO_2CH_2C(CH_3)_3$, and $R_4$ is

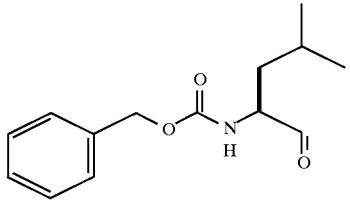

164. $R_1$ is H, Z and $Z_1$ together form

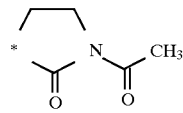

and $R_4$ is

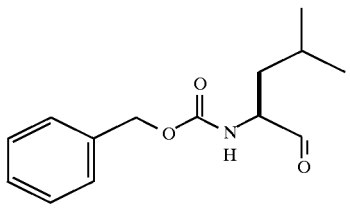

where C=O is preferably cis to the $R_1$ group

165. $R_1$ is H, Z is H, $Z_1$ is $CO_2CH_2CH_3$, and $R_4$ is

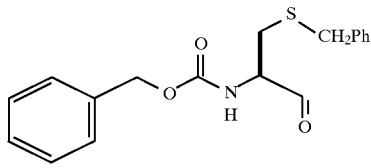

166. $R_1$ is H, Z is H, $Z_1$ is $CO_2CH_2CH_3$, and $R_4$ is

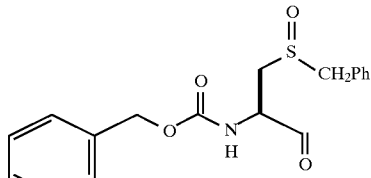

167. $R_1$ is H, Z is H, Z is $CO_2CH_2CH_3$, and $R_4$ is

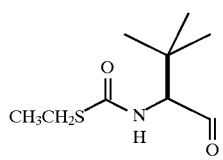

168. $R_1$ is H, Z is $CH_3$, $Z_1$ is $CO_2CH_2CH_3$, and $R_4$ is

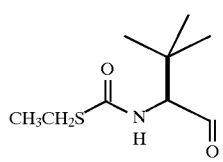

169. $R_1$ is H, Z and $Z_1$ together form

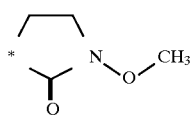

and $R_4$ is

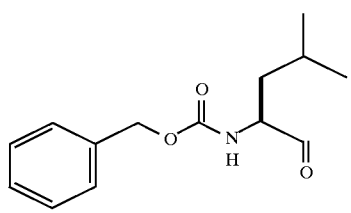

where C=O is preferably cis to $R_1$

170. $R_1$ is H, Z is H, $Z_1$ is $CO_2CH_2CH_3$, and $R_4$ is

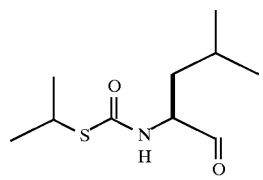

171. $R_1$ is H, Z is $CH_3$, $Z_1$ is $CO_2CH_2CH_3$, and $R_4$ is

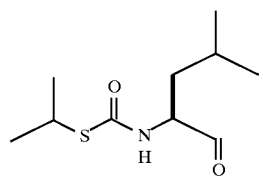

172. $R_1$ is H, Z is H, $Z_1$ is $CO_2CH_2CH_3$, and $R_4$ is

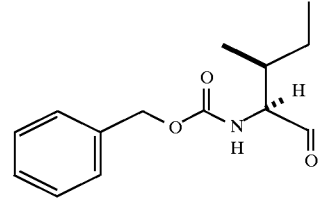

173. $R_1$ is H, Z is H, $Z_1$ is $CO_2CH_2CH_3$, and $R_4$ is

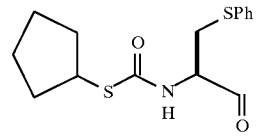

Compounds 174–188, also having the formula XIV:

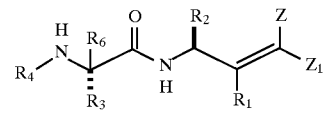

wherein $R_6$ is H, $R_2$ is $CH_2CH_2C(O)NH_2$, $R_1$ is H, and

174. Z is H, $Z_1$ is $CO_2CH_2CH_3$, $R_3$ is

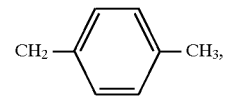

and $R_4$ is

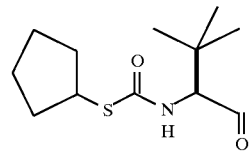

175. Z is $CH_3$, $Z_1$ is $CO_2CH_2CH_3$, $R_3$ is

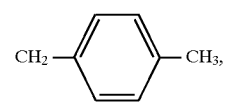

and $R_4$ is

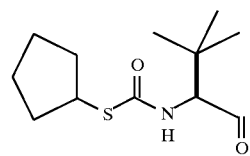

176. Z is H, $Z_1$ is $CO_2CH_2CH_3$, $R_3$ is

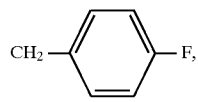

and $R_4$ is

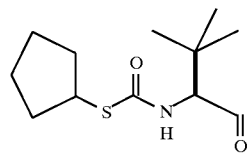

177. Z is $CH_3$, $Z_1$ is $CO_2CH_2CH_3$, $R_3$ is

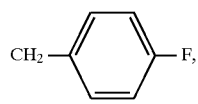

and $R_4$ is

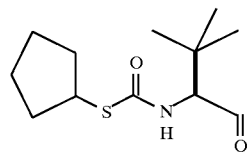

178. Z is H, $Z_1$ is $CO_2CH_2CH_3$, $R_3$ is $CH_2Ph$, and $R_4$ is

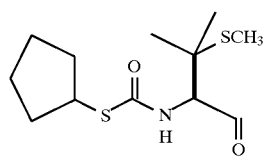

179. Z is H, $Z_1$ is $CO_2CH_2CH_3$, $R_3$ is $CH_2Ph$, and $R_4$ is

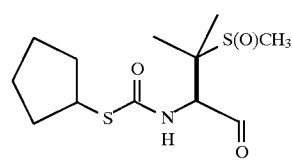

180. Z is H, $Z_1$ is $CO_2CH_2CH_3$, $R_3$ is $CH_2Ph$, and $R_4$ is

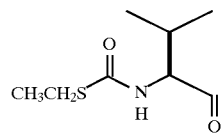

181. Z and $Z_1$ together form

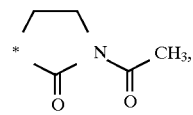

$R_3$ is

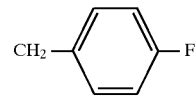

and $R_4$ is

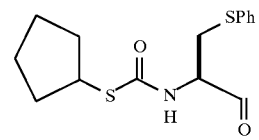

where C=O is preferably cis to the $R_1$ group

182. Z is H, $Z_1$ is $CO_2CH_2CH_3$, $R_3$ is $CH_2Ph$, and $R_4$ is

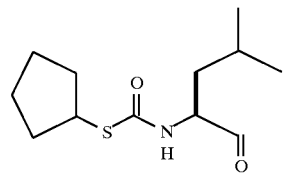

183. Z is H, $Z_1$ is $CO_2CH_2CH_3$, $R_3$ is

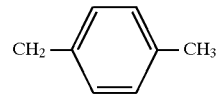

and $R_4$ is

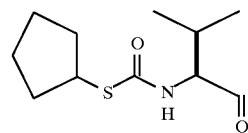

184. Z is H, $Z_1$ is $CO_2CH_2CH_3$, $R_3$ is

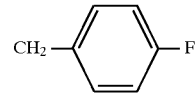

and $R_4$ is

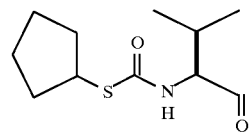

185. Z is H, Z$_1$ is CO$_2$CH$_2$CH$_3$, R$_3$ is

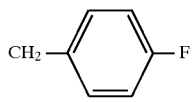

and R$_4$ is

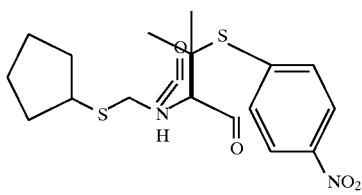

186. Z is H, Z$_1$ is CO$_2$CH$_2$Ph, R$_3$ is

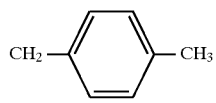

and R$_4$ is

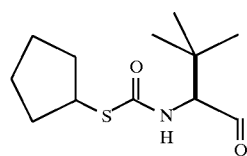

187. Z is CH$_3$, Z$_1$ is CO$_2$CH$_2$CH$_3$, R$_3$ is CH$_2$Ph and R$_4$ is

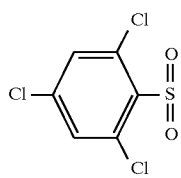

188. Z is H, Z$_1$ is CO$_2$CH$_2$CH$_2$OCH$_3$, R$_3$ is

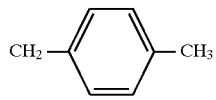

and R$_4$ is

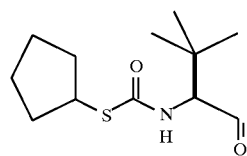

189. R$_3$ is

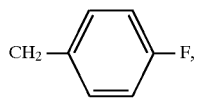

R$_4$ is

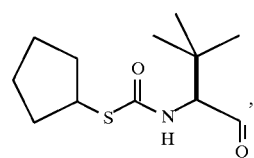

and Z and Z$_1$ together form

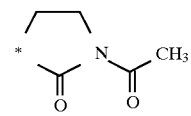

where C=O is preferably cis to the R$_1$ group

190. Z is H, Z$_1$ is CO$_2$CH$_2$CH$_3$, R$_3$ is

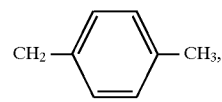

and R$_4$ is

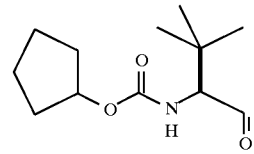

Other compounds according to the invention include the following compounds of formula III:

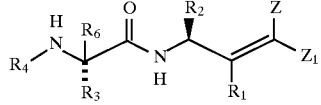

wherein R$_6$ is H, R$_1$ is H, R$_3$ is CH$_2$Ph, R$_2$ is CH$_2$CH$_2$C(O)NH$_2$, Z is H, Z$_1$ is CO$_2$CH$_2$CH$_3$, and R$_4$ is selected from the following:

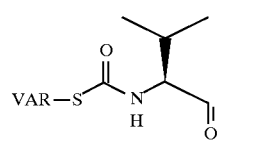

1c.

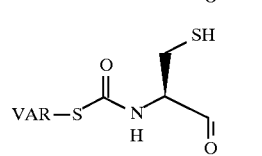

2c.

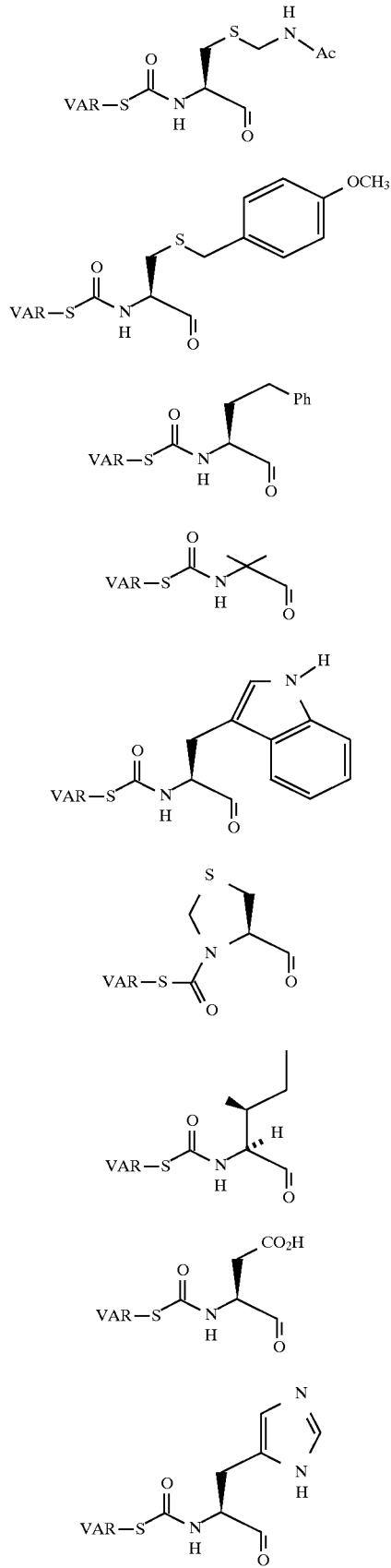
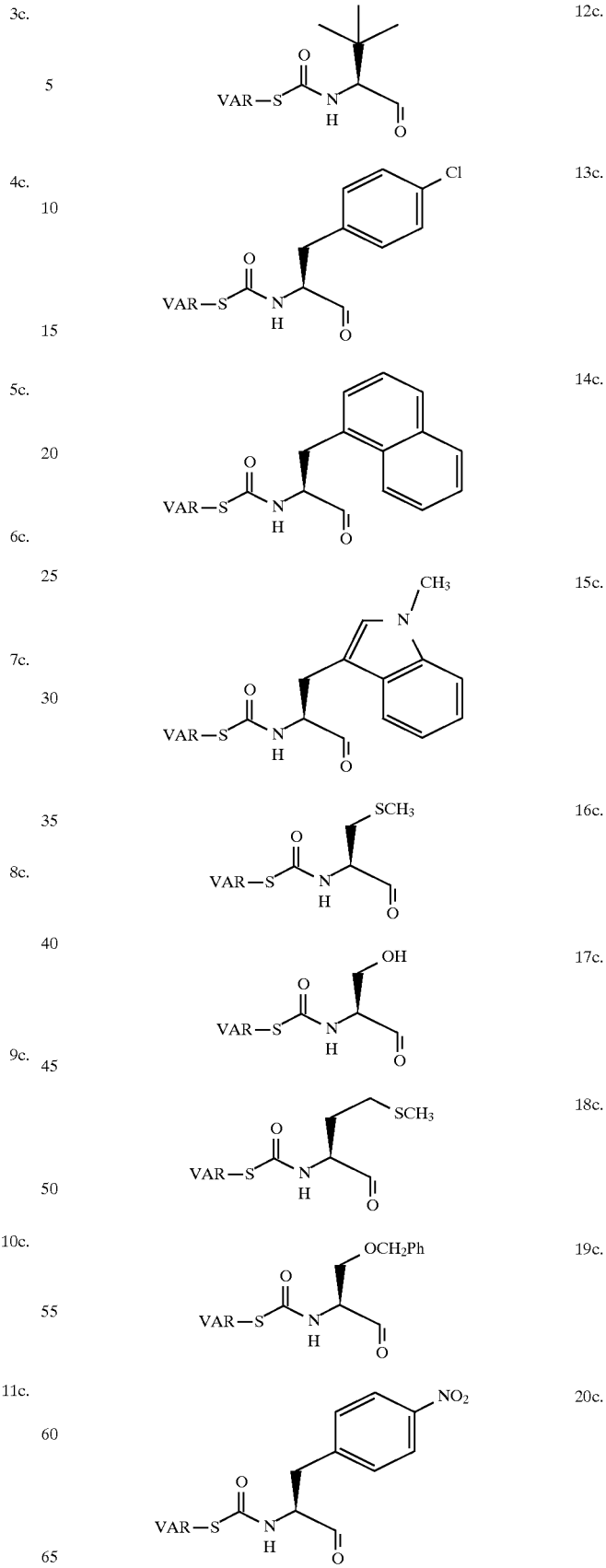

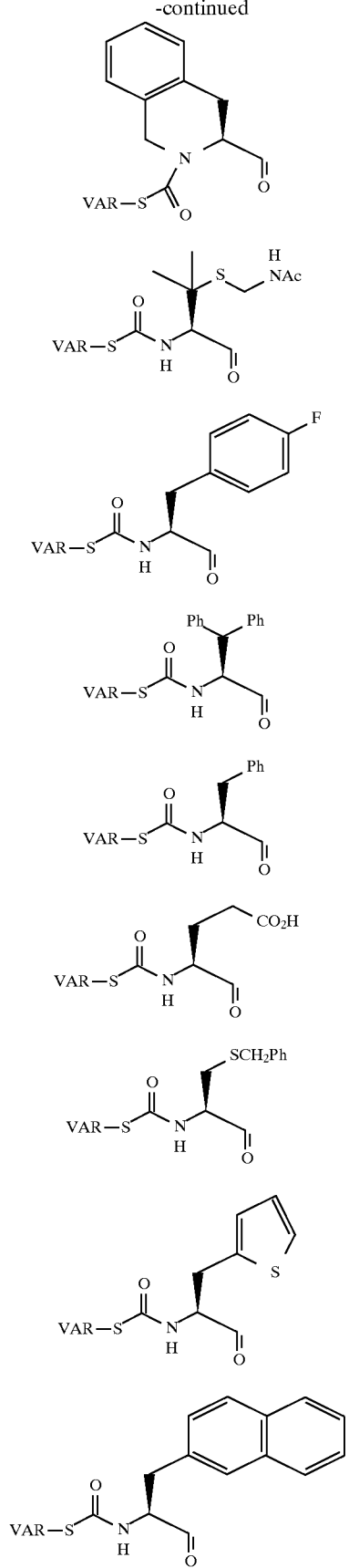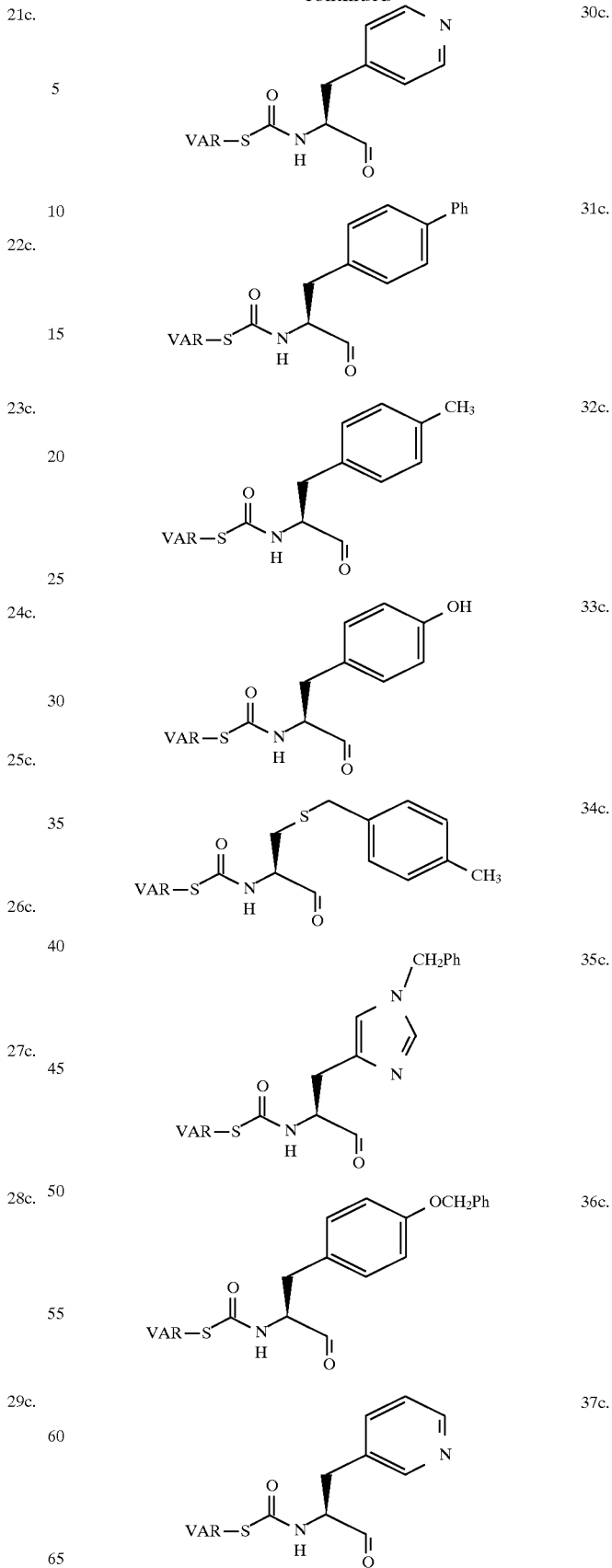

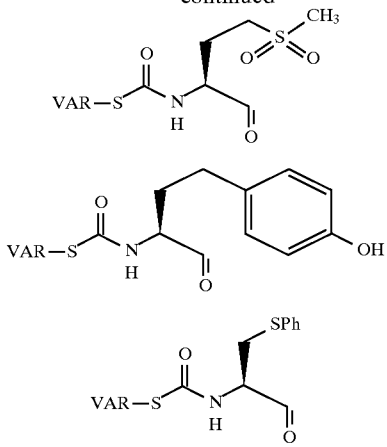

wherein VAR is selected from —CH$_2$CH$_3$, —CH(CH$_3$)$_2$, —CH$_2$CH(CH$_3$)$_2$, —CH$_2$—Ph,

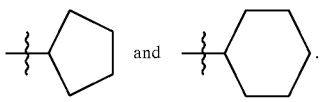

The present invention is further directed to methods of inhibiting picornaviral 3C protease activity that comprises contacting the protease for the purpose of such inhibition with an effective amount of a compound of formula I or a pharmaceutically acceptable prodrug, salt, or solvate thereof. For example, one can inhibit picornaviral 3C protease activity in mammalian tissue by administering a compound of formula I or II or a pharmaceutically acceptable prodrug, salt, or solvate thereof. More particularly, the present invention is directed to methods of inhibiting rhinoviral protease activity.

The activity of the inventive compounds as inhibitors of picornaviral 3C protease activity may be measured by any of the methods available to those skilled in the art, including in vivo and in vitro assays. Examples of suitable assays for activity measurements include the Antiviral HI-HeLa Cell Culture Assay and the Normal Human Bronchial Epithelial Cell Assay, both described herein.

Administration of the compounds of the formulas I and II, or their pharmaceutically acceptable prodrugs, salts, and solvates, may be performed according to any of the accepted modes of administration available to those skilled in the art. Illustrative examples of suitable modes of administration include, but are not limited to, oral, nasal, parenteral, topical, transdermal and rectal.

The inventive compounds of formulas I and II, and their pharmaceutically acceptable prodrugs, salts, and solvates, may be administered as a pharmaceutical composition in any suitable pharmaceutical form recognizable to the skilled artisan. Suitable pharmaceutical forms include, but are not limited to, solid, semisolid, liquid, or lyopholized formulations, such as tablets, powders, capsules, suppositories, suspensions and aerosols. The pharmaceutical composition may also include suitable excipients, diluents, vehicles and carriers, as well as other pharmaceutically active agents, depending upon the intended use.

Acceptable methods of preparing suitable pharmaceutical forms of the pharmaceutical compositions are known to those skilled in the art. For example, pharmaceutical preparations may be prepared following conventional techniques of the pharmaceutical chemist involving steps such as mixing, granulating and compressing when necessary for tablet forms, or mixing, filling and dissolving the ingredients as appropriate, to give the desired products for oral, parenteral, topical, intravaginal, intranasal, intrabronchial, intraocular, intraural and/or rectal administration.

Solid or liquid pharmaceutically acceptable carriers, diluents, vehicles or excipients may be employed in the pharmaceutical compositions. Illustrative solid carriers include starch, lactose, calcium sulphate dihydrate, terra alba, sucrose, talc, gelatin, pectin, acacia, magnesium stearate, and stearic acid. Illustrative liquid carriers may include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g. solution), or a nonaqueous or aqueous liquid suspension.

A dose of the pharmaceutical composition contains at least a therapeutically effective amount of the active compound (i.e., a compound of formula I or II or a pharmaceutically acceptable prodrug, salt, or solvate thereof) and preferably is made up of one or more pharmaceutical dosage units. The selected dose may be administered to a mammal, for example, a human patient, in need of treatment mediated by inhibition of 3C protease activity, by any known method of administering the dose including topical, for example, as an ointment or cream; orally, rectally, for example, as a suppository; parenterally by injection; or continuously by intravaginal, intranasal, intrabronchial, intraaural or intraocular infusion.

A "therapeutically effective amount" is intended to mean that amount of a compound of formula I or II that, when administered to a mammal in need thereof, is sufficient to effect treatment for disease conditions alleviated by the inhibition of the activity of one or more picarnoviral 3C proteases, such as human rhinoviruses, human poliovirus, human coxsackieviruses, encephalomyocarditis viruses, menigovirus, and hepatitis A virus. The amount of a given compound of formula I or II that will correspond to a "therapeutically effective amount" will vary depending upon factors such as the particular compound, the disease condition and the severity thereof, the identity of the mammal in need thereof, but can nevertheless be readily determined by one of skill in the art.

"Treating" or "treatment" is intended to mean at least the mitigation of a disease condition in a mammal, such as a human, that is alleviated by the inhibition of the activity of one or more picarnoviral 3C proteases, such as human rhinoviruses, human poliovirus, human coxsackieviruses, encephalomyocarditis viruses, menigovirus, and hepatitis A virus, and includes:

(a) prophylactic treatment in a mammal, particularly when the mammal is found to be predisposed to having the disease condition but not yet diagnosed as having it;

(b) inhibiting the disease condition; and/or (c) alleviating, in whole or in part, the disease condition.

The inventive compounds, and their salts, solvates, and prodrugs, may be prepared by employing the techniques available in the art using starting materials that are readily available. Certain novel and exemplary methods of preparing the inventive compounds are described below.

Preferably, the inventive compounds of formulas I and II are prepared by the novel X methods of the present invention, including the four general methods shown below. In each of these general methods, R$_1$, R$_2$, R$_3$, R$_4$, R$_5$, R$_6$, Z, and Z$_1$ are as defined above.

General Method I:

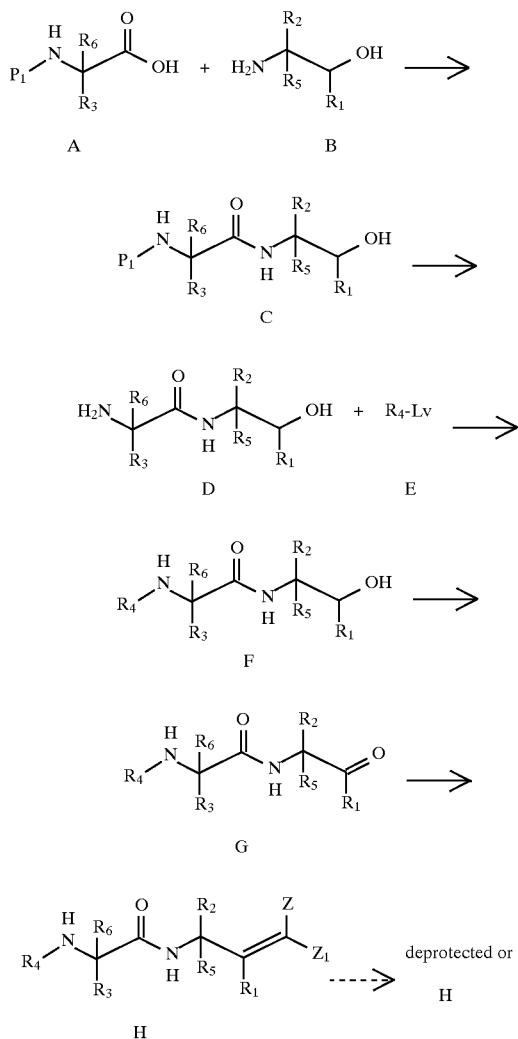

In General Method I, protected amino acid A, where $P_1$ is an appropriate protecting group for nitrogen, is subjected to an amide forming reaction with amino alcohol (or salt thereof) B to produce amide C. Amide C is then deprotected to give free amine (or salt thereof) D. Amine D and compound E, where "Lv" is an appropriate leaving group, are subjected to a bond forming reaction generating compound F. Compound F is oxidized to intermediate G, which is then transformed into unsaturated product H. If protecting groups are used on any R groups ($R_1$–$R_6$) and/or on Z and/or $Z_1$, product H is deprotected and/or further modified to yield "deprotected or modified H."

An alternative method to prepare intermediate F is described as follows:

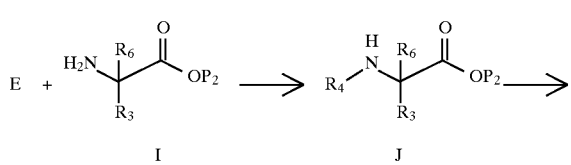

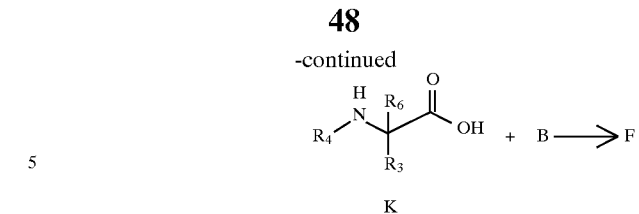

Compound E and amino acid (or salt thereof) I, where $P_2$ is an appropriate protecting group for oxygen, are subjected to a bond forming reaction to produce intermediate J. Intermediate J is deprotected to yield free carboxylic acid K, which is subsequently subjected to an amide forming reaction with amino alcohol (or salt thereof) B to generate intermediate F.

Amino alcohol B can be prepared as follows:

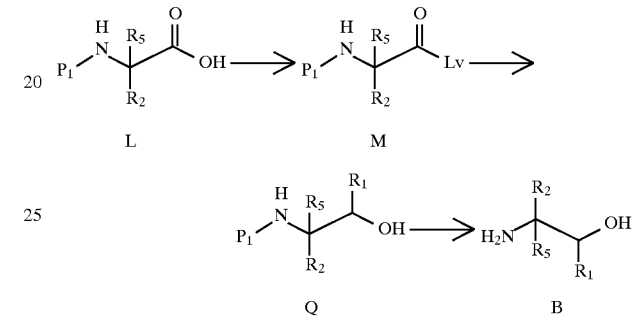

Amino acid L, where $P_1$ is an appropriate protecting group for nitrogen, is converted to carbonyl derivative M, where "Lv" is a leaving group. Compound M is subjected to a reaction where "Lv" is reduced to protected amino alcohol Q. Amino alcohol Q is deprotected to give amino alcohol B.

General Method II:

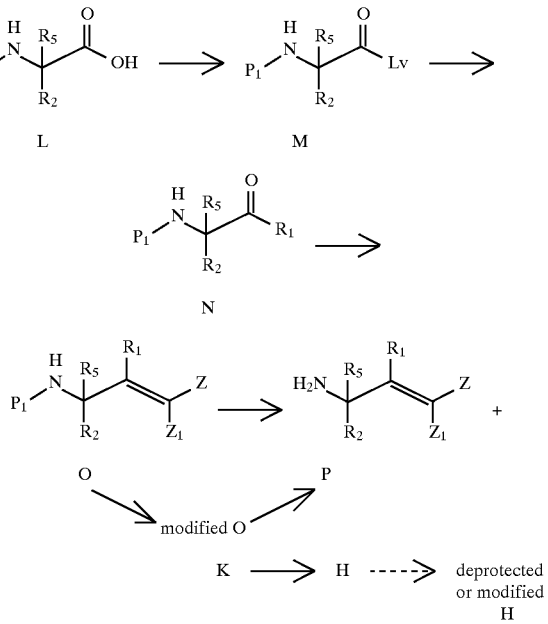

In General Method II, amino acid L, where $P_1$ is an appropriate protecting group for nitrogen, is converted to a carbonyl derivative M, where "Lv" is a leaving group. Compound M is subjected to a reaction where "Lv" is replaced by $R_1$ to give derivative N. Derivative N is then transformed into unsaturated product O. Unsaturated compound O is deprotected to give free amine (or salt thereof) P, or modified one or more times at $R_2$, $R_5$, Z and/or $Z_1$ to give one or more modified O compounds.

Modified O is then deprotected to give amine (or salt thereof) P. Amine P is subsequently subjected to an amide forming reaction with carboxylic acid K, prepared as described in General Method I, to give final product H. If protecting groups were used on any R group ($R_1$–$R_6$) and/or on Z and/or $Z_1$, product H is deprotected and/or further modified to yield "deprotected or modified H."

An alternative method to prepare intermediate N is described as follows:

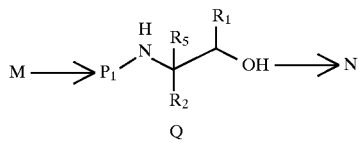

Compound M is subjected to a reaction where "Lv" is reduced to protected amino alcohol Q. Amino alcohol Q is subsequently oxidized to derivative N.

General Method III:

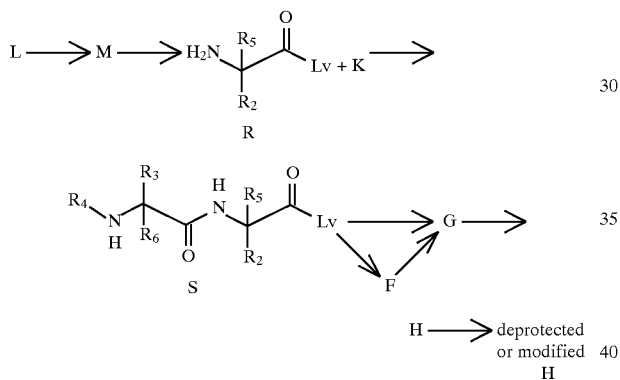

In General Method III, amino acid L, where $P_1$ is an appropriate protecting group for nitrogen, is converted to a carbonyl derivative M, where "Lv" is a leaving group. Derivative M is deprotected to give free amine (or salt thereof) R, which subsequently is subjected to an amide forming reaction with carboxylic acid K to give intermediate S. Intermediate S is then either converted directly to carbonyl intermediate G, or successively reduced to alcohol F, which is then oxidized to G. Intermediate G is subjected to a reaction to yield the unsaturated final product H. If protecting groups were used on any R groups ($R_1$–$R_6$) and/or on Z and/or $Z_1$, product H is deprotected and/or further modified to yield "deprotected or modified H."

General Method IV

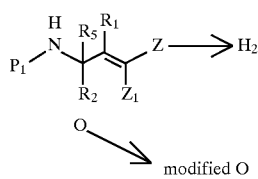

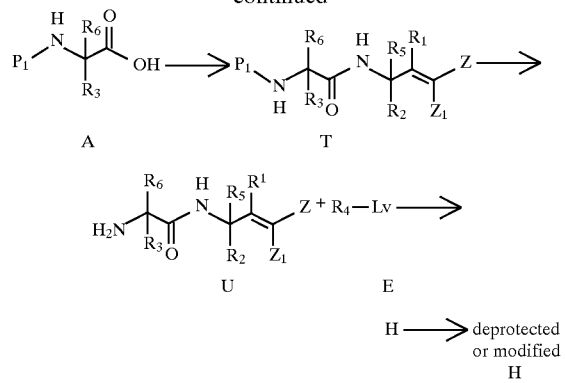

In General Method IV, free amine (or salt thereof) P, prepared from intermediate O as described in General Method II, is converted to amide T by reaction with amino acid A, where $P_1$ is an appropriate protecting group for nitrogen. Compound T is farther deprotected to free amine (or salt thereof) U, which is subsequently converted to H with reactive intermediate E. If protecting groups were used on any R groups ($R_1$–$R_6$) and/or on Z and/or $Z_1$, product H is deprotected and/or further modified to yield "deprotected or modified H."

Preferably the compound of formulas I or II can be prepared by one of four specific methods. For example, compounds 4, 12, 14, 16, 20, 23, 24, 26–30, 35, and 36 can be prepared by Specific Method I:

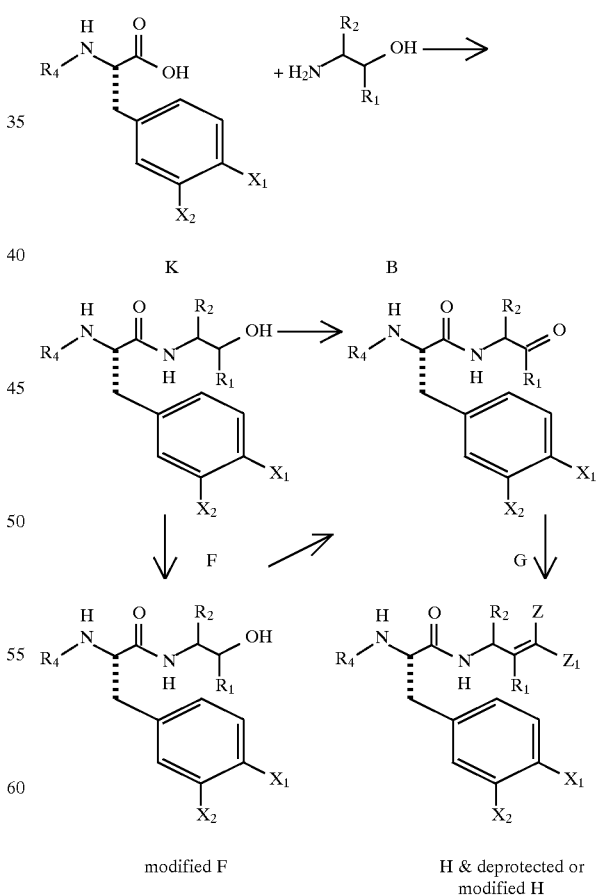

In Specific Method I, carboxylic acid K, CBZ-L-Leu-L-Phe, which can be purchased from Bachem or prepared as described in General Method I, is subjected to an amide forming reaction with amino alcohol (or salt thereof) B to generate intermediate F. Intermediate F is oxidized to intermediate G, which is then transformed into unsaturated product H. In the case of Compound 12, intermediate F is oxidized to modified F, which is then oxidized to intermediate G. If protecting groups were used on any R groups ($R_1$–$R_6$) and/or on Z and/or $Z_1$, product H is deprotected and/or further modified to yield "deprotected or modified H."

For example, compounds 1–3, 6–11, 17–19, 21, 22, 25, 37–40, and 74–77 can be prepared by Specific Method II:

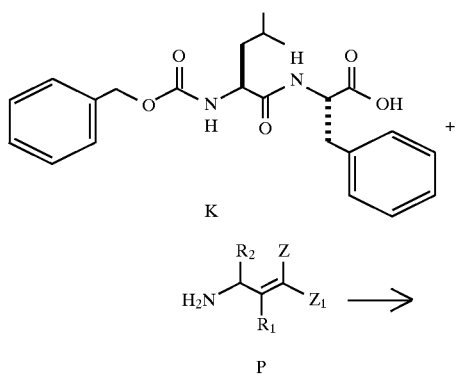

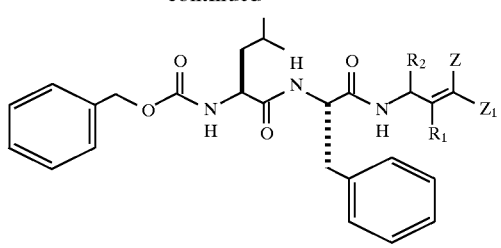

H & deprotected or modified H

In Specific Method II, intermediate P (or salt thereof), prepared as described in General Method II, is subjected to an amide forming reaction with carboxylic acid K, CBZ-L-Leu-L-Phe, which can be purchased from Bachem or prepared as described in General Method I, to give final product H. If protecting groups were used on any R group ($R_1$–$R_6$) and/or on Z and/or $Z_1$, product H is deprotected and/or further modified to yield "deprotected or modified H."

For example, compounds 5, 13, and 15 can be prepared by Specific Method III:

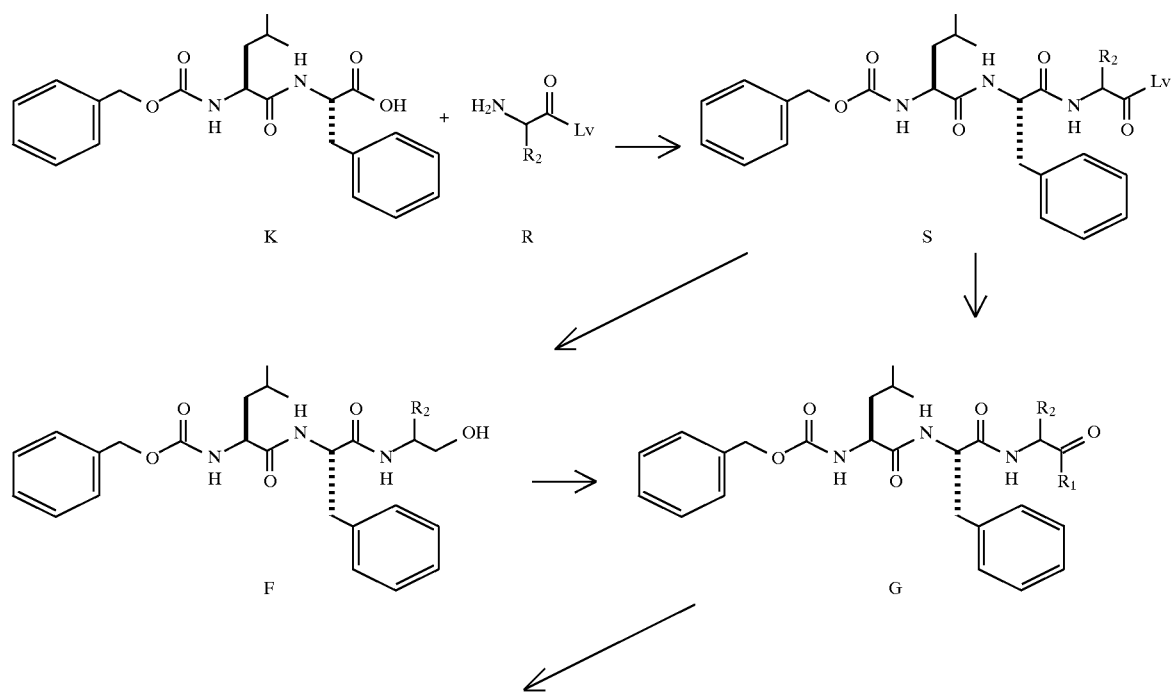

-continued

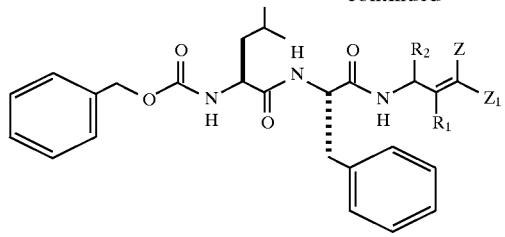

H & deprotected or modified H

In Specific Method III, free amine (or salt thereof) R, prepared as described in General Method III, is subjected to an amide forming reaction with carboxylic acid K, CBZ-L-Leu-L-Phe, which can be purchased from Bachem or prepared as described in General Method I, to give intermediate S. Intermediate S is then either converted directly to carbonyl intermediate G, in the case of compounds 13 and 15, or reduced to alcohol F, which is then oxidized to intermediate G, in the case of compound 5. Intermediate G is subjected to a reaction to yield the unsaturated final product H. If protecting groups were used on any R groups ($R_1$–$R_6$) and/or on Z and/or $Z_1$, product H is deprotected and/or further modified to yield "deprotected or modified H."

For example, compounds 31–34 can be prepared by Specific Method IV:

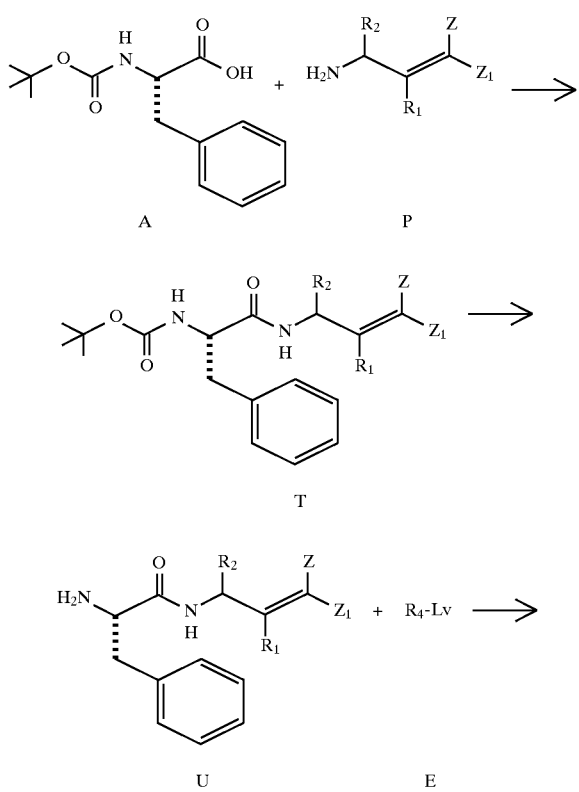

-continued

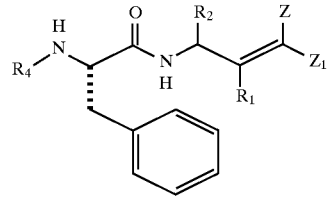

H & deprotected or modified H

In Specific Method IV, free amine (or salt thereof) P, prepared as described in General Method II, is converted to amide T by reaction with protected amino acid A, which can be purchased from Bachem, Advanced Chemtech, and Synthetech. Compound T is further deprotected to free amine (or salt thereof) U, which is subsequently converted to H with reactive intermediate E. If protecting groups were used on any R groups ($R_1$–$R_6$) and/or on Z and/or $Z_1$, product H is deprotected and/or further modified to yield "deprotected or modified H."

Suitable protecting groups for nitrogen are recognizable to those skilled in the art and include, but are not limited to benzyloxycarbonyl, t-butoxycarbonyl, 9-fluorenylmethoxycarbonyl, p-methoxybenxyloxycarbonyl, trifluoroacetamnide, and p-toluenesulfonyl. Suitable protecting groups for oxygen are recognizable to those skilled in the art and include, but are not limited to —$CH_3$, —$CH_2CH_3$, tBu, —$CH_2Ph$, —$CH_2CH=CH_2$, —$CH_2OCH_2CH_2Si(CH_3)_3$, and —$CH_2CCl_3$. Other examples of suitable protecting groups for nitrogen or oxygen can be found in T. Green & P. Wuts, *Protective Groups in Organic Synthesis* (2nd ed. 1991), which is incorporated herein by reference.

Suitable leaving groups are recognizable to those skilled in the art and include, but are not limited to, Cl, Br, I, sulfonates, O-alkyl groups,

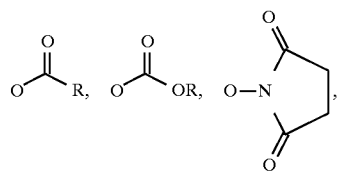

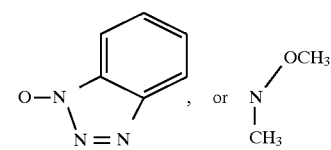

Other examples of suitable leaving groups are described in J. March, *Advanced Organic Chemistry, Reactions, Mechanisms, and Structure* (4th ed. 1992) at pages 205, 351–56, 642–43, 647, 652–53, 666, 501, 520–21, 569, 579–80, 992–94, 999–1000, 1005, and 1008, which are incorporated herein by reference.

EXAMPLES

Examples of the processes used to make several of the compounds of formulas I and II are set forth below. The structures of the compounds of the following Examples were confirmed by one or more of the following: proton magnetic resonance spectroscopy, infrared spectroscopy, elemental microanalysis, mass spectrometry, thin layer chromatography and melting point.

Proton magnetic resonance (NMR) spectra were determined using a Tech-Mag or Varian UNITYplus 300 spectrometer operating at a field strength of 300 megahertz (MHz). Chemical shifts are reported in parts per million (δ) and setting the references such that in $CDCl_3$ the $CHCl_3$ is at 7.26 ppm, in acetone-$d_6$ the acetone is at 2.02 ppm, and in DMSO-$d_6$ the DMSO is at 2.49 ppm. Peak multiplicities are designated as follows: s, singlet; d, doublet; dd, doublet of doublets; ddd, doublet of doublet of doublets; t, triplet; q, quartet; bs, broad singlet; bt, broad triplet; m, multiplet. Mass spectra (FAB; fast atom bombardment) were determined at the Scripps Research Institute Mass Spectometry Facility, San Diego, Calif. Infrared absorption (IR) spectra were taken on a MIDAC Corporation FTIR or a Perkin-Elmer 1600 series FTIR spectrometer.

Elemental microanalysis were performed by Atlantic Microlab Inc. Norcross, Ga. and gave results for the elements stated with ±0.4% of the theoretical values. Flash chromatography was performed using Silica gel 60 (Merck Art 9385). Thin layer chromatographs (TLC) were performed on precoated sheets of silica 60 $F_{254}$ (Merck Art 5719). Melting points were determined on a Mel-Temp apparatus and are uncorrected. Anhydrous N,N-Dimethylformamide (DMF), N,N-dimethylacetamide (DMA), dimethysulfoxide (DMSO), were used as is. Tetrahydrofuran (THF) was distilled from sodium benzophenone ketyl under nitrogen.

$Et_2O$ refers to diethyl ether. Pet. ether refers to petroleum ether having a boiling range of 36°–53° C. TFA refers to trifluoroacetic acid. $Et_3N$ refers to triethylamine. Other abbreviations include: methanol (MeOH), ethanol (EtOH), ethyl acetate (EtOAc), acetyl (Ac), methyl (Me), phenyl (Phe), triphenylmethyl (Tr), benzyloxycarbonyl (CBZ), tert-butoxycarbonyl (BOC), m-chloroperoxybenzoic acid (m-CPBA), alanine (Ala), glutamine (Gln), leucine (Leu), methionine (Met), phenylalanine (Phe), penicillamine (Pen). Additionally, "L" represents natural amino acids, "D" represent unnatural amino acids, and "DL" represents racemic mixtures.

A simplified naming system was used to identify intermediates and final products. Amino acid and peptide alcohols are given the suffix 'ol' (for example methioninol). Amino acid and peptide aldehydes are given the suffix 'al' (for example methioninal). When naming final products, italicized amino acid abbreviations represent modifications at the C-terminus of that residue where the following apply:

1. acrylic acid esters are reported as either "E" (trans) or "Z" (cis) propenoates,
2. acrylonitriles are reported as either E or Z propenonitriles,
3. acrylamides are reported as either E or Z propenamides, except in the case of the compound 21, which is reported as 1-Pyrrolidin-1-yl-3-(CBZ-L-Leu-L-Phe-L-Gln)-E-Propenone,
4. vinyl sulfones, vinyl phosphonates, or vinyl aryls are reported as E or Z vinyl sulfones, vinyl phosphonates or aryls, and
5. vinyl ketones are reported as either E or Z en-2-ones.

Example 1

Preparation of Compound 12: Ethyl-3-[CBZ-L-Leu-L-Phe-L-Met(sulfoxide)]-E-Propenoate Preparation of Intermediate CBZ-L-Leu-L-Phe-L-Methioninol CBZ-L-Leu-L-Phe (3.02 g, 7.3 mmol) was dissolved in 75 mL of $CH_2Cl_2$. To this solution was added N-hydroxysuccinimide (0.91 g, 7.7 mmol) and 2 mL of DMF, and stirring was continued until all solids had gone into solution. N,N'-Dicyclohexylcarbodiimide (1.60 g, 7.7 mmol) was added to the reaction mixture, and the reaction was stirred at room temperature for one hour. The mixture was then filtered into a separate flask containing S-(–)-methioninol (1.06 g, 7.7 mmol) dissolved in a minimum of DMF, removing the N,N'-dicyclohexylurea precipitate. The reaction was allowed to stir overnight at room temperature. The solvents were removed under vacuum, and the resulting crude product was purified by flash chromatography (anhydrous $NH_3$/MeOH/$CHCl_3$, 0.5:4.5:9.5) on silica gel to give 3.72 g (96%) of white solid: IR (KBr) 3293, 3065, 2955, 1696, 1645, 1539, 1236, 698 $cm^{-1}$; $^1$H NMR (DMSO-$d_6$) δ 0.80 (m, 6 H), 1.31 (m, 2 H), 1.51 (m, 2 H), 1.82 (m, 1 H), 2.00 (s, 3 H), 2.43 (m, 2 H), 2.78–3.29 (m, 4 H), 3.72 (m, 1H), 3.97 (m, 1 H), 4.45 (m, 1 H), 4.66 (t, 1 H, J=5.5 Hz), 5.01 (s, 2 H), 7.15–7.39 (m, 10 H), 7.43 (d, 1H, J=8.1 Hz), 7.62 (d, 1 H, J=8.5 Hz), 7.95 (d, 1 H, J=8.1 Hz). Anal. ($C_{28}H_{39}N_3O_5S$) C, H, N.

Preparation of Intermediate CBZ-L-Leu-L-Phe-L-Methioninol (sulfoxide)

CBZ-L-Leu-L-Phe-L-methioninol (1.50 g, 2.80 mmol) was dissolved in 50 mL of $CH_2Cl_2$. A total amount of 0.61 g (3.5 mmol) of m-CPBA was added portionwise over a period of five hours as the reaction was stirred at room temperature. After an additional hour, the reaction was poured into saturated $NaHCO_3$/$CH_2Cl_2$. The organic layer was separated, washed with brine, and dried ($Na_2SO_4$). After removal of the solvent, the crude residue was flash chromatographed on a short flash silica gel column eluting with 5% MeOH/$CHCl_3$. The product was obtained as a white glassy solid (1.38 g, 90%): IR (KBr) 3295, 3063, 2955, 1694, 1644, 1541, 1263, 1234, 1043, 698 $cm^{-1}$; $^1$H NMR (DMSO-$d_6$) δ 0.81 (m, 6 H), 1.32 (m, 2 H), 1.59 (m, 2 H), 1.92 (m, 1H), 2.47 (s, 3 H), 2.55–3.29 (m, 6 H), 3.73 (m, 1 H), 3.97 (m, 1 H), 4.42 (m, 1 H), 4.75 (t, 1 H, J=5.5 Hz), 5.01 (m, 2 H), 7.16–7.39 (m, 10 H), 7.44 (d, 1 H, J=7.7 Hz), 7.73 (d, I H, J=8.8 Hz), 7.98 (m, 1 H). Anal. ($C_{28}H_{39}N_3O_6S$) C, H, N, S.

Preparation of Intermediate CBZ-L-Leu-L-Phe-L-Methioninal (sulfoxide)

CBZ-L-Leu-L-Phe-L-methioninol (sulfoxide) (1.38 g, 2.53 mmol) was dissolved in DMSO. o-Iodoxybenzoic acid (2.12 g, 7.59 mmol) was added, requiring a few minutes of stirring at room temperature to dissolve. After three hours, the DMSO was removed under reduced pressure. The residue was twice diluted with $CH_2Cl_2$, and the solvent was evaporated to remove any residual DMSO. The residue was diluted with a minimum of acetone, and the white precipitate was filtered off. The filtrate was concentrated to near dryness and dissolved in EtOAc, which produced more of the white precipitate, which was again filtered off. The filtrate was washed with a 10% $Na_2S_2O_3$/10% $NaHCO_3$ solution, water, and brine before drying over $Na_2SO_4$. Upon removal of the organic solvent, the residue was twice taken up in benzene and evaporated to remove any residual water, giving 0.98 g (71%) of a white glassy solid which was used immediately without further purification: $^1$H NMR (DMSO-$d_6$) δ 0.81 (m, 6H), 1.30 (m, 2H), 1.50 (m, 1H), 1.97 (m, 1H), 2.48 (s, 3H), 2.55–3.27 (m, 5H), 3.70 (m, 1H), 4.47 (m, 1H), 4.71 (m, 1H), 5.00 (s, 2H), 7.20–7.40 (m, 1OH), 7.93 (m, 1H), 8.08 (m, 1H), 8.51 (m, 1H), 9.22 (s, 1H); (M+H) 544.

Preparation of Product—Ethyl-3-[CBZ-L-Leu-L-Phe-L-Met(sulfoxide)]-E-Propenoate

CBZ-L-Leu-L-Phe-L-Methioninal (sulfoxide) (0.98 g, 1.80 mmol) was dissolved in 50 mL of THF. (Carbethoxymethylene)triphenyl-phosphorane (1.11 g, 2.16 mmol) was added, and the reaction was stirred at room temperature overnight. The solvent was removed in vacuo, and the residue subjected to flash column chromatography eluting with 2% MeOH/$CHCl_3$. The product was obtained (0.82 g, 74%) as a white solid: $^1$H NMR (DMSO-$d_6$) δ 0.81 (m, 6H), 1.21 (t, 3H, J=7 Hz), 1.34 (m, 2H), 1.54 (m, 1H), 1.78 (m, 1H), 1.93 (m, 1H), 2.49 (s, 3H), 2.50–3.05 (m, 4H), 3.99 (m, 1H), 4.10 (q, 2H, J=7 Hz), 4.51 (m, 2H), 5.00 (dd, 2H, J=17.3, 4.4 Hz), 5.62 (m, 1H), 6.72 (m, 1H), 7.19 (m, 5H), 7.34 (m, 5H), 7.43 (d, 1H, J=8.1 Hz), 8.08 (d, 1H, J=7.4 Hz), 8.13 (d, 1H, J=8.5 Hz); (M+H) 614; HRMS calcd for $C_{32}H_{43}N_3O_7S$+Cs 746.1876 (M+Cs), found 746.1850. Anal. ($C_{32}H_{43}N_3O_7S$) C, H, N, S.

Example 2

Preparation of Compound 4: Ethyl-3-[CBZ-L-Leu-L-Phe-L-(-Ac-amino)-Ala]-E-Propenoate Preparation of Intermediate CBZ-L-(N-Ac-amino)-Ala CBZ-L-Amino-Ala (1.5 g, 6.3 mmol) was suspended in 50 mL of $H_2O$ with stirring. Acetic anhydride (5.0 mL) was added slowly to this suspension over a 30 minute period, during which time the starting material dissolved. The reaction mixture was stirred for an additional 1 hour at room temperature and then evaporated to dryness under vacuum. The resulting oil was dissolved in 30 mL $CHCl_3$ and left for 12 hours. The solid that formed was collected by filtration, washed with 30 mL of $CHCl_3$ and dried yielding 1.29 g (73%) of product as a white solid: IR (KBr) 3271, 3125, 3065, 1734, 1703, 1614, 1545, 1289, 1244, 1053, 727 cm$^{-1}$; $^1$H NMR (DMSO-$d_6$) δ 1.84 (s, 3H), 3.2–3.55 (m 2H), 4.13 (m, 1H), 5.08 (s, 2H), 7.12–7.41 (m, 5H), 7.54 (d, 1H, J=8.1 Hz), 8.02 (bt, 1H, J=5.5 Hz), 12.78 (bs, 1H); Anal. ($C_{13}H_{16}N_2O_5$) C, H, N.

Preparation of Intermediate CBZ-L-(N-Ac-amino)-Ala-OMe

Anhydrous HCl gas was slowly bubbled at 0° C. into a stirred suspension of CBZ-L-(N-Ac-amino)-Ala (1.21 g, 4.3 mmol) in MeOH (43 mL) until the solid was dissolved. Stirring was continued for 30 minutes at 0° C. whereupon the methanolic HCl was carefully evaporated to dryness. The methyl ester was formed as a white solid in quantitative yield and used without further purification: IR (KBr) 3323, 3285, 3094, 2957, 1755, 1736, 1686, 1651, 1531, 1277, 1057, 736, 600 cm$^{-1}$; $^1$H NMR (DMSO-$d_6$) δ 1.78 (s, 3H), 3.22–3.47 (m, 2H), 3.61 (s, 3H), 4.15 (m, 1H), 5.02 (s, 2H), 7.24–7.36 (m, 5H), 7.64 (d, 1H, J=7.7 Hz), 7.97 (bt, 1H, J=6.3 Hz); Anal. ($C_{14}H_{18}N_2O_5$) C, H, N.

Preparation of Intermediate CBZ-L-(N-Ac-amino)-Alaninol

To a solution of CBZ-L-(N-Ac-amino)-Ala-OMe (1.8 g, 6.12 mmol) in 50 mL anhydrous THF/EtOH (2:1) was added LiCl (0.52 g, 12.24 mmol). Upon dissolution, $NaBH_4$ (0.46 g, 12.24 mmol) was added, and the mixture was stirred at room temperature for 12 hours. The reaction mixture was evaporated to near dryness, whereupon 45 mL of $H_2O$ was added. The pH of this mixture was adjusted to 2–3 using concentrated HCl, followed by extraction with EtOAc (300 mL). The organic layer was washed with $H_2O$ (50 mL), dried over $Na_2SO_4$, filtered and concentrated. The residue was purified by flash column chromatography (10% MeOH/$CHCl_3$) to give 1.38 g (85%) of a white solid: IR (KBr) 3303, 3082, 2951, 2926, 1689, 1645, 1547, 1284, 1061, 1046, 756, 698 cm$^{-1}$; $^1$H NMR (DMSO-$d_6$) δ 1.78 (s, 3H), 3.03 (m, 1H), 3.16–3.28 (m, 3H), 3.49 (m, 1H), 5.00 (s, 2H), 6.95 (d, 1H, J=8.1 Hz), 7.29–7.38 (m, 5H), 7.83 (bt, 1H, J=5.5 Hz); Anal. ($C_{13}H_{18}N_2O_4$) C, H, N.

Preparation of Intermediate L-(N-Ac-amino)-Alaninol

To a solution of CBZ-L-(N-Ac-amino)-alaninol (1.36 g, 5.11 mmol) in 40 mL MeOH, 10% Pd on carbon (0.15 g) was added with stirring while under an argon atmosphere. The reaction vessel was evacuated under vacuum and then put under an atmosphere of hydrogen using a balloon. The mixture was stirred for 2 hours. At this time the hydrogen gas was evacuated, and the catalyst was removed by filtration. The solvent was removed under vacuum. Addition of EtOAc and reconcentration gave a white hygroscopic solid in quantitative yield which was used without further purification: mp=80°–82° C.; $^1$H NMR (DMSO-$d_6$) δ 1.79 (s, 31), 2.66 (m, 1H), 2.86 (m, 1H), 3.06 (m, 1H), 3.21 (2H, m), 3.4 (bs, 2H), 4.55 (bs, 1H), 7.76 (bs, 1H). Anal. ($C_5H_{12}N_2O_2$) C, H, N.

Preparation of Intermediate CBZ-L-Leu-L-Phe-L-(N-Ac-amino)-Alaninol

This compound was prepared from CBZ-L-Leu-L-Phe and L-(N-Ac-amino)-alaninol using the procedure described in Example 1 for the preparation of CBZ-L-Leu-L-Phe-L-methioninol. The compound was purified by column chromatography (7% MeOH/$CHCl_3$) to give a white solid (81%): IR (KBr) 3302, 2955, 1694, 1651, 1539, 1454, 1236, 1047, 698 cm$^{-1}$; $^1$H NMR (DMSO-$d_6$) δ 0.80 (s, 6H), 1.32 (m, 2H), 1.47 (m, 1H), 1.79 (s, 3H), 2.81 (m, 1H), 2.97 (m, 2H), 3.14–3.25 (m,. 3H), 3.71 (m, 1H), 3.95 (m, 1H), 4.42 (m, 1H), 4.67 (t, 1H, J=5.5 Hz), 5.00 (m, 2H), 7.16–7.34 (m, 101H), 7.45 (d, 1H, J=8.1 Hz), 7.70 (m, 2H), 7.88 (d, 1H, J=8.1 Hz); Anal. ($C_{28}H_{38}N_4O_6$) C, H, N.

Preparation of Intermediate CBZ-L-Leu-L-Phe-L-(N-Ac-amino)-Alaninal

This compound was prepared in 73% yield as a white solid from CBZ-L-Leu-L-Phe-L-(N-Ac-amino)-alaninol using the procedure described in Example 1 for the preparation of CBZ-L-Leu-L-Phe-L-methioninal (sulfoxide). The product was used immediately without further purification. The product existed as a mixture of aldehyde and aldehyde hydrate. IR (KBr) 3294, 2957, 1695, 1649, 1539, 1263, 698 cm$^{-1}$; $^1$H NMR (DMSO-$d_6$) δ 0.81 (dd, 6H, J=8.8, 6.2 Hz), 1.31 (m, 2H), 1.50 (m, 1H), 1.76 (s, hydrate), 1.78 (s, 3H), 2.83 (m, 1H), 3.00 (m, 1H), 3.20 (d, J=9.6 Hz, hydrate), 3.35 (m, 1H), 3.80 (m, hydrate), 3.97 (m, 2H), 4.16 (m, 1H), 4.37 (m, hydrate), 4.44 (m, hydrate), 4.54 (m, 1H), 5.01 (s, 2H), 6.28 (d, 1H, J=7.0 Hz, hydrate), 6.41 (d, 1H, J=6.6 Hz, hydrate), 7.12–7.50 (m, 10H), 7.63 (t, 1H, J=7.9 Hz), 7.87 (m, 1H), 7.98 (d, 1H, J=8.1 Hz), 8.40 (d, 1H, J=7.0 Hz), 9.26 (s, 1H); Anal. ($C_{28}H_{36}N_4O_6$.0.5 $H_2O$) C, H, N.

Preparation of Product—Ethyl-3-[CBZ-L-Leu-L-Phe-L-(N-Ac-amino)-Ala]-E-Propenoate This compound was prepared in 55% yield as a white solid from CBZ-L-Leu-L-Phe-L-(N-Ac-amino)-alaninal and (carbethoxymethylene)triphenylphosphorane using the procedure described in Example 1 for the preparation of compound 12, ethyl-3-[CBZ-L-Leu-L-Phe-L-Met(sulfoxide)-E-propenoate. The product was purified by flash column chromatography (3% MeOH/CHCl$_3$). $^1$H NMR (DMSO-d$_6$) δ 0.81 (dd, 6H, J=9.2, 6.6 Hz), 1.21 (t, 3H, J=7.2 Hz), 1.34 (m, 2H), 1.53 (m, 1H), 1.78 (s, 3H), 2.80–3.28 (m, 4H), 3.99 (m, 1H), 4.10 (q, 2H, J=7.0 Hz), 4.43 (m, 2H), 5.01 (m, 2H), 5.61 (d, 1H, J=15.4 Hz), 6.61 (dd, 1H, J=15.4, 5.2 Hz), 7.10–7.34 (m, 10H), 7.44 (d,1H, J=7.7 Hz), 7.70 (m, 2H), 7.82 (t, 1H, J=5.5 Hz), 8.05 (m, 2H); HRMS calcd for C$_{32}$H$_{42}$N$_4$O$_7$+Cs 727.2108 (M+Cs), found 727.2137. Anal. (C$_{32}$H$_{42}$N$_4$O$_7$) C, H, N.

Example 3

Preparation of Compound 2: Ethyl-3-[CBZ-L-Leu-L-Phe-L-(Tr-Gln)]-E-Propenoate

Preparation of Intermediate BOC-L-(Tr-Gln)-N(Me)OMe

Isobutyl chloroformate (0.611 mL, 4.71 mmol) was added to a solution of BOC-L-(Tr-Gln) (2.30 g, 4.71 mmol) and 4-methylmorpholine (1.04 mL, 9.46 mmol) in CH$_2$CL$_2$ at 0° C. The reaction mixture was stirred at 0° C. for 20 minutes then N,O-dimethylhydroxylamine hydrochloride (0.459 g, 4.71 mmol) was added. The resulting solution was stirred at 0° C. for 15 minutes and at 23° C. for 4 hours, then was partitioned between water (150 0mL) and a 1:1 mixture of EtOAc and hexanes (2×150 mL). The combined organic layers were dried over Na$_2$SO$_4$ and were concentrated. Purification of the residue by flash column chromatography (40% hexanes in EtOAc) afforded the product (2.22 g, 89%) as a white foam: R$_f$=0.22 (50% EtOAc in hexanes); IR (KBr) 3411, 3329, 3062, 1701, 1659 cm$^{-1}$; $^1$H NMR (CDCl$_3$) δ 1.42 (s, 9H), 1.63–1.77 (m, 1H), 2.06–2.17 (m, 1H), 2.29–2.43 (m, 2H), 3.17 (s, 3H), 3.64 (s, 3H), 4.73 (bs, 1H), 5.38–5.41 (m, 1H), 7.20–7.31 (m, 15H); Anal. (C$_{31}$H$_{37}$N$_3$O$_5$) C, H, N.

Preparation of Intermediate BOC-L-(Tr-Glutaminal)

Diisobutylaluminum hydride (7.84 mL of 1.5M solution in toluene, 11.76 mmol) was added to a solution of BOC-L-(Tr-Gln)-N(Me)OMe (2.50 g, 4.70 mmol) in THF at −78° C., and the reaction mixture was stirred at −78° C. for 4 hours. Methanol (3 mL) and 1.0M HCl (6 mL) were added sequentially, and the mixture was warmed to 23° C. The resulting suspension was diluted with Et$_2$O (150 mL) and was washed with 1.0M HCl (3× 100 mL), half-saturated NaHCO$_3$ (100 mL), and water (100 mL). The organic layer was dried over MgSO$_4$, filtered, and concentrated to give crude aldehyde (2.01 g, 91%) as a white solid: mp=114°–116° C.; R$_f$=0.42 (50% EtOAc in hexanes); IR (KBr) 3313, 1697, 1494 cm$^{-1}$; $^1$H NMR (CDCl$_3$) δ 1.44 (s, 9H), 1.65–1.75 (m, 1H), 2.17–2.23 (m, 1H), 2.31–2.54 (m, 2H), 4.11 (bs, 1H), 5.38–5.40 (m, 1H), 7.11 (s, 1H), 7.16–7.36 (m, 15H), 9.45 (s, 1H).

Preparation of Intermediate Ethyl-3-[BOC-L-(Tr-Gln)]-E-Propenoate

Sodium bis(trimethylsilyl)amide (3.38 mL of a 1.0M solution in THF, 3.3 mmol) was added to a solution of triethyl phosphonoacetate (0.732 mL, 3.39 mmol) in THF (100 mL) at −78° C., and the resulting solution was stirred for 20 minutes at that temperature. BOC-L-(Tr-Glutaminal) (1.60 g, 3.39 mmol) in THF (20 mL) was added via cannula, and the reaction mixture was stirred for 4 hours at −78° C. then was partitioned between 1.0M 5HCl (150 mL) and a 1:1 mixture of EtOAc and hexanes (2×150 mL). The organic layers were dried over Na$_2$SO$_4$ and concentrated. Purification of the residue by flash column chromatography (40% EtOAc in hexanes) provided ethyl-3-[BOC-L-(Tr-Gln)]-E-propenoate (1.53 g, 83%) as a white foam: R$_f$=0.60 (50% EtOAc in hexanes); IR (cm$^{-1}$) 3321, 1710; $^1$H NMR (CDCl$_3$) δ 1.27 (t, 3 H, J=7.2 Hz), 1.42 (s, 9H), 1.70–1.78 (m, 1H), 1.80–1.96 (m, 11H), 2.35 (t, 2H, J=7.0 Hz), 4.18 (q, 2H, J=7.2 Hz), 4.29 (bs, 1H), 4.82–4.84 (m, 1H), 5.88 (dd, 1H, J=15.7, 1.6 Hz), 6.79 (dd, 1H, J=15.7, 5.3 Hz), 6.92 (s, 1H), 7.19–7.34 (m, 15H); Anal. (C$_{33}$H$_{38}$N$_2$O$_5$) C, H, N.

Preparation of Product Ethyl-3-[CBZ-L-Leu-L-Phe-L-(Tr-Gln)]-E-Propenoate

Ethyl-3-[BOC-L-(Tr-Gln)]-E-propenoate (0.224 g, 0.422 mmol) was dissolved in 1,4-dioxane (3 ) mL) and cooled to 0° C. A solution of HCl in 1,4-dioxane (4.0M, 3 mL, 12 mmol) was added dropwise, and the reaction solution was allowed to warm to room temperature. After being stirred for 2 hours, the solution was diluted with 1:1 CH$_2$Cl$_2$/EtOAc (50 mL) and added to a solution of NaOH (16 mmol) in saturated aqueous NaHCO$_3$ (50 mL). After vigorous shaking, the phases were separated, and the aqueous phase was washed 2 more times with 1:1 CH$_2$Cl$_2$/EtOAc (50 mL). The combined organic phases were dried over Na$_2$SO$_4$ and concentrated to give 0.164 g (88%) of the crude free amine, which was used without further purification.

The crude amine (0.371 mmol, 1.0 equiv) was dissolved in dry CH$_2$Cl$_2$ (5 mL). CBZ-L-Leu-L-Phe (0.176 g, 0.427 mmol), 1-hydroxybenzotriazole hydrate (0.081 g, 0.599 mmol), 4-methylmorpholine (0.175 mL, 1.59 mmol), and 1-(3-dimethylaminopropyl)-3-ethylcarbodiimide hydrochloride (0.114 g, 0.595 mmol) were added sequentially. After being stirred for 18 hours at 23° C., the reaction mixture was poured into water (40 mL) and extracted with 1:1 CH$_2$Cl$_2$/EtOAc (3×50 mL). The combined organic layers were dried over Na$_2$SO$_4$ and were concentrated. The residue was purified by flash column chromatography (50% EtOAc in hexanes) to give the product (0.163 g, 49%) as a white solid: mp=192°–194° C.; IR (KBr) 3295, 3049, 1696, 1654 cm$^{-1}$; $^1$H NMR (CDCl$_3$) δ 0.84 (d, 3H, J=6.5 Hz), 0.86 (d, 3H, J=6.5 Hz), 1.24–1.32 (mi, 1H), 1.28 (t, 3H, J=7.2 Hz), 1.43–1.75 (m, 3H), 1.91–2.06 (m, 1H), 2.20–2.38 (m, 2H), 2.93–3.02 (m, 3H), 3.07–3.18 (m, 1H), 3.95–4.02 (m, 1H), 4.17 (q, 2H, J=7.2 Hz), 1.43–4.55 (m, 2H), 4.82–4.95 (m, 2H), 5.69 (d, 1H, J=15.7 Hz), 6.46 (d, 1H, J=7.5 Hz), 6.60 (d, 1H, J=8.1 Hz), 6.69 (dd, 1H, J=15.7, 5.1 Hz), 7.09–7.38 (m, 27H); Anal. (C$_{51}$H$_6$N$_4$O$_7$) C, H, N.

Example 4

Preparation of Compound 3: Ethyl-3-(CBZ-L-Leu-L-Phe-L-Gln)-E-Propenoate

Preparation of Product—Ethyl-3-(CBZ-L-Leu-L-Phe-L-Gln)-E-Propenoate

Compound 2, ethyl-3-[CBZ-L-Leu-L-Phe-L-(Tr-Gln)]-E-propenoate (0.15 g, 0.18 mmol), prepared as described in Example 3, was dissolved in 1 :1 CH$_2$Cl$_2$/TFA (5 mL) at 23° C. and the bright yellow solution was stirred 30 minutes, whereupon the solvent was evaporated. CCl$_4$ (10 mL) was added, and the resulting solution was concentrated twice. Addition of Et$_2$O (10 mL) to the oily residue quickly gave a white precipitate. After stirring 10 minutes, the solid was collected by filtration and washed sequentially with acetone (2×10 mL) and Et$_2$O (2×10 mL) then was dried in vacuo to give ethyl-3-(CBZ-L-Leu-L-Phe-L-Gln)-E-propenoate (0.057 mg, 53%) as a white solid: mp=219°–221° C.; IR (KBr) 3300, 3065, 1672 cm$^{-1}$; $^1$H NMR (DMSO-d$_6$) δ 0.78 (d, 3H, J=6.8 Hz), 0.82 (d, 3H, J=6.5 Hz), 1.21 (t, 3H, J=7.0 Hz), 1.25–1.37 (m, 2H), 1.42–1.54 (m, 1H), 1.58–1.80 (m, 2H), 2.02–2.09 (m, 2H), 2.84 (dd, 1H, J=13.2, 8.9 Hz), 2.97 (dd, 1H, J=13.2,−5.8 Hz), 3.93–4.01 (m, 1H), 4.11 (q, 2H, J=7.0 Hz), 4.33–4.52 (m, 2H), 4.97 (d, 1H, J=12.3 Hz), 5.04 (d, 1H J=12.3 Hz), 5.64 (d, 1H, J=15.9 Hz), 6.69 (dd, 1H, J=15.9, 5.4 Hz), 6.76 (s, 1H), 7.13–7.37 (m, 1H), 7.43 (d, 1H, J=7.8 Hz), 7.99 (d, 1H, J=8.1 Hz), 8.04 (d, 1H, J=8.1 Hz); Anal. ($C_{32}H_{42}N_4O_7$) C, H, N.

Example 5

Preparation of Compound 7: Methyl-3-(CBZ-L-Leu-L-Phe-L-Gln)-Z-Propenoate

Preparation of Intermediate Methyl-3-[BOC-L-(Tr-Gln)]-Z-Propenoate 18-crown-6 (0.867 g, 3.28 mmol) was evaporated from toluene (40 mL) and then dissolved in dry THF (14 mL) under argon. Bis(2,2,2-trifluoroethyl)(methoxycarbonylmethyl)phosphonate (0.111 mL, 0.525 mmol) was added, and the reaction mixture was cooled to −78° C. After dropwise addition of a solution of potassium bis(trimethylsilyl)-amide in toluene (0.5M, 1.26 mL, 0.63 mmol), the reaction mixture was stirred for 25 minutes. A solution of BOC-L-(Tr-glutaminal) (0.310 g, 0.656 mmol) in dry THF (4 mL) was added dropwise, and, after stirring 1 hour more, saturated aqueous $NH_4Cl$ (2 mL) was added. The reaction mixture was allowed to warm to room temperature, and the THF was evaporated. Water (10 mL) was added to the residue, which was then extracted with $CH_2Cl_2$ (3×30 mL). The combined organic phases were dried over $Na_2SO_4$ and concentrated. The residue was purified by flash column chromatography (35% EtOAc/hexanes) to give the product (0.181 g, 52%) as a glass: IR (thin film) 3326, 1713, 1690, 1666, 1514 cm$^{-1}$; $^1$H NMR (CDCl$_3$) δ 1.41 (s, 9H), 1.84–1.93 (m, 2H), 2.37–2.44 (m, 2H), 3.68 (s, 3H), 5.10 (m, 2H), 5.80 (d, 1H, J=11.8 Hz), 6.03 (m, 1H), 6.88 (bs, 1H), 7.18–7.32 (m, 15H).

Preparation of Intermediate Methyl-3-[CBZ-L-Leu-L-Phe-L-(Tr-Gln)]-Z-Propenoate

Methyl-3-[BOC-L-(Tr-G an)]-Z-propenoate (0.143 g, 0.271 mmol) was dissolved in 1,4-dioxane (3 mL) at room temperature. A solution of HCl in 1,4-dioxane (4.0M, 3 mL) was added dropwise, and the reaction solution was stirred for 2 hours under an argon balloon. Then the solvent was evaporated to give the crude amine salt as a glassy residue, which was used without further purification. This amine salt, CBZ-L-Leu-L-Phe (0.112 g, 0.272 mmol), and 1-hydroxybenzotriazole hydrate (0.055 g, 0.40 mmol) were dissolved in dry $CH_2Cl_2$ (5 mL) under argon at room temperature. 4-Methylmorpholine (0.149 mL, 1.36 mmol), and 1-(3-dimethylaminopropyl)-3-ethylcarbodiimide hydrochloride (0.078 g, 0.40 mmol) were then added sequentially. After stirring for 3 hours, water (10 mL) was added, and the mixture was extracted with $CH_2Cl_2$ (3×30 mL). The combined organic phases were dried over $Na_2SO_4$ and concentrated. The residue was purified by flash column chromatography (33% acetone in hexanes) to give the product (0.132 g, 59%) as a white foam: IR (thin film) 3296, 1708, 1650, 1517 cm$^{-1}$; Anal. ($C_{50}H_{54}N_4O_7$) C, H, N.

Preparation of Product—Methyl-3-(CBZ-L-Leu-L-Phe-L-Gln)-Z-Propenoate

Methyl-3-[CBZ-L-Leu-L-Phe-L-(Tr-Gln)]-Z-propenoate (0.110 g, 0.134 mmol) was dissolved in 1:1 $CH_2Cl_2$/TFA (4 mL), giving a bright yellow solution, which was stirred for 30 minutes under an argon balloon. $CCl_4$ (7 mL) was added, and the solution was concentrated twice. The residue was triturated with $Et_2O$ (3 mL) to give a white solid, which was collected by filtration and dried in vacuo (0.040 g, 51%): mp=185°–188° C.; IR (KBr) 3401, 3283, 1719, 1690, 1643, 1538 cm$^{-1}$; $^1$H NMR (DMSO-d$_6$) δ 0.78 (d, 3H, J=6.6 Hz), 0.82 (d, 3H, J=6.5 Hz), 1.22–1.38 (m, 2H), 1.43–1.54 (m, 1H), 1.58–1.75 (m, 2H), 1.92–2.09 (m, 2H), 2.77–2.90 (m, 2H), 3.65 (s, 3H), 3.91–4.00 (m, 1H), 4.37–4.46 (m, 1H), 4.99 (d, 1 H, J=12.6 Hz), 5.04 (d, I H, J=12.6 Hz), 5.18–5.25 (m, 1H), 5.79 (d, 1H, J=11.5 Hz), 5.92 (dd, 1H, J=11.5, 8.7 Hz), 6.72 (s, 1H), 7.14–7.36 (m, 1 1H), 7.43 (d, 1H, J=8.0 Hz), 7.76 (d, 1H, J=8.1 Hz), 8.01 (d, 1H, J=8.0 Hz); Anal. ($C_{31}H_{40}N_4O_7$) C, H, N.

Example 6

Preparation of Compound 11: Methyl-3-(CBZ-L-Leu-L-Phe-L-Gln)-E-Propenoate

Preparation of Intermediate Methyl-3-[BOC-L-(Tr-Gln)]-E-Propenoate

Sodium bis(trimethylsilyl)amide (0.978 mL of a 1.0M solution in THF, 0.978 mmol) was added to a solution of trimethyl phosphonoacetate (0.144 mL, 0.890 mmol) in THF (20 mL) at −78° C., and the resulting solution was stirred for 15 minutes at that temperature. BOC-L-(Tr-Glutaminal) (0.420 g, 0.889 mmol) in THF (10 mL) was added via cannula, and the reaction mixture was stirred for 2 hours at −78° C., then was partitioned between 0.5M HCl (100 1L) and a 1:1 mixture of EtOAc and hexanes (2×100 mL). The organic layers were dried over $Na_2SO_4$ and were concentrated. Purification of the residue by flash column chromatography (gradient elution, 30–40% EtOAc in hexanes) provided methyl-3-[BOC-L-(Tr-Gln)]-E-propenoate (0.460 g, 96%) as a white solid: mp 110°–112° C.; IR (thin film) 3318, 1708, 1665 cm$^{-1}$; $^1$H NMR (CDCl$_3$) δ 1.42 (s, 9H), 1.72–1.82 (m, 1H), 1.91–1.98 (m, 1H), 2.34–2.41 (m, 2H), 3.72 (s, 3H), 4.29 (s, br, 1H), 4.78–4.81 (m, 1H), 5.89 (dd, 1H, J=15.6, 1.6 Hz), 6.80 (dd, 1H, J=15.6, 5.3 Hz), 6.87 (s, 1H), 7.19–7.33 (m, 15H).

Preparation of Intermediate Methyl-3-[CBZ-L-Leu-L-Phe-L-(Tr-Gln)]-E-Propenoate

Using the procedure described in Example 28 for the preparation of ethyl-2-fluoro-3-[CBZ-L-Leu-L-Phe-L-(Tr-Gln)]-E-propenoate, methyl-3-[BOC-L-(Tr-Gln)]-E-propenoate (0.157 g, 0.297 mmol) was deprotected and coupled with CBZ-L-Leu-L-Phe (0.123 g, 0.298 mmol) to provide methyl-3-[CBZ-L-Leu-L-Phe-L-(Tr-Gln)]-E-propenoate (0.176 g, 72%) as a white foam: $^1$H NMR (CDCl$_3$) δ 0.84 (d, 3H, J=6.7 Hz), 0.86 (d, 3H, J=6.7 Hz), 1.45–1.61 (m, 3H), 1.67–1.75 (m, 1H), 1.94–1.96 (m, 1H), 2.20–2.35 (m, 2H), 2.95–3.15 (m, 2H), 3.72 (s, 3H), 3.94–4.01 (m, 1H), 4.46–4.49 (m, 1H), 4.83–4.93 (m, 3H), 5.72 (d, 1H, J=15.8 Hz), 6.45 (d, 1H, J=7.2 Hz), 6.63 (d, 1H, J=8.1 Hz), 6.71 (dd, 1H, J=15.8, 5.1 Hz), 7.01–7.38 (m, 27H).

Preparation of Product—Methyl-3-(CBZ-L-Leu-L-Phe-L-Gln)-E-Propenoate

Using the procedure described in Example 4 for the preparation of compound 3, methyl-3-[CBZ-L-Leu-L-Phe-L-(Tr-Gln)]-E-propenoate (0.087 g, 0.106 mmol) was deprotected to provide methyl-3-(CBZ-L-Leu-L-Phe-L-Gln)-E-propenoate (0.015 g, 25%) as a white solid: mp=220° C. (dec); $^1$H NMR (DMSO-d$_6$) δ 0.79 (d, 3H, J=10.9 Hz), 0.81 (d, 3H, J=10.9 Hz), 1.26–1.34 (m, 2H), 1.47–1.49 (m, 1H), 1.61–1.76 (m, 2H), 2.06 (t, 2H, J=7.6 Hz), 2.84 (dd, 1H, J=13.5, 9.0 Hz), 2.97 (dd, 1H, J=13.5, 5.6 Hz), 3.65 (s, 3H), 3.93–3.97 (m, 1H), 4.38 (s, br, 1H), 4.44–4.49 (m, J1), 4.97 (d, 1H, J=12.5 Hz), 5.04 (d, I H, J=12.5 Hz), 5.68 (d, 1 H, J=15.6 Hz), 6.70 (dd, l1H, J=15.6, 5.5 Hz), 6.76 (s, l1H), 7.19 (s, br, 7H), 7.34 (s, br, 4H), 7.44 (d, l1H, J=7.5 Hz), 7.99 (d, 1 H, J=8.1 Hz), 8.05 (d, 1H, J=8.1 Hz).

Example 7

Preparation of Compound 13: 4-(CBZ-L-Leu-L-Phe-L-Gln)-E-3-Butene-2-one

Preparation of Intermediate CBZ-L-Leu-L-Phe-L-(Tr-Gln)-N(Me)OMe

BOC-L-(Tr-Gln)-N(Me)OMe (0.807 g, 1.52 mmol) was dissolved in 1,4-dioxane (4.5 mL) at room temperature. A solution of HCl in 1,4-dioxane (4.0M, 4.5 mL) was added dropwise, and the reaction solution was stirred for 2.5 hours under an argon balloon. The solvent was evaporated to give the crude amine salt as a white foam, which was used without further purification. This amine salt, CBZ-L-Leu-L-Phe (0.626 g, 1.52 mmol) and 1-hydroxybenzotriazole hydrate (0.308 g, 2.28 mmol) were stirred in dry $CH_2Cl_2$ (12 mL) under argon at room temperature. 4-Methylmorpholine (0.840 mL, 7.64 mmol), and 1-(3-dimethylaminopropyl)-3-ethylcarbodiimide hydrochloride (0.436 g, 2.27 mmol) were added sequentially. After stirring for 3 hours, the reaction solution was poured into water (25 mL), and the aqueous layer was extracted 3 times with $CH_2Cl_2$ (70 mL, 40 mL, and 30 mL). The combined organic phases were dried over $Na_2SO_4$ and concentrated. The residue was purified by flash column chromatography (40% acetone in hexanes) to give the product (0.826 g, 66%) as a white foam: IR (thin film) 3300, 1643, 1525 $cm^{-1}$.

Preparation of Intermediate CBZ-L-Leu-L-Phe-L-(Tr-Glutaminal)

CBZ-L-Leu-L-Phe-L-(Tr-Gln)-N(Me)OMe (0.768 g, 0.930 mmol) was dissolved in dry THF (12 mL) under argon and cooled to −78° C. A solution of diisobutylaluminum hydride in toluene (1.5M, 2.17 mL, 3.26 mmol) was added dropwise. After stirring 3 hours, methanol (0.7 mL) was added slowly, followed by 1N HCl (1 mL). The reaction mixture was allowed to warm to nearly room temperature and was then diluted with 5:1 $CH_2Cl_2$/EtOAc (120 mL). The resulting mixture was washed with 1N HCl (2×15 mL), half-saturated $NaHCO_3$ (15 mL) and brine (25 mL). The organic phase was dried over $MgSO_4$ and concentrated to give the product as an off-white foam (0.606 g, 85%), which was used without further purification. An analytical sample was purified by column chromatography (36% acetone in hexanes): IR (thin film) 3295, 1708, 1660, 1531 $cm^{-1}$; $^1H$ NMR (CDCl) δ 0.80 (d, 3H, J=6.2 Hz), 0.87 (d, 3H, J=6.4 Hz), 1.27–1.59 (m, 3M), 1.71–1.83 (m, 1H), 2.07–2.15 (m, 1H), 2.22–2.29 (m, 2H), 2.96 (dd, 1H, J=13.7, 7.4 Hz), 3.08 (dd, 1H, J=13.7, 6.2 Hz), 3.99–4.08 (m, 1H), 4.11–4.20 (m, 1H), 4.55–4.64 (m, 1l), 4.92 (bs, 2H), 5.17 (d, 1H, J=6.7 Hz), 6.70 (d, 1H, J=7.4 Hz), 7.08–7.35 (m, 27H), 9.26 (s, 1H); Anal. ($C_{47}H_{50}N_4O_6$) C, H, N.

Preparation of Intermediate 4-[CBZ-L-Leu-L-Phe-L-(Tr-Gln)]-E-3-Butene-2-one

CBZ-L-Leu-L-Phe-L-(Tr-Glutaminal) (0.605 g, 0.789 mmol) and 1-triphenylphosphoranylidene-2-propanone (0.251 g, 0.788 mmol) were stirred in dry THF (7 mL) at room temperature, under argon, giving a yellow solution. After stirring 20 hours, the solvent was evaporated, and the residue was purified by flash column chromatography (36% acetone in hexanes) to give the product (0.425 g, 67%) as a white foam: IR (thin film) 3299, 1666, 1519 $cm^{-1}$.

Preparation of Product—4-(CBZ-L-Leu-L-Phe-L-Gln)-E-3-Butene-2-one

This compound was prepared in 54% yield from 4-[CBZ-L-Leu-L-Phe-L-(Tr-Gln)]-E-3-butene-2-one using the procedure described in Example 26 for the preparation of compound 14, 3-(CBZ-L-Leu-L-Phe-DL-Gln)-E-propenonitrile: mp=194°–196° C. (dec); IR (KBr) 3413, 3284, 1684, 1643, 1537 $cm^{-1}$; $^1H$ NMR (DMSO-$d_6$) δ 0.79 (d, 3H, J=6.6 Hz), 0.82 (d, 3H, J=6.6 Hz), 1.23–1.39 (m, 2H), 1.44–1.55 (m, 1H), 1.60–1.84 (m, 2H), 2.05–2.12 (m, 2H), 2.17 (s, 3H), 2.84 (dd, 1H, J=13.6, 8.7 Hz), 2.99 (dd, 1H, J=13.6, 5.7 Hz), 3.93–4.02 (m, 1H), 4.34–4.44 (m, 1H), 4.46–4.55 (m, 1H), 4.98 (d,1H, J=12.6 Hz), 5.04 (d, 1H, J=12.6 Hz), 5.84 (d,1H, J=16.0 Hz), 6.64 (dd,1H, J=16.0, 5.4 Hz), 6.77 (s, 1H), 7.15–7.37 (m, 1 1H), 7.43 (d, 1H, J=7.9 Hz), 7.99 (d, 1H, J=8.1 Hz), 8.06 (d, 1H, J=8.1 Hz); Anal. ($C_{31}H_{40}N_4O_6$) C, H, N.

Example 8

Preparation of Compound 5: Ethyl-3-[CBZ-L-Leu-L-Phe-L-[N-(2-pyrrolidinone)]-Ala]-E-Propenoate Preparation of Intermediate CBZ-L-[N-(4-Chlorobutyryl)-amino]-Ala-OMe Acetyl chloride (19.6 g, 250 mmol) was slowly added to a solution of MeOH (300 mL) at 0° C. After 10 minutes, CBZ-L-amino-Ala (10 g., 42 mmol) was added, and the reaction was allowed to stir for 12 hours at room temperature. Removal of solvent under vacuum provided 13.5 g of crude CBZ-L-amino-Ala-OMe as the hydrochloride salt. The crude ester was taken up in 200 mL $CH_2Cl_2$, to which was added $Et_3N$ (10.6 g, 105 mmol) and then 4-chlorobutyryl chloride (7.1 g, 50.4 mmol) at 0° C. The reaction was allowed to warm to room temperature and was stirred for 4 hours. At this time the reaction mixture was added to brine. The organic layer was extracted, washed with 1N HCl, brine, dried over $MgSO_4$, and concentrated yielding, 19 g of crude material. The material was purified by flash column chromatography (50% EtOAc-hexanes), giving an 87% yield of product. $^1H$ NMR (CDCl$_3$) δ 2.07 (m, 2H), 2.35 (t, 2H, J=7.0 Hz), 3.57 (t, 2H, J=6.3 Hz), 3.67 (t, 2H, J=5.9 Hz), 3.77 (s, 3H), 4.45 (m, 1H), 5.12 (s, 2H), 5.84 (d, 1H, J=6.3 Hz), 6.00 (bs, 1H), 7.37 (s, 5H).

Preparation of Intermediate CBZ-L-[N-(2-pyrrolidinone)]-Ala-OMe

A solution of CBZ-L-[N-(4-chlorobutyryl)-amino]-Ala-OMe (14.6 g, 39 mmol) in DMF (400 mL) was cooled to 0° C. To the solution was added NaH (1.87 g of a 60% dispersion in oil, 46.8 mmol), and the mixture was stirred at room temperature for 4 hours. The DMF was removed under high vacuum, and the residue was taken up in EtOAc, washed with 1N HCl, saturated aqueous $NaHCO_3$, brine, dried over $MgSO_4$ and concentrated. The material was purified by flash column chromatography (100% EtOAc), giving 7.0 g (56%) of product. $^1H$ NMR 6 (CDCl$_3$) 1.97 (m, 2H), 2.35 (m, 2H), 3.36 (m, 1H), 3.40–3.60 (m, 3H), 3.77 (s, 3H), 4.52 (m, 1H), 5.13 (d, 2H, J=5.6 Hz), 5.83 (d, 1H, J=6.3 Hz), 7.37 (m, 5H).

Preparation of Intermediate L-[N-(2-pyrrolidinone)]-Ala-OMe-HCl

This compound was prepared from CBZ-L-[N-(2-pyrrolidinone)]-Ala-OMe by catalytic hydrogenation as described in Example 2 for the preparation of L-(N-Ac-amino)alaninol, except methanolic HCl was used in order to isolate the product as the HCl salt. $^1H$ NMR (CDCl$_3$), δ 2.03 (m, 2H), 2.39 (m, 2H), 3.14 (bs, 2H), 3.40–3.70 (m, 5H), 3.75 (s, 3H).

Preparation of Intermediate CBZ-L-Leu-L-Phe-L-[N-(2-pyrrolidinone)]-Ala-OMe

This compound was prepared from CBZ-L-Leu-L-Phe and L-[N-(2-pyrrolidinone)]-Ala-OMe.HCl using the procedure described in Example 1 for the preparation of CBZ-L-Leu-L-Phe-L-methioninol. $^1H$ NMR (CDCl$_3$), δ 0.89 (m, 6H), 1.36 (m, 2H), 1.56 (m, 1H), 1.61 (m, 2H), 2.04 (m, 3H), 2.31 (m, 2H), 3.07–3.70 (m, 6H), 3.75 (s, 3H), 4.11 (m, 1H), 4.71 (m, 1H), 5.13 (bs, 1H), 5.18 (bs, 1H), 6.76–6.88 (m, rotomers, 1H), 7.10–7.45 (m, 10H).

Preparation of Intermediate CBZ-L-Leu-L-Phe-L-[N-(2-pyrrolidinone)]-Alaninol

This compound was prepared by the reduction of CBZ-L-Leu-L-Phe-L-[N-(2-pyrrolidinone)]-Ala-OMe with $NaBH_4$ and LiCl using the procedure described in Example 2 for the preparation of CBZ-L-(N-Ac-amino)-alaninol.

Preparation of Intermediate CBZ-L-Leu-L-Phe-L-[N-(2-pyrrolidinone)]-Alaninal

This compound was prepared from CBZ-L-Leu-L-Phe-L-[N-(2-pyrrolidinone)]-alaninol using the procedure described in Example 1 for the preparation of CBZ-L-Leu-L-Phe-L-methioninal (sulfoxide). Anal. ($C_{30}H_{38}N_4O_6 \cdot 1.4 H_2O$) C, H, N.

Preparation of Product—Ethyl-3-[CBZ-L-Leu-L-Phe-L-[N-(2-pyrrolidinone)]-Ala]-E-Propenoate This compound was prepared from CBZ-L-Leu-L-Phe-L-[N-(2-pyrrolidinone)]-alaninal and (carbethoxymethylene)triphenylphosphorane using the procedure described in Example 1 for the preparation of compound 12, ethyl-3-[CBZ-L-Leu-L-Phe-L-Met(sulfoxide)-E-propenoate. $^1$H NMR (DMSO-$d_6$) δ 0.80 (d, 6H, J=7.0 Hz), 0.95–1.40 (m, 7H), 1.49 (m, 1H), 1.82 (m, 2H), 2.12 (m, 2H), 2.60–3.10 (m, 2H), 3.20 (m, 2H), 3.81 (m, 1H), 4.00 (m, 1H), 4.10 (m, 2H), 4.49 (m, 1H), 4.72 (m, 1H), 5.01 (bs, 1H), 5.70 (d, 0.5H-rotomer-J=16.5 Hz), 5.97 (d, 0.5H-rotomer-J=16.5 Hz), 6.70 (d, 0.5H -rotomer-J=16.5 Hz), 6.80 (d, 0.5H-rotomer-J=16.5 Hz), 7.20 (d, 2H, J=7.4 Hz), 7.34 (m, 3H), 7.60 (m, 5H), 8.04 (m, 1H), 8.23 (m, 1H). HRMS calcd for $C_{34}H,4N_4O_7$+Cs 753.2264 (M+Cs), found 753.2295.

Example 9

Preparation of Compound 16: Ethyl-3-[CBZ-L-Leu-L-Phe-L-(-carbamyl-amino)-Ala]-E-Propenoate Preparation of Intermediate CBZ-L-(N-BOC-amino)-Ala To a stirred solution of NaOH (1.23 g, 30.76 mmol) in 36 mL of $H_2O$ and 24 mL tert-butanol was added CBZ-L-amino-Ala (7.15 g, 30 mmol). To this solution was added di-tert-butyl dicarbonate (6.88 g, 31.5 mmol). Stirring was continued at room temperature for 12 hours, at which time the solution was washed with pet. ether (2×150 mL). The organic layers were washed with saturated aqueous $NaHCO_3$ (3×20 mL), and the aqueous layers were combined and acidified at 0° C. with 25% aqueous $KHSO_4$ to pH 2–3. This milky white mixture was then extracted with a large excess of $Et_2O$, dried over anhydrous $Na_2SO_4$, and concentrated to yield 9.13 g (90%) of product as a white solid, which was used without further purification. $^1$H NMR (DMSO-$d_6$) δ 1.35 (s, 9H), 3.21 (m, 2H), 4.05 (m, 1H), 5.02 (s, 2H), 6.83 (bt, 1H, J=6.6 Hz), 7.34 (m, 5H), 7.41 (d, 1H, J=8.1 Hz), 12.65 (bs, 1H). This compound was further characterized as its corresponding methyl ester.

Preparation of Intermediate CBZ-L-(N-BOC-amino)-Ala-OMe.

A solution of diazomethane in $Et_2O$, generated from N-methyl-N-nitroso-p-toluenesulfonamide (7.7 g, 36.0 mmol), 70 mL $Et_2O$, 16 mL EtOH, 12 mL $H_2O$ and KOH (7.65 g, 13.6 mmol) was carefully distilled into a stirred solution of CBZ-L-(N-BOC-amino)-Ala (7.8 g, 23.0 mmol) in 50 mL $Et_2O$ and 10 mL EtOH at 0° C. The yellow solution was stirred for 30 minutes. The cold solution was then brought to room temperature, and argon was bubbled into the reaction flask to remove any excess diazomethane. After the solution turned colorless, it was concentrated to give the methyl ester as a white solid in quantitative yield. mp 72°–74° C.; IR (KBr) 3418, 3331, 3005, 2955, 1753, 1724, 1676, 1552, 1525, 1298, 1045, 699 cm$^{-1}$; $^1$H NMR (CDCl$_3$) δ 1.41 (s, 9H), 3.55 (m, 2H), 3.76 (s, 3H), 4.40 (m, 2H), 4.82 (m, 1H), 5.11 (s, 2H), 5.77 (m, 1H), 7.35 (m, 5H). Anal. ($C_{17}H_{24}N_2O_6$) C, H, N.

Preparation of Intermediate CBZ-L-(N-BOC-amino)-Alaninol

Using the borohydride reduction procedure described in Example 2 for the preparation of CBZ-L-(N-Ac-amino)-alaninol, CBZ-L-(N-BOC-amino)-Ala-OMe was converted to the corresponding alcohol and isolated in 96% yield without column chromatography purification. mp=116°–119° C.; IR (KBr) 3327, 3277, 3065, 2976, 1699, 1682, 1543, 1315, 1250, 1062, 1001, 696 cm$^{-1}$; $^1$H NMR (DMSO-$d_6$) δ 1.35 (s, 9H), 2.90–3.10 (m, 4H), 3.55 (m 1H), 4.60 (bt, 1H, J=5.5 Hz), 4.99 (s, 2H), 6.72 (bt, 1H, J=5.5 Hz), 6.86 (d, 1H, J=8.1 Hz), 7.34 (m, 5H). Anal. ($C_{16}H_{24}N_2O_5$) C, H, N.

Preparation of Intermediate L-N-BOC-amino)-Alaninol

Using the hydrogenation procedure described in Example 2 for the preparation of L-(N-Ac-amino)-alaninol, the CBZ group was removed from CBZ-L-(N-BOC-amino)-alaninol to give the amino alcohol in 98% yield. mp=61°–64° C.; IR (KBr) 3362, 2980, 2935, 1680, 1534, 1370, 1287, 1175, 1059, 642 cm$^{-1}$; $^1$H NMR (DMSO-$d_6$) δ 1.36 (s, 9H), 2.64 (m, 1H), 2.72 (m, 1H), 2.93 (m, 1H), 3.13 (m, 1H), 3.32 (m, 2H), 4.45 (bs, 1H), 6.67 (bs, 1H); Anal. ($C_8H_{18}N_2O_3$) C, H, N.

Preparation of Intermediate CBZ-L-Leu-L-Phe-L-(N-BOC-amino)-Alaninol

This compound was prepared from L-(N-BOC-amino)-alaninol and CBZ-L-Leu-L-Phe using the coupling procedure described in Example 2 for the preparation of CBZ-L-Leu-L-Phe-L-(N-Ac-amino)-alaninol. The reaction mixture was purified by flash column chromatography (5% saturated anhydrous $NH_3$ in MeOH/$CH_2Cl_2$) to give a white solid in 90% yield. IR (KBr) 3420, 3327, 3289, 3032, 2953, 1694, 1643, 1535, 1284, 1036, 696 cm$^{-1}$; $^1$H NMR (DMSO-$d_6$) δ 0.80 (dd, 6H, J=11.2, 6.4 Hz), 1.35 (s, 9H), 1.55 (m 2H), 1.72 (m, 1H), 2.89 (m, 2H), 3.19 (m, 2H), 3.78 (m, 1H), 3.92 (m, 1H), 4.44 (m, 1H), 4.62 (t, 1H, J=5.5 Hz), 5.01 (d, 2H, J=5.9 Hz), 6.63 (bt, 1H, J=5.5 Hz), 7.18 (m, 5H), 7.34 (m, 5H), 7.45 (d, 1H, J=8.1 Hz), 7.60 (d, 1H, J=7.7 Hz), 7.85 (d, 1H, J=8.1 Hz). Anal. ($C_{31}H_{44}N_4O_7$) C, H, N.

Preparation of Intermediate CBZ-L-Leu-L-Phe-L-(N-BOC-amino)-Alaninal

This compound was prepared in 90% yield as a white solid from CBZ-L-Leu-L-Phe-L-(N-BOC-amino)-alaninol using the procedure described in Example 1 for the preparation of CBZ-L-Leu-L-Phe-L-methioninal (sulfoxide). The product was used immediately without further purification. The product existed as a mixture of aldehyde and aldehyde hydrate. IR (KBr) 3299, 3067, 2959, 2934, 1696, 1647, 1535, 1254, 1171, 747, 698 cm$^{-1}$; $^1$H NMR (DMSO-$d_6$) δ 0.80 (dd, 6H, J=9.0, 6.8 Hz), 1.35 (s, 9H), 1.41 (m, 2H), 1.69 (m, 1H), 2.80–3.01 (m, 2H), 3.29 (m, 2H), 3.97 (m, 1H), 4.10 (m, 1H), 4.60 (m, 1H), 5.00 (s, 2H), 5.56 (d, J=7.4 Hz, hydrate), 6.78 (t, 1H, J=6.3 Hz), 7.20 (m, 5H), 7.33 (m, 5H), 7.40 (d, 1H, J=8.1 Hz), 7.97 (d, 1H, J=8.1 Hz), 8.39 (d, 1H, J=6.6 Hz), 9.26 (s, 1H); HRMS calcd for $C_{31}H_{42}N_4O_7$+Cs 715.2108 (M+Cs), found 715.2133. Anal. ($C_{31}H_{42}N_4O_7 \cdot 0.5 H_2O$) C, H, N.

Preparation of Intermediate Ethyl-3-[CBZ-L-Leu-L-Phe-L-N-BOC-amino)-Ala]-E-Propenoate This compound was prepared in approximately 40% yield as a white foaming solid from CBZ-L-Leu-L-Phe-L-(N-BOC-amino)-alaninal and (carbethoxymethylene)-triphenylphosphorane using the procedure described in Example 1 for the preparation of compound 12, ethyl-3-

[CBZ-L-Leu-L-Phe-L-Met(sulfoxide)-E-propenoate. The product was partially purified (impure with triphenylphosphine oxide as determined by NMR) by flash column chromatography (4% MeOH/CH$_2$Cl$_2$). $^1$H NMR (DMSO-d$_6$) δ 0.80 (dd, 6H, J=9.6, 6.3 Hz), 1.19 (t, 3H, J=6.8 Hz), 1.34 (s, 9H), 1.45–1.70 (m, 3H), 2.82–3.05 (m, 4H), 3.99 (m, 1H), 4.08 (q, 2H, J=7.0 Hz), 4.46 (m, 2H), 5.01 (m, 2H), 5.64 (d, 1H, J=16.2 Hz), 6.61 (dd, 1H, J=16.2, 5.5 Hz), 6.85 (bt, 1H, J=5.2 Hz), 7.18 (m, 5H), 7.34 (m, 5H), 7.42 (d, 1H, J=5.5 Hz), 7.96 (d, 1H, J=7.4 Hz), 8.01 (d, 1H, J=7.4 Hz); HRMS calcd for C$_{35}$H$_{48}$N$_4$O$_8$+Na 675.3370 (M+Na), found 675.3363.

Preparation of Intermediate Ethyl-3-(CBZ-L-Leu-L-Phe-L-amino-Ala)-E-Propenoate

To a stirred solution of ethyl-3-[CBZ-L-Leu-L-Phe-L-(N-BOC-amino)-Ala]-E-propenoate (0.14 g, 0.215 mmol) in 12 mL CH$_2$Cl$_2$, cooled to 0° C., was added 0.65 mL TFA dropwise. The reaction was followed by TLC (silica, 10% MeOH/CH$_2$Cl$_2$) until there was a disappearance of starting material. At this time the reaction mixture was taken up in 100 mL EtOAc and washed with saturated NaHCO$_3$ (3×10 mL). The organic layer was then washed with H$_2$O then saturated brine and dried over anhydrous Na$_2$SO$_4$. Concentration of the solution gave a residue, which was purified by flash column chromatography (8% MeOH/CH$_2$Cl$_2$) to give a beige foam in 84% yield. $^1$H NMR (DMSO-d$_6$) δ 0.80 (dd, 6H, J=9.4, 6.8 Hz), 1.22 (t, 3H, J=7.2 Hz), 1.31 (m, 2H), 1.51 (m, 1H), 2.64 (m, 2H), 2.91 (m, 2H), 3.99 (m, 1H), 4.10 (q, 2H, J=7.4 Hz), 4.36 (m, 1H), 4.49 (m, 1H), 5.02 (m, 2H), 5.60 (d, 1H, J=16.2 Hz), 6.76 (dd, 1H, J=15.6, 5.0 Hz), 7.20 (m, 5H), 7.34 (m, 5H), 7.46 (d, 1H, J=7.0 Hz), 7.95 (d, 1H, J=8.5 Hz), 8.05 (d, 1H, J=5.9 Hz); MS calcd for C$_{35}$H$_{48}$N$_4$O$_8$+H 553 (M+H), found 553.

Preparation of Product—Ethyl-3-[CBZ-L-Leu-L-Phe-L-N-carbamyl-amino)-Ala]-F-Propenoate To a stirred solution of bis (4-nitrophenyl) carbonate (66 mg, 0.22 mmol) in 2 mL CH$_2$Cl$_2$, was added a solution of ethyl-3-[CBZ-L-Leu-L-Phe-L-amino-Ala]-E-propenoate (0.10 g, 0.18 mmol) in 2 mL CH$_2$Cl$_2$. The mixture was stirred for 3 hours at which time 2 mL of saturated anhydrous methanolic ammonia was added. The yellow solution was allowed to stir for 30 minutes longer, diluted with 100 mL CH$_2$Cl$_2$, and washed repeatedly with 1N NaOH to remove 4-nitrophenol. The organic layer was washed with dilute HCl, H$_2$O, and brine, and dried over anhydrous Na$_2$SO$_4$. This solution was concentrated, and the residue was subjected to flash column chromatography (5% MeOH/CH$_2$Cl) to yield a white solid in 20% yield. IR (KBr) 3470, 3291, 2978, 2926, 1715, 1645, 1539, 1281, 1045, 698 cm$^{-1}$; $^1$H NMR (DMSO-d$_6$) δ 0.81 (dd, 6H, J=9.0, 6.8 Hz), 1.21 (t, 3H, J=7.0 Hz), 1.30 (m, 2H), 1.48 (m, 1H), 2.92 (m, 2H), 3.10 (m, 2H), 3.97 (m, 1H), 4.10 (q, 2H, J=7.0 Hz), 4.40 (m, 2H), 5.01 (m, 2H), 5.54 (bs, 2H), 5.61 (d, J=16.5 Hz), 6.04 (t, 1H, J=7.7 Hz), 6.71 (dd, J=15.8, 5.2 Hz), 7.20 (m, 5H), 7.34 (m, 5H), 7.46 (d, 1H, J=7.4 Hz), 8.01 (d, 1H, J=7.0 Hz), 8.11 (d, 1H, J=8.5 Hz); HRMS calcd for C$_{31}$H$_{41}$N$_5$O$_7$+Cs 728.2060 (M+Cs), found 728.2078 Anal. (C$_{31}$H$_{41}$N$_5$O$_7$) C, H, N.

Example 10

Preparation of Compound 17: Isopropyl-3-(CBZ-L-Leu-L-Phe-L-Gln)-E-Propenoate

Preparation of Intermediate 3-[BOC-L-(Tr-Gln)]-E-Propenoic Acid

Ethyl-3-[BOC-L-(Tr-Gln)]-E-propenoate (1.874 g, 3.46 mmol), prepared as decribed in Example 3, was taken up in 20 mL EtOH and treated with 1N NaOH solution (7.95 mL, 7.95 mmol) dropwise, via addition funnel, over 2 hours. The resulting solution was stirred at room temperature for 1.5 hours, whereupon the reaction mixture was poured into water and washed with ether. The aqueous layer was acidified to pH 3 with 1N HCl, and extracted 3 times with EtOAc. The organic phase was separated and dried over MgSO$_4$ and concentrated to provide 3-[BOC-L-(Tr-Gln)]-E-propenoic acid (1.373 g, 77%) as an off-white foam. No further purification was needed: IR (thin film) 3315, 1698, 1666 cm$^{-1}$; $^1$H NMR(CDCl$_3$) δ 1.42 (s, 9H), 1.76 (m, 1H), 1.83–1.98 (m, 1H), 2.37 (t, 2H, J=7.0 Hz), 4.30 (m, 1H), 4.88 (m, 1H), 5.85 (d, 1H, J=15.3 Hz), 6.86 (dd, 1H, J=15.5, 5.1 Hz), 6.92 (s, 1H), 7.25 (m, 15H).

Preparation of Intermediate Isopropyl-3-[BOC-L-(Tr-Gln)]-E-Propenoate

3-BOC-L-(Tr-Gln)]-E-Propenoic acid (0.500 g, 0.973 mmol), isopropanol (0.008 mL, 1.07 mmol), and 4-dimethylaminopyridine (0.012 g, 0.0973 mmol) were taken up in 10 mL dry CH$_2$Cl, and treated with 1-(3-dimethylaminopropyl)-3-ethylcarbodiimide hydrochloride (0.196 g, 1.07 mmol). The resulting solution was stirred at room temperature overnight, concentrated in vacuo, and purified by flash column with 50% EtOAc/hexanes to provide isopropyl-3-[BOC-L-(Tr-Gln)]-E-propenoate (0. 106 g, 20%) as a white foam: R$_f$=0.8 (50% EtOAc/hexanes); IR 3320, 1711 cm$^{-1}$; $^1$H NMR(CDCl$_3$) δ 1.25 (d, 6H, J=6.23 Hz), 1.43 (s, 9H), 1.72 (m, 1H), 1.96 (m, 1H), 2.37 (t, 2H, J=7.16 Hz), 4.30 (bs, 1H), 4.74 (m, 1H), 5.05 (m, 1H), 5.86 (dd, 1H, J=15.9, 5.0 Hz), 6.78 (dd, 1H, J=15.6, 5.0 Hz), 6.89 (1,s, 1H), 7.26 (m, 15H); Anal. (C$_{34}$H$_{40}$N$_2$O$_5$) C, H, N.

Preparation of Intermediate Isopropyl-3-[CBZ-L-Leu-L-Phe-L-(Tr-Gln)]-E-Propenoate Isopropyl-3-[BOC-L-(Tr-Gln)]-E-propenoate (0.087 g, 0.191 mmol) was deprotected and coupled with CBZ-L-Leu-L-Phe (0.079 g, 0.191 mmol) using the procedure described in Example 3 for the preparation of ethyl-3-[BOC-L-(Tr-Gln)]-E-propenoate, to provide the product (0.064 g, 40%) as a white foam: R$_f$=0.7 (50% EtOAc/hexanes); IR (thin film) 3283, 1707 cm$^{-1}$; $^1$H NMR (CDCl$_3$) δ 0.86 (m, 6H), 1.03 (m, 1H), 1.23 (m, 6H), 1.72 (m, 1H), 1.96 (m, 1H), 2.28 (m, 2H), 2.54 (m, 1H), 2.70 (m, 1H), 2.78 (m, 1H), 2.95–3.25 (m, 4H), 3.99 (m, 1H), 4.85–5.13 (m, 4H), 5.66 (d, 1H, J=15.9 Hz), 6.45 (d, 1H, J=7.5 Hz), 6.55 (d, 1H, J=7.5 Hz), 6.68 (m, 1H), 7.12–7.36 (m, 25H); MS (M+Cs) 983.

Preparation of Product—Isopropyl-3-(CBZ-L-Leu-L-Phe-L-Gln)-E-Propenoate

Using the procedure described in Example 4 for the preparation of compound 3, ethyl-3-(CBZ-L-Leu-L-Phe-L-Gln)-E-propenoate, isopropyl-3-[CBZ-L-Leu-L-Phe-L-(Tr-Gln)]-E-propenoate (0.059 g, 0.0694 mmol) was deprotected to provide the product (0.024 g, 57%) as a white solid: mp=180°–182° C.; R$_f$=0.6 (10% MeOH/CHCl$_3$); IR (KBr) 3272, 1705 cm$^{-1}$; $^1$H NMR (DMSO-d$_6$) δ 0.70 (m, 1H), 0.80 (dd, 6H, J=10.6, 6.5 Hz), 1.21 (dd, 6H, J=6.2, 2.5 Hz), 1.32 (m, 1H), 1.70 (m, 1H), 2.05 (t, 2H, J=7.6 Hz), 2.83 (m, 1H), 2.97 (m, 1H), 3.99 (m, 1H), 4.37–4.49 (m, 4H), 4.91–5.06 (m, 4H), 5.60 (d, 1H, J=15.3 Hz), 6.67 (dd, 1H, J=15.6, 5.6 Hz), 6.76 (bs, 1H), 7.19 (m, 5H), 7.34 (m, 5H), 7.44 (d, 1H, J=7.2 Hz), 8.01 (m, 2H); Anal. (C$_{33}$H$_{44}$N$_4$O$_7$·1.0 CH$_2$Cl$_2$) C, H, N.

Example 11

Preparation of Compound 18: Cyclopentyl-3-(CBZ-L-Leu-L-Phe-L-Gln)-E-Propenoate Preparation of Intermediate Cyclopentyl-3-[BOC-L-(Tr-Gln)]-E-Propenoate Using the procedure described in Example 10 for the preparation of isopropyl-3-[BOC-L-(Tr-Gln)]-E-propenoate, 3-[BOC-L-(Tr-Gln)]-E-propenoic acid (0.50 g, 0.973 mmol) was coupled with cyclopentanol (0.1 mL, 1.07 mmol) to provide cyclopentyl-3-[BOC-L-(Tr-Gln)]-E-propenoate (0.123 g, 22%) as a white foam: $R_f$=0.7 (EtOAc/hexanes); IR (thin film) 3319, 1708 cm$^{-1}$; $^1$H NMR (CDCl$_3$) δ 1.27 (m, 2H), 1.44 (s, 9H), 1.59–1.89 (m, 8H), 2.38 (t, 2H, J=7.2 Hz), 4.32 (bs, 1H), 4.55 (m, 1H), 5.22 (m, 1H), 5.87 (d, 1H, J=15.6 Hz), 6.77 (dd, 1H, J=15.1, 4.1 Hz), 6.90 (bs, 1H), 7.20–7.33 (m, 15H).

Preparation of Intermediate Cyclopentyl-3-[CBZ-L-Leu-L-Phe-L-(Tr-Gln)]-E-Propenoate Using the procedure described in Example 4 for the preparation of compound 3, ethyl-3-[CBZ-L-Leu-L-Phe-L-(Tr-Gln)]-E-propenoate, cyclopentyl-3-[BOC-L-(Tr-Gln)]-E-propenoate (0.077 g, 0.160 mmol) was deprotected and coupled with CBZ-L-Leu-L-Phe (0.068 g, 0.160 mmol) to provide cyclopentyl-3-[CBZ-L-Leu-L-Phe-L-(Tr-Gln)]-E-propenoate (0.052 g, 36%) as a white foam: $R_f$=0.4 (50% EtOAc/hexanes); IR (thin film) 3401, 3319, 1708 cm$^{-1}$; $^1$H NMR (CDCl$_3$) δ 0.84 (m, 6H), 1.05 (m, 1H), 1.28 (m, 1H), 1.46–1.71 (m, 9H), 1.85 (m, 1H), 2.28 (m, 2H), 2.98–3.12 (m, 4H), 3.99 (m 1H), 4.47 (m, 2H), 4.83–5.21 (m, 4H), 5.65 (d 1H, J=15.9 Hz), 6.50 (d, 1H, J=7.2 Hz), 6.59 (d, 1H, J=8.1 Hz), 6.65 (dd, 1H, J=15.9, 5.4 Hz), 7.04–7.35 (m 25H); MS (M+Cs) 1009.

Preparation of Product—Cyclopentyl-3-(CBZ-L-Leu-L-Phe-L-Gln)-E-Propenoate

Using the procedure described in Example 4 for the preparation of compound 3, ethyl-3-(CBZ-L-Leu-L-Phe-L-Gln)-E-propenoate, cyclopentyl-3-[CBZ-L-Leu-L-Phe-L-(Tr-Gln)]-E-propenoate (0.052 g, 0.059 mmol) was deprotected to provide the product (0.014 g, 36%) as a white solid: mp=182°–185° C.; $R_f$=0.5 (10% MeOH/CHCl,); IR (thin film) 3389, 3295, 1707 cm$^{-1}$; $^1$H NMR (Acetone-d$_6$) δ 0.85 (dd, 6H, J=10.6, 6.5 Hz), 1.08 (m, 1H), 1.48 (m, 1H), 1.60–1.70 (m, 11H), 1.89 (m, 1H), 2.22 (m, 2H), 2.96 (m, 1H), 3.18 (dd, 1H, J=13.9, 5.8 Hz), 4.00 (d, 1H, J=6.8 Hz), 4.08 (m, 1H), 4.59 (m, 2H), 4.97–5.16 (m, 4H), 5.76 (d, 1H, J=15.3 Hz), 6.71 (m, 2H), 7.15–7.41 (m, 10H), 7.51 (d, 1H, J=7.8 Hz); HRMS calcd for $C_{35}H_{46}N_7O_7$+Cs 767.2421 (M+Cs) found 767.2435.

Example 12

Preparation of Compound 19: Cyclopentylmethyl-3-(CBZ-L-Leu-L-Phe-L-Gln)-E-Propenoate Preparation of Intermediate Cyclopentylmethyl-3-[BOC-L-(Tr-Gln)]-E-Propenoate Using the procedure described in Example 10 for the preparation of isopropyl-3-[BOC-L-(Tr-Gln)]-E-propenoate, 3-[BOC-L-(Tr-Gln)]-E-propenoic acid (0.50 g, 0.973 mmol) was coupled with cyclopentylmethanol (0.12 mL, 1.07 mmol) to provide this ester (0.298 g, 51%) as a pale yellow oil: $R_f$=0.7 (50% EtOAc/hexanes); IR (thin film) 3336, 1707 cm$^{-4}$; $^1$H NMR (CDCl$_3$) δ 1.28 (m, 2H), 1.43 (s, 9H), 1.54–1.62 (m, 5H), 1.72–1.78 (m, 4H), 2.37 (t, 2H, J=7.2 Hz), 4.01 (d, 2H, J=7.2 Hz), 4.31 (bs, 1H), 4.78 (m, 1H), 5.90 (dd, 1H, J=15.9, 1.6 Hz), 6.80 (dd, 1H, J=15.9, 5.3 Hz), 6.90 (bs, 1H), 7.19–7.34 (m, 15H); Anal ($C_{37}H_{44}N_2O_5$) C, H, N.

Preparation of Intermediate Cyclopentylmethyl-3-[CBZ-L-Leu-L-Phe-L-(Tr-Gln)]-E-Propenoate Using the procedure described in Example 4 for the preparation of compound 3, ethyl-3-[CBZ-L-Leu-L-Phe-L-(Tr-Gln)]-E-propenoate, cyclopentylmethyl-3-[B OC-L-(Tr-Gln)]-E-propenoate (0.150 g, 0.310 mmol) was deprotected and coupled with CBZ-L-Leu-L-Phe (0.128 g, 0.310 mmol) to provide the product (0.062 g, 22%) as an off-white foam: $R_f$=0.4 (50% EtOAc/hexanes); IR (thin film) 3413, 3295, 1708 cm$^{-1}$; $^1$H NMR (CDCl$_3$) δ 0.84 (m, 6H), 1.05 (m, 1H), 1.46–1.65 (m, 10H), 1.74 (m, 1H), 2.25 (m, 2H), 2.93–3.11 (m, C 4H), 3.93–4.02 (m, 3H), 4.20 (m, 1H), 4.48 (m, 1H), 4.86–5.11 (m, 4H), 5.70 (d, 1H, J=15.0 Hz), 6.46 (d, 1H, J=6.9 Hz), 6.54 (d, 1H, J=8.4 Hz), 6.70 (m, 1H), 6.78 (m, 1H), 7.14–7.36 (m, 25H); MS (M+Cs) 1023.

Preparation of Product—Cyclopentylmethyl-3-(CBZ-L-Leu-L-Phe-L-Gln)-E-Propenoate

Using the procedure described in Example 4 for the preparation of compound 3, ethyl-3-(CBZ-L-Leu-L-Phe-L-Gln)-E-propenoate, cyclopentylmethyl-3-[CBZ-L-Leu-L-Phe-L-(Tr-Gln)]-E-propenoate (0.062 g, 0.070 mmol) was deprotected to provide compound 11 (0.021 g, 47%) as a white solid: mp=145°–148° C.; $R_f$=0.4 (10% MeOH/CHCl$_3$); IR (thin film) 3401, 3295, 1713 cm$^{-1}$; $^1$H NMR (acetone-d$_6$) δ 0.86 (dd, 6H, J=10.6, 6.5 Hz), 1.09 (m, 1H), 1.20–1.85 (m, 13H), 2.21 (m, 2H), 2.99 (m, 1H), 3.18 (m, 1H), 3.99 (m, 2H), 4.10 (m, 2H), 4.59 (m, 2H), 4.98–5.16 (m, 4H), 5.83 (d, 1H, J=14.6 Hz), 6.67–6.98 (m, 2H), 7.20–7.45 (m, 10H), 7.55 (m, 1H); HRMS calcd for $C_{36}H_{48}N_7O_7$+Cs 781.2577 (M+Cs) found 781.2559.

Example 13

Preparation of Compound 21: 1-Pyrrolidin-1-yl-3-(CBZ-L-Leu-L-Phe-L-Gln)-E-Propenone Preparation of Intermediate 1-Pyrrolidin-1-yl-3-[BOC-L-(Tr-Gln)]-E-Propenone 3-[BOC-L-(Tr-Gln)]-E-Propenoic acid (1.09 g, 2.12 mmol) was coupled with pyrrolidine (0.18 mL, 2.12 mmol) by dissolving both in 30 1L dry CH$_2$Cl$_2$ and treating with 1-(3-dimethylaminopropyl)-3-ethylcarbodiimide hydrochloride (0.610 g, 3.18 mmol), 1-hydroxybenzotriazole hydrate (0.430 g, 3.18 mmol), Et$_3$N (1.18 mL, 8.48 mmol) and stirring at room temperature overnight. The reaction mixture was poured into 50 mL 1N HCl, and the layers were separated. The organic layer was washed with 1N HCl and then a saturated NaHCO$_3$ solution. The organic layer was dried over MgSO$_4$ and concentrated to give a yellow residue, which was then subjected to column chromatography using a 5% MeOH/CHCl$_3$ to yield the product (0.661 g, 55%) as a white foam: $R_f$=0.5 (5% MeOH/CHCl$_3$); IR (thin film) 3291, 1696 cm$^{-1}$; $^1$H NMR (CDCl$_3$) δ 1.42 (s, 9H), 1.89 (m, 6H), 2.37 (m, 2H), 3.44–3.53 (m, 4H), 4.28 (bs, 1H), 4.82 (d, 1H, J=7.8 Hz), 6.17 (dd, 1H, J=15.3, 1.6 Hz), 6.71 (dd, 1H, J=15.4, 6.1 Hz), 6.93 (bs, 1H), 7.19–7.32 (m, 15H); Anal ($C_{35}H_{41}N_3O_4$CH$_2$Cl$_2$) C, H, N.

Preparation of Intermediate 1-Pyrrolidin-1-yl-3-[CBZ-L-Leu-L-Phe-L-(Tr-Gln)]-E-Propenone Using the procedure described in Example 3 for the preparation of compound 2, ethyl-3-[CBZ-L-Leu-L-Phe-L-(Tr-Gln)]-E-propenoate, 1-pyrrolidin-1-yl-3-[BOC-L-(Tr-Gln)]-E-propenone (0.613 g, 1.166 mmol) was deprotected and coupled with CBZ-L-Leu-L-Phe (0.481 g, 1.166 mmol), yielding 1-pyrrolidin-1-yl-3-[CBZ-L-Leu-L-Phe-L-(Tr-Gln)]-E-propenone (0.668 g, 67%) as a white foam: $R_f$=0.5 (10% MeOH/CHCl$_3$); IR (thin film) 3294, 1702 cm$^{-1}$; $^1$H NMR (CDCl$_3$) δ 0.84 (m, 6H), 1.31 (m, 1H), 1.46 (m, 1H), 1.81–1.94 (m, 6H), 2.28 (m, 2H), 2.96 (m, 1H), 3.15 (m, 1H), 3.39–3.50 (m, 4H), 3.95 (m, 2H), 4.87–5.11 (m, 4H), 6.14 (d, 1H, J=15.3 Hz), 6.45 (d, 1H, J=7.8 Hz), 6.67 (dd, 1H, J=14.8, 4.8 Hz), 6.82 (d, 1H, J=8.1 Hz), 7.08–7.33 (m, 25H), 7.44 (d, 1H, J=8.1 Hz); MS (M+H) 862.

Preparation of Product—1-Pyrrolidin-1-yl-3-(CBZ-L-Leu-L-Phe-L-Gln)-E-Propenone

Using the procedure described in Example 4 for the preparation of compound 3, ethyl-3-(CBZ-L-Leu-L-Phe-L-Gln)-E-propenoate, l-pyrrolidin-1-yl-3-[CBZ-L-Leu-L-Phe-L-(Tr-Gln)]-E-propenone (0.668 g, 0.776 mmol) was deprotected to provide this final product (0.320 g, 67%) as a white solid: mp=195°–196° C. (dec); $R_f$=0.4 (10% MeOH/CHCl$_3$); IR (thin film) 3289, 1684 cm$^{-1}$; $^1$H NMR (DMSO-d$_6$) δ 0.79 (dd, 6H, J=12.1, 6.5 Hz), 1.29 (m, 1H), 1.47 (m, 1H), 1.68–1.87 (m, 6H), 2.05 (m, 2H), 2.84 (m, 1H), 3.01 (m, 1H), 3.29–3.40 (m, 4H), 3.94 (m, 1H), 4.44 (m, 2H), 5.01 (m, 2H), 6.14 (d, 1H, J=14.9 Hz), 6.507 (dd, 1H, J=15.4, 5.8 Hz), 6.76 (bs, 11H), 7.14–7.35 (m, 10H), 7.46 (d, 1H, J=7.8 Hz), 7.95–8.02 (m, 2H); HRMS calcd for $C_{34}H_{45}N_5O_6$ 620.3448 (M+H), found 620.3437; Anal. ($C_{34}H_{45}N_5O_6$.0.2 CH$_2$Cl$_2$) C, H, N.

Example 14

Preparation of Compound 22: N,N-Dimethyl-3-(CBZ-L-Leu-L-Phe-L-Gln)-E-Propenamide Preparation of Intermediate N,N-Dimethyl-3-[BOC-L-(Tr-Gln)]-E-Propenamide Using the procedure described in Example 13 for the preparation of 1-pyrrolidin-1-yl-3-[BOC-L-(Tr-Gln)]-E-propenone, 3-[BOC-L-(Tr-Gln)]-E-propenoic acid (1.05 g, 2.04 mmol) was coupled with N,N-dimethylamine (0.167 g, 2.04 mmol) to provide the amide (0.848 g, 77%) as a white foam: $R_f$=0.6 (10% MeOH/CHCl$_3$); IR (thin film) 3297, 1690 cm$^{-1}$; $^1$H NMR (CDCl$_3$) δ 1.42 (s, 9H), 1.81 (m, 1H), 1.93 (m, 1H), 2.38 (m, 2H), 2.98 (s, 3H), 3.03 (s, 3H), 4.27 (bs, 1H), 4.84 (d, 1H, J=7.2 Hz), 6.31 (dd, 1H, J=15.1, 1.4 Hz), 6.65 (dd, 1H, J=15.3, 5.9 Hz), 6.94 (bs, 1H), 7.19–7.33 (m, 15H); Anal ($C_{33}H_{39}N_3O_4$.0.9 CH$_2$Cl$_2$) C, H, N.

Preparation of Intermediate N,N-Dimethyl-3-[CBZ-L-Leu-L-Phe-L-(Tr-Gln)]-E-Propenamide Using the procedure described in Example 3 for the preparation of compound 2, ethyl-3-L[CBZ-L-Leu-L-Phe-L-(Tr-Gln)]-E-propenoate, N,N-dimethyl-3-[B OC-L-(Tr-Gln)]-E-propenamide (0.726 g, 1.567 mmol) was deprotected and coupled with CBZ-L-Leu-L-Phe (0.646 g, 1.567 mmol) to provide the product (0.417 g, 32%) as a white foam: $R_f$=0.5 (10% MeOH/CHCl$_3$); IR (thin film) 3291, 1702 cm$^{-1}$; $^1$H NMR (CDCl$_3$) δ 0.84 (m, 6H), 1.30 (m, 1H), 1.47 (m, 1H), 1.74 (m, 1H), 1.94 (m, 3H), 2.56 (s, 3H), 2.96 (m, 1H), 3.15 (m, 1H), 2.99 (d, 6H, J=13.4 Hz), 3.94 (m, 1H), 4.54 (m, 2H), 4.87 (s, 2H), 5.00 (d, 2H, J=5.3 Hz), 6.28 (d, 1H, J=14.9 Hz), 6.42 (d, 1H, J=7.8 Hz), 6.63 (dd, 1H, J=15.3, 5.0 Hz), 6.81 (d, 1H, J=8.4 Hz), 7.06 (bs 1H), 7.10–7.36 (m, 25H); Anal ($C_{51}H_{57}N_5O_6$.3.0 H$_2$O) C, H, N.

Preparation of Product—N,N-Dimethyl-3-(CBZ-L-Leu-L-Phe-L-Gln)-E-Propenamide

Using the procedure described in Example 4 for the preparation of compound 3, ethyl-3-(CBZ-L-Leu-L-Phe-L-Gln)-E-propenoate, N,N-dimethyl-3-[CBZ-L-Leu-L-Phe-L-(Tr-Gln)]-E-propenamide (0.417 g, 0.5 mmol) was deprotected to provide N,N-dimethyl-3-(CBZ-L-Leu-L-Phe-L-Gln)-E-propenamide (0.214 g, 72%) as a white solid: mp=174°–175° C. (dec); $R_f$=0.34 (MeOH/CHCl$_3$); IR (thin film) 3284, 1684 cm$^{-1}$; $^1$H NMR (DMSO-d$_6$) δ 0.79 (dd, 6H, J=12.1, 6.5 Hz), 1.30 (m, 1H), 1.47 (m, 1H), 1.70 (m, 2H), 2.06 (m, 2H), 2.84 (m, 1H), 2.98 (s, 3H), 3.03 (s, 3H), 3.94 (m, 1H), 4.44 (m, 2H), 4.95–5.07 (m, 4H), 6.27 (d, 1H, J=15.3 Hz), 6.47 (dd, 1H, J=15.3, 5.6 Hz), 6.75 (bs, 1H), 7.14–7.35 (m, 1 OH), 7.46 (d, 1H, J=7.5 Hz) 7.96–8.01 (m, 2H); HRMS calcd for $C_{32}H_{43}N_5O_6$ 594.3291 (M+H), found 594.3281. Anal. ($C_{32}H_{43}N_5O_6$.1.0 CH$_2$Cl$_2$) C, H, N.

Example 15

Preparation of Compound 24: 1-Phenyl-3-(CBZ-L-Leu-L-Phe-L-Gln)-E-Propenone

Preparation of Intermediate 2-(2-[CBZ-L-Leu-L-Phe-L-(Tr-Gln)] -E-Vinyl) Pyridine 2-Picolyltriphenylphosphonium chloride/NaNH$_2$ (0.345 g, 0.76 mmol) was dissolved in 10 mL of THF. CBZ-L-Leu-L-Phe-L-(Tr-Glutaminal) (0.53 g, 0.69 mmol) was dissolved in 5 mL of THF and added dropwise to the yield solution at room temperature, which was allowed to stir overnight. The solvent was removed in vacuo, and the crude product purified by column chromatography eluting with a gradient of 1–5% MeOH in CHCl$_3$ to give 0.353 g (61%) of a white glassy solid: IR (KBr) 3295, 3061, 2953, 1952, 1881, 1649, 1539, 1234, 1045, 972, 750, 696 cm$^{-1}$; $^1$H NMR (DMSO-d$_6$) δ 0.78 (t, 6H, J=7.0 Hz), 1.30 (m, 2H), 1.46 (m, 1H), 1.70 (m, 2H), 2.27 (m, 2H), 2.78 (m, 1H), 3.03 (m, 1H), 3.97 (m, 1H), 4.42 (m,1H), 4.52 (m,1H), 4.96 (d, 1H, J=12.0 Hz), 5.03 (d, 1H, J=12.0 Hz), 6.38 (d, 1H, J=16.0 Hz), 6.60 (dd, 1H, J=16.0, 6.0 Hz), 7.10–7.34 (m, 27H), 7.42 (d, 1H, J=8.0 Hz), 7.73 (t, 1H, J=7.5 Hz), 7.92 (d, 1H, J=8.5 Hz), 8.07 (d, 1H, J=8.5 Hz), 8.49 (d, 1H, J=5.0 Hz), 8.59 (s, 1H); MS (M+H) 842. Anal. ($C_{53}H_{55}N_5O_5$.0.75 H$_2$O) C, H, N.

Preparation of Intermediate 2-[2-(CBZ-L-Leu-L-Phe-L-Gln)-E-Vinyl] Pyridine

Using the procedure described in Example 32 for the preparation of compound 20, diethyl-[2-(CBZ-L-Leu-L-Phe-L-Gln)-E-vinyl] phosphonate, 2-[2-(CBZ-L-Leu-L-Phe-L-Gln)-E-vinyl] pyridine was synthesized from 2-(CBZ-L-Leu-L-Phe-L-Tr-Gln)-E-vinyl pyridine in 69% yield as a white solid: IR (KBr) 3291, 3059, 2955, 2359, 1694, 1641, 1539, 1234, 1119, 1047, 970, 743, 698 cm$^{-1}$; $^1$H NMR (DMSO-d$_6$) δ 0.78 (m, 6H), 1.32 (m, 2H), 1.49 (m, 1H), 1.77 (m, 2H), 2.11 (t, 2H, J=7.0 Hz), 2.86 (m, 1H), 3.01 (m, 1H), 3.96 (m, 1H), 4.41 (m, 1H), 4.51 (m, 1H), 4.98 (d, 1H, J=13.0 Hz), 5.04 (d, 1H, J=13.0 Hz), 6.39 (d, 1H, J=16.0 Hz), 6.60 (dd, 1H, J=16.0, 6.0 Hz), 6.75 (bs, 1H), 7.08–7.34 (m, 13H), 7.45 (d, 1H, J=8.0 Hz), 7.73 (dt, 1H, J=7.5, 1.5 Hz), 7.97 (d, 1H, J=8.0 Hz), 8.07 (d, 1 H, J=8.0 Hz), 8.50 (d, 1H, J=4.0 Hz); HRMS calcd for $C_{34}H_4$,N5O, 600.3186 (M+H), found 600.3198. Anal. ($C_{34}H_{41}N_5O_5$.1.0 H$_2$O) C, H, N.

Preparation of Intermediate 1-Phenyl-3-[CBZ-L-Leu-L-Phe-L-(Tr-Gln)]-E-Propenone

Using the procedure described in Example 1 for the preparation of compound 12, ethyl-3-[CBZ-L-Leu-L-Phe-L-Met(sulfoxide)-E-propenoate, this compound was synthesized from CBZ-L-Leu-L-Phe-L-Tr-glutaminal and (benzoylmethylene)triphenylphosphorane to give 0.38 g of crude material (impure with triphenylphosphine oxide), which was used without further purification.

Preparation of Product—1-Phenyl-3-(CBZ-L-Leu-L-Phe-L-Gln)-E-Propenone

To 0.38 g of 1-phenyl-3-[CBZ-L-Leu-L-Phe-L-(Tr-Gln)]-E-propenone, impure with triphenylphosphine oxide, was added 10 mL of CH$_2$Cl$_2$. TFA (1 mL) was added to this solution, and the reaction was stirred at room temperature for four hours. The reaction was poured into an EtOAc/saturated NaHCO, solution and agitated until white solids began to precipitate out of the organic layer. The aqueous layer was separated, and the solids filtered and washed with EtOAc to give compound 14 (0.0795 g, 20% yield from the aldehyde; 2 steps) as a white solid: IR (KBr) 3408, 3293, 3063, 2955, 1653, 1539, 1449, 1283, 1234, 1121, 1047, 970, 698 cm$^{-1}$; $^1$H NMR (DMSO-d$_6$) δ 0.78 (m, 6H), 1.31 (m, 2H), 1.45 (m, 1H), 1.76 (m, 2H), 2.11 (t, 2H, J=8.0 Hz), 2.89 (m, 1H), 3.01 (m, 1H), 3.97 (m, 1H), 4.51 (m, 2H), 4.97 (d, 1H, J=13.0 Hz), 5.05 (d, 1H, J=13.0 Hz), 6.76 (dd, 1H, J=15.0, 5.0 Hz), 6.77 (bs, 1H), 6.91 (d, 1H, J=15.0 Hz), 7.02–7.34 (m, 11H), 7.47 (d, 1H, J=7.0 Hz), 7.54 (m, 2H), 7.66 (t, 1H, J=7.0 Hz), 7.93 (d, 2H, J=7.0 Hz), 8.04 (d, 1H, J=8.0 Hz), 8.10 (d, 1H, J=8.5 Hz); HRMS calcd for C$_3$,H$_{43}$N$_4$O$_6$ 627.3182 (M+H), found 627.3199. Anal. (C$_{36}$H$_{43}$N$_4$O$_6$) C, H, N.

Example 16

Preparation of Compound 26: Ethyl-3-[N-(4-Methoxyindole-2-Carbonyl)-L-(4-Cl-Phe)-L-Gln]-E-Propenoate Preparation of Intermediate BOC-L-(4-Cl-Phe)-L-(Tr-Glutaminol)

BOC-L4-Cl-Phe (0.90 g, 3.0 mmol) was dissolved in 30 mL of THF. Carbonyldiimidazole (0.49 g, 3.0 mmol) was added, and the reaction was allowed to stir at room temperature for one hour. L-(Tr-Glutaminol) (1.12 g, 3 mmol) was added, and the reaction was stirred overnight at room temperature. The solvent was removed in vacuo, and the product was purified by flash column chromatography eluting with 3% MeOH/CHCl$_3$ to yield 1.57 g (80%) of a white solid: IR (KBr) 3416, 3302, 3057, 3024, 2978, 2934, 1663, 1491, 1447, 1366, 1250, 1165, 752, 700 cm$^{-1}$; $^1$H NMR (DMSO-d$_6$) δ 1.28 (s, 9H), 1.44 (m, 1H), 1.66 (m, 1H), 2.26 (m, 2H), 2.72 (m, 1H), 2.91 (m, 1H), 3.18 (m, 2H), 3.64 (m, 1H), 4.07 (m, 1H), 4.67 (t, 1H, J=5.0 Hz), 7.05–7.32 (m, 19H), 6.86 (d, 1H, J=8.5 Hz), 7.62 (d, 1H, J=8.5 Hz), 8.48 (s, 1H). Anal. (C$_{38}$H$_{42}$N$_3$O$_5$Cl.1.0 H$_2$O) C, H, N.

Preparation of Intermediate L-(4-Cl-Phe)-L-(Tr-Glutaminol) Hydrochloride Salt

BOC-L-(4-Cl-Phe)-L-(Tr-Glutaminol) (1.57 g., 2.4 mmol) was dissolved in a minimum amount of CH$_2$Cl$_2$ (~5 mL) followed by 50 mL of Et$_2$O. Anhydrous HCl gas was bubbled into the solution until a white solid precipitated from solution. The reaction was allowed to stir at room temperature overnight, and the resulting solid was filtered and washed with Et$_2$O, giving 1.19 g (84%) of a white crystalline material: IR (KBr) 3246, 3057, 3028, 2934, 1668, 1494, 1447, 1089, 700cm$^{-1}$; $^1$H NMR (DMSO-d$_6$) δ 1.48 (m, 1H), 1.71 (m, 1H), 2.30 (m, 2H), 2.94–3.17 (m. 3H), 3.27 (m, 1H), 3.67 (br, 2H), 3.98 (m, 1H), 7.07–7.40 (m, 19H), 8.28 (bs, 3H), 8.34 (d, 1H, J=8.8 Hz), 8.54 (s, 1H). Anal. (C$_{33}$H$_{34}$N$_3$O$_3$Cl.1.0HCl.0.75 H$_2$O) C, H, N.

Preparation of Intermediate N-(4-Methoxyindole-2-Carbonyl)-L-(4-Cl-Phe)-L-(Tr-Glutaminol)

4-Methoxyindole-2-carboxylic acid (0.36 g, 1.87 mmol) was suspended in 10 mL of CH$_2$Cl$_2$. To this suspension was added N-hydroxysuccinimide (0.23 g, 1.97 mmol) and 2 mL of DMF to dissolve all solids. Dicyclohexylcarbodiimide (0.41 g, 1.97 mmol) was added, and the reaction mixture was stirred at room temperature for 4 hours. At this time the mixture was then filtered into a separate flask containing (1.17 g, 1.97 mmol) of L-(4-Cl-Phe)-L-(Tr-glutaminol)-HCl salt, 0.41 mL (2.95 mmol) of Et$_3$N, 10 mL of CH$_2$Cl$_2$, and 2 mL of DMF, removing the N,N'-dicyclohexylurea precipitate. The reaction was allowed to stir overnight at room temperature. The solvents were removed in vacuo, and the resulting crude product was purified by flash column chromatography eluting with 3% (anhydrous NH$_3$/MeOH)/CHCl$_3$ to afford 0.53 g (39%) of a white solid: IR (KBr) 3290, 3057, 2933, 1653, 1491, 1360, 1257, 1098, 754, 698 cm$^{-1}$; $^1$H NMR (DMSO-d$_6$) δ 1.50 (m, 1H), 1.74 (m, 1H), 2.28 (m 2H), 3.02 (m, 2H), 3.24 (m, 2H), 3.66 (m, 1H), 3.87 (s, 3H), 4.65 (m, 1H), 4.70 (m, 1H), 6.49 (m, 1H, J=7.3 Hz), 6.94–7.38 (m, 22H), 7.86 (d, 1H, J=8.8 Hz), 8.49 (d, 1H, J=8.8 Hz), 8.53 (s, 1H), 11.50 (s, 1H). Anal. (C$_{43}$H$_{41}$N$_4$O$_5$Cl.0.75 H$_2$O) C, H, N.

Preparation of Intermediate N-(4-Methoxyindole-2-Carbonyl)-L-(4-Cl-Phe)-L-(Tr-Glutaminal)

N-(4-Methoxyindole-2-carbonyl)-L-(4-Cl-Phe)-L-(Tr-glutaminol) (1.13 g, 1.55 mmol) was dissolved in 15 mL of DMSO. o-Iodoxybenzoic acid (1.30 g, 4.66 mmol) was added to this solution, and dissolved after a few minutes of stirring at room temperature. After two hours the DMSO was removed under reduced pressure. The residue was twice diluted with CH$_2$Cl$_2$, and the solvent was evaporated to remove any residual DMSO. The residue was diluted with EtOAc, and the white precipitate was triturated and filtered off. The organic solvent was washed with 10% Na$_2$S$_2$O$_3$/10% NaHCO$_3$ solution, water, and brine before drying over Na$_2$SO$_4$. The solvent was removed to give 0.85 g (76%) of a white glassy solid which was used immediately without further purification: $^1$H NMR (DMSO-d$_6$) δ 1.72 (m, 2H), 2.32 (m, 2H), 3.04 (m, 1H), 3.11 (m, 11H), 3.87 (m, 311), 4.05 (m, 1H), 4.81 (m, 1H), 6.49 (d, 1H, J=7.3 Hz), 6.94–7.39 (m, 22H), 8.60 (m, 2H), 8.63 (s, 1H), 9.34 (s, 1H), 11.48 (s, 1H).

Preparation of Intermediate Ethyl-3-[N-(4-Methoxyindole-2-Carbonyl)-L-(4-Cl-Phe)-L-(Tr-Gln)]-E-Propenoate Using the procedure described in Example 1 for the preparation of compound 12, ethyl-3-[CBZ-L-Leu-L-Phe-L-Met(sulfoxide)-E-propenoate, this compound was synthesized from N-(4-methoxyindole-2-carbonyl)-L-(4-Cl-Phe)-L-(Tr-glutaminal) in 59% yield as a white solid: IR (KBr) 3302, 3057, 2934, 1958, 1896, 1659, 1491, 1260, 1096, 1036, 833, 756, 700 cm$^{-1}$; $^1$H NMR (DMSO-d$_6$) δ 1.22 (t, 3H, J=6.0 Hz), 1.72 (m, 2H), 2.24 (m, 2H), 3.05 (m, 2H), 3.88 (s, 3H), 4.12 (q, 2H, J=6.0 Hz),4.43 (m, 1H), 4.78 (m, 1H), 5.74 (d, 1H, J=14.0 Hz), 6.50 (d, 1H, J=7.7 Hz), 6.77 (dd, 1H, J=16.0, 5.0 Hz), 6.93–7.57 (m, 22H), 8.33 (d, 1H, J=7.7 Hz), 8.56 (d, 1H, J=7.7 Hz), 8.60 (s, 1H), 11.51 (s, 1H). Anal. (C$_{47}$H$_{45}$N$_4$O$_6$Cl.0.5 H$_2$O) C, H, N.

Preparation of Product—Ethyl-3-[N-(4-Methoxyindole-2-Carbonyl)-L-(4-Cl-Phe)-L-Gln]-E-Propenoate Using the procedure described in Example 32 for the preparation of compound 20, diethyl-[2-(CBZ-L-Leu-L-Phe-L-Gln)-E-vinyl] phosphonate, this compound was synthesized by deprotection of ethyl-3-[N-(4-methoxyindole-2-carbonyl)-L-(4-Cl-Phe)-L-(Tr-Gln)]-E-propenoate. The product was purified by flash silica gel chromatography eluting with 2–3% MeOH/CHCl$_3$ to give 0.16 g (73%) of an off-yellow solid: IR (KBr) 3420, 3289, 2930, 2838, 1722, 1663, 1622, 1541, 1261, 1184, 1101, 976, 754 cm$^{-1}$; $^1$H NMR (DMSO-d$_6$) δ 1.21 (t, 3H, J=7.0 Hz), 1.74 (m, 2H), 2.11 (t, 2H, J=8.0 Hz), 3.02 (m, 2H), 3.88 (s, 3H), 4.12 (q, 2H, J=7.0 Hz), 4.42 (m, 1H), 4.68 (m, 1H), 5.74 (dd, 1H, J=16.0, 1.5 Hz), 6.47 (d, 1H, J=5.0 Hz), 6.75 (bs, 1H), 6.76–6.81 (m, 2H), 6.96 (d, 1H, J=8.5 Hz), 7.07 (t, 1H, J=8.0 Hz), 7.24–7.38 (m, 5H), 8.33 (d, 1H, J=8.0Hz), 8.58 (d, 1H, J=8.5 Hz), 11.52 (s, 1H); HRMS calcd for C$_{28}$H$_{31}$N$_4$O$_6$Cl+ Cs 687.0986 (M+Cs), found 687.0976. Anal. (C$_{28}$H$_{31}$N$_4$O$_6$Cl) C, H, N.

Example 17—Preparation of Compound 27: Ethyl-3-[N-(4-Methoxyindole-2-Carbonyl)-L-(4-F-Phe)-L-Gln]-E-Propenoate Preparation of Intermediate BOC-L-(4-F-Phe)-L-(Tr-Glutaminol)

Using the procedure described in Example 16 for the preparation of BOC-L-(4-Cl-Phe)-L-(Tr-glutaminol), this compound was synthesized from BOC-L-4-F-Phe and L-(Tr-glutaminol) in 80% yield. White solid: IR (KBr) 3416, 3308, 3057, 2978, 2932, 1663, 1510, 1368, 1223, 1167, 1051, 752, 700 cm$^{-1}$; $^1$H NMR (DMSO-d$_6$) δ 1.28 (s, 9H), 1.44 (m, 1H), 1.68 (m, 1H), 2.25 (m, 2H), 2.70 (m, 1H), 2.90 (m, 1H), 3.25 (m, 2H), 3.63 (m, 1H), 4.10 (m, 1H), 4.67 (t, 1H, J=5.0 Hz), 7.04–7.28 (m, 19H), 6.85 (d, 1H, J=8.5 Hz), 7.61 (d, 1H, J=8.0 Hz), 8.48 (s, 1H). Anal. (C$_{38}$H$_{42}$N$_3$O$_5$F 0.75 H$_2$O) C, H, N.

Preparation of Intermediate L-(4-F-Phe)-L-(Tr-Glutaminol) Hydrochloride Salt

Using the procedure described in Example 16 for the preparation of L-(4-Cl-Phe)-L-(Tr-glutaminol) hydrochloride salt, this salt was synthesized from BOC-L-(4-F-Phe)-L-(Tr-glutaminol) in 79% yield. White crystalline solid: IR (KBr) 3245, 3057, 2361, 1668, 1510, 1447, 1223, 766, 700 cm$^{-1}$; $^1$H NMR (DMSO-d$_6$) δ 1.47 (m, 1H), 1.72 (m, 1H), 2.30 (m, 2H), 2.94–3.16 (m, 3H), 3.23 (m, 1H), 3.65 (bs, 2H), 3.95 (m, 1H), 7.09–7.32 (m, 19H), 8.28 (m, 4H), 8.54 (s, 1H). Anal. (C$_{33}$H$_{34}$N$_3$O$_3$F1.0HCl 1.0 H$_2$O) C, H, N.

Preparation of Intermediate N-(4-Methoxyindole-2-Carbonyl)-L-(4-F-Phe)-L-(Tr-Glutaminol)

Using the procedure described in Example 16 for the preparation of N-(4-methoxyindole-2-carbonyl)-L-(4-Cl-Phe)-L-(Tr-glutaminol), this intermediate was synthesized from 4-methoxyindole-2-carboxylic acid and L-(4-F-Phe)-L-(Tr-glutaminol) HCl salt, in 40% yield. White solid: IR (KBr) 3314, 3059,2938, 1956, 1888, 1653, 1510, 1361, 1255, 1097, 835, 756, 700 cm$^{-1}$; $^1$H NMR (DMSO-d$_6$) δ 1.58 (m, 1H), 1.81 (m, 1H), 2.28 (m, 2H), 3.02 (m, 2H), 3.23 (m, 2H), 3.67 (m, 1H), 3.87 (s, 3H), 4.69 (m, 2H), 6.49 (m, 1H, J=7.3 Hz), 6.94–7.39 (m, 22H), 7.84 (d, 1H, J=8.5 Hz), 8.48 (d, 1H, J=8.5 Hz), 8.53 (s, 1H), 11.49 (s, 1H). Anal. (C$_{43}$H$_{41}$N$_4$O$_5$F 1.0H$_2$O) C, H, N.

Preparation of Intermediate N-(4-Methoxyindole-2-Carbonyl)-L-(4-F-Phe)-L-(Tr-Glutaminal)

Using the oxidation procedure described in Example 16 for the preparation of N-(4-methoxyindole-2-carbonyl)-L-(4-Cl-Phe)-L-(Tr-glutaminal), this aldehyde was prepared in 80% yield from N-(4-methoxyindole-2-carbonyl)-L-(4-F-Phe)-L-(Tr-glutaminol). Glassy white solid: $^1$H NMR (DMSO-d$_6$) δ 1.72 (m, 2H), 2.37 (m, 2H), 3.03 (m, 1H), 3.17 (m, 1H), 3.87 (s, 3H), 4.09 (m, 1H), 4.74 (m, 1H), 6.49 (d, 1H, J=7.7 Hz), 6.94–7.41 (m, 22H), 8.58 (m, 2H), 8.63 (s, 1H), 9.32 (s, 1H), 11.49 (s, 1H).

Preparation of Intermediate Ethyl-3-[N-(4-Methoxyindole-2-Carbonyl)-L-(4-F-Phe)-L-(Tr-Gln)]-E-Propenoate Using the procedure described in Example 1 for the preparation of compound 12, ethyl-3-[CBZ-L-Leu-L-Phe-L-Met(sulfoxide)-E-propenoate, this vinyl ester was synthesized from N-(4-methoxyindole-2-carbonyl)-L-(4-F-Phe)-L-(Tr-glutaminal) and (carbethoxymethylene)triphenylphosphorane in 60% yield. White solid: IR (KBr) 3300, 3061, 2938, 1958, 1890, 1653, 1510, 1368, 1260, 1100, 1036, 835, 756, 700 cm$^{-1}$; $^1$H NMR (DMSO-d$_6$) δ 1.20 (t, 3H, J=7.0 Hz), 1.70 (m, 2H), 2.35 (m, 2H), 3.01 (m, 2H), 3.87 (s, 3H), 4.11 (q, 2H, J=7.0 Hz), 4.41 (m, 1H), 4.67 (m, 1H), 5.68 (d, 1H, J=16.0 Hz), 6.49 (d, 1H, J=7.7 Hz), 6.74 (dd, 1H, J=16.0, 5.0 Hz), 6.97–7.38 (m, 22H), 8.31 (d, 1H, J=8.5 Hz), 8.55 (d, 1H, J=8.5 Hz), 8.58 (s, 1H), 11.51 (s, 1H). Anal. (C$_{47}$H$_{45}$N$_4$O$_6$F 1.0H$_2$O) C, H,N.

Preparation of Product—Ethyl-3-[N-(4-Methoxyindole-2-Carbonyl)-L-(4-F-Phe)-L-Gln]-E-Propenoate Using the procedure described in Example 32 for the preparation of compound 20, diethyl-[2-(CBZ-L-Leu-L-Phe-L-Gln)-E-vinyl] phosphonate, this compound was synthesized by deprotection of ethyl-3-[N-(4-methoxyindole-2-carbonyl)-L-(4-F-Phe)-L-(Tr-Gln)]-E-propenoate in 50% yield: White crystalline solid: IR (KBr) 3422, 3293, 2932, 1719, 1665, 1620, 1541, 1510, 1369, 1261, 1182, 1101, 752 cm$^{-1}$; $^1$H NMR(DMSO-d$_6$) δ 1.21 (t, 3H, J=7.0 Hz), 1.73 (m, 2H), 2.10 (t, 2H, J=8.0 Hz), 3.02 (m, 2H), 3.88 (s, 3H), 4.13 (q, 2H, J=7.0 Hz), 4.43 (m, 1H), 4.67 (m, 1H), 5.67 (dd, 1H, J=16.0, 1.5 Hz), 6.49 (d, 1H, J=7.0 Hz), 6.75 (bs, 1H), 6.76 (dd, 1H, J=16.0, 5.5 Hz), 6.96 (d, 1H, J=8.5 Hz), 7.03–7.10 (m, 3H), 7.23 (bs, 1H), 7.31–7.39 (m, 3H), 8.31 (d, 1H, J=8.0 Hz), 8.57 (d, 1H, J=8.0 Hz), 11.51 (s, 1H); HRMS calcd for C$_{28}$H$_{31}$N$_4$O$_6$F+Cs 671.1282 (M+Cs), found 671.1288. Anal. (C$_{28}$H$_{31}$N$_4$O$_6$F) C, H, N.

Example 18—Preparation of Compound 28: Ethyl-3-[N-(4-Methoxyindole-2-Carbonyl)-L-(3-F-Phe)-L-Gln]-E-Propenoate Preparation of Intermediate BOC-L-(3-F-Phe)-L-(Tr-Glutaminol)

Using the procedure described in Example 16 for the preparation of BOC-L-(4-Cl-Phe)-L-(Tr-glutamninol), this compound was synthesized from BOC-L-3-F-Phe and L-(Tr-glutaminol) in 74% yield. White solid: IR (KBr) 3410, 3302, 3059, 3030, 2974, 2934, 1663, 1491, 1448, 1250, 1167,1051, 752, 700 cm$^{-1}$; $^1$H NMR (DMSO-d$_6$) δ 1.28 (s, 9H), 1.46 (m, 1H), 1.71 (m, 1H), 2.26 (m, 2H), 2.74 (m, 1H), 2.95 (m, 1H), 3.19 (m, 2H), 3.65 (m, 1H), 4.11 (m, 1H), 4.67 (t, 1H, J=5.0 Hz), 6.97–7.32 (m, 19H), 6.89 (d, 1H, J=8.5 Hz), 7.58 (d, 1H, J=8.5 Hz), 8.48 (s, 1H). Anal. (C$_{38}$H$_{42}$N$_3$O$_5$F 1.0 H$_2$O) C, H, N.

Preparation of Intermediate L-(3-F-Phe)-L-(Tr-Glutaminol) Hydrochloride Salt

Using the procedure described in Example 16 for the preparation of L-(4-Cl-Phe)-L-(Tr-glutaminol) hydrochloride salt, this salt was synthesized from BOC-L-(3-F-Phe)-L-(Tr-glutaminol) in 88% yield. White crystalline solid: IR (KBr) 3231, 3047, 1668, 1491, 1447, 1254, 1145, 1036, 752, 700 cm$^{-1}$; $^1$H NMR (DMSO-d$_6$) δ 1.45 (m, 1H), 1.72 (m, 1H), 2.30 (m, 2H), 2.96–3.11 (m, 3H), 3.25 (m, 1H), 3.70 (m, 1H), 4.03 (m, 1H), 7.06–7.38 (m, 19H), 8.30 (bs, 4H), 8.54 (s, 1H). Anal. (C$_{33}$H$_{34}$N$_3$O$_3$F 1.0 HCl 0.5 H$_2$O) C, H, N.

Preparation of Intermediate N-(4-Methoxyindole-2-Carbonyl)-L-(3-F-Phe)-L-(Tr-Glutaminol)

Using the procedure described in Example 16 for the preparation of N-(4-methoxyindole-2-carbonyl)-L-(4-Cl-Phe)-L-(Tr-glutaminol), this intermediate was synthesized from 4-methoxyindole-2-carboxylic acid and L-(3-F-Phe)-L-(Tr-glutaiminol) HCl salt, in 60% yield. White solid: IR (KBr) 3291, 3057, 2936, 1956, 1890, 1653, 1361, 1256, 1100, 754, 698 cm$^{-1}$; $^1$H NMR (DMSO-d6) δ 1.58 (m, 1H), 1.81 (m, 1H), 2.28 (m, 2H), 3.02 (m, 2H), 3.28 (m, 2H), 3.70 (m, 1H), 3.87 (s, 3H), 4.68 (m, 2H), 6.49 (m, 1H, J=7.7 Hz), 6.94–7.28 (m, 22H), 7.85 (d, 1H, J=8.5 Hz), 8.50 (d, 1H, J=8.5 Hz), 8.53 (s, 1H), 11.50 (s, 1H). Anal. (C$_{43}$H$_{41}$N$_4$O$_5$F 1.0H$_2$O) C, H, N.

Preparation of Intermediate N-(4-Methoxyindole-2-Carbonyl)-L-(3-F-Phe)-L-(Tr-Glutaminal)

Using the oxidation procedure described in Example 16 for the preparation of N-(4-methoxyindole-2-carbonyl)-L-(4-Cl-Phe)-L-(Tr-glutaminal), this aldehyde was prepared in 77% yield from N-(4-methoxyindole-2-carbonyl)-L-(3-F-Phe)-L-(Tr-glutaminol) and was used immediately. Glassy white solid: $^1$H NMR (DMSO-$d_6$) δ 1.68 (m, 2H), 2.37 (m, 2H), 3.04 (m, 1H), 3.18 (m, 1H), 3.87 (m, 3H), 4.05 (m, 1H), 4.81 (m, 1H), 6.49 (d, 1H, J=7.7 Hz), 6.94–7.30 (m, 22H), 8.60 (m, 2H), 8.62 (s, 1H), 9.33 (s, 1H), 11.48 (s, 1H).

Preparation of Intermediate Ethyl-3-[N-(4-Methoxyindole-2-Carbonyl)-L-(3-F-Phe)-L-(Tr-Gln)]-E-Propenoate Using the procedure described in Example 1 for the preparation of compound 12, ethyl-3-[CBZ-L-Leu-L-Phe-L-Met(sulfoxide)-E-propenoate, this vinyl ester was synthesized from N-(4-methoxyindole-2-carbonyl)-L-(3-F-Phe)-L-(Tr-glutaminal) and (carbethoxymethylene)triphenylphosphorane in 68% yield. White solid: IR (KBr) 3293, 3057, 2934, 1956, 1894, 1657, 1491, 1368, 1260, 1100, 1036, 978, 756, 700 cm$^{-1}$; $^1$H NMR (DMSO-$d_6$) δ 1.20 (t, 3H, J=7.0 Hz), 1.69 (m, 2H), 2.25 (m, 2H), 3.02 (m, 2H), 3.87 (s, 3H), 4.11 (q, 2H, J=7.0 Hz), 4.42 (m, 1H), 4.69 (m, 1H), 5.71 (d, 1H, J=16.0 Hz), 6.49 (d, 1H, J=8.0 Hz), 6.75 (dd, 1H, J=16.0, 5.0 Hz), 6.91–7.29 (m, 22H), 8.32 (d, 1H, J=8.0 Hz), 8.56 (d, 1H, J=8.0 Hz), 8.59 (s, 1H), 11.51 (s, 1H). Anal. ($C_{47}H_{45}N_4O_6F$ 0.5 $H_2O$) C, H, N.

Preparation of Product—Ethyl-3-[N-(4-Methoxyindole-2-Carbonyl)-L-(3-F-Phe)-L-Gln]-E-Propenoate Using the procedure described in Example 32 for the preparation of compound 20, diethyl-[2-(CBZ-L-Leu-L-Phe-L-Gln)-E-vinyl]phosphonate, this compound was synthesized by deprotection of ethyl-3-[N-(4-methoxyindole-2-carbonyl)-L-(3-F-Phe)-L-(Tr-Gln)]-E-propenoate in 52% yield. White solid: IR (KBr) 3283, 2932, 1663, 1539, 1370, 1256, 1188, 1098, 1036, 978, 752 cm$^{-1}$; $^1$H NMR (DMSO-$d_6$) δ 1.21 (t, 3H, J=7.0 Hz), 1.73 (m,2H), 2.11 (t, 2H, J=7.0 Hz), 3.07 (m, 2H), 3.88 (s, 3H), 4.11 (q, 2H, J=7.0 Hz), 4.49 (m, 1H), 4.75 (m, 1H), 5.72 (dd, 1H, J=16.0, 1.5 Hz), 6.49 (d, 1H, J=7.7 Hz), 6.80 (m, 2H), 6.98–7.31 (m, 8H), 8.32 (d, 1H, J=8.0 Hz), 8.58 (d, 1H, J=8.0 Hz), 11.52 (s, 1H); HRMS calcd for $C_{28}H_{31}N_4O_6F$ 539.2306 (M+H), found 539.2317. Anal. ($C_{28}H_{31}N_4O_6F$) C, H, N.

Example 19—Preparation of Compound 30: Ethyl-3-(CBZ-L-Phe-L-Gln)-E-Propenoate

Preparation of Intermediate Ethyl-3-[CBZ-L-Phe-L-(Tr-Gln)]-E-Propenoate

Ethyl-3-[BOC-L-(Tr-Gln)]-E-propenoate (0.60 g, 1.1 mmol), prepared as in Example 3, was deprotected and coupled with CBZ-L-Phe (0.31 g, 1.04 mmol) using the procedure described in Example 28 for the preparation of ethyl-2-fluoro-3-[CBZ-L-Leu-L-Phe-L-(Tr-Gln)]-E-propenoate to provide ethyl-3-[CBZ-L-Phe-L-(Tr-Gln)]-E-propenoate (0.400 g, 53%) as a white foam: IR (thin film) 3298, 1651 cm$^{-1}$; $^1$H NMR (CDCl$_3$) δ 1.21 (t, 3H, J=7.2 Hz), 1.65–1.75 (m, 1H), 1.90–1.93 (m, 1H), 2.29 (s, br, 2H), 2.98–3.00 (m, 2H), 4.12 (q, 2H, J=7.2 Hz), 4.25–4.30 (m, 1H), 4.93 (d, 1H, J=12.3 Hz), 4.50 (s, br, 1H), 5.01 (d, 1H, J=12.3 Hz), 5.23 (d, 1H, J=6.2 Hz), 5.63 (d, 1H, J=15.6 Hz), 6.39 (d, 1H, J=7.2 Hz), 6.61 (dd, 1H, J=15.6, 5.6 Hz), 6.79 (s, 1H), 7.11–7.34 (m, 25H); Anal. ($C_{45}H_{45}N_3O_6$) C, H, N.

Preparation of Product—Ethyl-3-(CBZ-L-Phe-L-Gln)-E-Propenoate

Using the procedure described in Example 4 for the preparation of compound 3, Ethyl-3-[CBZ-L-Phe-L-(Tr-Gln)]-E-propenoate (0.40 g, 0.58 mmol) was deprotected to provide ethyl-3-(CBZ-L-Phe-L-Gln)-E-propenoate (0.15 g, 78%) as a white solid: mp=184°–186° C.; IR (thin film) 3287, 1637, 1533 cm$^{-1}$; $^1$H NMR (DMSO-$d_6$) δ 1.21 (t, 3H, J=7.2 Hz), 1.64–1.80 (m, 2H), 2.08 (t, 2H, J=7.6 Hz), 2.73–2.80 (m, 1H), 2.94 (dd, 1H, J=13.7, 5.3 Hz), 4.11 (q, 2H, J=7.2 Hz), 4.20–4.26 (m, 1H), 4.28–4.39 (m, 1H), 4.95 (s, 2H), 5.69 (d, 1H, J=15.9 Hz), 6.70 (d, 1H, J=5.3 Hz), 6.75–6.77 (m, 2H), 7.17–7.35 (m, 11H), 7.53 (d, 1H, J=8.4 Hz), 8.20 (d, 1H, J=8.1 Hz); Anal. ($C_{26}H_{31}N_3O_6$) C, H, N.

Example 20—Preparation of Compound 31: Ethyl-3-[N-(Propylsulfonyl)-L-Phe-L-Gln]-E-Propenoate

Preparation of Intermediate Ethyl-3-[BOC-L-Phe-L-(Tr-Gln)]-E-Propenoate

Ethyl-3-[BOC-L-(Tr-Gln)]-E-propenoate (2.26 g, 4.16 mmol), prepared as in Example 3, was dissolved in 1,4-dioxane (15 mL). A solution of HCl in 1,4-dioxane (4.0M, 15 mL) was added dropwise. The reaction solution was stirred at room temperature for 2 hours, then poured into a solution of aqueous NaOH (1M, 80 mL) in saturated aqueous NaHCO$_3$ (120 mL). The resulting mixture was extracted with CH$_2$Cl$_2$ (2×200 mL). The combined organic phases were dried over NA$_2$SO$_4$ and concentrated to give the free amine intermediate as a slightly yellow solid, which was used without further purification. This crude amine, BOC-L-Phe (1.10 g, 4.15 mmol), and 1-hydroxybenzotriazole hydrate (0.843 g, 6.24 mmol) were stirred in dry CH$_2$Cl$_2$ (35 mL) under argon at room temperature. 4-Methylmorpholine (1.83 mL, 16.6 mmol) and 1-(3-dimethylaminopropyl)-3-ethylcarbodiimide hydrochloride (1.20 g, 6.26 mmol) were added sequentially. After stirring for 3.5 hours, the reaction mixture was poured into water (100 mL), and the mixture was extracted with CH$_2$Cl$_2$ (2×100 mL). The combined organic phases were dried over NA$_2$SO$_4$ and concentrated. The residue was purified by column chromatography (33% acetone in hexanes) to give the product (1.94 g, 68%) as a white foam: IR (thin film) 3413, 3310, 1708, 1660 cm$^{-1}$; $^1$H NMR (CDCl$_3$) δ 1.30 (t, 3H, J=7.2 Hz), 1.39 (s, 9H), 1.64–1.77 (m, 1H), 1.88–2.00 (m, 1H), 2.25–2.31 (m, 2H), 2.94–3.07 (m, 2H), 4.18 (q, 2H, J=7.2 Hz), 4.49–4.59 (m, 1H), 4.95 (bs, 1H), 5.66 (d, 1H, J=15.9 Hz), 6.29 (m, 1H), 6.64 (dd, 1H, J=15.9, 5.3 Hz), 6.81 (bs, 1H), 7.14–7.34 (m, 21H); Anal. ($C_{42}H_{47}N_3O_6$) C, H, N.

Preparation of Intermediate Ethyl-3-[L-Phe-L-(Tr-Gln)]-E-Propenoate

Ethyl-3-[BOC-L-Phe-L-(Tr-Gln)]-E-propenoate (0.300 g, 0.435 mmol) was dissolved in 1,4-dioxane (2 mL). A solution of HCl in 1,4-dioxane (4.0M, 2 mL) was added dropwise. The reaction solution was stirred at room temperature for 2.5 hours, then poured into a solution of aqueous NaOH (1M, 10 mL) in saturated aqueous NAHCO$_3$ (20 mL). The resulting mixture was extracted with CH$_2$Cl$_2$ (3×40 mL). The combined organic phases were dried over Na$_2$SO$_4$ and concentrated to give the product as a foam (0.257 g, quantitative) which was used without further purification.

Preparation of Intermediate Ethyl-3-[N-(Propylsulfonyl)-L-Phe-L-(Tr-Gln)]-E-Propenoate Ethyl-3-[L-Phe-L-(Tr-Gln)]-E-propenoate was dissolved in dry CH$_2$Cl$_2$ (7 mL) under argon and cooled to 0° C. NEt$_3$ (0.067 mL, 0.48 mmol) and 1-propanesulfonyl chloride (0.054 mL, 0.48 mmol) were added sequentially. After stirring for 1 hour, the reaction mixture was allowed to warm to room temperature. More NEt$_3$ (0.100 mL, 0.714 mmol) and 1-propanesulfonyl chloride (0.086 mL, 0.76 mmol) were added. After 1.5 hours more, the solvent was evaporated and the residue was purified by column chromatography (50% EtOAc in hexanes) to give the product as a foam (0.121 g, 40%): IR (thin film) 3292, 1713, 1652, 1312, 1144 cm$^{-1}$; $^1$H NMR (CDCl$_3$) δ 0.80 (t, 3H, J=7.5 Hz), 1.28 (t, 3H, J=7.2 Hz), 1.34–1.58 (m, 2H), 1.67–1.81 (m, 1H), 1.92–2.04 (m, 1H), 2.32–2.56 (m, 4H, 2.79 (dd, 1H, J=13.9, 8.9 Hz), 3.05 (dd, 1H, J=13.9, 5.5 Hz), 3.96–4.05 (m, 1H), 4.17 (q, 2H, J=7.2 Hz), 4.49–4.59 (m, 1H), 5.14 (d, 1H, J=8.7 Hz), 5.75 (dd, 1H, J=15.9, 1.7 Hz), 6.72 (dd, 1H,J= 15.9, 5.3 Hz), 6.94 (s, 1H), 7.02 (d, 1H,J=8.1 Hz), 7.12–7.33 (m, 20H); HRMS (M+Cs) calcd for C$_{40}$H$_{45}$N$_3$O$_6$S 828.2083, found 828.2063.

Preparation of Product—Ethyl-3-[N-(Propylsulfonyl)-L-Phe-L-Gln]-E-Propenoate

Ethyl-3-[N-propylsulfonyl)-L-Phe-L-(Tr-Gln)]-E-propenoate (0.100 g, 0.143 mmol) was dissolved in CH$_2$Cl$_2$/TFA 1:1 (4 mL) under argon. The bright yellow solution was stirred at room temperature for 30 minutes. CCl$_4$ (4 mL) was added and the solution was concentrated to dryness. The residue was triturated with Et$_2$O (3 mL) to give a white precipitate which was collected by filtration and washed with Et$_2$O (2×2 mL) to give the product (0.048 g, 74%): mp=161–162° C; IR (KBr) 3284, 3213, 1708, 1666, 1543, 1314, 1138 cm$^{-1}$; $^1$H NMR (acetone-d$_6$) δ 0.83 (t, 3H, J=7.5 Hz), 1.25 (t, 3H, J=7.2 Hz), 1.39–1.62 (m, 2H), 1.73–2.02 (m, 2H), 2.23–2.30 (m, 2H), 2.54–2.72 (m, 2H), 2.92 (dd, 1H, J=13.5, 8.9 Hz), 3.15 (dd, 1H, J=13.5, 6.1 Hz), 4.14 (q, 2H, J=7.2 Hz), 4.12–4.21 (m, 1H), 4.53–4.63 (m, 1H), 5.79 (dd, 1H, J=15.7, 1.7 Hz), 6.18 (bs, 1H), 6.30 (d, 1H, J=8.7 Hz), 6.78 (dd, 1H, J=15.7, 5.4 Hz), 6.75 (bs, 1H), 7.19–7.35 (m, 5H), 7.59 (d, 1H, J=8.1 Hz); Anal. (C$_{21}$H$_{31}$N$_3$O$_6$S) C, H, N.

Example 21—Preparation of Compound 32: Ethyl-3-[N-(Benzylsulfonyl)-L-Phe-L-Gln]-E-Propenoate Preparation of Intermediate Ethyl-3-[N-(Benzylsulfonyl)-L-Phe-L-(Tr-Gln)]-E-Propenoate Ethyl-3-[L-Phe-L-(Tr-Gln)]-E-propenoate (0.250 g, 0.424 mmol) was dissolved in dry CH$_2$Cl$_2$ (7 mL) under argon and cooled to 0° C. Triethylamine (0.118 mL, 0.847 mmol) and α-toluenesulfonyl chloride (0.162 g, 0.850 mmol) were added sequentially. After stirring for 45 min, the solvent was evaporated and the residue was purified by column chromatography (47% EtOAc in hexanes) to give the product as a white foam (0.154g,49%): IR (thin film) 3296, 1708, 1663, 1316, 1154cm$^{-1}$; $^1$H NMR(CDCl$_3$) δ 1.29 (t, 3H, J=7.2 Hz), 1.59–1.72 (m, 1H), 1.91–2.03 (m, 1H), 2.31–2.37 (m, 2H), 2.82 (dd, 1H, J=13.7, 7.2 Hz), 2.92 (dd, 1H, J=13.7, 7.2 Hz), 3.78–3.87 (m, 1H), 3.90 (d, 1H, J=13.9 Hz), 3.97 (d, 1H, J=13.9 Hz), 4.17 (q, 2H, J=7.2 Hz), 4.44–4.54 (m, 1H), 4.96 (d, 1H, J=7.8 Hz), 5.59 (dd, 1H, J=15.7, 1.7 Hz), 6.51 (d, 1H, J=7.5 Hz), 6.63 (dd, 1H, J=15.7, 5.1 Hz), 6.91 (s, 1H), 7.03–7.07 (m, 2H), 7.17–7.40 (m, 23H); Anal. (C$_{44}$H$_{45}$N$_3$O$_6$S) C, H, N.

Preparation of Product—Ethyl-3-[N-(Benzylsulfonyl)-L-Phe-L-Gln]-E-Propenoate

This compound was prepared in 72% yield from ethyl-3-[N-(benzylsulfonyl)-L-Phe-L-(Tr-Gln)]-E-propenoate using the procedure described in Example 20 for the preparation of ethyl-3-[N-(propylsulfonyl)-L-Phe-L-Gln]-E-propenoate: mp=165°–167° C.; IR (KBr) 3330, 3201, 1713, 1660, 1314 cm$^{-1}$; $^1$H NMR (acetone-d$_6$) δ 1.25 (t, 3H, J=7.2 Hz), 1.72–1.99 (m, 2H), 2.22–2.30 (m, 2H), 2.96 (dd, 1H, J=13.5, 7.3 Hz), 3.10 (dd, 1H, J=13.5, 7.0 Hz), 4.03–4.22 (m, 5H), 4.51–4.62 (m, 1H), 5.72 (dd, 1H, J=15.6, 1.6 Hz), 6.18 (bs, 1H), 6.33 (d, 1H, J=8.4 Hz), 6.72 (bs, 1H), 6.73 (dd, 1H, J=15.6, 5.4 Hz), 7.19–7.35 (m, 10H), 7.55 (d, 1H, J=8.1 Hz); Anal. (C$_{25}$H$_{31}$N$_3$O$_6$S) C, H, N.

Example 22—Preparation of Compound 33: Ethyl-3-[N-(Ethylsulfonyl)-L-Phe-L-Gln]-E-Propenoate Preparation of Intermediate Ethyl-3-[N-(Ethylsulfonyl)-L-Phe-L-(Tr-Gln)]-E-Propenoate This compound was prepared in 46% yield from ethyl-3-[L-Phe-L-(Tr-Gln)]-E-propenoate and ethanesulfonyl chloride using the procedure described in Example 21 for the preparation of ethyl-3-[N-(benzylsulfonyl)-L-Phe-L-(Tr-Gln)]-E-propenoate. The material was purified by flash column chromatography (50% EtOAc in hexanes): IR (thin film) 3295, 1713, 1666, 1314, 1143 cm$^{-1}$; $^1$H NMR (CDCl$_3$) δ 1.04 (t, 3H, J=7.5 Hz), 1.29 (t, 3H, J=7.2 Hz), 1.68–1.81 (m, 1H), 1.95–2.06 (m, 1H), 2.33–2.43 (m, 2H), 2.45–2.58 (m, 1H), 2.59–2.72 (m, 1H), 2.86 (dd, 1H, J=13.7, 8.4 Hz), 3.09 (dd, 1H, J=13.7, 5.6 Hz), 3.96–4.04 (m, 1H), 4.19 (q, 2H, J=7.2 Hz), 4.50–4.59 (m, 1H), 4.91 (bs, 1H), 5.72 (dd, 1H, J=15.9, 1.9 Hz), 6.71 (dd, 1H, J=15.9, 5.3 Hz), 6.87 (s, 1H), 6.96 (d, 1H, J=7.8 Hz), 7.13–7.34 (m, 20H); Anal. (C$_{39}$H$_{43}$N$_3$O$_6$S) C, H, N.

Preparation of Product Ethyl-3-[N-(Ethylsulfonyl)-L-Phe-L-Gln]-E-Propenoate

This compound was prepared in 82% yield from ethyl-3-[N-(ethylsulfonyl)-L-Phe-L-(Tr-Gln)]-E-propenoate using the procedure described in Example 20 for the preparation of compound 31, ethyl-3-[N-(propylsulfonyl)-L-Phe-L-Gln]-E-propenoate: mp=150°–151° C.; IR (KBr) 3284, 3225, 1713, 1655, 1314, 1138 cm$^{-1}$; $^1$H NMR (acetone-d$_6$) δ1.05 (t, 3H, J=7.3 Hz), 1.26 (t, 3H, J=7.2 Hz), 1.74–1.87 (m, 1H), 1.90–2.02 (m, 1H), 2.22–2.33 (m, 2H), 2.62–2.84 (m, 2H), 2.95 (dd, 1H, J=13.7, 8.7 Hz), 3.15 (dd, 1H, J=13.7, 6.2 Hz), 4.16 (q, 2H, J=7.2 Hz), 4.13–4.23 (m, 1H), 4.54–4.64 (m, 1H), 5.78 (dd, 1H, J=15.9, 1.6 Hz), 6.22 (bs, 1H), 6.34 (d, 1H, J=9.0 Hz), 6.78 (bs, 1H), 6.78 (dd, 1H, J=15.9, 5.6 Hz), 7.21–7.35 (m, 5H), 7.61 (d, 1H, J=8.1 Hz); Anal. (C$_{20}$H$_{29}$N$_3$O$_6$S) C, H, N.

Example 23—Preparation of Compound 34: Ethyl-3-[N-(Phenylsulfonyl)-L-Phe-L-Gln]-E-Propenoate Preparation of Intermediate Ethyl-3-[N-(Phenylsulfonyl)-L-Phe-L-(Tr-Gln)]-E-Propenoate This compound was prepared in 55% yield from ethyl-3-[L-Phe-L-(Tr-Gln)]-E-propenoate and benzenesulfonyl chloride using the procedure described in Example 21 for the preparation of ethyl-3-[N-(benzylsulfonyl)-L-Phe-L-(Tr-Gln)]-E-propenoate. The material was purified by flash column chromatography (47% EtOAc in hexanes): IR (thin film) 3295, 1713, 1660, 1308, 1161 cm$^{-1}$; $^1$H NMR (CDCl$_3$) δ 1.29 (t, 3H, J=7.2 Hz), 1.59–1.72 (m, 1H), 1.83–1.95 (m, 1H), 2.12–2.33 (m, 2H), 2.82–2.94 (m, 2H), 3.82–3.91 (m, 1H), 4.18 (q, 2H, J=7.2 Hz), 4.31–4.41 (m, 1H), 5.05 (d, 1H, J=7.8 Hz), 5.67 (dd, 1H, J=15.7, 1.7 Hz), 6.60 (dd, 1H, J=15.7, 5.4 Hz), 6.72 (d, 1H, J=7.8 Hz), 6.79 (s, 1H), 6.91–6.97 (m, 2H), 7.13–7.40 (m, 20H), 7.48–7.54 (m, 1H), 7.58–7.62 (m, 2H); Anal. ($C_{43}H_{43}N_3O_6S$) C, H, N.

Preparation of Product Ethyl-3-[N-(Phenylsulfonyl)-L-Phe-L-Gln]-E-Propenoate This compound was prepared in 83% yield from ethyl-3-[N-(phenylsulfonyl)-L-Phe-L-(Tr-Gln)]-E-propenoate using the procedure described in Example 20 for the preparation of ethyl-3-[N-(propylsulfonyl)-L-Phe-L-Gln]-E-propenoate: mp=173°–175° C.; IR (KBr) 3284, 3201, 1708, 1660, 1314, 1161 cm$^{-1}$; $^1$H NMR (acetone-d$_6$) δ 1.24 (t, 3H, J=7.2 Hz), 1.59–1.85 (m, 2H), 2.07–2.19 (m, 2H), 2.85 (dd, 1H, J=13.5, 7.6 Hz), 2.99 (dd, 1H, J=13.5, 6.7 Hz), 4.03–4.16 (m, 1H), 4.13 (q, 2H, J=7.2 Hz), 4.30–4.40 (m, 1H), 5.65 (dd, 1H, J=15.7, 1.6 Hz), 6.21 (bs, 1H), 6.63 (dd, 1H, J=15.7, 5.6 Hz), 6.74 (bs, 1H), 6.75 (d, 1H, J=8.7 Hz), 7.07–7.29 (m, 5H), 7.42–7.61 (m, 4H), 7.67–7.80 (m, 2H); Anal. ($C_{24}H_{29}N_3O_6S$) C, H, N.

Example 24—Preparation of Compound 35: Ethyl-3-[CBZ-L-Leu-L-(4-F-Phe)-L-Gln]-E-Propenoate

Preparation of Intermediate CBZ-L-Leu-L-(4-F-Phe)-L-(Tr-Glutaminol)

Using the procedure described in Example 16 for the preparation of N-(4-methoxyindole-2-carbonyl)-L-(4-Cl-Phe)-L-(Tr-glutaminol), this intermediate was synthesized from CBZ-L-Leu and the free base of L-(4-F-Phe)-L-(Tr-glutaminol)-HCl, in 68% yield as a white solid: IR (KBr) 3304, 3063, 2955, 1651, 1510, 1223, 1038,752, 698 cm$^{-1}$; $^1$H NMR (DMSO-d$_6$) δ 0.79 (m, 6H), 1.34 (m, 2H), 1.46 (m, 2H), 1.72 (m, 1H), 2.25 (m, 2H), 2.80 (m, 1H), 2.99 (m, 1H), 3.16 (m, 1H), 3.26 (m, 1H), 3.64 (m, 1H), 3.95 (m, 1H), 4.47 (m, 1H), 4.66 (t, 1H, J=5.5 Hz), 4.97 (d, 1H, J=12.5 Hz), 5.02 (d, 1H, J=12.5 Hz), 7.01 (t, 2H, J=8.8 Hz), 7.15–7.37 (m, 22H), 7.42 (d, 1H, J=7.7 Hz), 7.69 (d, 1H, J=8.5 Hz), 7.87 (d, 1H, J=8 Hz), 8.54 (s, 1H).

Preparation of Intermediate CBZ-L-Leu-L-(4-F-Phe)-L-(Tr-Glutaminal)

Using the oxidation procedure described in Example 16 for the preparation of N-(4-methoxyindole-2-carbonyl)-L-(4-Cl-Phe)-L-(Tr-glutaminal), this aldehyde was prepared from CBZ-L-Leu-L-(4-F-Phe)-L-(Tr-glutaminol) in 92% yield as a white glassy solid, which was used immediately without furrter purification.

Preparation of Intermediate Ethyl-3-[CBZ-L-Leu-L-(4-F-Phe)-L-(Tr-Gln)]-E-Propenoate Using the procedure described in Example 1 for the preparation of compound 12, ethyl-3-[CBZ-L-Leu-L-Phe-L-Met(sulfoxide)-E-propenoate, (carbethoxymethylene)triphenyl-phosphorane and CBZ-L-Leu-L-(4-F-Phe)-L-(Tr-glutaminal) were stirred together in THF giving 0.37 g of the crude material contaminated with triphenylphosphine oxide which was subsequently used without further purification. A small amount (27 mg) was purified by flash column chromatography (MeOH/CHCl$_3$) for spectral analysis: $^1$H NMR (DMSO-d$_6$) δ 0.79 (t, 6H, J=7.0 Hz), 1.20 (t, 3H, J=7.0 Hz), 1.23–1.82 (m, 5H), 2.25 (m, 2H), 2.85 (m, 1H), 2.95 (m, 1H), 3.96 (m, 1H), 4.10 (q, 2H, J=7.0 Hz), 4.34 (m, 1H), 4.48 (m, 1H), 4.96 (d, 1H, J=13.0 Hz), 5.02 (d, 1H, J=13.0 Hz), 5.57 (d, 1H, J=15.0 Hz), 6.67 (dd, 1H, J=15.0, 5.5 Hz), 7.01 (t, 2H, J=9.0 Hz), 7.13–7.32 (m, 22H), 7.39 (d, 1H, J=8.0 Hz), 7.99 (d, 1H, J=8.0 Hz), 8.07 (d, 1H, J=8.0 Hz), 8.58 (s, 1H).

Preparation of Product Ethyl-3-[CBZ-L-Leu-L-(4-F-Phe)-L-Gln)-E-Propenoate

This compound was prepared by the deprotection of ethyl-3-[CBZ-L-Leu-L-(4-F-Phe)-L-(Tr-Gln)]-E-propenoate using the procedure describe in Example 32 for the preparation of compound 20, but in the absence of triisopropylsilane. The product was isolated as a white solid in 58% yield (2 steps from CBZ-L-Leu-L-(4-F-Phe)-L-(Tr-glutaminal). IR (KBr) 3439, 3293, 3067, 2961, 1692, 1643, 1539, 1227, 1045, 984, 835, 698 cm$^{-1}$; $^1$H NMR (DMSO-d$_6$) δ 0.80 (m, 6H), 1.21 (t, 3H, J=7.0 Hz), 1.26 (m, 2H), 1.45 (m, 1H), 1.71 (m, 2H), 2.06 (t, 2H, J=7.5 Hz), 2.81 (m, 1H), 2.94 (m, 1H), 3.97 (m, 1H), 4.10 (q, 2H, J=7.0 Hz), 4.37 (m, 1H), 4.47 (m, 1H), 4.98 (d, 1H, J=12.5 Hz), 5.04 (d, 1H, J=12.5 Hz), 5.59 (d, 1H, J=16.0 Hz), 6.68 (dd, 1H, J=16.0, 5.5 Hz), 6.76 (bs, 1H), 7.01 (t, 2H, J=8.8 Hz), 7.19–7.34 (m, 8H), 7.43 (d, 1H, J=8.0 Hz), 8.05 (m, 2H); HRMS calcd for $C_{32}H_{41}N_4O_7F$+Cs 745.2014 (M+Cs), found 745.2040 Anal. ($C_{32}H_{41}N_4O_7F$ 1.25 H$_2$O) C, H, N.

Example 25—Preparation of Compound 15: 3-(CBZ-L-Leu-L-Phe-L-Gln)-E-Propenoic Acid

Preparation of Intermediate tert-Butyl-3-[CBZ-L-Phe-L-(Tr-Gln)]-E-Propenoate To 0.20 g (0.261 mmol) of CBZ-L-Leu-L-Phe-L-(Tr-glutaminal) was added 3 mL of dry THF. To this stirred solution was added (tert-butoxycarbonylmethylene) triphenylphosphorane (0.098 g, 0.261 mmol). The reaction mixture was stirred at room temperature overnight. The solvent was removed in vacuo, and the residue was subjected to column chromatography with hexanes:EtOAc (6.5:3.5). The product was obtained in 69% yield as a white foam.

Preparation of Product 3-(CBZ-L-Leu-L-Phe-L-Gln)-E-Propenoic Acid tert-Butyl-3-[CBZ-L-Leu-L-Phe-L-(Tr-Gln)]-E-propenoate (0.157 g, 0.181 mmol) was dissolved in an excess of TFA, and 10 drops of water were added. The mixture was stirred at room temperature for 1 hour and evaporated to dryness. CCl$_4$ was added and the mixture was concentrated in vacuo to azeotrope any remaining water. The residue was slurried in Et$_2$O and the resulting white solid was filtered and dried to give 0.053 g (52%). mp=219°–220° C. (dec); IR (thin film); 2949, 1690, 3269, 1639 cm$^{-1}$; $^1$H NMR (DMSO-d$_6$) δ 0.80 (dd, 6H, J=9.0, 6.5 Hz), 1.23–1.38 (m, 2H), 1.41–1.56 (m, 1H), 1.61–1.79 (m, 2H), 2.0–2.1 (m, 2H), 2.84 (dd, 1H, J=13.6, 8.9 Hz), 2.99 (dd, 1H, J=13.5, 5.1 Hz), 3.91 (m, 1H), 4.32–4.41 (m, 1H), 4.44–4.54 (m, 1H), 5.01 (dd, 1H, J=12.5, 12.1 Hz), 5.64 (d, 1H, J=15.6 Hz), 6.64 (dd, 1H, J=15.6, 5.6 Hz), 6.76 (bs, 1H), 7.14–7.38 (m, 11H), 7.43 (d, 1H, J=7.5 Hz), 7.97 (d, 1H, J=8.1 Hz), 8.04 (d, 1H, J=8.1 Hz), 12.28 (bs, 1H).

Example 26—Preparation of Compound 14: 3-(CBZ-L-Leu-L-Phe-DL-Gln)-E-Propenonitrile

Preparation of Intermediate 3-[BOC-DL-(Tr-Gln)]-E-Propenonitrile

A solution of diethyl cyanomethylphosphonate (0.202 mL, 1.25 mmol) in dry THF (25 mL) was cooled to −78° C. After dropwise addition of a solution of sodium bis (trimethylsilyl)amide in THF (1.0M, 1.25 mL), the reaction solution was stirred for 20 minutes. A solution of BOC-L-(Tr-glutaminal) (0.590 g, 1.25 mmol) in dry THF (5 mL) was added dropwise, and, after stirring 50 minutes more, saturated aqueous NH₄CL (4 mL) was added. The reaction mixture was allowed to warm to room temperature, and the THF was evaporated. Water (10 mL) was added to the residue, which was then extracted with CH$_2$Cl$_2$ (3×30 mL). The combined organic phases were dried over NA$_2$SO$_4$ and concentrated. The residue was purified by flash column chromatography (38% EtOAc in hexanes) to give the product (0.407 g, 66%) as a white foam: IR (thin film) 3321, 2225, 1694, 1515 cm$^{-1}$; $^1$H NMR (CDCl$_3$) δ 1.42 (s, 9H), 1.67–1.81 (m, 1H), 1.82–1.97 (m, 1H), 2.34–2.42 (m, 2H), 4.23 (bs, 1H), 4.97–5.06 (m, 1H), 5.39 (dd, 1H, J=16.3, 1.6 Hz), 6.56 (dd, 1H, J=16.3, 5.3 Hz), 6.77 (bs, 1H), 7.15–7.33 (m, 15H).

Preparation of Intermediate (CBZ-L-Leu-L-Phe)$_2$O

CBZ-L-Leu-L-Phe (1.5 g, 3.6 mmol) was dissolved in dry CH$_2$Cl$_2$ (25 mL) at room temperature under argon. 1-(3-Dimethylaminopropyl)-3-ethylcarbodiimide hydrochloride (0.697 g, 3.64 mmol) was added. The reaction solution was stirred for 20 hours, then diluted with CH$_2$Cl$_2$ (20 mL) and washed with water (2×20 mL). The combined organic phases were dried over NA$_2$SO$_4$ and concentrated to give the anhydride product as a white semi-solid residue (1.18 g, 80%), which was used immediately in the next step of the reaction without further purification or analysis.

Preparation of Intermediate 3-[CBZ-L-Leu-L-Phe-DL-(Tr-Gln)]-E-Propenonitrile

3-[BOC-DL-(Tr-Gln)]-E-Propenonitrile (0.349 g, 0.704 mmol) was stirred in 2-propanol (9 mL) at room temperature. Perchloric acid (60%, 3.2 mL) was added dropwise. The resulting solution was stirred for 1 hour under an argon balloon, diluted with CH$_2$Cl$_2$ (100 mL), and poured into a solution of aqueous 1N NaOH/aqueous saturated NAHCO$_3$ (40 mL:70 mL). The phases were mixed and separated. The aqueous phase was washed again with CH$_2$Cl$_2$ (2×100 mL). The combined organic phases were dried over Na$_2$SO$_4$ and then concentrated to give the crude amine as a white solid (0.314 g), which was used without further purification. This amine was dissolved in acetone (15 mL) and added to the crude (CBZ-L-Leu-L-Phe)$_2$O (1.18 g, 1.46 mmol) in a round bottom flask. The reaction solution was stirred at room temperature under an argon balloon. After stirring for 4.5 hours, the solvent was evaporated, and the residue was purified by flash column chromatography (30% EtOAc in hexanes, then 30% acetone in hexanes) to give the product (0.448 g, 81%) as a white foam: IR (thin film) 3298, 2226, 1672, 1519 cm$^{-1}$; Anal. (C$_{49}$H$_{51}$N$_5$O$_5$) C, H, N.

Preparation of Product 3-(CBZ-L-Leu-L-Phe-DL-Gln)-E-Propenonitrile

3-[CBZ-L-Leu-L-Phe-DL-(Tr-Gln)]-E-Propenonitrile (0.381 g, 0.482 mmol) was dissolved in 1:1 CH$_2$Cl$_2$/TFA (14 mL) under argon, giving a bright yellow solution. After stirring for 30 minutes, the solvent was evaporated. CCl$_4$ (15 mL) was added, and the resulting solution was concentrated (3 times). The residue was triturated with Et$_2$O (8 mL) to give a white solid, which was collected by filtration. This solid was then stirred in acetonitrile (4 mL), collected by filtration, washed with acetonitrile (4 mL), washed with Et$_2$O (6 mL), and dried in vacuo (0.099 g, 38%): mp=178°–184° C.; IR (KBr) 3401, 3284, 2225, 1689, 1650, 1537 cm$^{-1}$; $^1$H NMR (DMSO-d$_6$) (2 diastereomers) δ 0.69 (d, 3H, J=5.3 Hz), 0.73 (d, 3H, J=5.1 Hz), 0.80 (d, 3 H, J=6.6 Hz), 0.83 (d, 3H, J=6.6 Hz), 1.10–1.20 (m, 3H), 1.26–1.40 (m, 2H), 1.46–1.85 (m, 5H), 1.99–2.09 (m, 4H), 2.76 (dd, 1H, J=13.4, 10.9 Hz), 2.83–2.99 (m, 2H), 3.10 (dd, 1H, J=13.6, 4.3 Hz), 3.85–3.93 (m, 1H), 3.96–4.05 (m, 1H), 4.28–4.52 (m, 4H), 4.90–5.07 (m, 5H), 5.71 (d, 1H, J=16.4 Hz), 6.68 (dd, 1H, J=16.4, 4.6 Hz), 6.78 (s, 2H), 6.88 (dd, 1H, J=16.3, 4.7 Hz), 7.16–7.37 (m, 22H), 7.41–7.47 (m, 2H), 7.96 (d, 1H, J=8.2 Hz), 8.03–8.10 (m, 2H), 8.38 (d, 1H, J=8.2 Hz); Anal. (C$_{30}$H$_{37}$N$_5$O$_5$) C, H, N.

Example 27—Preparation of Compound 6: N-Ethyl-3-(CBZ-L-Leu-L-Phe-L-Gln)-E-Propenamide Preparation of Intermediate N-Ethyl-3-[BOC-L-(Tr-Gln)]-E-Propenamide Isobutyl chloroformate (0.161 mL, 1.24 mmol) was added to a solution of 3-[BOC-L-(Tr-Gln)]-E-propenoic acid (0.639 g, 1.24 mmol) and 4-methylmorpholine (1.36 mL, 12.4 mmol) in CH$_2$Cl$_2$ at 0° C. The resulting solution was stirred for 20 minutes at 0° C., then ethylamine hydrochloride (0.810 g, 9.93 mmol) was added. The reaction mixture was warmed to 23° C. and was stirred for 24 hours, then was partitioned between water (100 mL) and a 9:1 mixture of CH$_2$Cl$_2$ and CH$_3$OH (2×100 mL). The organic layers were dried over NA$_2$SO$_4$ and were concentrated. Purification of the residue by flash column chromatography (5% CH$_3$OH/CH$_2$Cl$_2$) provided an oil, which was triturated with EtOAc to afford a white solid. The solid was filtered, washed with EtOAc (2×20 mL), and was air-dried to give N-ethyl-3-[BOC-L-(Tr-Gln)]-E-propenamide (0.055 g, 8%): mp=240° C. (dec); IR (thin film) 3255, 3085, 1715, 1665, 1612, 1529 cm$^{-1}$; $^1$H NMR (CDCl$_3$) δ 1.15 (t, 3H, J=7.2 Hz), 1.42 (s, 9H), 1.63–1.80 (m, 1H), 1.83–2.05 (m, 1H), 2.34–2.39 (m, 2H), 3.29–3.38 (m, 2H), 4.26 (s, br, 1H), 4.75 (s, br, 1H), 5.43 (s, br, 1H), 5.81 (d, 1H, J=15.4 Hz), 6.65 (dd, 1H, J=15.4, 5.9 Hz), 6.85 (s, 1H), 7.19–7.33 (m, 15H); Anal. (C$_{33}$H$_{37}$N$_3$O$_4$) C, H, N.

Preparation of Intermediate N-Ethyl-3-[CBZ-L-Leu-L-Phe-L-(Tr-Gln)]-E-Propenamide N-Ethyl-3-[BOC-L-(Tr-Gln)]-E-propenamide (0.040 g, 0.074 mmol) was deprotected and coupled with CBZ-L-Leu-L-Phe (0.030 g, 0.073 mmol) using the procedure described in Example 28 for the preparation of ethyl-2-fluoro-3-[CBZ-L-Leu-L-Phe-L-(Tr-Gln)]-E-propenoate to provide N-ethyl-3-[CBZ-L-Leu-L-Phe-L-(Tr-Gln)]-E-propenamide (0.043 g, 70%) as a white solid: mp=190° C. (dec); IR (thin film) 3283, 3067, 1693, 1642, 1535 cm$^{-1}$; $^1$H NMR (CDCl$_3$) δ 0.83 (d, 3H, J=9.0 Hz), 0.85 (d, 3H, J=9.0 Hz), 1.14 (t, 2H, J=7.3 Hz), 1.21–1.32 (m, 1H), 1.37–1.52 (m, 2H), 1.71–1.78 (m, 1H), 1.94–2.05 (m, 1H), 2.26 (t, 2H, J=7.3 Hz), 2.91 (dd, 1H, J=13.8, 7.6 Hz), 3.16 (dd, 1H, J=13.8, 6.2 Hz), 3.26–3.35 (m, 2H), 3.94–4.01 (m, 1H), 4.53–4.55 (m, 2H), 4.89–4.94 (m, 3H), 5.56–5.65 (m, 2H), 6.51 (d, 1H, J=8.1 Hz), 6.60 (dd, 1H, J=15.1, 4.8 Hz), 6.81 (d, 1H, J=8.4 Hz), 7.02 (s, 1H), 7.10–7.36 (m, 26H); Anal. (C$_{51}$H$_{57}$N$_5$O$_6$) C, H, N.

Preparation of Products N-Ethyl-3-(CBZ-L-Leu-L-Phe-L-Gln)-E-Propenamide

Using the procedure described in Example 4 for the preparation of compound 3, N-ethyl-3-[CBZ-L-Leu-L-Phe-L-(Tr-Gln)]-E-propenamide was deprotected to produce the product. mp=230° C. (dec), R$_f$=0.28 (10% MeOH in CH$_2$Cl$_2$); IR (KBr) 3404, 3075, 2943, 1692, 1643 cm$^{-1}$; $^1$H NMR (DMSO-d$_6$) δ 0.78 (d, 3H, J=11.5 Hz), 0.80 (d, 3H, J=11.5 Hz), 1.02 (t, 3H, J=7.3 Hz), 1.24–1.29 (m, 2H), 1.32–1.47 (m, 1H), 1.67–1.71 (m, 2H), 2.03–2.08 (m, 2H), 2.77–2.85 (m, 1H), 2.99–3.16 (m, 3H), 3.91–3.98 (m, 1H), 4.29–4.34 (m, 1H), 4.48–4.49 (m, 1H), 4.97 (d, 1H, J=12.5 Hz), 5.04 (d, 1H, J=12.5 Hz), 5.85 (d, 1H, J=15.3 Hz), 6.43 (dd, 1H, J=15.4, 6.4 Hz), 6.75 (s, 1H), 7.20 (bs, 7H), 7.30–7.34 (m, 4H), 7.41 (d, 1H, J=7.8 Hz), 7.90 (d, 1H, J=7.8 Hz), 7.97 (t, 1H, J=5.1 Hz), 8.08 (d, 1H, J=8.1 Hz); Anal. ($C_{32}H_{43}N_5O_6$) C, H, N.

Example 28—Preparation of Compound 8: Ethyl-2-Fluoro-3-(CBZ-L-Leu-L-Phe-L-Gln)-E-Propenoate Preparation of Intermediate Ethyl-2-Fluoro-3-[BOC-L-(Tr-Gln)]-E-Propenoate Sodium bis(trimethylsilyl)amide (0.264 mL of a 1.0M solution in THF, 0.264 mmol) was added to a solution of triethyl-2-fluoro-2-phosphonoacetate (0.054 mL, 0.266 mmol) in THF (10 mL) at −78° C., and the resulting solution was stirred for 15 minutes at that temperature. BOC-L-(Tr-Glutaminal) (0.125 g, 0.264 mmol) in THF (10 mL) was added via cannula, and the reaction mixture was stirred for 30 minutes at −78° C. then was partitioned between 0.5M HCl (100 mL) and a 1:1 mixture of EtOAc and hexanes (2×100 mL). The organic layers were dried over $NA_2SO_4$ and were concentrated. Purification of the residue by flash column chromatography (30% EtOAc in hexanes) provided ethyl-2-fluoro-3-[BOC-L-(Tr-Gln)]-E-propenoate (0.094 g, 63%) as a white foam: IR (thin film) 3324, 1724, 1670 cm$^{-1}$; $^1$H NMR (CDCl$_3$) δ 1.33 (t, 3H, J=7.2 Hz), 1.41 (s, 9H), 1.92–2.05 (m, 2H), 2.39 (t, 2H, J=7.2 Hz), 4.28 (q, 2H, J=7.2 Hz), 5.00 (bs, 2H), 5.74 (dd, 1H, J=19.8, 8.6 Hz), 6.78 (s, 1H), 7.14–7.32 (m, 15H); Anal. ($C_{33}H_{37}FN_2O_5$) C, H, N.

Preparation of Intermediate Ethyl-2-Fluoro-3-[CBZ-L-Leu-L-Phe-L-(Tr-Gln)]-E-Propenoate.

A solution of HCl in 1,4-dioxane (4 mL of a 4.0M solution, 16 mmol) was added to a solution of ethyl-2-fluoro-3-[BOC-L-(Tr-Gln)]-E-propenoate (0.310 g, 0.553 mmol) in the same solvent (4 mL) at 23° C. The reaction mixture was stirred for 4 hours at 23° C., then was concentrated. The resulting oil was dissolved in $CH_2Cl_2$, and CBZ-L-Leu-L-Phe (0.228 g, 0.553 mmol), 1-hydroxybenzotriazole hydrate (0.112 g, 0.828 mmol), 4-methylmorpholine (0.182 mL, 1.67 mmol), and 1-(3-dimethylaminopropyl)-3-ethyl-carbodiimide hydrochloride (0.159 g, 0.829 mmol) were added sequentially. The reaction mixture was stirred for 12 hours at 23° C., then was partitioned between water (100 mL) and EtOAc (2×100 mL). The organic layers were dried over $NA_2SO_4$ and were concentrated. Purification of the residue by flash column chromatography (5% $CH_3OH/CH_2Cl_2$) afforded ethyl-2-fluoro-3-[CBZ-L-Leu-L-Phe-L-(Tr-Gln)]-E-propenoate (0.203 g, 43%) as a white foam: IR (thin film) 3394, 3066, 1724, 1647 cm$^{-1}$; $^1$H NMR (CDCl$_3$) δ 0.84 (d, 3H, J=5.9 Hz), 0.86 (d, 3H, J=6.2 Hz), 1.32 (t, 3H, J=7.0 Hz), 1.37–1.57 (m, 3H), 1.82–1.84 (m, 2H), 2.26–2.29 (m, 2H), 2.97–2.99 (m, 2H), 3.99–4.05 (m, 1H), 4.26 (q, 2H, J=7.0 Hz), 4.46–4.49 (m, 1H), 4.95 (s, 2H), 5.06 (d, 1H, J=6.5 Hz), 5.16–5.21 (m, 1H), 5.54 (dd, 1H, J=19.9, 9.7 Hz), 6.55 (d, 1H, J=7.5 Hz), 6.79 (d, 1H, J=7.5 Hz), 6.99 (s, 1H), 7.07–7.42 (m, 25H); Anal. ($C_{51}H_{55}FN_4O_7$) C, H, N.

Preparation of Product Ethyl-2-Fluoro-3-(CBZ-L-Leu-L-Phe-L-Gln)-E-Propenoate

Using the procedure described in Example 4 for the preparation of compound 3, ethyl-2-fluoro-3-[CBZ-L-Leu-L-Phe-L-(Tr-Gln)]-E-propenoate was deprotected to produce the product. mp=210°–211° C., $R_f$=0.57 (10% MeOH in $CH_2Cl_2$); IR (KBr) 3401, 3300, 3072, 2943, 1693, 1648 cm$^{-1}$; $^1$H NMR (DMSO-d$_6$) δ 0.79 (d, 3H, J=10.9 Hz), 0.82 (d, 3H, J=10.9 Hz), 1.27 (t, 3H, J=7.2.Hz), 1.32–1.49 (m, 3H), 1.65–1.80 (m, 2H), 1.99–2.06 (m, 2H), 2.78–2.96 (m, 2H), 3.96–4.01 (m, 1H), 4.25 (q, 2H, J=7.2 Hz), 4.39–4.41 (m, 1H), 4.97–5.07 (m, 3H), 5.65 (dd, 1H, J=21.2, 10.0 Hz), 6.74 (s, 1H), 7.16–7.30 (m, 7H), 7.32–7.34 (m, 4H), 7.44 (d, 1H, J=8.1 Hz), 7.94 (d, 1H, J=8.1 Hz), 8.03 (d, 1H, J=7.8 Hz) Anal. ($C_{32}H_{41}FN_4O_7$) C, H, N.

Example 29—Preparation of Compound 9: Methyl-[2-(CBZ-L-Leu-L-Phe-L-Gln)-E-Vinyl] Sulfone Preparation of Intermediate Methyl-(2-[BOC-L-(Tr-Gln)]-E-Vinyl) Sulfone Sodium bis(trimethylsilyl)amide (1.04 mL of a 1.0M solution in THF, 1.04 mmol) was added to a solution of methanesulfonylmethyl-phosphinic acid diethyl ether (0.217 g, 0.943 mmol) in THF (30 mL) at −78° C., and the resulting solution was stirred for 15 minutes at that temperature. BOC-L-(Tr-Glutaminal) (0.446 g, 0.944 mmol) in THF (15 mL) was added via cannula, and the reaction mixture was stirred for 30 minutes at −78° C. then was partitioned between 0.5M HCl (100 mL) and a 1:1 mixture of EtOAc and hexanes (2×100 mL). The organic layers were dried over $NA_2SO_4$ and were concentrated. Purification of the residue by flash column chromatography (40% hexanes in EtOAc) provided methyl-(2-[BOC-L-(Tr-Gln)]-E-vinyl) sulfone (0.359 g, 69%) as a white foam: IR (thin film) 3348, 1688, 1495 cm$^{-1}$; $^1$H NMR (CDCl$_3$) δ 1.43 (s, 9H), 1.64–1.81 (m, 1H), 1.83–2.01 (m, 1H), 2.40 (t, 2H, J=6.7Hz), 2.91 (s, 3H), 4.35 (s, br, 1H), 5.01–5.04 (m, 1H), 6.42 (dd, 1H, J=15.0, 1.7 Hz), 6.78 (s, 1H), 6.78 (dd, 1H, J=15.0, 5.0 Hz), 7.18–7.33 (m, 15H); Anal. ($C_{31}H_{36}N_2O_5S$) C, H, N.

Preparation of Intermediate Methyl-(2-[CBZ-L-Leu-L-Phe-L-(Tr-Gln)]-E-Vinyl) Sulfone.

Using the procedure described in Example 28 for the preparation of ethyl-2-fluoro-3-[CBZ-L-Leu-L-Phe-L-(Tr-Gln)]-E-propenoate, methyl-(2-[BOC-L-(Tr-Gln)]-E-vinyl) sulfone (0.359 g, 0.654 mmol) was deprotected and coupled with CBZ-L-Leu-L-Phe (0.270 g, 0.655 mmol) to provide methyl-(2-[CBZ-L-Leu-L-Phe-L-(Tr-Gln)]-E-vinyl) sulfone (0.160 g, 29%) as a white foam: IR (thin film) 3296, 3061, 1649, 1529 cm$^{31\ 1}$; $^1$H NMR (CDCl$_3$) δ 0.84 (d, 3H, J=8.9 Hz), 0.86 (d, 3H, J=8.9 Hz), 1.24–1.36 (m, 2H), 1.42–1.55 (m, 2H), 1.72–1.75 (m, 1H), 1.96–1.99 (m, 1H), 2.23–2.32 (m, 2H), 2.85 (s, 3H), 2.97 (dd, 1H, J=13.8, 7.5 Hz), 3.13 (dd, 1H, J=13.8, 6.1 Hz), 3.92–3.99 (m, 1H), 4.43–4.56 (m, 2H), 4.88 (s, br, 2H), 4.95 (d, 1H, J=5.9 Hz), 6.20 (d, 1H, J=14.9 Hz), 6.47 (d, 1H, J=7.2 Hz), 6.70 (dd, 1H, J=14.9, 4.4 Hz), 6.98 (d, 1H, J=8.1 Hz), 7.09–7.38 (m, 25H).

Preparation of Product—Methyl-[2-(CBZ-L-Leu-L-Phe-L-Gln)-E-Vinyl] Sulfone

Using the procedure described in Example 4 for the preparation of compound 3, methyl-(2-[CBZ-L-Leu-L-Phe-L-(Tr-Gln)]-E-vinyl) sulfone was deprotected to produce the product. mp=220° C. (dec), $R_f$=0.44 (10% MeOH in $CH_2Cl_2$); IR (KBr) 3413, 3284, 3049, 2951, 1690, 1649 cm$^{-1}$; $^1$H NMR (DMSO-d$_6$) δ 0.79 (d, 3H, J=10.6 Hz), 0.81 (d, 3H, J=10.6 Hz), 1.27–1.38 (m, 2H), 1.40–1.50 (m, 1H), 1.63–1.80 (m, 2H), 2.08 (t, 2H, J=7.5 Hz), 2.82–2.89 (m, 1H), 2.96 (s, 3H), 2.98–3.04 (m, 1H), 3.94–3.99 (m, 1H), 4.45–4.53 (m, 2H), 4.98 (d, 1H, J=12.5 Hz), 5.05 (d, 1H, J=12.5 Hz), 6.38 (d, 1H, J=14.9), 6.60 (dd, 1H, J=15.4, 5.1 Hz), 6.78 (s, 1H), 7.17–7.31 (m, 7H), 7.34–7.36 (m, 4H), 7.43 (d, 1H, J=8.1 Hz), 8.01 (d, 1H, J=8.1 Hz), 8.13 (d, 1H, J=8.1 Hz); Ana;l. ($C_{30}H_{40}N_4O_7S$) C, H, N.

Example 30—Preparation of Compound 10: Phenyl-[2-(CBZ-L-Leu-L-Phe-L-Gln)-E-Vinyl] Sulfone Preparation of Intermediate Phenyl-(2-[BOC-L-(Tr-Gln)]-E-Vinyl) Sulfone Sodium bis(trimethylsilyl)amide (1.14 mL of a 1.0M solution in THF, 1.14 mmol) was added to a solution of benzenesulfonylmethyl-phosphinic acid diethyl ether (0.304 g, 1.04 mmol) in THF (20 mL) at −78° C., and the resulting solution was stirred for 15 minutes at that temperature. BOC-L-(Tr-Glutaminal) (0.491 g, 1.04 mmol) in THF (10 mL) was added via cannula, and the reaction mixture was stirred for 30 minutes at −78° C. then was partitioned between 0.5M HCl (100 mL) and a 1:1 mixture of EtOAc and hexanes (2×100 mL). The organic layers were dried over $NA_2SO_4$ and were concentrated. Purification of the residue by flash column chromatography (gradient elution, 30–40% EtOAc in hexanes) provided phenyl-(2-[BOC-L-(Tr-Gln)]-E-vinyl) sulfone (0.540 g, 85%) as a white foam: IR (thin film) 3347, 2250, 1688, 1493 cm$^{-1}$; $^1$H NMR (CDCl$_3$) δ 1.37 (s, 9H), 1.73–1.81 (m, 1H), 1.83–1.94 (m, 1H), 2.38 (t, 2H, J=6.7 Hz), 4.33 (s, br, 1H), 4.88–4.90 (m, 1H), 6.37 (dd, 1H, J=15.3, 1.6 Hz), 6.79–6.86 (m, 2H), 7.17–7.32 (m, 15H), 7.49–7.54 (m, 2H), 7.58–7.63 (m, 1H), 7.83–7.87 (m, 2H); Anal. ($C_{36}H_{38}N_2O_5S$) C, H, N.

Preparation of Intermediate Phenyl-(2-[CBZ-L-Leu-L-Phe-L-(Tr-Gln)]-E-Vinyl) Sulfone Using the procedure described in Example 28 for the preparation of ethyl-2-fluoro-3-[CBZ-L-Leu-L-Phe-L-(Tr-Gln)]-E-propenoate, phenyl-(2-[BOC-L-(Tr-Gln)]-E-vinyl) sulfone (0.205 g, 0.336 mmol) was deprotected and coupled with CBZ-L-Leu-L-Phe (0.138 g, 0.335 mmol) to provide phenyl-(2-[CBZ-L-Leu-L-Phe-L-(Tr-Gln)]-E-vinyl) sulfone (0.100 g, 33%) as a white foam: IR (thin film) 3298, 3061, 1652, 1518 cm$^{-1}$; $^1$H NMR (CDCl$_3$) δ 0.81 (d, 3H, J=6.9 Hz), 0.83 (d, 3H, J=6.9 Hz), 1.24–1.69 (m, 5H), 1.91 (s, br, 1H), 2.16–2.31 (m, 2H), 2.91 (dd, 1H, J=13.5, 7.5 Hz), 3.05 (dd, 1H, J=13.5, 6.7 Hz), 3.91–3.98 (m, 1H), 4.38–4.45 (m, 1H), 4.54 (s, br, 1H), 4.87 (s, br, 1H), 5.06 (d, 1H, J=6.2 Hz), 6.12 (d, 1H, J=15.3 Hz), 6.57 (d, 1H, J=7.2 Hz), 6.75 (dd, 1H, J=15.3, 4.4 Hz), 6.85 (d, 1H, J=8.4 Hz), 7.05 (d, 1H, J=7.2 Hz), 7.10–7.37 (m, 24H), 7.40–7.62 (m, 3H), 7.79–7.82 (m, 2H); Anal. ($C_{54}H_{56}N_4O_7S$) C, H, N.

Preparation of Product—Phenyl-[2-(CBZ-L-Leu-L-Phe-L-Gln)-E-Vinyl] Sulfone

Using the procedure described in Example 4 for the preparation of compound 3, phenyl-(2-[CBZ-L-Leu-L-Phe-L-(Tr-Gln)]-E-vinyl) sulfone was deprotected to produce the product. mp=230° C. (dec), $R_f$=0.40 (10% MeOH in CH$_2$Cl$_2$); IR (KBr) 3400, 3288, 3062, 2960, 1685, 1644 cm$^{-1}$; $^1$H NMR (DMSO-d$_6$) δ 0.78 (d, 3H, J=10.6 Hz), 0.81 (d, 3H, J=10.6 Hz), 1.26–1.39 (m, 2H), 1.47–1.59 (m, 1H), 1.61–1.66 (m, 1H), 1.76–1.79 (m, 1H), 2.04 (t, 2H, J=7.0 Hz), 2.77–2.96 (m, 2H), 3.95–4.00 (m, 1H), 4.43–4.45 (m, 2H), 4.96 (d, 1H, J=12.6 Hz), 5.02 (d, 1H, J=12.6 Hz), 6.33 (d, 1H, J=14.9 Hz), 6.74–6.81 (m, 2H), 7.11–7.18 (m, 7H), 7.20–7.38 (m, 4H), 7.42 (d, 1H, J=7.8 Hz), 7.65 (d, 2H, J=7.8 Hz), 7.71 (d, 1H, J=7.5 Hz), 7.82 (d, 2H, J=6.9 Hz), 8.00 (d, 1H, J=7.8 Hz), 8.09 (d, 1H, J=8.1 Hz); Anal. ($C_{35}H_{42}N_4O_7S$) C, H, N.

Example 31—Preparation of Compound 11: Ethyl-2-Fluoro-3-[BOC-L-(Cyanomethyl)-Ala]-E-Propenoate Preparation of Intermediate BOC-L-Gln-OMe To a solution of BOC-L-Gln (20 g, 81 mmol) in 50 mL of EtOAC and MeOH at 0° C. was added diazomethane in 250 mL of Et$_2$O with stirring. The resulting yellow solution was stirred at 0° C. for 5 minutes and then warmed up to room temperature and stirred for 20 minutes. Argon gas was then bubbled through the yellow reaction mixture to remove excess diazomethane. The crude product was concentrated and purified by crystallization from methyl-tert-butyl ether. Yield 100%. $^1$H NMR (CDCl$_3$) δ 1.45 (s, 9H), 1.96 (m, 1H), 2.21 (m, 1H), 2.36 (m, 2H), 3.76 (s, 3H,), 4.34 (m, 1H), 5.32 (m, 1H), 5.44 (bs, 1H), 6.16 (bs, 1H). Anal. ($C_{11}H_{20}N_2O_5$) C, H, N.

Preparation of Intermediate BOC-L-(Cyanomethyl)-Ala-OMe

To a solution of BOC-L-Gln-OMe (10 g, 38 mmol) in 100 mL of pyridine at 0° C. was added 3.5 mL of POCl$_3$ dropwise. The reaction was warmed to room temperature and stirred overnight. The reaction mixture was diluted with 100 mL EtOAc and washed with 1N HCl (2×50 mL). The organics were combined and dried over $NA_2SO_4$, concentrated to yield the crude product which was purified by flash column chromatography (1:4 EtOAc/hexane) to give the product in 67% yield. $^1$H NMR (CDCl$_3$) δ 1.45 (s, 9H), 2.03 (m, 1H), 2.27 (m, 1H), 2.46 (m, 2H), 3.80 (s, 3H), 4.38 (m, 1H), 5.20 (m, 1H).

Preparation of Intermediate BOC-L-(Cyanomethyl)-Alaninol

This compound was prepared in 84% yield from BOC-L-(cyanomethyl)-Ala-OMe using the procedure described in Example 2 for the preparation of CBZ-L-(N-Ac-amino)-alaninol. The compound was purified by flash column chromatography (50:50 EtOAc/hexane). $^1$H NMR (CDCl$_3$) δ 1.45 (s, 9H), 1.92 (m, 2H), 2.19 (m, 1H), 2.46 (m, 2H), 3.71 (m, 3H), 4.83 (m, 1H). Anal. ($C_{10}H_{18}N_2O_3$0.4 H$_2$O) C, H, N.

Preparation of Intermediate BOC-L-(Cyanomethyl)-Alaninal

To a solution of oxalyl chloride (1.63 g, 12.57 mmol) in CH$_2$Cl$_2$ (30 mL) at −78° C. was added DMSO dropwise (2.01 g, 25.74 mmol). After the addition, the reaction was stirred for 5 minutes. A solution of BOC-L-(cyanomethyl)-alaninol (2.5 g, 11.7 mmol) in 20 mL was added at −78° C. with stirring. After 20 minutes, the reaction was treated with NEt$_3$ (8.15 mL, 58.5 mmol) and stirred for another 20 minutes. Water (40 mL) was added at −60° C., and then the reaction was warmed up to room temperature. The water layer was separated and extracted with EtOAc (2×50 mL). The organic layers were combined and dried over MgSO$_4$, and then concentrated to give 2.1 g crude product which was purified by flash column chromatography using a gradient of 3:7 EtOAc/hexane to 5:5 EtOAc/hexane to give the aldehyde in 60% yield. $^1$H NMR (CDCl$_3$) δ 1.37 (m, 3H), 1.42 (s, 9H), 1.46 (s, 9H), 1.91 (m, 1H), 2.55–2.30 (m, 3H), 4.25 (m, 1H), 5.27 (m, 1H), 9.63 (s, 1H).

Preparation of Intermediate Ethyl-2-Fluoro-3-[BOC-L-(Cyanomethyl)-Ala]-E-Propenoate A solution of triethyl 2-fluoro-phosphonoacetate (0.31 g, 1.27 mmol) in 4 mL THF was cooled at −78° C. and then n-BuLi (0.56 mL of 2.5M solution in hexanes, 1.39 mmol) was added. The resulting solution was stirred at −78° C. for 20 minutes, and then a solution of BOC-L-(cyanomethyl)-alaninal (0.124 g, 0.58 mmol) in 2 mL THF was added to the reaction mixture. The reaction was allowed to stir at −78° C. for 1 hour and then warmed up to room temperature and stirred overnight. Aqueous 6N HCl (10 mL) was added to the reaction, and the organic layer was separated and washed with brine (2×10 mL) and concentrated. The crude product was purified by flash column chromatography (30:70 EtOAc/hexane) to give 0.07 g. product (55% yield). $^1$H NMR (CDCl$_3$) δ 2.2–1.8 (m, 2H), 2.45 (m, 2H), 4.33 (m, 2H), 4.77 (m, 1H), 5.01 (m, 1H,), 5.89 (m, 1H). Anal. (C$_{14}$H$_{21}$N$_2$O$_4$F0.15 H$_2$O) C, H,.N. MS calcd for C$_{14}$H$_{21}$N$_2$O$_4$F (M+Na), found 323.

Production of Product—Ethyl-2-Fluoro-3-[CBZ-L-Leu-L-Phe-L-(Cyanomethyl)-Ala]-E-Propenoate A solution of ethyl-2-fluoro-3-[BOC-L-(cyanomethyl)-Ala]-E-propenoate (0.055 g, 0.18 mmol) in 1 mL CH$_2$Cl$_2$ was cooled to 0° C., and 0.3 mL of TFA was added. The reaction was then warmed to room temperature, stirred for 3 hours, concentrated, and trace amounts of water were removed by toluene azeotrope. This crude product was dissolved in 2 mL DMF and a solution of benzotriazol-1-yloxytris(dimethylamino)phosphonium hexafluorophosphate (BOP) (0.12 g, 0.27 mmol), CBZ-L-Leu-L-Phe (0.11 g, 0.27 mmol), and Et$_3$N (0.075 mL, 0.54 mmol) was added at 0° C., and the reaction was stirred for 4 hours. This reaction was diluted with saturated aqueous NaHCO$_3$ solution and extracted with EtOAc (3×15 mL). The organics layers were combined and dried with MgSO$_4$ and concentrated. The residue was purified by flash column chromatography using a solvent gradient of 1% MeOH/CH$_2$Cl$_2$ to 5% MeOH/CH$_2$Cl$_2$ yielding the product in 37% (2-steps). Anal (C$_{32}$H$_{39}$N$_4$O$_6$F) C, H, N. HRMS calcd for C$_{32}$H$_{39}$N$_4$O$_6$F+Na 617.2751 (M+Na), found 617.2738.

Example 32—Preparation of Compound 20: Diethyl-[2-(CBZ-L-Leu-L-Phe-L-Gln)-E-Vinyl] Phosphonate Preparation of Intermediate CBZ-L-(Tr-Gln)

CBZ-L-Gln (28.03 g, 100 mmol) was dissolved in 300 mL of glacial acetic acid. To this solution was added triphenylmethanol (26.83 g, 100 mmol), acetic anhydride (18.87 mL, 200 mmol), and 0.5 mL of sulfuric acid. The reaction was heated to 55° C., stirring for one hour. After cooling to room temperature the mixture was concentrated under reduced pressure to one-third the original volume. Ice water was added, and the product extracted with EtOAc. The organic layer was washed with water and brine, dried over MgSO$_4$, and concentrated. The crude product was recrystallized from CH$_2$Cl$_2$/hexane, and the resulting crystals washed with Et$_2$O, yielding 37.27 g (71%) as a white solid: IR (KBr) 3418, 3295, 3059, 3032, 2949, 2515, 1699, 1628, 1539, 1504, 1447, 1418, 1341, 1242, 1209, 1061, 748, 696 cm$^{-1}$; $^1$H NMR (DMSO-d$_6$) δ 1.71 (m, 1H), 1.88 (m, 1H), 2.38 (m, 2H), 3.97 (m, 1H), 5.04 (s, 2H), 7.14–7.35 (m, 20H), 7.52 (d, 1H, J=7.7 Hz), 8.60 (s, 1H).

Preparation of Intermediate CBZ-L-(Tr-Gln)OMe

CBZ-L-(Tr-Gln) (0.26 g, 0.5 mmol) was added to a stirring solution of 0.25 mL of acetyl chloride in 5 mL of MeOH, and stirring was continued at room temperature for 1 hour. The solvent was removed in vacuo, and the residue dissolved in 100 ml CH$_2$Cl$_2$. The organic layer was washed with water, saturated NaHCO$_3$, and brine followed by drying over Na$_2$SO$_4$. The crude product was purified on a short flash silica gel column, eluting with 20% EtOAc/hexane. The product (0.23 g, 84%) was obtained as a white solid: IR (KBr) 3405, 3277, 3057, 3034, 2953, 1724, 1643, 1532, 1493, 1447, 1207, 1042, 750, 698 cm$^{-1}$; $^1$H NMR (DMSO-d$_6$) δ 1.16 (t, 1H, J=7.0 Hz), 1.77 (m, 1H), 1.97 (m, 1H), 3.61 (s, 3H), 4.99 (m, 1H), 5.03 (s, 2H), 7.02–7.55 (m, 20H), 7.69 (d, 1H, J=7.7 Hz), 8.59 (s, 1H). Anal. (C$_{33}$H$_{32}$N$_2$O$_5$) C, H, N.

Preparation of Intermediate CBZ-L-(Tr-Glutaminol)

CBZ-L-(Tr-Gln)OMe (1.50 g, 2.79 mmol) was dissolved in 20 mL of THF and 10 mL of EtOH. LiCl (0.24 g, 5.6 mmol) was added, and the mixture stirred for 10 minutes until all solids had dissolved. NaBH$_4$ (0.21 g, 5.6 mmol) was added, and the reaction stirred overnight at room temperature. The solvents were removed in vacuo, the residue taken up in water, and the pH was adjusted to 2–3 with 10% HCl. The product was extracted with EtOAc, and the organic layer was washed with water and brine before drying over MgSO$_4$. The crude product was purified on a short flash silica gel column, eluting with an increasing gradient of EtOAc/benzene, yielding 1.02 g (72%) of a white glassy solid: IR (KBr) 3408, 3318, 3057, 3032, 2947, 1699, 1674, 1516, 1447, 1240, 1059, 752, 698 cm$^{-1}$; $^1$H NMR (DMSO-d$_6$) δ 1.40 (m, 1H), 1.72 (m, 1H), 2.26 (m, 2H), 3.17–3.50 (m, 3H), 4.64 (t, 1H, J=5.0 Hz), 5.00 (s, 2H), 7.00–7.40 (m, 20H), 6.96 (d, 1H, J=8.5 Hz), 8.54 (s, 1H). Anal. (C$_{32}$H$_{32}$N$_2$O$_4$) C, H, N.

Preparation of Intermediate L-(Tr-Glutaminol)

This amino alcohol was prepared from CBZ-L-(Tr-glutaminol) in 98% yield using the procedure described in Example 2 for the preparation of L-(N-Ac-amino)-alaninol. IR (KBr) 3255, 3057, 3016, 2916, 1642, 1527, 1491, 1446, 1057, 1036, 750, 700, 636 cm$^{-1}$; $^1$H NMR (DMSO-d$_6$) δ 1.29 (m, 1H), 1.53 (m, 1H), 2.29 (m, 2H), 3.08 (m, 1H), 3.18 (m, 2H), 3.38 (bs, 2H), 4.43 (bs, 1H), 7.14–7.28 (m, 15H), 8.62 (s, 1H). Anal. (C$_{24}$H$_{26}$N$_2$O$_2$) C, H, N.

Preparation of Intermediate CBZ-L-Leu-L-Phe-L-(Tr-Glutaminol)

Using the procedure described in Example 1 for the preparation of CBZ-L-Leu-L-Phe-L-methioninol, this derivative was synthesized from CBZ-L-Leu-L-Phe and L-Tr-glutaminol in 62% yield as awhite solid: IR (KBr) 3302, 3057, 3032, 2951, 1954, 1885, 1657, 1520, 1238, 1045, 746, 698 cm$^{-1}$; $^1$H NMR (DMSO-d$_6$) δ 0.79 (t, 6H, J=7.0 Hz), 1.30 (m, 2H), 1.44 (m, 2H), 1.75 (m, 1H), 2.22 (m, 2H), 2.82 (m, 1H), 2.97 (m, 1H), 3.14 (m, 1H), 3.25 (m, 1H), 3.63 (m, 1H), 3.95 (m, 1H), 4.48 (m, 1H), 4.65 (t, 1H, J=5.0 Hz), 4.96 (d, 1H, J=13.0 Hz), 5.02 (d, 1H, J=13.0 Hz), 7.07–7.33 (m, 25H), 7.42 (d, 1H, J=8.0 Hz), 7.66 (d, 1H, J=8.5 Hz), 7.86 (d, 1H, J=8.0 Hz), 8.52 (s, 1H). Anal. (C$_{47}$H$_{52}$N$_4$O$_6$ 0.5 H$_2$O) C, H, N.

Preparation of Intermediate CBZ-L-Leu-L-Phe-L-(Tr-Glutaminal)

Using the procedure described in Example 1 for the preparation of CBZ-L-Leu-L-Phe-L-methioninal, this aldehyde was synthesized from CBZ-L-Leu-L-Phe-L-(Tr-glutaminol) in 92% yield as a white glassy solid, which was used immediately. $^1$H NMR (DMSO-d$_6$) δ 0.79 (t, 6H, J=7.0

Hz), 1.00–1.98 (m, 5H), 2.27 (m, 2H), 2.84 (m, 1H), 3.02 (m, 1H), 3.98 (m, 2H), 4.58 (m, 1H), 4.99 (s, 2H), 7.14–7.32 (m, 25H), 7.39 (d, 1H, J=8.0 Hz), 7.97 (d, 1H, J=8.5 Hz), 8.38 (d, 1H, J=8.0 Hz), 8.60 (s, 1H), 9.20 (s, 1H).

Preparation of Intermediate Diethyl-(2-[CBZ-L-Leu-L-Phe-L-(Tr-Gln)]-E-Vinyl) Phosphonate Tetraethyl methylenediphosphonate (0.21 mL, 0.86 mmol) was dissolved in 10 mL of THF and cooled to 0° C. Potassium bis(trimethylsilyl)amide (0.5M in toluene) was added dropwise via syringe, and the reaction stirred at 0° C. for 30 minutes. After cooling the reaction to −30° C. a solution of CBZ-L-Leu-L-Phe-L-(Tr-glutaminol) (0.63 g, 0.82 mmol) in 6 mL of THF was added dropwise. The reaction was allowed to warm slowly to room temperature and stirred overnight. The solvent was removed by evaporation, and the crude product was purified by flash column chromatography eluting with 1% (saturated anhydrous $NH_3$/MeOH)/ $CHCl_3$ to afford 0.50 g (68%) of a white crystalline solid: IR (KBr) 3289, 3059, 3032, 2957, 1667, 1532, 1447, 1246, 1026, 968, 748, 698 cm$^{-1}$; $^1$H NMR (DMSO-$d_6$) δ 0.78 (t, 6H, J=7.0 Hz), 1.20 (m, 6H), 1.15–1.78 (m, 5H), 2.25 (m, 2H), 2.85 (m, 1H), 2.97 (m, 1H), 3.86–4.07 (m, 5H), 4.32 (m, 1H), 4.51 (m, 1H), 4.95 (d, 1H, J=13.0 Hz), 5.02 (d, 1H, J=13.0 Hz), 5.52 (t, 1H, J=19.0 Hz), 6.48 (t, 1H, J=19.0 Hz), 7.07–7.32 (m, 25H), 7.41 (d, 1H, J=8.0 Hz), 7.97 (d, 1H, J=8.5 Hz), 8.05 (d, 1H, J=8.0 Hz), 8.59 (s, 1H); MS (M+H) 901, (M−H) 899. Anal. ($C_{52}H_{61}N_4O_8P$ 2.5 $H_2O$) C, H, N.

Preparation of Product Diethyl-[2-(CBZ-L-Leu-L-Phe-L-Gln)-E-Vinyl] Phosphonate

The protected amide diethyl-[2-(CBZ-L-Leu-L-Phe-L-Tr-Gln)-E-vinyl] phosphonate (0.469 g, 0.52 mmol) was dissolved in 10 mL of $CH_2Cl_2$. Triisopropylsilane (0.52 mL) was added as a triphenylmethyl cation scavenger. TFA (1.0 mL) was added, and the reaction was stirred overnight at room temperature. The reaction was poured into EtOAc and washed with saturated $NaHCO_3$ solution. The organic layer was separated and washed with water and brine followed by drying over $MgSO_4$. The product was purified by flash column chromatography eluting with 2–3% MeOH/$CHCl_3$ to give in 67% yield of a white solid: IR (KBr) 3291, 3063, 2955, 1647, 1541, 1236, 1026, 968, 746, 698 cm$^{-1}$; $^1$H NMR (DMSO-$d_6$) δ 0.79 (m, 6H), 1.21 (t, 6H, J=7.0 Hz), 1.28 (m, 2H), 1.52 (m, 1H), 1.63 (m, 1H), 1.75 (m, 1H), 2.06 (m, 2H), 2.85 (m, 1H), 3.00 (m, 1H), 3.92 (m, 5H), 4.34 (m, 1H), 4.50 (m, 1H), 4.97 (d, 1H, J=13.0 Hz), 5.04 (d, 1H, J=13.0 Hz), 5.54 (t, 1H, J=19.0 Hz), 6.49 (t, 1H, J=19.0 Hz), 6.77 (bs, 1H), 7.15–7.34 (m, 11H), 7.44 (d, 1H, J=8.0 Hz), 8.00 (d, 1H, J=8.5 Hz), 8.03 (d, 1H, J=8.0 Hz); HRMS calcd for $C_{33}H_{48}N_4O_P$ 659.3210 (M+H), found 659.3223. Anal. ($C_{33}H_{48}N_4O_8P$) C, H, N.

Example 33—Preparation of Compound 29: Ethyl-3-[N-(1-Tr-4-Methoxyindole-2-Carbonyl)-L-(4-Cl-Phe)-L-Gln]-E-Propenoate Preparation of Product—Ethyl-3-[N-(1-Tr-4-Methoxyindole-2-Carbonyl)-L-(4-Cl-Phe)-L-Gln]-E-Propenoate This compound was prepared by the deprotection of ethyl-3-[N-(4-methoxyindole-2-carbonyl)-L-(4-Cl-Phe)-L-(Tr-Gln)]-E-propenoate, using the procedure described in Example 32 for the preparation of compound 20, but in the absence of triisopropylsilane. $^1$H NMR (DMSO-$d_6$) δ 1.20 (t, 3H, J=7.0 Hz), 1.74 (m, 2H), 2.03 (t, 2H, J=8.0 Hz), 2.94 (m, 2H), 3.89 (s, 3H), 4.11 (q, 2H, J=7.0 Hz), 4.46 (m, 1H), 4.60 (m, 1H), 5.70 (d, 1H, J=15.0 Hz), 6.54 (d, 1H, J=7.8 Hz), 6.70 (dd, 1H, J=15.0, 5.7 Hz), 6.75 (bs, 1H), 6.87 (d, 1H, J=8.5 Hz), 7.06 (m, 5H), 7.31 (m, 18H), 7.72 (bs, 1H), 8.26 (d, 1H, J=8.2 Hz), 8.61 (d, 1H, J=8.1 Hz); HRMS calcd for $C_{47}H_{45}N_4O_6Cl$+Cs 929.2082 (M+Cs), found 929.2078 Anal. ($C_{47}H_{45}N_4O_6Cl$ 1.0 $H_2O$) C, H, N.

Example 34—Preparation of Compound 167: Ethyl-3-[Ethylthiocarbonyl-L-α-(t-Butyl-Gly)-L-Phe-L-Gln]-E-Propenoate.

Preparation of Intermediate CBZ-L-Phe-L-(Tr-Glutaminol).

Using the procedure described in Example 16 for the preparation of BOC-L-(4-Cl-Phe)-(Tr-glutaminol), CBZ-L-Phe-L-(Tr-glutaminol) was synthesized from CBZ-L-Phe and L-(Tr-glutaminol) in 67% yield as a white glassy solid: IR (KBr) 3304, 3059, 3030, 2936, 1956, 1887, 1809, 1659, 1495, 1446, 1246, 1036, 750, 698 cm$^{-1}$; $^1$H NMR (DMSO-$d_6$) δ 1.47 (m, 1H), 1.72 (m, 1H), 2.26 (m, 2H), 2.75 (m, 1H), 2.94 (m, 1H), 3.18 (m, 1H), 3.26 (m, 1H), 3.66 (m, 1H), 4.21 (m, 1H), 4.66 (m, 1H), 4.90 (m, 2H), 7.15–7.30 (m, 25H), 7.43 (d, 1H, J=8.5 Hz), 7.72 (d, 1H, J=9.0 Hz), 8.49 (s, 1H). Anal. ($C_{41}H_{41}N_3O_5$.1.0 $H_2O$) C, H, N.

Preparation of Intermediate L-Phe-L-(Tr-Glutaminol).

Using the procedure described in Example 2 for the preparation of L-(N-Ac-amino)-alaninol, L-Phe-L-(Tr-Glutaminol) was synthesized from CBZ-L-Phe-L-(Tr-glutaminol) in quantitative yield as a white glassy solid: IR (KBr) 3293, 3061, 3026, 2938, 2361, 1669, 1495, 1446, 752, 700 cm$^{-1}$; $^1$H NMR (DMSO-$d_6$) δ 1.46 (m, 1H), 1.78 (m, 1H), 2.28 (m, 2H), 3.10 (m, 2H), 3.21 (m, 1H), 3.25 (m, 1H), 3.62 (m, 1H), 3.86 (t, 1H, J=6.0 Hz), 4.72 (m, 1H), 7.10–7.32 (m, 20H), 8.14 (d, 1H, J=8.0 Hz), 8.53 (s, 1H). MS calcd for $C_{33}H_{35}N_3O_3$+H 522, found 522. Anal. ($C_{33}H_{35}N_3O_3$.0.55 $CH_2Cl_2$) C, H, N.

Preparation of Intermediate BOC-L-α-(t-Butyl-Gly)-L-Phe-L-(Tr-Glutaminol).

L-Phe-L-(Tr-Glutaminol) (0.65 g, 1.25 mmol) was dissolved in 5 mL of DMF. Diisopropylethylamine (0.44 mL, 2.5 mmol) was added, followed by 0.29 g (1.25 mmol) of BOC-L-α-t-butylglycine. The reaction was cooled to 0° C. and HATU [O-(7-azabenztriazol-1-yl)-1,1,3,3-tetramethyluronium hexafluorophosphate] (0.48 g, 1.25 mmol) was added. The reaction mixture was allowed to warm to rt at which time the DMF was removed in vacuo. The residue was dissolved with EtOAc, and the organic phase washed consecutively with 10% aq HCl solution, sat. $NaHCO_3$ solution, $H_2O$, and brine. The solvent was dried ($MgSO_4$) and filtered, and the residue purified by flash silica gel chromatography using a gradient solvent system (0–1.5% MeOH/$CHCl_3$) to give 0.78 g (85%) of a white amorphous solid: IR (KBr) 3314, 2967, 1657, 1495, 1368, 1246, 1169, 1057, 752, 700 cm$^{-1}$; $^1$H NMR (DMSO-$d_6$) δ 0.78 (s, 9H), 1.37 (s, 10H), 1.72 (m, 1H), 2.23 (m, 2H), 2.80 (m, 1H), 2.92 (m, 1H), 3.08 (m, 1H), 3.21 (m, 1H), 3.60 (m, 1H), 3.83 (d, 1H, J=9.0 Hz), 4.55 (m, 1H), 4.59 (t, 1H, J=5.5 Hz), 6.42 (d, 1H, J=9.0 Hz), 7.14–7.28 (m, 20H), 7.67 (d, 1H, J=8.0 Hz), 7.95 (d, 1H, J=8.0 Hz), 8.45 (s, 1H); Anal. ($C_{44}H_{54}N_4O_6$.1.0 $H_2O$) C, H, N.

Preparation of Intermediate L-α-(t-Butyl-Gly)-L-Phe-L-(Tr-Glutaminol) Hydrochloride Salt.

BOC-L-α-(t-butyl-Gly)-L-Phe-L-(Tr-glutaminol) (0.745 g, 1.01 mmol) was dissolved in 2 mL of $CH_2Cl_2$ followed by 20 mL of Et$_2$O. Dry HCl gas was carefully bubbled into the solution until the white solid stopped precipitating. The reaction mixture hwas concentrated, and 2–3 mL of THF was added which redissolved the white solids. Thin layer chromatography indicated that the reaction went to completion. The THF was removed under vacuum and white solids were washed thoroughly with an excess of Et$_2$O and dried to yield L-α-(t-butyl-Gly)-L-Phe-L-(Tr-glutaminol) hydrochloride salt in 95% yield. IR(KBr) 3258, 3057, 2967, 1661, 1520, 700 cm$^{-1}$; $^1$H NMR (DMSO-d$_6$) δ 0.95 (s, 9H), 1.44 (m, 1H), 1.72 (m, 1H), 2.13 (m, 1H), 2.25 (m, 1H), 2.97 (m, 2H), 3.06 (m, 1H), 3.15 (m, 1H), 3.60 (m, 2H), 4.25 (bs, 1H), 4.55 (m, 1H), 7.13–7.27 (m, 20H), 7.89 (d, 1H, J=8.0 Hz), 8.13 (bs, 2H), 8.49 (s, 1H), 8.61 (d, 1H, J=7.7 Hz); Anal. (C$_{39}$H$_{46}$N$_4$O$_4$. HCl 1.0 H$_2$O) C, H, N.

Preparation of Intermediate Ethylthiocarbonyl-L-α-(t-Butyl-Gly)-L-Phe-L-(Tr-Glutaminol).

L-α-(t-Butyl-Gly)-L-Phe-L-(Tr-glutaminol) hydrochloride salt (0.61 g, 0.91 mmol) was dissolved in 9 mL of CH$_2$Cl$_2$. Triethylamine (0.26 mL, 1.87 mmol) was added, followed by the addition of 0.097 g (0.91 mL) of ethyl chlorothiolformate. After stirring for five minutes at rt, the solvent was removed under reduced pressure, and the residue was purified by column chromatography on silica gel eluting with a gradient solvent system (0–2% MeOH/CHCl$_3$) to give 0.47 g (71%) of a white amorphous solid: IR(KBr) 3300, 3059, 3026, 2967, 1649, 1493, 1194, 750, 698 cm$^{-1}$; $^1$H NMR (DMSO-d$_6$) 0.83 δ (s, 9H), 1.16 (t, 3H, J=7.0 Hz), 1.42 (m, 1H), 1.69 (m, 1H), 2.23 (m, 2H), 2.75 (q, 2H, J=7.0 Hz), 2.80 (m, 1H), 2.96 (m, 1H), 3.08 (m, 1H), 3.18 (m, 1H), 3.62 (m, 1H), 4.25 (d, 1H, J=9.0 Hz), 4.48 (m, 1H), 5.75 (t, 1H, J=5.0 Hz), 7.10–7.28 (m, 20H), 7.60 (d, 1H, J=8.5 Hz), 7.93 (d, 1H, J=9.0 Hz), 8.09 (d, 1H, J=7.7 Hz), 8.48 (s, 1H); Anal. (C$_{42}$H$_{50}$N$_4$O$_5$S) C, H, N.

Preparation of Intermediate Ethylthiocarbonyl-L-α-(t-Butyl-Gly)-L-Phe-L-(Tr-Glutaminal).

Using the general procedure described in Example 1 for the preparation of CBZ-L-Leu-L-Phe-L-methioninal (sulfoxide), ethylthiocarbonyl-L-α-(t-butyl-Gly)-L-Phe-L-(Tr-glutaminal) was synthesized from ethylthiocarbonyl-L-α-(t-butyl-Gly)-L-Phe-L-(Tr-glutaminol) in quantitative yield and isolated as a white amorphous solid and used without further purification: $^1$H NMR (DMSO-d$_6$) δ 0.83 (s, 9H), 1.16 (t, 3H, J=7.0 Hz), 1.55 (m, 1H), 1.86 (m, 1H), 2.26 (m, 2H), 2.74 (q, 2H, J=7.0 Hz), 2.85 (m, 1H), 2.98 (m, 1H), 3.90 (m, 1H), 4.25 (d, 1H, J=9.0 Hz), 4.59 (m, 1H), 7.14–7.28 (m, 20H), 7.93 (d, 1H, J=9.0 Hz), 8.18 (d, 1H, J=7.7 Hz), 8.38 (d, 1H, J=6.6 Hz), 8.52 (s, 1H), 9.13 (s, 1H).

Preparation of Intermediate Ethyl-3-[Ethylthiocarbonyl-L-α-(t-Butyl-Gly)-L-Phe-L-(Tr-Gln)]-E-Propenoate.

Using the procedure described in Example 1 for the preparation of ethyl-3-[CBZ-L-Leu-L-Phe-L-Met (sulfoxide)]-E-propenoate, ethyl-3-[ethylthiocarbonyl-L-α-(t-butyl-Gly)-L-Phe-L-(Tr-Gln)]-E-propenoate was synthesized from ethylthiocarbonyl-L-α-(t-butyl-Gly)-L-Phe-L-(Tr-glutaminal) (0.22 g, 0.30 mmol) to give 0.28 g of material contaminated with triphenylphosphine oxide which was used without further purification: white amorphous solid: $^1$H NMR (DMSO-d$_6$) δ 0.83 (s, 9H), 1.21 (m, 6H), 1.60 (m, 2H), 2.25 (m, 2H), 2.74 (q, 2H, J=7.0 Hz), 2.82 (m, 1H), 2.92 (m, 1H), 4.09 (q, 2H, J=7.0 Hz), 4.25 (d, 1H, J=9.0 Hz), 4.34 (m, 1H), 4.52 (m, 1H), 5.53 (d, 1H, J=15.5 Hz), 6.63 (dd, 1H, J=15.5, 5.5 Hz), 7.08–7.28 (m, 20H), 7.93 (d, 1H, J=9.0 Hz), 8.07 (d, 1H, J=7.7 Hz), 8.16 (d, 1H, J=7.7 Hz), 8.51 (s, 1H).

Preparation of Product—Ethyl-3-[EthyIthiocarbonyl-L-α-(t-ButyI-Gly)-L-Phe-L-Gln]-E-Propenoate.

Ethyl-3-[ethylthiocarbonyl-L-α-(t-butyl-Gly)-L-Phe-L-(Tr-Gln)]-E-propenoate, impure with triphenylphosphine oxide (0.28 g), was dissolved in 6 mL of CH$_2$Cl$_2$. TFA (0.6 mL) was added, and the reaction stirred at rt for 4 hours. The reaction was poured into an EtOAc/ sat. NaHCO$_3$ solution and agitated until white solids began to precipitate out of the organic layer. The aqueous layer was separated, and the solids were filtered and washed with EtOAc to give 0.074 g of a white solid (45% yield from the ethylthiocarbonyl-L-α-(t-butyl-Gly)-L-Phe-L-(Tr-glutaminal); 2 steps): IR(KBr) 3302, 2967, 1645, 1541, 1196 cm$^{-1}$; $^1$H NMR (DMSO-d$_6$) δ 0.83 (s, 9H), 1.18 (m, 6H), 1.67 (m, 2H), 2.03 (m, 2H), 2.75 (q, 2H, J=7.0 Hz), 2.86 (m, 1H), 2.93 (m, 1H), 4.10 (q, 2H, J=7.0 Hz), 4.25 (d, 1H, J=9.0 Hz), 4.35 (m, 1H), 4.49 (m, 1H), 5.55 (d, 1H, J=15.5 Hz), 6.64 (dd, 1H, J=15.5, 5.5 Hz), 6.73 (bs), 7.19 (m, 6H), 7.97 (d, 1H, J=8.5 Hz), 8.07 (d, 1H, J=8.0 Hz), 8.15 (d, 1H, J=7.7 Hz); HRMS calcd for C$_{27}$H$_{40}$N$_4$O$_6$S+Cs 681.1723, found 681.1738. Anal. (C$_{27}$H$_{40}$N$_4$O$_6$S) C, H, N.

Example 35—Preparation of Compound 168: Ethyl-2-Methyl-3-[Ethylthiocarbonyl-L-α-(t-Butyl-Gly)-L-Phe-L-Gln]-E-Propenoate.

Preparation of Intermediate Ethyl-2-Methyl-3-[Ethylthiocarbonyl-L-α-(t-Butyl-Gly)-Phe-L-(Tr-Gln)]-E-Propenoate.

Using the procedure described in Example 1 for the preparation of ethyl-3-[CBZ-L-Leu-L-Phe-L-Met (sulfoxide)]-E-propenoate, ethyl-2-methyl-3-[ethylthiocarbonyl-L-α-(t-butyl-Gly)-L-Phe-L-(Tr-Gln)]-E-propenoate was synthesized from ethylthiocarbonyl-L-α-(t-butyl-Gly)-L-Phe-L-(Tr-glutaminal) (0.22 g, 0.30 mmol) and (carbethoxyethylidene)triphenylphosphorane (0.14 g, 0.37 mmol). The product (0.31 g), a white amorphous solid, contaminated with triphenylphosphine oxide, was isolated after column chromatography and used without further purification: $^1$H NMR (DMSO-d$_6$) δ 0.83 (s, 9H), 1.18 (m, 6H), 1.54 (m, 1H), 1.66 (m, 1H), 1.73 (s, 3H), 2.21 (m, 2H), 2.75 (q, 2H, J=7.0 Hz), 2.80 (m, 1H), 2.88 (m, 1H), 4.12 (q, 2H, J=7.0 Hz), 4.24 (d, 1H, J=9.0 Hz), 4.44 (m, 2H), 6.27 (d, 1H, J=8.5 Hz), 7.13–7.27 (m, 20H), 7.95 (d, 1H, J=9.0 Hz), 8.03 (d, 1H, J=8.0 Hz), 8.09 (d, 1H, J=7.0 Hz), 8.51 (s, 1H).

Preparation of Product—Ethyl-2-Methyl-3-[Ethylthiocarbonyl-L-α-(t-Butyl-Gly)-L-Phe-L-Gln]-E-Propenoate.

Using the procedure described in Example 34 for the preparation of ethyl-3-[ethylthiocarbonyl-L-α-(t-butyl-Gly)-L-Phe-L-Gln]-E-propenoate, ethyl-2-methyl-3-[ethylthiocarbonyl-L-α-(t-butyl-Gly)-L-Phe-L-Gln]-E-propenoate was synthesized from ethyl-2-methyl-3-[ethylthiocarbonyl-L-α-(t-butyl-Gly)-L-Phe-L-(Tr-Gln)]-E-propenoate and isolated as a white glassy solid after purification by column chromatography on silica gel using a gradient solvent system (0–2% MeOH/CHCl$_3$) (58% yield; two steps from ethylthiocarbonyl-L-α-(t-butyl-Gly)-L-Phe-L-(Tr-glutaminal): IR (KBr) 3302, 2967, 1647, 1541, 1261, 1202 cm$^{-1}$; $^1$H NMR (DMSO-d$_6$) δ 0.83 (s, 9H), 1.18 (m, 6H), 1.65 (m, 1H), 1.69 (m, 1H), 1.77 (s, 3H), 2.00 (m, 2H), 2.75 (q, 2H, J=7.0 Hz), 2.86 (m, 2H), 4.12 (q, 2H, J=7.0 Hz), 4.24 (d, 1H, J=9.0 Hz), 4.42 (m, 2H), 6.26 (d, 1H, J=8.5 Hz), 6.71 (bs, 1H), 7.15 (m, 6H), 7.96 (d, 1H, J=9.0 Hz), 8.03 (d, 1H, J=7.7 Hz), 8.07 (d, 1H, J=7.0 Hz); HRMS calcd for $C_{28}H_{42}N_4O_6S+Cs$ 695.1879, found 695.1864. Anal. ($C_{28}H_{42}N_4O_6S.0.2$ $CHCl_3$) C, H, N.

Example 36—Preparation of Compound 178:

Ethyl-3-[Cyclopentylthiocarbonyl-L-(S-Me-Pen)-L-Phe-L-Gln]-E-Propenoate.

Preparation of Intermediate BOC-L-(S-Me-Pen)-L-Phe-L-(Tr-Glutaminol).

L-Phe-L-(Tr-Glutaminol) (0.64 g, 1.25 mmol) was dissolved in 4 mL of DMF. Diisopropylethylamine (0.43 mL, 2.46 mmol) was added, followed by BOC-S-methyl-L-penicillamine (0.32 g, 1.25 mmol; generated from the BOC-S-methyl-L-penicillamine dicyclohexylammonium salt (Sigma Chemical, St. Louis, Mo.) and aq HCl/EtOEt extraction and drying by benzene azeotrope). The solution was cooled to 0° C., HATU(O-7-azabenzotriazol-1-yl)-1,1,3,3-tetramethyluronium hexafluorophosphate] (0.468.g, 1.25 mmol) was added, and the reaction mixture was allowed to warm to rt. The DMF was then removed in vacuo, the residue was dissolved with EtOAc, and the organic phase was washed consecutively with 10% HCl solution, sat $NaHCO_3$, $H_2O$, and brine. The organic phase was dried over $MgSO_4$, filtered, and concentrated to give a residue which was purified by column chromatography on silica gel using a gradient solvent system (0–1% MeOH/CHCl$_3$) to yield 0.76 g (81%) of a white amorphous solid: IR (KBr) 3308, 2937, 1695, 1677, 1506, 1493, 1448, 1367, 1246, 1165, 700 cm$^{-1}$; $^1$H NMR (DMSO-d$_6$) δ 1.07 (s, 3H), 1.19 (s, 3H), 1.37 (s, 9H), 1.66–1.75 (m, 2H), 1.94 (s, 3H), 2.19–2.25 (m, 2H), 2.78–2.83 (m, 1H), 2.95–3.01 (m, 1H), 3.06–3.12 (m, 1H), 3.19–3.23 (m, 1H), 3.62–3.65 (m, 1H), 4.12 (d, 1H, J=3.0 Hz), 4.48–4.55 (m, 1H), 4.59–4.62 (m, 1H), 6.50 (d, 1H, J=9.0 Hz), 7.14–7.28 (m, 20H), 7.62 (d, 1H, J=6.0 Hz), 8.21 (d, 1H, J=6.0 Hz), 8.47 (s, 1H). MS calcd for $C_{44}H_{54}N_4O_6S+H$ 767, found 767.

Preparation of Intermediate L-(S-Me-Pen)-L-Phe-L-Tr-Glutaminol) Hydrochloride Salt.

To a solution of BOC-L-(S-Me-Pen)-L-Phe-L-(Tr-glutaminol) (0.69 g, 0.91 mmol) in 6 mL of 1,4-dioxane was added 4 mL of 4M HCl/1,4-dioxane. The reaction mixture was stirred at rt for 3 h under an argon atmosphere. At this time the solvent was removed in vacuo to give 0.61 g (97%) of a white solid which was used without further purification: IR (KBr) 3313, 3057, 2926, 1664, 1493, 1448, 750, 700 cm$^{-1}$; $^1$H NMR (DMSO-d$_6$) δ 1.18 (s, 3H), 1.39 (s, 3H), 1.66–1.78 (m, 2H), 2.01 (s, 3H), 2.06–2.15 (m, 1H), 2.27–2.39 (m, 1H), 2.83–3.08 (m, 2H), 3.14–3.29 (m, 2H), 3.33–3.40 (m, 3H), 3.59–3.68 (m, 1H), 3.84–3.89 (m, 1H), 7.13–7.27 (m, 20H), 7.91 (d, 1H, J=9.0 Hz), 8.15–8.26 (m, 2H), 8.52 (s, 1H), 8.76 (d, 1H, J=6.0 Hz).

Preparation of Intermediate Cyclopentylthiocarbonyl-L-(S-Me-Pen)-L-Phe-L-(Tr-Glutaminol).

A solution of cyclopentyl chlorothiolformate (0.133 g, 0.81 mmol), prepared as described in Example 37, in 2 mL of $CH_2Cl_2$ was added dropwise to a solution of L-(S-Me-Pen)-L-Phe-L-(Tr-glutaminol) hydrochloride salt (0.57 g, 0.81 mmol) in 10 mL of $CH_2Cl_2$. To this solution was added 0.24 mL(7 mmol) of $Et_3N$. The reaction mixture was stirred for 15 min at rt, and the solvent was removed under vacuum. The residue was purified by column chromatography on silica gel chromatography using a gradient solvent system (0–2% MeOH/CHCl$_3$) to give 0.512 g (80%) of a white amorphous solid: IR (KBr) 3358, 2939, 1649, 1516, 1448, 1190, 700 cm$^{-1}$; $^1$H NMR (DMSO-d$_6$) δ 1.13 (s, 3H), 1.23 (s, 3H), 1.37–1.63 (m, 10H), 1.96 (s, 3H), 1.98–2.01 (m, 1H), 2.16–2.33 (m, 1H), 2.7–2.89 (m, 1H), 3.07–3.23 (m, 2H), 3.24–3.28 (m, 1H), 3.53–3.57 (m, 1H), 3.59–3.66 (m, 1H), 4.37–4.47 (m, 1H), 4.54–4.60 (m, 2H), 7.14–7.28 (m, 20H), 7.55 (d, 1H, J=9.0 Hz), 7.99 (d, 1H, J=9.0 Hz), 8.36 (d, 1H, J=6.0 Hz), 8.49 (s, 1H). MS calcd for $C_{45}H_{54}N_4O_5S_2+H$ 795, found 795.

Preparation of Intermediates Cyclopentylthiocarbonyl-L-(S-Me-Pen)-L-Phe-L-(Tr-Glutaminal) & Cyclopentylthiocarbonyl-L-[S(O)-Me-Pen]-L-Phe-L-(Tr-Glutaminal).

Cyclopentylthiocarbonyl-L-(S-Me-Pen)-L-Phe-L-(Tr-glutaminol) (0.46 g, 0.58 mmol) was dissolved in 10 mL of anh DMSO. o-Iodoxybenzoic acid (0.48 g, 1.73 mmol) was added, and the reaction mixture was stirred at rt for 3 h. The DMSO was removed under high vacuum. The residue was twice diluted with $CH_2Cl_2$ and the solvent was evaporated to remove any residual DMSO. The residue was diluted with EtOAc, and triturated to form a white solid which was filtered off. The filtrate was washed with an aq 10% $Na_2S_2O_3$/10% NaHCO$_3$ solution, water and brine and dried over $MgSO_4$. Filtration and concentration gave 0.40 g (87%) of a white glassy solid which was used without further purification. The product was shown to be a mixture of the sulfide and sulfoxide by NMR analysis. $^1$H NMR (DMSO$_6$) (mixture of sulfide and sulfoxide) δ 1.12 (s), 1.24 (s), 1.32 (s), 1.45–1.66 (m), 1.95–2.13 (m), 2.29 (s), 2.40 (s), 2.53 (s), 2.82–2.87 (m), 2.99–3.23 (m), 3.52–3.57 (m), 3.95–4.03 (m), 4.55–4.83 (m), 7.14–7.28 (m), 7.89–8.06 (m), 8.41–8.58 (m), 9.15 (s), 9.18 (s).

Preparation of Intermediates Ethyl-3-[Cyclopentylthiocarbonyl-L-(S-Me-Pen)-L-Phe-L-(Tr-Gln)]-E-Propenoate & Ethyl-3-(Cyclopentylthiocarbonyl-L-[S(O)-Me-Pen]-L-Phe-L-[Tr-Gln])-E-Propenoate.

The mixture of cyclopentylthiocarbonyl-L-(S-Me-Pen)-L-Phe-L-(Tr-glutaminal) and cyclopentylthiocarbonyl-L-[S(O)-Me-Pen]-L-Phe-L-(Tr-glutaminal) (0.40 g, approximately 0.51 mmol) was dissolved in 10 mL of anh THF. To this solution was added (carbethoxymethylene) triphenylphosphorane (0.21 g, 0.61 mmol), and the reaction mixture was stirred overnight at rt. The solvent was removed in vacuo, and the residue was purified by column chromatography on silica gel using a gradient solvent system (0–2% MeOH/CHCl$_3$) to give 0.184 g of the sulfide product and 0.132 g sulfoxide product (contaminated with triphenylphosphine oxide): Ethyl-3-[cyclopentylthiocarbonyl-L-(S-Me-Pen)-L-Phe-L-(Tr-Gln)]-E-propenoate: $^1$H NMR (DMSO-d$_6$) δ 1.14 (s, 3H), 1.21 (t, 3H, J=6.0 Hz), 1.24 (s, 3H), 1.46–1.68 (m, 10H), 1.96 (s, 3H), 2.25–2.31 (m, 2H), 2.78–2.85 (m, 1H), 2.96–3.00 (m, 1H), 3.54–3.72 (m, 1H), 4.05–4.13 (m, 2H), 4.32–4.47 (m, 1H), 4.49–4.55 (m, 1H), 4.56–4.59 (m, 1H), 5.57 (d, 1H, J=15.0 Hz), 6.64 (dd, 1H, J=15.0, 3.0 Hz), 7.13–7.26 (m, 20H), 7.99–8.04 (m, 2H), 8.45 (d, 1H, J=9.0 Hz), 8.55 (s, 1H). Ethyl-3-(cyclopentylthiocarbonyl-L-[S(O)-Me-Pen]-L-Phe-L-[Tr- Gln])-E-propenoate: $^1$H NMR (DMSO-$d_6$) (mixture of diastereomers): δ 1.11–1.15 (m), 1.19–1.23 (m), 1.35–1.66 (m), 1.98–2.00 (m), 2.18–2.35 (m), 2.41 (s), 2.64–2.83 (m), 2.89–3.02 (m), 3.51–3.56 (m), 4.11 (q, J=6.0 Hz), 4.34–4.40 (m), 4.48–4.59 (m), 4.63–4.66 (m), 5.51–5.57 (m), 6.61–6.68 (m), 7.13–7.28 (m), 8.12–8.24 (m), 8.42–8.53 (m), 8.55–8.57 (m).

Preparation of Product—Ethyl-3-[Cyclopentylthiocarbonyl-L-(S-Me-Pen)-L-Phe-L-Gln]-E-Propenoate Ethyl-3 -[cyclopentylthiocarbonyl-L-(S-Me-Pen)-L-Phe-L-(Tr-Gln)]-E-propenoate (0.184 g) was dissolved in 10 mL $CH_2Cl_2$. To this solution was added 1 mL of trifluoroacetic acid, and the reaction mixture was stirred at rt overnight. The solvent was removed under vacuum and the residue was purified by column chromatography on silica gel using a gradient solvent system (0–2% MeOH/CHCl$_3$) to give 0.044 g (24%; 3 steps from cyclopentylthiocarbonyl-L-(S-Me-Pen)-L-Phe-L-(Tr-glutaminol)) as a white amorphous solid: IR (KBr) 3296, 2984, 1787, 1655, 1560, 1541, 1280, 1194 cm$^{-1}$; $^1$H NMR (DMSO-$d_6$) δ 1.14 (s, 3H), 1.21 (t, 3H, J=6.0 Hz), 1.25 (s, 3H), 1.40–1.70 (m, 10H), 2.02 (s, 3H), 2.05–2.24 (m, 2H), 2.79–2.86 (m, 1H), 2.93–3.00 (m, 1H), 3.43–3.55 (m, 1H), 4.09 (q, 2H, J=6.0 Hz), 4.31–4.36 (m, 1H), 4.43–4.50 (m, 1H), 4.56 (d, 1H, J=6.0 Hz), 5.58 (d, 1H, J=15.0 Hz), 6.65 (dd, 1H, J=15.0, 6.0 Hz), 6.75 (bs, 1H), 7.15–7.21 (m, 6H), 7.99–8.06 (m, 2H), 8.45 (d, 1H, J=6.0 Hz). HRMS calcd for $C_{30}H_{44}N_4O_6S_2$+Cs 753.1757, found 753.1737. Anal. ($C_{30}H_{44}N_4O_6S_2$) C, H, N, S.

Example 37—Preparation of Compound 173: Ethyl-3-[Cyclopentylthiocarbonyl-L-(S-Ph-Cys)-L-Phe-L-Gln]-E-Propenoate.

Preparation of Intermediate Cyclopentyl Chlorothiolformate.

Cyclopentanethiol (10.7 mL, 0.1 mol) was dissolved in 200 mL of $CH_2Cl_2$. Triphosgene (11.13 g, 37.5 mmol) was added and the reaction mixture was cooled to 0° C. Et$_3$N (14.1 mL, 0.1 mol) was added dropwise, and the reaction was allowed to warm to room temperature over a period of one hour. The solvent was carefully removed under reduced pressure at 20° C. due to the volatility of the product. The resulting residue was taken up in Et$_2$O, and the solids were filtered and washed with more Et$_2$O. The solvent was again carefully removed under reduced pressure, and the was product purified by distillation (85% yield): colorless liquid (bp 70°–74° C.; 1 torr): IR(neat) 1756, 830 cm$^{-1}$; $^1$H NMR (benzene-$d_6$) δ 1.01–1.23 (m, 6H), 1.49–1.60 (m, 2H), 3.20–3.29 (m, 1H).

Preparation of Intermediate BOC-L-(S-Ph-Cys).

To a suspension of 19.73 g (0.1 mol) L-(S-Ph-Cys) (purchased from Davos Chemical Corp., Englewood Cliffs, N.J.) in 72 mL of tert-butanol was added a solution of NaOH (4.1 g, 0.1025 mol) in 100 mL $H_2O$. Once the suspension became a clear solution di-tert-butyl dicarbonate (22.92 g, 0.105 mol) was added. The clear solution became a slurry and was allowed to stir at rt overnight. At this time the turbid solution was washed twice with pet. ether. The organic layer was washed 3 times with a sat NaHCO$_3$ solution and the aqueous layers were combined. The aqueous layer was then carefully acidified to pH 2-3 with a sat KHSO$_4$ solution and extracted with a large excess of EGO. The organic phase was dried over Na$_2$SO$_4$, filtered and concentrated under vacuum to give 27.4 g (92%) of BOC-L-(S-Ph-Cys) as white solid. Any residual $H_2O$ and/or tert-butanol was removed by benzene azeotrope before using the material. $^1$H NMR (DMSO-$d_6$) δ 1.36 (s, 9H), 3.10 (dd, 1H, J=13.6, 9.6 Hz), 3.34 (dd, 1H, J=13.6, 4.4 Hz), 4.01 (m, 1H), 7.20 (m, 2H), 7.34 (m, 3H), 12.82 (bs, 1H).

Preparation of Intermediate BOC-L-(S-Ph-Cys)-L-Phe-L-(Tr-glutaminol).

BOC-L-(S-Ph-Cys) (0.45 g, 1.5 mmol) was dissolved in 2 mL of DMF and 2 mL of $CH_2Cl_2$. To this solution was added N-hydroxysuccinimide (0.17 g, 1.5 mmol), followed by dicyclohexylcarbodiimide (0.31 g, 1.5 mmol). The reaction was stirred at rt for 2 h. The mixture was then filtered into a separate flask containing L-Phe-L-(Tr-glutaminol) (0.78 g, 1.5 mmol) dissolved in 4 mL of DMF and 2 mL of $CH_2Cl_2$. The reaction mixture was stirred overnight and the solvent was removed in vacuo. The residue was purified by column chromatography on silica gel using a gradient solvent system (0–2% MeOH/CHCl$_3$) to give 1.06 g (88%) of a white amorphous solid: IR (KBr) 3304, 3061, 2972, 2928, 1645, 1516, 1493, 1367, 1248, 1165, 1024, 742, 698 cm$^{-1}$; $^1$H NMR (DMSO-$d_6$) δ 1.35 (s, 9H), 1.35–1.43 (m, 1H), 1.70–1.74 (m, 1H), 2.20–2.33 (m, 2H), 2.82–2.92 (m, 1H), 2.93–3.10 (m, 1H), 3.11–3.23 (m, 2H), 3.24–3.32 (m, 2H), 3.58–3.68 (m, 1H), 3.80–3.98 (m, 1H), 4.58–4.64 (m, 1H), 4.65–4.77 (m, 1H), 7.14–7.30 (m, 26H), 7.75 (d, 1H, J=6.0 Hz), 7.83 (d, 1H, J=6.0 Hz), 8.51 (s, 1H). MS calcd for $C_{47}H_{52}N_4O_6S$+H 801, found 801.

Preparation of Intermediate L-(S-Ph-Cys)-L-Phe-L-(Tr-glutaminol) Hydrochloride Salt.

Using the procedure described in Example 36 for the preparation of L-(S-Me-Pen)-L-Phe-L-(Tr-glutaminol) hydrochloride salt, L-(S-Ph-Cys)-L-Phe-L-(Tr-glutaminol) hydrochloride salt was synthesized from BOC-L-(S-Ph-Cys)-L-Phe-L-(Tr-glutaminol) to give 0.182 g of white solid which was used without further purification: IR (KBr) 3325, 3057, 2949, 1685, 1655, 1560, 1493, 1448, 746, 700 cm$^{-1}$; $^1$H NMR (DMSO-$d_6$) δ 1.41–1.67 (m, 1H), 1.69–1.81 (m, 1H), 2.26–2.44 (m, 2H), 2.86–2.97 (m, 1H), 2.98–3.23 (m, 1H), 3.25–3.43 (m, 4H), 3.60–3.84 (m, 2H), 4.02–4.20 (m, 1H), 4.44–4.60 (m, 1H), 7.08–7.48 (m, 25H), 7.87 (d, 1H, J=6.0 Hz), 8.46 (bs, 3H), 8.55 (s, 1H), 8.87 (d, 1H, J=6.0 Hz).

Preparation of Intermediate Cyclopentylthiocarbonyl-L-(S-Ph-Cys)-L-Phe-L-(Tr-Glutaminol).

Using the procedure described in Example 36 for the preparation of cyclopentylthiocarbonyl-L-(S-Me-Pen)-L-Phe-L-(Tr-glutaminol), cyclopentylthiocarbonyl-L-(S-Ph-Cys)-L-Phe-L-(Tr-glutaminol) was synthesized from L-(S-Ph-Cys)-L-Phe-L-(Tr-glutaminol) hydrochloride salt in 75% yield: white amorphous solid: IR (KBr) 3288, 3059, 2960, 1637, 1494, 1448, 1205, 746, 700 cm$^{-1}$; $^1$H NMR (DMSO-$d_6$) δ 1.42–1.98 (m, 10H), 1.99–2.26 (m, 1H), 2.48–2.50 (m, 1H), 2.96–2.98 (m, 1H), 3.01–3.19 (m, 1H), 3.19–3.55 (m, 6H), 3.64–3.85 (m, 1H), 4.36–4.40 (m, 1H), 4.46–4.58 (m, 1H), 7.14–7.30 (m, 25H), 7.68 (d, 1H, J=6.0 Hz), 8.01 (d, 1H, J=6.0 Hz), 8.41 (d, 1H, J=6.0 Hz), 8.52 (s, 1H). MS calcd for $C_{48}H_{52}N_4O_5S_2$+H 829, found 829.

Preparation of Intermediate Cyclopentylthiocarbonyl-L-(S-Ph-Cys)-L-Phe-L-(Tr-Glutaminal).

Using the procedure described in Example 36 for the preparation of cyclopentylthiocarbonyl-L-(S-Me-Pen)-L-

Phe-L-(Tr-glutaminal) and cyclopentylthiocarbonyl-L-[S(O)-Me-Pen]-L-Phe-L-(Tr-glutaminal), cyclopentylthiocarbonyl-L-(S-Ph-Cys)-L-Phe-L-(Tr-glutaminal) was synthesized from cyclopentylthiocarbonyl-L-(S-Ph-Cys)-L-Phe-L-(Tr-glutaminol) in 98% yield: white amorphous solid used without further purification: $^1$H NMR (DMSO-d$_6$) δ 1.45–1.70 (m, 8H), 2.02–2.28 (m, 3H), 2.35–2.51 (m, 1H), 2.95–3.02 (m, 2H), 3.04–3.22 (m, 1H), 3.24–3.36 (m, 1H), 3.56–3.59 (m, 1H), 4.02–4.08 (m, 1H), 4.47–4.59 (m, 1H), 4.60–4.80 (m, 1H), 7.20–7.36 (m, 25H), 8.22 (d, 1H, J=6.0 Hz), 8.43–8.48 (m, 2H), 8.65 (s, 1H), 9.27 (s, 1H).

Preparation of Intermediate Ethyl-3-[Cyclopentylthiocarbonyl-L-(S-Ph-Cys)-L-Phe-L-(Tr-Gln)]-E-Propenoate.

Using the procedure described in Example 1 for the preparation of ethyl-3-[CBZ-L-Leu-L-Phe-L-Met(sulfoxide)]-E-propenoate, ethyl-3-[cyclopentylthiocarbonyl-L-(S-Ph-Cys)-L-Phe-L-(Tr-Gln)]-E-propenoate was synthesized from cyclopentylthiocarbonyl-L-(S-Ph-Cys)-L-Phe-L-(Tr-glutaminal) to give 0.26 g of material contaminated with triphenylphosphine oxide (after column chromatography) which was used without further purification: $^1$H NMR (DMSO-d$_6$) δ 1.19 (t, 3H, J=6.0 Hz), 1.47–1.59 (m, 10H), 1.93–2.23 (m, 1H), 2.25–2.34 (m, 1H), 2.83–2.93 (m, 1H), 2.95–3.16 (m, 1H), 3.19–3.29 (m, 2H), 3.51–3.56 (m, 1H), 4.09 (q, 2H, J=6.0 Hz), 4.35–4.44 (m, 2H), 4.46–4.48 (m, 1H), 5.64 (d, 1H, J=15.0 Hz), 6.68 (dd, 1H, J=15.0, 3.0 Hz), 7.13–7.29 (m, 25H), 8.07 (d, 1H, J=6.0 Hz), 8.13 (d, 1H, J=6.0 Hz), 8.42 (d, 1H, J=6.0 Hz), 8.58 (s, 1H).

Preparation of Product—Ethyl-3-[Cyclopentylthiocarbonyl-L-(S-Ph-Cys)-L-Phe-L-Gln]-E-Propenoate.

Using the procedure described in Example 34 for the preparation of ethyl-3-[ethylthiocarbonyl-L-α-(t-butyl-Gly)-L-Phe-L-Gln]-E-propenoate, ethyl-3-[cyclopentylthiocarbonyl-L-(S-Ph-Cys)-L-Phe-L-Gln]-E-propenoate was synthesized from ethyl-3-[cyclopentylthiocarbonyl-L-(S-Ph-Cys)-L-Phe-L-(Tr-Gln)]-E-propenoate in 35% yield (2 steps from cyclopentylthiocarbonyl-L-(S-Ph-Cys)-L-Phe-L-(Tr-glutaminal)): white amorphous solid: IR (Pr) 3294, 1712, 1655, 1633, 1545, 1203, 738, 700 cm$^{-1}$; $^1$H NMR (DMSO-d$_6$) δ 1.19 (t, 3H, J=6.0 Hz), 1.56–1.76 (m, 10H), 1.98–2.08 (m, 2H), 2.84–2.99 (m, 2H), 3.17–3.39 (m, 2H), 3.51–3.76 (m, 1H), 4.08 (q, 2H, J=6.0 Hz), 4.39–4.45 (m, 3H), 5.64 (d, 1H, J=15.0 Hz), 6.69 (dd, 1H, J=15.0, 3.0 Hz), 6.77 (bs, 1H), 7.18–7.32 (m, 11H), 8.08 (d, 1H, J=6.0 Hz), 8.18 (d, 1H, J=6.0 Hz), 8.43 (d, 1H, J=6.0 Hz). HRMS calcd for C$_{33}$H$_{42}$N$_4$O$_6$S$_2$+Cs 787.1600, found 787.1618. Anal. (C$_{33}$H$_{42}$N$_4$O$_6$S$_2$) C, H, N, S.

Example 38—Preparation of Compound 174: Ethyl-3-[Cyclopentylthiocarbonyl-L-α-(t-Butyl-Gly)-L-(4-Me-Phe)-L-Gln]-E-Propenoate.

Preparation of Intermediate Fmoc-L-(4-Me-Phe)-L-(Tr-Glutaminol).

Using the procedure described in Example 1 for the preparation of CBZ-L-Leu-L-Phe-L-methioninol, this derivative was synthesized from Fmoc-L-4-Me-Phe (purchased from Neosystems Laboratories, Strasbourg, France) and L-(Tr-glutaminol) in 85% yield and isolated as a white solid. IR (KBr) 3316, 3283, 3024, 2946, 1694, 1667, 1448, 1256, 1041, 760, 700 cm$^{-1}$; $^1$H NMR (DMSO-d$_6$) δ 1.56 (m, 1H), 1.77 (m, 1H), 2.22 (s, 3H), 2.26 (m, 2H), 2.74 (m, 1H), 2.90 (m, 1H), 3.17 (m, 1H), 3.69 (m, 1H), 4.03–4.23 (m, 4H), 7.03–7.54 (m, 21H), 7.39 (t, 2H, J=7.4 Hz), 7.50 (d, 1H, J=8.5 Hz), 7.59 (d, 1H, J=7.4 Hz), 7.60 (d, 1H, J=7.7 Hz), 7.70 (d, 1H, J=8.8 Hz), 7.87 (d, 2H, J=7.4 Hz), 8.45 (s, 1H); MS calcd for C$_{49}$H$_{47}$N$_3$O$_5$+Cs 890, found 890.

Preparation of Intermediate L-(4-Me-Phe)-L-(Tr-Glutaminol).

To a solution of Fmoc-L-(4-Me-Phe)-L-(Tr-glutaminol) (3.25 g, 4.29 mmol) in anh DMF (10 mL) was added piperidine (0.51 mL, 5.15 mmol). The solution was stirred and monitored by TLC. Upon consumption of the starting material, the reaction mixture was concentrated to a residue and then subjected to column chromatography on silica gel (5% MeOH/CH$_2$Cl$_2$) to afford the product as white solid in 87% yield. IR (KBr) 3326, 3054, 3030, 2953, 2872, 1651, 1516, 1491, 1447, 1036, 700 cm$^{-1}$; $^1$H NMR (DMSO-d$_6$) δ 1.47 (m, 1H), 1.75 (m, 3H), 2.13 (m, 1H), 2.23 (s, 3H), 2.57 (dd, 1H, J=13.2, 8.1 Hz), 2.88 (dd, 1H, J=13.6, 4.8 Hz), 3.20 (m, 1H), 3.30 (m, 1H), 3.66 (m, 1H), 4.64 (t, 1H, J=5.5 Hz), 7.07 (m, 4H), 7.10–7.28 (m, 15H), 7.62 (d, 1H, J=8.8 Hz), 8.54 (s, 1H); MS calcd for C$_{34}$H$_{37}$N$_3$O$_3$+Na 558, found 558.

Preparation of Intermediate Cyclopentylthiocarbonyl-L-α-(t-Butyl-Gly).

A stirred suspension of L-α-(t-butyl-Gly) (0.656 g, 5.0 mmol) in 18 mL CH$_2$Cl$_2$, and diisopropylethylamine (3.5 mL, 20 mmol) was cooled to 0° C. To this mixture chlorotrimethylsilane (0.83 mL, 6.5 mmol) was added dropwise. The slurry was allowed to warm to rt, and the mixture was stirred for about 2 h. At this time the mixture was recooled to 0° C., and cyclopentyl chlorothiolformate (0.823 g, 5.0 mmol) was added dropwise. The slurry became a pale yellow solution after stirring at rt for approximately 5 h. The solution was concentrated, redissolved in an excess of EtOAc and washed with H$_2$O, 10% aq KHSO$_4$, H$_2$O and brine. The organic phase was dried over MgSO$_4$, filtered and concentrated to give cyclopentylthiocarbonyl-L-α-(t-butyl-Gly) as a yellow oil in nearly quantitative yield which was azeotroped with benzene to remove any residual water before being used in the next step. IR (film) 3324, 2965, 2920, 2872, 1726, 1642, 1518, 1202 cm$^{-1}$; $^1$H NMR (CDCl$_3$) δ 1.03 (s, 9H), 1.48–1.73 (m, 6H), 2.10 (m, 2H), 3.72 (m, 1H), 4.46 (m, 1H), 5.79 (m, 1H); MS calcd for C$_{12}$H$_{21}$NO$_3$S+Na 282, found 282.

Preparation of Intermediate Cyclopentylthiocarbonyl-L-α-(t-Butyl-Gly)-L-(4-Me-Phe)-L-(Tr-Glutaminol).

This preparation was carried out following the procedure of L. A. Carpino, *J. Am. Chem. Soc.* 1993, 115, 4397. Cyclopentylthiocarbonyl-L-α-(t-butyl-Gly) (0.325 g, 1.25 mmol) was dissolved in 8.0 mL of DMF. Diisopropylethylamine (0.45 mL, 2.5 mmol) was added, followed by 0.67 g (1.25 mmol) of N-Me-L-(4-Me-Phe)-L-(Tr-glutaminol). The reaction was cooled to 0° C. and O-(7-azabenzotriazol-1-yl)-1,1,3,3-tetramethyluronium hexafluorophosphate (HATU) (0.476 g, 1.25 mmol) was added. The reaction mixture was allowed to warm to rt whereupon the DMF was removed in vacuo. The residue was dissolved with EtOAc, and the organic phase washed consecutively with 1N HCl, a sat NaHCO$_3$ solution, H$_2$O, and brine. The solvent was dried over MgSO$_4$, filtered, and concentrated to give a residue which was subjected to column chromatography on silica gel (gradient; 2–5% MeOH/CHCl$_3$) to give 0.95 g (98%) of a white amorphous solid: IR(KBr) 3302, 2957, 2876, 1669, 1645, 1537, 1447, 1196, 700 cm$^{-1}$; $^1$H NMR (CDCl$_3$) δ 0.88 (s, 9H), 1.48–1.70 (m, 9H), 1.85 (m, 1H), 2.04 (m, 2H), 2.28 (s, 3H), 2.32 (m, 2H), 2.92 (m, 2H), 3.25 (dd, 1H, J=8.1, 3.5 Hz), 3.30 (dd, 1H, J=10.9, 3.7 Hz), 3.66 (m, 1H), 3.72 (m, 1H), 4.14 (m, 1H), 4.47 (m, 1H), 6.04 (d, 1H, J=7.7 Hz), 6.52 (d, 1H, J=7.7 Hz), 6.60 (d, 1H, J=7.0Hz), 7.05 (m, 5H), 7.24 (m, 15H). MS calcd for C$_{46}$H$_{56}$N$_4$O$_5$S+Na 799, found 799.

Preparation of Intermediate Cyclopentylthiocarbonyl-L-α-(t-Butyl-Gly)-L-(4-Me-Phe)-L-(Tr-Glutaminal).

Using the general procedure described in Example 1 for the preparation of CBZ-L-Leu-L-Phe-L-methioninal (sulfoxide), cyclopentylthiocarbonyl-L-α-(t-butyl-Gly)-L-(4-Me-Phe)-L-(Tr-glutaminal) was synthesized from cyclopentylthiocarbonyl-L-α-(t-butyl-Gly)-L-(4-Me-Phe)-L-(Tr-glutaminol) in quantitative yield and isolated as a white amorphous solid and used without further purification: IR(film) 3302, 3061, 3030, 2961, 2870, 1730, 1644, 1514, 1493, 1196, 911, 733, 700 cm$^{-1}$; $^1$H NMR (CDCl$_3$) δ 0.90 (s, 9H), 1.46–1.68 (m, 8H), 1.86 (m, 1H), 2.00–2.24 (m, 2H), 2.28 (s, 3H), 2.31 (m, 1H), 2.96 (m, 2H), 3.58 (m, 1H), 4.05 (m, 1H), 4.14 (m, 1H), 4.52 (m, 1H), 5.88 (m, 1H), 6.28 (m, 1H), 6.90 (m, 1H), 7.07 (m, 5H), 7.25 (m, 15H), 9.30 (s, 1H); MS calcd for C$_{46}$H$_{54}$N$_4$O$_5$S.CH$_3$OH (methylhemiacetal)+Na 829, found 829.

Preparation of Intermediate Ethyl-3-[Cyclopentylthiocarbonyl-L-α-(t-Butyl-Gly)-L-(4-Me-Phe)-L-(Tr-Gln)]-E-Propenoate.

Using the procedure described in Example 1 for the preparation of ethyl-3-[CBZ-L-Leu-L-Phe-L-Met (sulfoxide)]-E-propenoate, ethyl-3-[cyclopentylthiocarbonyl-L-α-(t-butyl-Gly)-L-(4-Me-Phe)-L-(Tr-Gln)]-E-propenoate was synthesized from cyclopentylthiocarbonyl-L-α-(t-butyl-Gly)-L-(4-Me-Phe)-L-(Tr-glutaminal) (0.468 g, 0.627 mmol) to give 0.52 g of material contaminated with triphenylphosphine oxide after column chromatography on silica gel (gradient: 1–2.5% MeOH/CH$_2$Cl$_2$), which was used without further purification: white amorphous solid: IR(film) 3302, 3061, 2967, 2868, 1721, 1642, 1514, 1491, 1370, 1192, 1036, 911, 731, 700 cm$^{-1}$; $^1$H NMR (CDCl$_3$) δ 0.72 (s, 9H), 1.29 (t, 3H, J=7.0 Hz), 1.46–1.68 (m, 6H), 1.86–2.05 (m, 4H), 2.29 (s, 3H), 2.32 (m, 2H), 2.91 (m, 2H), 3.00 (m, 1H), 3.62 (m, 1H), 4.07 (m, 1H), 4.17 (q, 2H, J=7.2 Hz), 4.43 (m, 2H), 5.61 (dd, 1H, J =15.8, 1.5 Hz), 5.95 (m, 1H), 6.34 (m, 1H), 6.57 (m, 1H), 6.64 (dd, 1H, J=15.8, 5.5 Hz), 7.03 (m, 5H), 7.24 (m, 15H). MS calcd for C$_{50}$H$_{60}$N$_4$O$_6$S+Na 867, found 867.

Preparation of Product—Ethyl-3-[Cyclopentylthiocarbonyl-L-α-(t-Butyl-Gly)-L-(4-Me-Phe)-L-Gln]-E-Propenoate.

Using the procedure described in Example 34 for the preparation of ethyl-3-[ethylthiocarbonyl-L-α-(t-butyl-Gly)-L-Phe-L-Gln]-E-propenoate, ethyl-3-[cyclopentylthiocarbonyl-L-α-(t-butyl-Gly)-L-(4-Me-Phe)-L-Gln]-E-propenoate was synthesized from ethyl-3-[cyclopentylthiocarbonyl-L-α-(t-butyl-Gly)-L-(4-Me-Phe)-L-(Tr-Gln)]-E-propenoate and isolated as a white solid after purification by column chromatography on silica gel using a gradient solvent system (1–5% MeOH/CH$_2$Cl$_2$) (57% yield; two steps from cyclopentylthiocarbonyl-L-α-(t-butyl-Gly)-L-(4-Me-Phe)-L-(Tr-glutaminal): IR (KBr) 3318, 2973, 2951, 2868, 1715, 1651, 1539, 1371, 1192 cm$^{-1}$; $^1$H NMR (DMSO-d$_6$) δ 0.83 (s, 9H), 1.21 (t, 3H, J=7.2 Hz), 1.41–1.72 (m, 8H), 2.02 (m, 4H), 2.22 (s, 3H), 2.81 (m, 2H), 3.54 (m, 1H), 4.10 (q, 2H, J=7.0 Hz), 4.24 (d, 1H, J=9.3 Hz), 4.36 (m, 1H), 4.43 (m, 1H), 5.56 (dd, 1H, J=15.7, 1.4 Hz), 6.65 (dd, 1H, J=15.7, 5.5 Hz), 6.73 (s, 1H), 7.03 (m, 4H), 7.13 (s, 1H), 7.86 (d, 1H, J=9.3 Hz), 8.04 (d, 1H, J=8.4 Hz), 8.12 (d, 1H, J=7.8 Hz); HRMS calcd for C$_{31}$H$_{46}$N$_4$O$_6$S+Cs 735.2192, found 735.2180. Anal. (C$_{31}$H$_{46}$N$_4$O$_6$S) C, H, N, S.

Example 39—Preparation of Compound 175: Ethyl-2-Methyl-3-[Cyclopentylthiocarbonyl-L-α-(t-Butyl-Gly)-L-(4-Me-Phe)-L-Gln]-E-Propenoate.

Preparation of Intermediate Ethyl-2-Methyl-3-[Cyclopentylthiocarbonyl-L-α-(t-Butyl-Gly)-L-(4-Me-Phe)-L-(Tr-Gln)]-E-Propenoate.

Using the procedure described in Example 1 for the preparation of ethyl-3-[CBZ-L-Leu-L-Phe-L-Met (sulfoxide)]-E-propenoate, ethyl-2-methyl-3-[cyclopentylthiocarbonyl-L-α-(t-butyl-Gly)-L-(4-Me-Phe)-L-(Tr-Gln)]-E-propenoate was synthesized from cyclopentylthiocarbonyl-L-α-(t-butyl-Gly)-L-(4-Me-Phe)-L-(Tr-glutaminal) (0.466 g, 0.60 mmol) and (carbethoxyethylidene)triphenylphosphorane (0.24 g, 0.66 mmol) to give 0.487 g of material contaminated with triphenylphosphine oxide after column chromatography on silica gel (gradient: 1–2.5% MeOH/CH$_2$Cl$_2$) which was used without further purification. white amorphous solid: IR(film) 3302, 3063, 2967, 2870, 1711, 1642, 1516, 1491, 1250, 1194, 911, 731, 698 cm$^{-1}$; $^1$H NMR (CDCl$_3$) δ 0.88 (s, 9H), 1.31 (t, 3H, J=7.2 Hz), 1.50–1.77 (m, 6H), 1.81 (m, 2H), 1.82 (s, 3H), 2.06 (m, 2H), 2.28 (s, 3H), 2.31 (m, 2H), 2.93 (m, 2H), 3.64 (m, 1H), 4.04 (m, 1H), 4.20 (q, 2H, J=7.0 Hz), 4.40 (m, 1H), 4.58 (m, 1H), 5.90 (m, 1H), 6.30 (m, 3H), 7.01 (m, 5H), 7.24 (m, 15H). MS calcd for C$_{51}$H$_{62}$N$_4$O$_6$S+Na 881, found 881.

Preparation of Product—Ethyl-2-Methyl-3-[Cyclopentylthiocarbonyl-L-α-(t-Butyl-Gly)-L-(4-Me-Phe)-L-Gln]-E-Propenoate.

Using the procedure described in Example 34 for the preparation of ethyl-3-[ethylthiocarbonyl-L-α-(t-butyl-Gly)-L-Phe-L-Gln]-E-propenoate, ethyl-2-methyl-3-[cyclopentylthiocarbonyl-L-α-(t-butyl-Gly)-L-(4-Me-Phe)-L-Gln]-E-propenoate was synthesized from ethyl-2-methyl-3-[cyclopentylthiocarbonyl-L-α-(t-butyl-Gly)-L-(4-Me-Phe)-L-(Tr-Gln)]-E-propenoate and isolated as a white solid after purification by column chromatography on silica gel using a gradient solvent system (1–5% MeOH/CH$_2$Cl$_2$) (55% yield; two steps from cyclopentylthiocarbonyl-L-α-(t-butyl-Gly)-L-(4-Me-Phe)-L-(Tr-glutaminal): IR (KBr) 3324, 2963, 2870, 1707, 1647, 1550, 1516, 1257, 1196 cm$^{-1}$; $^1$H NMR (DMSO-d$_6$) δ 0.83 (s, 9H), 1.22 (t, 3H, J=7.2 Hz), 1.41–1.73 (m, 8H), 1.77 (m, 3H), 2.00 (m, 4H), 2.20 (s, 3H), 2.78 (m, 2H), 3.55 (m, 1H), 4.12 (q, 2H, J=7.0 Hz), 4.23 (d, 1H, J=9.0 Hz), 4.35 (m, 1H), 4.48 (m, 1H), 6.29 (dd, 1H, J=9.3, 1.2 Hz), 6.72 (s, 1H), 6.99 (m, 4H), 7.13 (s, 1H), 7.86 (d, 1H, J=9.0 Hz), 8.03 (m, 2H); HRMS calcd for C$_{32}$H$_{48}$N$_4$O$_6$S+Cs 749.2349, found 749.2336. Anal. (C$_{32}$H$_{48}$N$_4$O$_6$S) C, H, N, S.

Example 40—Preparation of Compound 176: Ethyl-3-[Cyclopentylthiocarbonyl-L-α-(t-Butyl-Gly)-L-(4-F-Phe)-L-Gln]-E-Propenoate.

Preparation of Intermediate Cyclopentylthiocarbonyl-L-α-(t-Butyl-Gly)-L-(4-F-Phe)-L-(Tr-Glutaminol).

This intermediate was prepared as a white solid in 75% yield from cyclopentylthiocarbonyl-L-α-(t-butyl-Gly) and the free base of L-(4-F-Phe)-L-(Tr-glutaminol) HCl using the procedure described to prepare cyclopentylthiocarbonyl-L-α-(t-butyl-Gly)-L-(4-Me-Phe)-L-(Tr-glutaminol). IR(KBr) 3299, 3063, 2969, 2870, 1651, 1510, 1447, 1225, 1192, 766, 700 cm$^{-1}$; $^1$H NMR (CDCl$_3$) δ 0.88 (s, 9H), 1.50–1.76 (m, 9H), 1.85 (m, 1H), 2.05 (m, 2H), 2.36 (m, 2H), 2.50 (m, 1H), 2.92 (m, 2H), 3.32 (m, 2H), 3.66 (m, 1H), 3.73 (m, 1H), 4.17 (m, 1H), 4.69 (m, 1H), 6.09 (d, 1H, J=7.0 Hz), 6.74 (m, 1H), 6.91 (m, 2H), 7.05 (m, 2H), 7.24 (m, 15H). MS calcd for C$_{46}$H$_{53}$N$_4$O$_5$SF+Na 803, found 803.

Preparation of Intermediate Cyclopentylthiocarbonyl-L-α-(t-Butyl-Gly)-L-(4-F-Phe)-L-(Tr-Glutaminal).

Using the general procedure described in Example 1 for the preparation CBZ-L-Leu-L-Phe-L-methioninal (sulfoxide), cyclopentylthiocarbonyl-L-α-(t-butyl-Gly)-L-(4-F-Phe)-L-(Tr-glutaminal) was synthesized from cyclopentylthiocarbonyl-L-α-(t-butyl-Gly)-L-(4-F-Phe)-L-(Tr-glutaminol) in quantitative yield and isolated as a white amorphous solid and used without further purification: IR(film) 3302, 3061, 3030, 2961, 2866, 1732, 1644, 1510, 1447, 1225, 1196, 911, 733, 700 cm$^{-1}$; $^1$H NMR (CDCl$_3$) δ 0.90 (s, 9H), 1.48–1.67 (m, 8H), 1.85 (m, 1H), 2.00–2.28 (m, 2H), 2.36 (m, 2H), 2.90 (dd, 1H, J=14.9, 6.1 Hz), 3.03 (dd, 1H, J=14.5, 6.8 Hz), 3.64 (m, 1H), 4.07 (m, 1H), 4.18 (m, 1H), 4.53 (m, 1H), 5.92 (m, 1H), 6.31 (m, 1H), 6.92 (m, 2H), 7.10 (m, 3H), 7.23 (m, 15H), 9.31 (s, 1H); MS calcd for C$_{45}$H$_{53}$N$_4$O$_5$SF.CH$_3$OH (methyl-hemiacetal)+Na 833, found 833.

Preparation of Intermediate Ethyl-3-[Cyclopentylthiocarbonyl-L-α-(t-Butyl-Gly)-L-(4-F-Phe)-L-(Tr-Gln)]-E-Propenoate.

Using the procedure described in Example 1 for the preparation of ethyl-3-[CBZ-L-Leu-L-Phe-L-Met (sulfoxide)]-E-propenoate, ethyl-3-[cyclopentylthiocarbonyl-L-α-(t-butyl-Gly)-L-(4-F-Phe)-L-(Tr-Gln)]-E-propenoate was synthesized from cyclopentylthiocarbonyl-L-α-(t-butyl-Gly)-L-(4-F-Phe)-L-(Tr-glutaminal) (0.343 g, 0.44 mmol) to give 0.377 g of material contaminated with triphenylphosphine oxide after column chromatography on silica gel (gradient: 1–2.5% MeOH/CH$_2$Cl$_2$) which was used without further purification: white amorphous solid: IR(KBr) 3314, 3285, 2969, 2936, 1723, 1651, 1510, 1447, 1370, 1190, 1038, 700 cm$^{-1}$; $^1$H NMR (CDCl$_3$) δ 0.88 (s, 9H), 1.28 (t, 3H, J=7.0 Hz), 1.48–1.78 (m, 8H), 1.83–2.15 (m, 4H), 2.32 (m, 2H), 2.85 (m, 1H), 3.00 (m, 1H), 3.61 (m, 1H), 4.16 (q, 2H, J=7.0 Hz), 4.39 (m, 2H), 5.54 (d, 1H, J=15.4 Hz), 6.17 (m, 1H), 6.63 (dd, 1H, J=15.4, 4.0 Hz), 6.91 (m, 2H), 7.01 (m, 2H), 7.28 (m, 15H), 7.45 (m, 1H), 7.54 (m, 1H), 7.63 (m, 1H). MS calcd for C$_{49}$H$_{57}$N$_4$O$_6$SF+Na 871, found 871.

Preparation of Product—Ethyl-3-[Cyclopentylthiocarbonyl-L-α-(t-Butyl-Gly)-L-(4-F-Phe)-L-Gln]-E-Propenoate.

Using the procedure described in Example 34 for the preparation of ethyl-3-[ethylthiocarbonyl-L-α-(t-butyl-Gly)-L-Phe-L-Gln]-E-propenoate, ethyl-3-[cyclopentylthiocarbonyl-L-α-(t-butyl-Gly)-L-(4-F-Phe)-L-Gln]-E-propenoate was synthesized from ethyl-3-[cyclopentylthiocarbonyl-L-α-(t-butyl-Gly)-L-(4-F-Phe)-L-(Tr-Gln)]-E-propenoate and isolated as a white solid after purification by column chromatography on silica gel using a gradient solvent system (1–5% MeOH/CH$_2$Cl$_2$) (56% yield; two steps from cyclopentylthiocarbonyl-L-α-(t-butyl-Gly)-L-(4-F-Phe)-L-(Tr-glutaminal): IR (KBr) 3310, 2961, 2868, 1713, 1649, 1512, 1192 cm$^{-1}$; $^1$H NMR (DMSO-d$_6$) δ 0.83 (s, 9H), 1.21 (t, 3H, J=7.2 Hz), 1.40–1.69 (m, 8H), 2.01 (m, 4H), 2.80 (dd, 1H, J=14.0, 8.1 Hz), 2.90 (dd, 1H, J=13.2, 7.0 Hz), 3.54 (quin, 1H, J=7.2 Hz), 4.09 (q, 2H, J=6.9 Hz), 4.28 (d, 1H, J=9.6 Hz), 4.38 (m, 1H), 4.47 (m, 1H), 5.48 (dd, 1H, J=15.6, 1.3Hz), 6.64 (dd, 1H,J=15.6, 5.3Hz), 6.74 (bs, 1H), 7.00 (t, 2H,J=8.8 Hz), 7.13 (bs, 1H), 7.20 (d, 1H, J=8.5 Hz), 7.22 (d, 1H, J=8.5 Hz), 7.88 (d, 1H, J=9.2 Hz), 8.08 (d, 1H, J=8.1 Hz), 8.18 (d, 1H, J=7.7 Hz); HRMS calcd for C$_{30}$H$_{43}$N$_4$O$_6$SF+Cs 739.1942, found 739.1954. Anal. (C$_{30}$H$_{43}$N$_4$O$_6$SF) C, H, N, S.

Example 41—Preparation of Compound 177: Ethyl-2-Methyl-3-[Cyclopentylthiocarbonyl-L-α-(t-Butyl-Gly)-L-(4-F-Phe)-L-Gln]-E-Propenoate.

Preparation of Intermediate Ethyl-2-Methyl-3-[Cyclopentylthiocarbonyl-L-α-(t-Butyl-Gly)-L-(4-F-Phe)-L-(Tr-Gln)]-E-Propenoate.

Using the procedure described in Example 1 for the preparation of ethyl-3-[CBZ-L-Leu-L-Phe-L-Met (sulfoxide)]-E-propenoate, ethyl-2-methyl-3-[cyclopentylthiocarbonyl-L-α-(t-butyl-Gly)-L-(4-F-Phe)-L-(Tr-Gln)]-E-propenoate was synthesized from cyclopentylthiocarbonyl-L-α-(t-butyl-Gly)-L-(4-F-Phe)-L-(Tr-glutaminal) (0.297 g, 0.38 mmol) and (carbethoxyethylidene)triphenylphosphorane (0.152 g, 0.42 mmol) to give 0.377 g of material contaminated with triphenylphosphine oxide after column chromatography on silica gel (gradient: 1–2.5% MeOH/CH$_2$Cl$_2$) which was used without further purification. white amorphous solid: IR(film) 3356, 3291, 3063, 2973, 2951, 1711, 1651, 1510, 1447, 1256, 1190, 752, 700 cm$^{-1}$; $^1$H NMR (CDCl$_3$) δ 0.90 (s, 9H), 1.31 (t, 3H, J=7.0 Hz), 1.51–1.83 (m, 11H), 2.17 (m, 2H), 2.28 (m, 2H), 2.75–3.02 (m, 2H), 3.66 (m, 1H), 4.16 (m, 3H), 4.45 (m, 1H), 4.60 (m, 1H), 6.30 (m, 2H), 6.58 (m, 1H), 6.78 (m, 1H), 6.88 (m, 2H), 6.98 (m, 3H), 7.20 (m, 15H). MS calcd for C$_{50}$H$_{59}$N$_4$O$_6$SF+Na 885, found 885.

Preparation of Product—Ethyl-2-Methyl-3-[Cyclopentylthiocarbonyl-L-α-(t-Butyl-Gly)-L-(4-F-Phe)-L-Gln]-E-Propenoate.

Using the procedure described in Example 34 for the preparation of ethyl-3-[ethylthiocarbonyl-L-α-(t-butyl-Gly)-L-Phe-L-Gln]-E-propenoate, ethyl-2-methyl-3-[cyclopentylthiocarbonyl-L-α-(t-butyl-Gly)-L-(4-F-Phe)-L-Gln]-E-propenoate was synthesized from ethyl-2-methyl-3-[cyclopentylthiocarbonyl-L-α-(t-butyl-Gly)-L-(4-F-Phe)-L-(Tr-Gln)]-E-propenoate and isolated as a white solid after purification by column chromatography on silica gel using a gradient solvent system (1–5% MeOH/CH$_2$Cl$_2$) (55% yield; two steps from cyclopentylthiocarbonyl-L-α-(t-butyl-Gly)-L-(4-F-Phe)-L-(Tr-glutaminal): IR (KBr) 3326, 2951, 2868, 1713, 1645, 1553, 1510, 1260, 1194 cm$^{-1}$; $^1$H NMR (DMSO-d$_6$) δ 0.83 (s, 9H), 1.22 (t, 3H, J=7.0 Hz), 1.41–1.75 (m, 8H), 1.77 (m, 3H), 1.92 (m, 4H), 2.77 (dd, 1H, J=13.8, 8.3 Hz), 2.85 ((dd, 1H, J=13.6, 7.0 Hz), 3.55 (quin, 1H, J=7.0 Hz), 4.12 (q, 2H, J=7.1 Hz), 4.22 (d, 1H, J=9.2 Hz), 4.38 (m, 1H), 4.45 (m, 1H), 6.24 (dd, 1H, J=9.2, 1.5 Hz), 6.72 (bs, 1H), 6.96 (t, 2H, J=8.8 Hz), 7.87 (d, 1H, J=8.8 Hz), 8.03 (d, 1H, J=8.1 Hz), 8.11 (d, 1H, J=7.7 Hz); HRMS calcd for C$_{31}$H$_{45}$N$_4$O$_6$SF+Cs 753.2098, found 753.2084. Anal. (C$_{31}$H$_{45}$N$_4$O$_6$SF) C, H, N, S.

Example 42—Preparation of Compound 179: Ethyl-3-(Cyclopentylthiocarbonyl-L-[S(O)-Me-Pen]-L-Phe-L-Gln)-E-Propenoate.

Preparation of Product Ethyl-3-(Cyclopentylthiocarbonyl-L-[S(O)-Me-Pen]-L-Phe-L-Gln)-E-Propenoate Using the procedure described in Example 36 for the preparation of ethyl-3-[cyclopentylthiocarbonyl-L-(S-Me- Pen)-L-Phe-L-Gln]-E-propenoate, ethyl-3-(cyclopentylthiocarbonyl-L-[S(O)-Me-Pen]-L-Phe-L-Gln)-E-propenoate was synthesized from ethyl-3-(cyclopentylthiocarbonyl-L-[S(O)-Me-Pen]-L-Phe-L-[Tr-Gln])-E-propenoate in 40% yield (3 steps from cyclopentylthiocarbonyl-L-(S-Me-Pen)-L-Phe-L-(Tr-glutaminol)): white amorphous solid: IR (KBr) 3302, 1662, 1541, 1458, 1205, 1138, 1028 cm$^{-1}$; $^1$H NMR (DMSO-d$_6$) (mixture of diastereomers) δ 1.03 (s), 1.12 (s), 1.21 (t, 3H, J=6.0 Hz), 1.42–1.76 (m), 2.0–2.21 (m), 2.34 (s), 2.42 (s), 2.80–2.87 (m), 2.93–3.11 (m), 3.47–3.60 (m), 4.10 (q, J=6.0 Hz), 4.35–4.40 (m), 4.44–4.52 (m), 4.64 (d, J=6.0 Hz), 5.58–5.62 (m), 6.60–6.70 (m), 6.75 (bs), 7.14–7.21 (m), 8.16–8.22 (m), 8.41 (d, J=9.0 Hz), 8.54 (d, J=9.0 Hz). HRMS calcd for $C_{30}H_{44}N_4O_7S_2$+Cs 769.1706, found 769.1727.

While the invention has been described in detail and with reference to specific embodiments thereof, it will be apparent to one skilled in the art that various changes and modifications can be made therein without departing from the spirit and scope thereof. Thus, it is intended that the present invention cover the modifications and variations, provided they come within the scope of the appended claims and their equivalents.

BIOCHEMICAL AND BIOLOGICAL EVALUATION

Inhibition of Rhinovirus Protease

Stock solutions (50 mM, in DMSO) of various compounds were prepared; dilutions were in the same solvent. Recombinant Rhinovirus 3C proteases from serotypes 14, 16, 2 or 89 were prepared by the following standard chromatographic procedures: (1) ion exchange using Q Sepharose Fast Flow from Pharmacia; (2) affinity chromatography using Affi-Gel Blue from Biorad; and (3) sizing using Sephadex G-100 from Pharmacia. Assays contained 2% DMSO, 50 mM tris pH 7.6, 1 mM EDTA, a compound at the indicated concentrations, approximately 1 μM substrate, and 50–100 nM protease. For $K_i$ determinations, the compound and the enzyme were preincubated for 10 minutes at 30° C. prior to addition of the substrate (substrate start). The $k_{obs/I}$ values were obtained from reactions initiated by addition of enzyme rather than substrate. RVP activity is measured in the fluorescence resonance energy transfer assay. The substrate was (N-terminal) DABCYL-(Gly-Arg-Ala-Val-Phe-Gln-Gly-Pro-Val-Gyl)-EDANS. In the uncleaved peptide, the EDANS fluorescence was quenched by the proximal DABCYL moiety. When the peptide was cleaved, the quenching was relieved, and activity was measured as an increase in fluorescence signal. Data was analyzed using standard non linear fitting programs (Enzfit), and are shown Table 1.

TABLE 1

| COMPOUND # | RVP | INHIB | $k_{obs/I}$ (M-1sec-1) |
|---|---|---|---|
| 1 | | 77 (50) | ND |
| 2 | | 6.6 μM ($K_i$) | ND |
| 3 | | 81 (0.1) | 37,000 |
| | (16) | | 6,500 |
| | (89) | | 3,400 |
| | (2) | | 1,900 |
| 4 | | 49 (0.5) | 790 |
| 5 | | 7.1 μM ($K_i$) | 221 |
| 6 | | 32 μM ($K_i$) | 350 |

TABLE 1-continued

| COMPOUND # | RVP | INHIB | $k_{obs/I}$ (M-1sec-1) |
|---|---|---|---|
| 7 | | 9.5 μM ($K_i$) | 2,400 |
| | (16) | 42 (1) | ND |
| 8 | | 36 μM ($K_i$) | 61 |
| 9 | | 20 (1) | 160 |
| 10 | | 55 (5) | 270 |
| 11 | | 28 μM ($K_i$) | 20,000 |
| 12 | | 4.3 μM ($K_i$) | 2,200 |
| 13 | | 6.5 μM ($K_i$) | 54,000 |
| | (16) | | 9,000 |
| | (2) | | 2,400 |
| | (89) | | 5,500 |
| 14 | | NI | ND |
| 15 | | 55 (50) | 27 |
| 16 | | 40(0.25) | 3,500 |
| 17 | | 1.25 μM ($K_i$) | 6,100 |
| 18 | | 15.3 μM ($K_i$) | 7,700 |
| 19 | | 35 μM ($K_i$) | 7,900 |
| 20 | | NI | ND |
| 21 | | 9.9 μM ($K_i$) | 2,100 |
| 22 | | 4.3 μM ($K_i$) | 1,300 |
| 23 | | 177 μM ($K_i$) | 120 |
| 24 | | ND | 500,000 |
| 25 | | 5.5 μM ($K_i$) | 3,700 |
| 26 | | 52 (0.1) | 5,400 |
| 27 | | 20 μM ($K_i$) | 3,000 |
| 28 | | 57 μM ($K_i$) | 4,000 |
| 29 | | ND | ND |
| 30 | | 373 μM ($K_i$) | 430 |
| 31 | | 25 (10) | 21 |
| 32 | | ND | 280 |
| 33 | | 24 (10) | 33 |
| 34 | | 25 (10) | 34 |
| 35 | | 16.5 μM ($K_i$) | 46,388 |
| | (2) | ND | 2,357 |
| | (16) | ND | 9,177 |
| 36 | | 15 μM ($K_i$) | 12,000 |
| 37 | | 18.8 μM ($K_i$) | 5,900 |
| 38 | | >50 μM ($K_i$) | 400 |
| 39 | | ND | 1,200 |
| 40 | | ND | 250 |
| 41 | | ND | 8,464 |
| 42 | | ND | 150,000 |
| 43 | | ND | 4,500 |
| 44 | | 12.6 μM ($K_i$) | 21,000 |
| 45 | | NI | ND |
| 46 | | ND | 120,000 |
| 49 | | ND | 460,000 |
| 51 | | ND | 310,000 |
| 52 | | ND | 15,000 |
| 53 | | ND | 11,320 |
| 56 | | 15 μM ($K_i$) | 5,624 |
| 59 | | 2.0 μM ($K_i$) | 200 |
| 60 | | 5.0 μM ($K_i$) | 575 |
| 61 | | ND | 125,940 |
| | (2) | ND | 14,000 |
| | (16) | ND | 25,000 |
| 62 | | ND | 600,000 |
| | (2) | ND | 600,000 |
| | (16) | ND | 300,000 |
| 65 | | 2.9 μM ($K_i$) | ND |
| 66 | | ND | 400,000 |
| 67 | | ND | 9,600 |
| 68 | | 15 μM ($K_i$) | 750 |
| 70 | | ND | 39,000 |
| 71 | | ND | 20,650 |
| 73 | | ND | 20,000 |
| | (2) | ND | 1,750 |
| | (16) | ND | 4,500 |
| 74 | | 2.4 μM ($K_i$) | |
| 75 | | ND | |
| 76 | | 30 μM ($K_i$) | ND |
| 77 | | 4.8 ND | |
| 78 | | 7.0 μM ($K_i$) | |
| 79 | | ND | 13,900 |
| 80 | | ND | 200,000 |
| 81 | | ND | 124,000 |
| 82 | | 26 μM ($K_i$) | 7,300 |

TABLE 1-continued

| COMPOUND # | RVP | INHIB | $k_{obs/I}$ (M-1sec-1) |
|---|---|---|---|
| 83 | | 8.0 μM ($K_i$) | ND |
| 84 | | ND | 18,650 |
| 85 | | 3.0 μM ($K_i$) | 6,500 |
| 86 | | 4.0 μM ($K_i$) | 12,000 |
| 87 | | 6.0 μM ($K_i$) | 5,430 |
| 88 | | >30 μM ($K_i$) | 8,960 |
| 89 | | 5 μM ($K_i$) | 53,360 |
| | (16) | ND | 2,800 |
| 90 | | ND | 10,918 |
| | (16) | ND | 3,600 |
| 91 | | 10 μM ($K_i$) | 5,427 |
| 92 | | ND | 445 |
| 93 | | 30 μM ($K_i$) | 3,444 |
| 94 | | 1.5 μM ($K_i$) | 5,800 |
| 95 | | ND | >1000 |
| 96 | | ND | 300 |
| 97 | | ND | 12,900 |
| 98 | | ND | 91 |
| 99 | | 10 (50) | ND |
| 100 | | ND | 1,200 |
| 101 | | ND | 11,288 |
| 102 | | 12 μM ($K_i$) | 3,845 |
| 103 | | ND | 29,200 |
| | (2) | ND | 1,106 |
| | (16) | ND | 3,354 |
| 104 | | 2.5 μM ($K_i$) | 8,000 |
| | (16) | 1.5 μM ($K_i$) | ND |
| 105 | | ND | 1,200 |
| 106 | | 2.0 μM ($K_i$) | 280,000 |
| | (2) | ND | 28,400 |
| | (16) | ND | 75,0900 |
| 107 | | 13.5 μM ($K_i$) | 3,655 |
| 108 | | ND | 4,694 |
| 109 | | ND | 1,348 |
| 110 | | ND | 9,072 |
| 111 | | 5.0 μM ($K_i$) | 2,065 |
| 112 | | 13 μM ($K_i$) | 6,800 |
| 113 | | ND | 8,877 |
| 114 | | ≧1.0 μM ($K_i$) | 82,320 |
| | (2) | ND | 1,971 |
| 115 | | 11 μM ($K_i$) | 4,485 |
| 116 | | ND | 23,670 |
| 117 | | ND | 18,760 |
| 118 | | 39 μM ($K_i$) | 1,448 |
| 119 | | 5.0 μM ($K_i$) | 69,800 |
| 120 | | 6.0 μM ($K_i$) | 91,300 |
| | (2) | ND | 8,900 |
| | (16) | ND | 20,034 |
| 121 | | 12 μM ($K_i$) | 238 |
| 122 | | ND | 1,252 |
| 123 | | ND | 890 |
| 124 | | ND | 1,000 |
| 125 | | ND | >500,000 |
| 126 | | ND | 29,000 |
| 127 | | ND | 28,347 |
| 128 | | ND | 22,691 |
| 129 | | ND | 230,000 |
| 130 | | 30–40 nM ($K_i$) | ND |
| 131 | | NI | NI |
| 132 | | 10 μM ($K_i$) | 10,800 |
| 133 | | ND | 9,600 |
| 134 | | ND | 1,769 |
| 135 | | ND | 16,270 |
| | (2) | ND | 671 |
| | (16) | ND | 3,465 |
| 136 | | ND | 4,210 |
| 137 | | ND | 2,344 |
| | (2) | ND | 643 |
| | (16) | ND | 1,157 |
| 138 | | 20 μM ($K_i$) | 1,769 |
| 139 | | ND | 43,140 |
| | (2) | ND | 691 |
| | (16) | ND | 1,259 |
| 140 | | ND | 7,122 |
| 141 | | ND | 2,309 |
| 142 | | ND | 2,929 |
| 143 | | ND | 2,963 |
| 144 | | ND | ND |
| 145 | | 10–20 μM ($K_i$) | ND |
| 146 | | ND | 62,500 |
| | (2) | ND | 7,790 |
| | (16) | ND | 16,900 |
| 147 | | ND | 18,600 |
| | (2) | ND | 1,000 |
| | (16) | ND | 4,290 |
| 148 | | 1.0 μM ($K_i$) | 57,000 |
| | (2) | ND | 8,300 |
| | (16) | ND | 14,800 |
| 149 | | ND | 39,940 |
| | (2) | ND | 2,840 |
| | (16) | ND | 7,700 |
| 150 | | ND | 573 |
| 151 | | >4.8 μM ($K_i$) | 39,750 |
| 152 | | 3.2 μM ($K_i$) | 38,900 |
| 153 | | 1.4 μM ($K_i$) | 141,200 |
| | (2) | ND | 13,350 |
| | (16) | ND | 30,650 |
| 154 | | 1.1 μM ($K_i$) | 78,900 |
| | (2) | ND | 5,400 |
| | (16) | ND | 13,900 |
| 155 | | 4.2 mM ($K_i$) | 59,425 |
| | (2) | ND | 1,390 |
| | (16) | ND | 5,250 |
| 156 | | ND | NI |
| 157 | | 6.0 μM ($K_i$) | 161,500 |
| | (2) | ND | 9,700 |
| | (16) | ND | 30,800 |
| 158 | | 17 μM ($K_i$) | 22,600 |
| | (2) | ND | 2,200 |
| | (16) | ND | 6,400 |
| 159 | | 0.5 μM ($K_i$) | 35,000 |
| | (2) | ND | 2,500 |
| | (16) | ND | 6,500 |
| 160 | | ND | 312,000 |
| | (2) | ND | 26,710 |
| | (16) | ND | 50,000 |
| 161 | | ND | 1,086,000 |
| | (2) | ND | 200,000 |
| | (16) | ND | 126,000 |
| 162 | | ND | 800,000 |
| | (2) | ND | 150,000 |
| | (16) | ND | 80,000 |
| 163 | | 3.6 μM ($K_i$) | 9,800 |
| 164 | | ND | 155,500 |
| 165 | | ND | 97,000 |
| | (2) | ND | 5,600 |
| | (16) | ND | 20,200 |
| 166 | | ND | 40,900 |
| | (2) | ND | 3,500 |
| | (16) | ND | 7,700 |
| 167 | | ND | 165,400 |
| | (2) | ND | 10,700 |
| | (16) | ND | 42,100 |
| 168 | | ND | 37,800 |
| 169 | | ND | 800 |
| 170 | | ND | 85,300 |
| | (2) | ND | 8,400 |
| | (16) | ND | 30,000 |
| 171 | | ND | 21,200 |
| | (2) | ND | 830 |
| | (16) | ND | 3,250 |
| 172 | | ND | 31,700 |
| | (2) | ND | 2,000 |
| | (16) | ND | 6,000 |
| 173 | | ND | 1,000,000 |
| | (2) | ND | 113,000 |
| | (16) | ND | 185,000 |
| 174 | | ND | 800,000 |
| 175 | | ND | 124,000 |
| 176 | | 0.48 μM ($K_i$) | 240,000 |
| 177 | | ND | 80,300 |
| 178 | | ND | 286,300 |
| 179 | | 0.36 μM ($K_i$) | 300,000 |
| 180 | | 0.42 μM ($K_i$) | 300,000 |

TABLE 1-continued

| COMPOUND # | RVP | INHIB | $k_{obs/I}$ (M-1sec-1) |
|---|---|---|---|
| 181 | | ND | 1,000,000 |
| 182 | | ND | 114,360 |
| 183 | | 0.55 μM ($K_i$) | 500,000 |
| | (16) | ND | 60,000 |
| 184 | | ND | 59,900 |
| 185 | | ND | 600,000 |
| 186 | | ND | 950,000 |
| 187 | | NI | ND |
| 188 | | 0.16 μM ($K_i$) | 580,000 |
| 189 | | ND | 386,000 |
| 190 | | ND | 29,230 |

In the above table, all data is for RVP serotype-14 unless otherwise noted in parentheses. All strains of human rhinovirus (HRV) were purchased from American Type Culture Collection (ATCC), except for serotype 14, which was produced from the infectious cDNA clone constructed and supplied to us by Dr. Roland Rueckert at the Institute for Molecular Virology, University of Wisconsin, Madison, Wis. The column designated INHIB represents the percent inhibition, with the concentration of the compound in μM indicated in parentheses, unless $K_i$ was assigned as designated by ($K_i$), at 10 minute preincubation with 50 nM RVP prior to addition of substrate was used. The data in the column designated $k_{obs/I}$ was measured from progress curves in enzyme start experiments. The designation NI indicates that no inhibition was obtained when 10 μM of a compound was used. The designation ND indicates that a value was not determined for that compound.

Antirhinoviral HI-HeLa Cell Culture Assay

In the Cell Protection Assay, the ability of compounds to protect cells against HRV infection was measured by the XTT dye reduction method. This method is described in Weislow, O. S., R. Kiser, D. L. Fine, J. Bader, R. H. Shoemaker, and M. R. Boyd, *J. Natl. Cancer Inst.* 1989, 81, 577–586, which is incorporated herein by reference.

HI-HeLa cells were infected with HRV-14 at a multiplicity of infection (m.o.i.) of 0.13 (virus particles/cell) or mock-infected with medium only. Infected or mock-infected cells were resuspended at $8 \times 10^5$ cells per mL and incubated with appropriate concentrations of compounds of formulas I and II. Two days later, XTT/PMS was added to test plates and the amount of formazan produced was quantified spectrophotometrically at 450/650 nm. The $EC_{50}$ was calculated as the concentration of compound that increased the percentage of formazan production in compound-treated, virus-infected cells to 50% of that produced by compound-free mock-infected cells. The 50% cytotoxic dose ($CC_{50}$) was calculated as the concentration of compound that decreased the percentage of formazan produced in compound-treated, mock-infected cells to 50% of that produced in compound-free, mock-infected cells. The therapeutic index (TI) was calculated by dividing the $CC_{50}$ the $EC_{50}$.

All strains of human rhinovirus (HRV) for use in this assay were purchased from American Type Culture Collection (ATCC), except for HRV serotype-14, which was produced from the infectious cDNA clone, constructed and supplied to us by Dr. Roland Rueckert the Institute for Molecular Virology, University of Wisconsin, Madison, Wis. HRV stocks were propagated, and antiviral assays were performed in HI-HeLa cells (ATCC). Cells were grown in Minimal Essential Medium, available from Life Technologies, with 10% fetal bovine serum.

The compounds were tested against control compounds WIN 51711, WIN 52084, and WIN 54954, all obtained from Sterling-Winthrop Pharmaceuticals, and control compound Pirodavir, obtained from Janssen Pharmaceuticals.

TABLE 2

| Compound # | $EC_{50}$ (μM) | $CC_{50}$ (μM) | TI |
|---|---|---|---|
| 1 | ND | ND | |
| 2 | 100 | >320 | >3.20 |
| 3 | 0.61 | >320 | >525 |
| 4 | 2.2 | >320 | >525 |
| 5 | 1.6 | 251 | 157 |
| 6 | >320 | >320 | |
| 7 | 3.2 | >320 | >100 |
| 8 | >320 | >320 | >5 |
| 9 | >320 | >320 | |
| 10 | 200 | >320 | >2 |
| 11 | 1.3 | >320 | >246 |
| 12 | 1.6 | >100 | >63 |
| 13 | 2.0 | 58.9 | 29 |
| 14 | 17.8 | 500 | 28 |
| 15 | >100 | >100 | |
| 16 | 32 | >100 | >3 |
| 17 | 1.8 | >100 | >56 |
| 18 | 0.64 | >100 | >156 |
| 19 | 1.35 | >100 | >74 |
| 20 | >320 | >320 | |
| 21 | 22.4 | >100 | >5 |
| 22 | 56.2 | 251 | >5 |
| 23 | >100 | >100 | |
| 24 | 4.0 | 16 | 4 |
| 25 | 3.1 | >100 | >33 |
| 26 | 2.0 | 44.7 | 22 |
| 27 | 3.5 | 160 | 46 |
| 28 | 4.5 | 63.1 | 14 |
| 29 | 27 | 500 | 19 |
| 30 | 5.6 | 100 | 18 |
| 31 | 50.1 | >100 | >2 |
| 32 | 10 | >100 | >10 |
| 33 | 79.4 | >100 | >1 |
| 34 | 100 | >100 | >1 |
| 35 | 1.8 | >320 | >178 |
| 36 | 5.6 | >320 | >57 |
| 37 | 4.0 | >100 | >25 |
| 38 | >320 | >320 | |
| 39 | >320 | >320 | |
| 40 | >100 | >100 | |
| 41 | 56 | 56 | 1 |
| 42 | 22.4 | 100 | >4 |
| 43 | 10 | 18 | >1 |
| 44 | 1.0 | >320 | >320 |
| 45 | >100 | >100 | |
| 46 | 3.2 | 45 | 14 |
| 49 | 2.4 | 19.1 | 8 |
| 51 | 32 | 32 | |
| 52 | 1.7 | 5.6 | 3 |
| 53 | 5.3 | >320 | >60 |
| 56 | 1.6 | >320 | >203 |
| 59 | >320 | >320 | |
| 60 | 158 | >320 | >2 |
| 61 | 0.89 | 56 | 63 |
| 62 | 1.6 | >100 | >63 |
| 65 | 158 | >320 | >2 |
| 66 | 1.4 | 6.3 | 5 |
| 67 | 5.2 | >320 | >62 |
| 68 | 16 | >320 | >20 |
| 70 | 1.2 | >320 | >267 |
| 71 | 14.1 | >320 | 23 |
| 73 | ND | | |
| 74 | 10 | 250 | 25 |
| 75 | 5.0 | >100 | >20 |
| 76 | >320 | >320 | |
| 77 | >320 | >320 | |
| 78 | 10 | 79.4 | 8 |
| 79 | 45 | >320 | >7 |
| 80 | 50 | >320 | >6 |
| 81 | 8.0 | 112 | 14 |
| 82 | 3.0 | >320 | >107 |
| 83 | 100 | >320 | >3 |

TABLE 2-continued

| Compound # | EC$_{50}$ ($\mu$M) | CC$_{50}$ ($\mu$M) | TI |
|---|---|---|---|
| 84 | 16 | >320 | >20 |
| 85 | 16 | >320 | >20 |
| 86 | 17 | >320 | >19 |
| 87 | 10.6 | >320 | >30 |
| 88 | 8.8 | >160 | >18 |
| 89 | 1.8 | 29 | 16 |
| 90 | 5.2 | >320 | >61 |
| 91 | 56 | >320 | >6 |
| 92 | 5.6 | 56 | 10 |
| 93 | >320 | >320 | |
| 94 | 46.8 | >320 | >7 |
| 95 | >320 | >320 | |
| 96 | 19.1 | 100 | 5 |
| 97 | >320 | >320 | |
| 98 | 100 | >320 | >3.2 |
| 99 | 141 | >320 | >2 |
| 100 | 11.1 | >320 | >29 |
| 101 | 2.0 | >320 | >160 |
| 102 | 5.6 | >320 | >57 |
| 103 | 1.7 | >320 | >188 |
| 104 | 5.2 | >320 | >61 |
| 105 | 14 | >320 | >23 |
| 106 | 0.27 | >320 | >1185 |
| 107 | 13.5 | >320 | >23 |
| 108 | 6.0 | >320 | >53 |
| 109 | 20 | >320 | >16 |
| 110 | 1.3 | >320 | >246 |
| 111 | 29.5 | >320 | >11 |
| 112 | 27 | >320 | >12 |
| 113 | 10 | >320 | >32 |
| 114 | 0.55 | >320 | >582 |
| 115 | 19 | >320 | >17 |
| 116 | 0.6 | >320 | >533 |
| 117 | 1.0 | >320 | >320 |
| 118 | 17.8 | >320 | >18 |
| 119 | 1.1 | >320 | >291 |
| 120 | 0.46 | >320 | >695 |
| 121 | >320 | >320 | |
| 122 | 1.78 | 10 | 5 |
| 123 | >320 | >320 | |
| 124 | 126 | >320 | >2 |
| 125 | >100 | 100 | |
| 126 | >320 | >320 | |
| 127 | >100 | ND | |
| 128 | >320 | >320 | |
| 129 | >320 | >320 | |
| 130 | 15.8 | >100 | >6 |
| 131 | >100 | >100 | |
| 132 | 5.6 | >320 | >57 |
| 133 | >177 | 177 | |
| 134 | 56.2 | >320 | >5 |
| 135 | 1.9 | >320 | >168 |
| 136 | >320 | >320 | |
| 137 | 223.9 | >320 | >1 |
| 138 | >41.7 | 41.7 | |
| 139 | 3.5 | >320 | >91 |
| 140 | 39 | >320 | >8 |
| 141 | 5.4 | >320 | >59 |
| 142 | 8.9 | >320 | >36 |
| 143 | 10 | >320 | >32 |
| 144 | 103.5 | >320 | >3 |
| 145 | >320 | >320 | |
| 146 | 0.38 | >320 | >842 |
| 147 | 205 | >320 | >1 |
| 148 | 0.25 | >320 | >1280 |
| 149 | 1.78 | >320 | >180 |
| 150 | >320 | >320 | |
| 151 | 0.32 | 177.8 | 555 |
| 152 | 1.78 | >320 | >180 |
| 153 | 0.12 | >320 | >2667 |
| 154 | 5.5 | >320 | >58 |
| 155 | 0.18 | >320 | >1778 |
| 156 | 35.5 | >320 | >9 |
| 157 | 0.56 | >320 | >571 |
| 158 | 5.9 | >320 | >54 |
| 159 | 2.4 | >320 | >133 |
| 160 | 5.0 | >320 | >64 |

TABLE 2-continued

| Compound # | EC$_{50}$ ($\mu$M) | CC$_{50}$ ($\mu$M) | TI |
|---|---|---|---|
| 161 | 0.17 | >100 | >588 |
| 162 | 0.32 | >100 | >312 |
| 163 | 0.5 | >100 | >200 |
| 164 | 0.71 | >100 | >141 |
| 165 | 0.20 | >100 | >500 |
| 166 | 5.6 | >100 | >18 |
| 167 | 0.083 | >100 | >1204 |
| 168 | 0.32 | >100 | >312 |
| 169 | 18 | >100 | >5 |
| 170 | 0.20 | >100 | >500 |
| 171 | 0.71 | >100 | >140 |
| 172 | 0.79 | >100 | >126 |
| 173 | 0.80 | >100 | >1250 |
| 174 | 0.056 | >100 | >1786 |
| 175 | 0.18 | >100 | >555 |
| 176 | 0.14 | >100 | >714 |
| 177 | 0.5 | >100 | >200 |
| 178 | 0.10 | >100 | >1000 |
| 179 | 1.78 | >100 | >56 |
| 180 | 0.056 | >100 | >1785 |
| 181 | 0.1 | >100 | >1000 |
| 182 | 0.18 | >100 | >556 |
| 183 | 0.03 | >100 | >3333 |
| 184 | 0.19 | >100 | >526 |
| 185 | 0.50 | >100 | >200 |
| 186 | ND | ND | |
| 187 | ND | ND | |
| 188 | ND | ND | |
| WIN 51711 | 0.78 | >60 | >77 |
| WIN 52084 | 0.07 | >10 | >143 |
| WIN 54954 | 2.13 | >63 | >30 |
| Pirodavir | 0.03 | >10 | >300 |

Normal Human Bronchial Epithelial Cell Assay

Normal human bronchial cells were obtained from cadavers and cultured. The cells were plated $2\times10^4$ per well in a 96 well plate. They were allowed to adhere and grow for 24 hours in 200 $\mu$L of serum-free bronchial/tracheal epithelial cell growth medium at 37° C. with 5% $CO_2$. Human Rhinovirus-serotype 10 (HRV-10) was purchased from American Type Culture Collection (ATCC). To start the assay, the supernatant was removed, and HRV-10 at an m.o.i. of 10 (virus particles/cell) was added to each well along with the appropiate amount of compound of formula I or II. The plate was then incubated at 34° C. After 3 hours the supernatant was removed, and 200 $\mu$L of media was added along with the same concentration of compound as used in the beginning of the assay. The plates were incubated for 3–4 days at 34° C. To determine the amount of cell growth, an MTT assay (0.5 mgs/mL), as described in Mosmann, T. J. *J. Immunol. Methods* 1983, 65, 55–63, which is incorporated herein by reference, was performed on the cells, and the plate was read at an optical density of 540 nm. The results of the assay are set forth in Table 3. The compounds were tested against control compound Pirodavir, obtained from Janssen Pharmaceuticals. The EC$_{50}$ was measured as described above for the HI-HeLa Cell Culture Assay.

TABLE 3

| Compound # | ED$_{50}$ ($\mu$M) |
|---|---|
| 3 | 0.04 |
| 4 | 0.15 |
| 5 | 0.001 |
| 11 | 0.0007 |
| 12 | 0.004 |

TABLE 3-continued

| Compound # | ED$_{50}$ ($\mu$M) |
|---|---|
| 13 | 0.0004 |
| 27 | 0.07 |
| 85 | 0.005 |
| pirodavir | 0.0075 |

Anticoxsackieviral HI-HeLa Cell Culture Assay

The ability of compounds to protect calls against CVB-3 infection was measured by the XTT dye reduction method, which is described in Weislow, O. S., R. Kiser, D. L. Fine, J. Bader, R. H. Shoemaker, and M. R. Boyd, 1989, J. Natl. Cancer Inst. 81:577–586, which is incorporated herein by reference. Specifically, HI-HeLa cells were infected with CVB-3 at a multiplicity of infection (m.o.i.) of 0.08 or mock-infected with medium only. Infected or mock-infected cells were resuspended at $8 \times 10^{50}$ cells per mL and incubated with appropriate concentrations of compound. One day later, XTT/PMS was added to test plates and the amount of formazan produced was quantified spectrophotometrically at 450/650 nm. The EC$_{50}$ was calculated as the concentration of compound that increased the percentage of formazan production in compound-treated, virus-infected cells to 50% of that produced by compound free, mock-infected cells. The 50% cytotoxic dose (CC$_{50}$) was calculated as the concentration of drug that decreased the percentage of formazan produced in compound treated, mock-infected cells to 50% of that produced in compound-free, mock-infected cells. The therapeutic index (TI) was calculated by dividing the CC$_{50}$ by the EC$_{50}$.

The Coxsackie strain B-3 (CVB-3) was purchased from American Type Culture Collection (ATCC). Virus stocks were propagated and antiviral assays were performed in Hi-HeLa cells (ATCC). Cells were grown in Minimal Essential Medium with 10% fetal bovine serum.

The compounds were tested against control compound WIN 54954, obtained from Sterling Winthrop Pharmaceuticals, and control compound Pirodavir, obtained from Janssen Pharmaceuticals.

TABLE 4

| Compound # | EC$_{50}$ ($\mu$M) | CC$_{50}$ ($\mu$M) | TI |
|---|---|---|---|
| 3 | 39.8 | >320 | >8 |
| 11 | 8.9 | >320 | >35 |
| 13 | >100 | >100 | |
| 21 | 158 | >320 | >2 |
| 23 | >100 | >100 | |
| 24 | 10 | 10 | 1 |
| 27 | 20 | 102.7 | >5 |
| 37 | 17.8 | >100 | >5.6 |
| 41 | >100 | >100 | |
| WIN 54954 | >100 | >100 | |
| Pirodavir | >100 | >100 | |

We claim:
1. A compound of the formula (I):

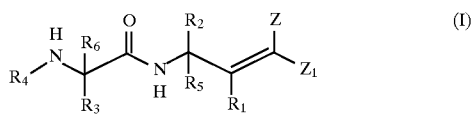

wherein:
R$_1$ is H, F, an alkyl group, OH, SH, an O-alkyl group, or an S-alkyl group; one of R$_2$ and R$_5$ is H or an alkyl group and the other is

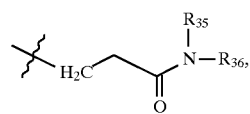

wherein R$_{35}$ is H, an alkyl group, or an aryl group, and R$_{36}$ is H or an alkyl group;
R$_3$ and R$_6$ are independently H, F, or an alkyl group;
R$_4$ is H, OH, or a suitable organic moiety;
Z and Z$_1$ are independently H, F, an alkyl group, a cycloalkyl group, an aryl group, —C(O)R$_{21}$, —CO$_2$R$_{21}$, —C(O)NR$_{21}$R$_{22}$, —C(O)NR$_{21}$OR$_{22}$, —C(S)R$_{21}$, —C(S)NR$_{21}$R$_{22}$, —NO$_2$, —SOR$_{21}$, —SO$_2$R$_{21}$, —SO$_2$NR$_{21}$R$_{22}$, —SO(NR$_{21}$)(OR$_{22}$), —SONR$_{21}$, —SO$_3$R$_{21}$, —PO(OR$_{21}$)$_2$, —PO(R$_{21}$)R$_{22}$), —PO(NR$_{21}$R$_{22}$)(OR$_{23}$), —PO(NR$_{21}$R$_{22}$)(NR$_{23}$R$_{24}$), —C(O)NR$_{21}$NR$_{22}$R$_{23}$, or —C(S)NR$_{21}$NR$_{22}$R$_{23}$,
wherein R$_{21}$, R$_{22}$, R$_{23}$, and R$_{24}$ are independently H, an alkyl group, a cycloalkyl group, an aryl group, an acyl group, or a thioacyl group, with the proviso that at least one of Z or Z$_1$ is a —CO$_2$R$_{50}$ group, where R$_{50}$ represents an alkyl group, a cycloalkyl group, or an aryl group;
or Z and Z$_1$ both as defined above, together with the atoms to which they are bonded, form a cyclic carboxylic acid ester group;
or a pharmaceutically acceptable prodrug, salt, or solvate thereof;
and wherein the compound, pharmaceutically acceptable prodrug, salt, or solvate thereof, has antipicornaviral activity with an EC$_{50}$ less than or equal to 100 $\mu$M in the HI-HeLa cell culture assay.

2. A compound of claim 1 wherein R$_1$ is H or F, or a pharmaceutically acceptable prodrug, salt, or solvate thereof.

3. A compound of claim 1 wherein R$_4$ is an acyl group or a sulfonyl group, or a pharmaceutically acceptable prodrug, salt, or solvate thereof.

4. A compound according to claim 1, wherein said compound has the formula

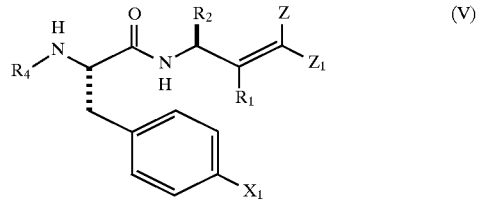

wherein:
R$_4$ is PhCH$_2$OC(O), X$_1$ is H, R$_2$ is CH$_2$CH$_2$C(O)NH$_2$, R$_1$ is H, Z is H, and Z$_1$ is CO$_2$CH$_2$CH$_3$; or
R$_4$ is CH$_3$CH$_2$CH$_2$SO$_2$, X$_1$ is H, R$_2$ is CH$_2$CH$_2$C(O)NH$_2$, R$_1$ is H, Z is H, and Z$_1$ is CO$_2$CH$_2$CH$_3$; or
R$_4$ is PhCH$_2$SO$_2$, X$_1$ is H, R$_2$ is CH$_2$CH$_2$C(O)NH$_2$, R$_1$ is H, Z is H, and Z$_1$ is CO$_2$CH$_2$CH$_3$; or
R$_4$ is CH$_3$CH$_2$SO$_2$, X$_1$ is H, R$_2$ is CH$_2$CH$_2$C(O)NH$_2$, R$_1$ is H, Z is H, and Z$_1$ is CO$_2$CH$_2$CH$_3$; or
R$_4$ is PhSO$_2$, X$_1$ is H, R$_2$ is CH$_2$CH$_2$C(O)NH$_2$, R$_1$ is H, Z is H, and Z$_1$ is CO$_2$CH$_2$CH$_3$;

or a pharmaceutically acceptable prodrug, salt, or solvate thereof.

5. A compound according to claim 1, wherein said compound has the formula IX:

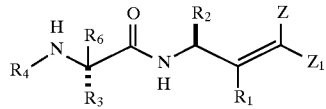

wherein $R_6$ is H, $R_1$ is H, $R_2$ is $CH_2CH_2C(O)NH_2$, Z is H, and $Z_1$ is $CO_2CH_2CH_3$, $R_3$ is $CH_2Ph$, and $R_4$ is

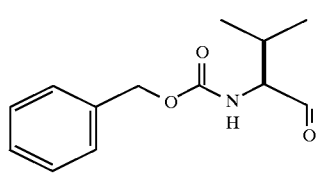

$Z_1$ is $CO_2CH_2Ch_3$, $R_3$ is $CH_2Ph$, and $R_4$ is

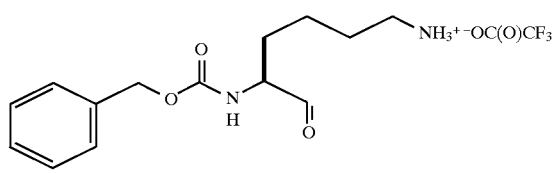

$Z_1$ is $CO_2CH_2CH_3$, $R_3$ is $CH_2Ph$, and $R_4$ is

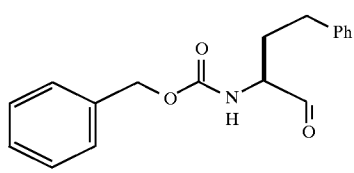

$Z_1$ is $CO_2CH_2CH_3$, $R_3$ is $CH_2Ph$, and $R_4$ is

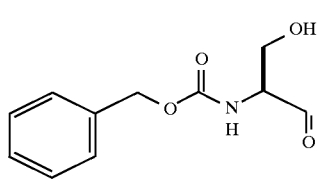

$Z_1$ is $CO_2CH_2CH_3$, $R_3$ is $CH_2Ph$, and $R_1$ is

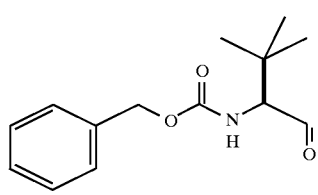

$Z_1$ is $CO_2CH_2CH_3$, $R_3$ is $CH_2Ph$, and $R_4$ is

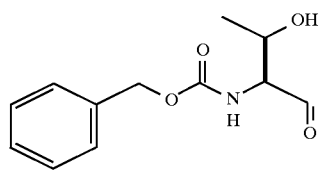

$Z_1$ is $CO_2CH_2CH_3$, $R_3$ is $CH_2Ph$, and $R_4$ is

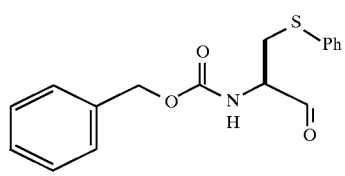

$Z_1$ is $CO_2CH_2CH_3$, $R_3$ is $CH_2Ph$, and $R_4$ is

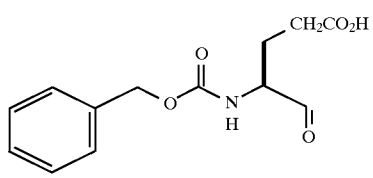

$Z_1$ is $CO_2CH_2CH_3$, $R_3$ is

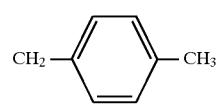

and $R_4$ is

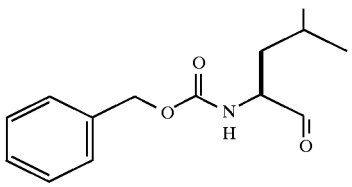

or a pharmaceutically acceptable prodrug, salt or solvate thereof.

6. A pharmaceutical composition comprising:
   (a) a therapeutically effective amount of a compound as defined in claim 1 or a pharmaceutically acceptable prodrug, salt, or solvate thereof; and
   (b) a pharmaceutically acceptable carrier, diluent, vehicle, or excipient.

7. A method of treating a mammalian disease condition mediated by picornaviral protease activity that comprises administering to a mammal for the purpose of said treating a therapeutically effective amount of a compound as defined in claim 1 or a pharmaceutically acceptable prodrug, salt, or solvate thereof.

8. A method of inhibiting the activity of a picornaviral 3C protease that comprises contacting the picornaviral 3C protease for the purpose of said inhibiting with an effective amount of a compound as defined in claim 1 or a pharmaceutically acceptable prodrug, salt, or solvate thereof.

9. A method of inhibiting the activity of a rhinoviral protease that comprises contacting the rhinoviral protease for the purpose of said inhibiting with an effective amount of a compound as defined in claim 1 or a pharmaceutically acceptable prodrug, salt, or solvate thereof.

10. A method of making a compound according to claim 1, comprising converting a compound of formula Q

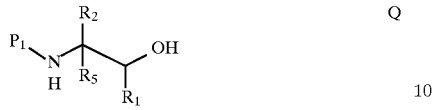

wherein $R_1$, $R_2$ and $R_5$ are as defined in claim 1, and $P_1$ is a protective group, or a salt or solvate thereof, to a compound of formula I, as defined in claim 1, or a pharmaceutically acceptable prodrug, salt or solvate thereof.

11. A method according to claim 10 wherein $P_1$ is benzyloxy carbonyl or t-butoxycarbonyl.

12. A method a making a compound according to claim 1, comprising converting a compound of the formula B:

wherein $R_1$, $R_2$ and $R_5$ are as defined in claim 1, or a salt or solvate thereof, to a compound of formula I, as defined in claim 1, or a pharmaceutically acceptable prodrug, salt or solvate thereof.

13. A method of making a compound according to claim 1, comprising converting a compound of formula O,

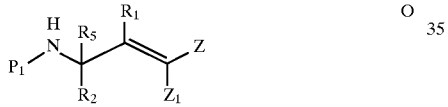

wherein $R_1$, $R_2$, $R_5$, Z and $Z_1$ are as defined in claim 1 and $P_1$ is a protective group, or a salt or solvate thereof, to a compound of formula I, as defined in claim 1, or a pharmaceutically acceptable prodrug, salt or solvate thereof.

14. A method according to claim 13, werein $P_1$ is benzyloxy carbonyl or t-butoxycarbonyl.

15. A method of preparing a compound according to claim 1, (comprising converting a compound of formula P:

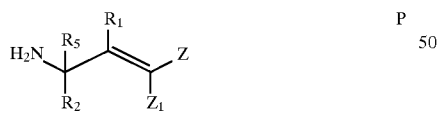

wherein $R_1$, $R_2$, $R_5$, Z and $Z_1$ are as defined in claim 1, or a salt or solvate thereof, to a compound of formula I, as defined in claim 1, or a pharmaceutically acceptable prodrug, salt solvate thereof.

16. A compound according to claim 1, or a pharmaceutically acceptable prodrug or a pharmaceutically acceptable salt, solvate, or any crystal form thereof, wherein said antipicornaviral activity is antirhinoviral activity.

17. A compound according to claim 1, or a pharmaceutically acceptable prodrug or a pharmaceutically acceptable salt, solvate, or any crystal form thereof, wherein said antipicornaviral activity is anticoxsackieviral activity.

18. A compound according to claim 1, wherein the compound has the formula II:

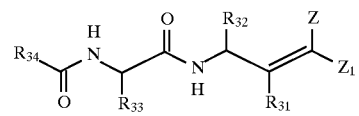

wherein:

$R_{31}$ is H, F, or an alkyl group;

$R_{32}$ is

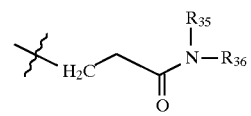

wherein:

$R_{35}$ is H, an alkyl group, or an aryl group, and $R_{36}$ is H or an alkyl group;

$R_{33}$ is H or an alkyl group;

$R_{34}$ is an alkyl group, a cycloalkyl group, an aryl group, an O-alkyl group, an O-cycloalkyl group, an O-aryl group, an S-alkyl group, an NH-alkyl group, an NH-aryl group, an N,N-dialkyl group, or an N,N-diaryl group;

or a pharmaceutically acceptable prodrug, salt, or solvate thereof.

19. A compound according to claim 1, wherein Z and $Z_1$ are independently H, an aryl group, —C(O)$R_{21}$, —CO$_2R_{21}$, —C(O)NR$_{21}R_{22}$, —C(O)NR$_{21}$OR$_{22}$, —C(S)R$_{21}$, —C(S)NR$_{21}R_{22}$, —NO$_2$, —SOR$_{21}$, —SO$_2R_{21}$, —SO$_2$NR$_{21}R_{22}$, —SO(NR$_{21}$)(OR$_{22}$), —SONR$_{21}$, —SO$_3R_{21}$, —C(O)NR$_{21}$NR$_{22}R_{23}$, or —C(S)NR$_{21}$NR$_{22}R_{23}$;

wherein $R_{21}$, $R_{22}$, and $R_{23}$ are independently H, an alkyl group, a cycloalkyl group, an aryl group, or an acyl group, with the proviso that at least one of Z or $Z_1$ is a —CO$_2R_{50}$ group, where $R_{50}$ is an alkyl group, a cycloalkyl group, or an aryl group;

or Z and $Z_1$ together with the atoms to which they are bonded, form a cyclic carboxylic acid ester group;

or a pharmaceutically acceptable prodrug, salt, or solvate thereof.

20. A compound according to claim 18, wherein $R_{32}$ is —CH$_2$CH$_2$C(O)NH$_2$ or —CH$_2$CH$_2$C(O)NHCPh$_3$;

or a pharmaceutically acceptable prodrug, salt, or solvate thereof.

21. A compound according to claim 1, wherein the compound has the formula III:

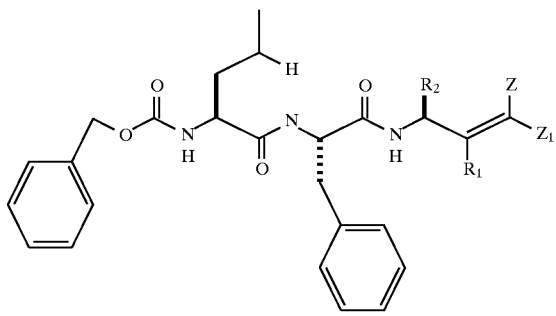

wherein:

$R_2$ is CH$_2$CH$_2$C(O)NHCPh$_3$, $R_1$ is H, Z is H, and $Z_1$ is CO$_2$CH$_2$CH$_3$, $R_2$ is CH$_2$CH$_2$C(O)NH$_2$, $R_1$ is H, Z is H, and $Z_1$ is CO$_2$CH$_2$CH$_3$, $R_2$ is $CH_2CH_2C(O)NH_2$, $R_1$ is H, Z is $CO_2CH_3$, and $Z_1$ is H, $R_2$ is $CH_2CH_2C(O)NH_2$, $R_1$ is H, Z is H, and $Z_1$ is $CO_2CH_3$, $R_2$ is $CH_2CH_2C(O)NH_2$, $R_1$ is H, Z is H, and $Z_1$ is $CO_2CH(CH_3)_2$, $R_2$ is $CH_2CH_2C(O)NH_2$, $R_1$ is H, Z is H, and $Z_1$ is

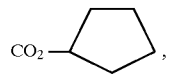

$R_2$ is $CH_2CH_2C(O)NH_2$, $R_1$ is H, Z is H, and $Z_1$ is

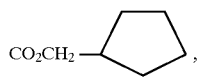

or $R_2$ is $CH_2CH_2C(O)NH_2$, $R_1$ is H, Z is H, and $Z_1$ is

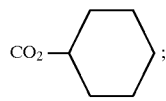

or a pharmaceutically acceptable prodrug, salt, or solvate thereof.

22. A compound according to claim 1, wherein the compound has the formula VII:

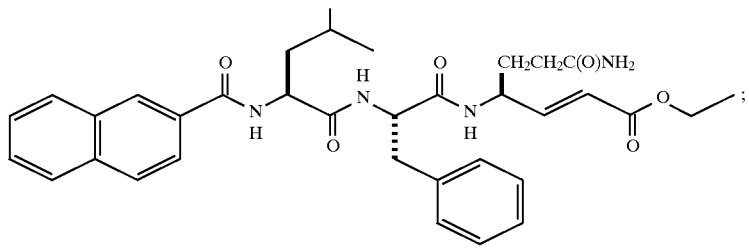

(VII)

or a pharmaceutically acceptable prodrug, salt, or solvate thereof.

23. A compound according to claim 1, wherein the compound has the formula VIII:

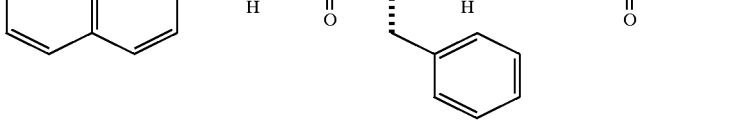

(VIII)

wherein:

$X_1$ is F, $R_2$ is $CH_2CH_2C(O)NH_2$, Y is CH, Z is H, and $Z_1$ is $CO_2CH_2CH_3$; or a pharmaceutically acceptable prodrug, salt, or solvate thereof.

24. A compound according to claim 1, wherein the compound has the formula III:

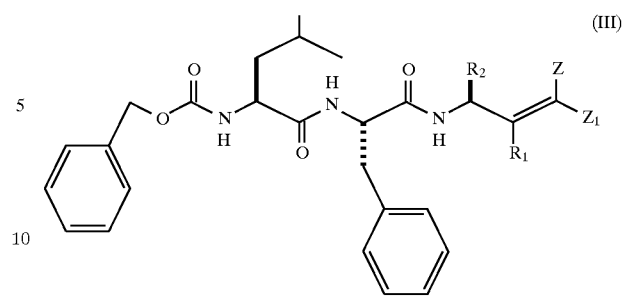

(III)

wherein $R_2$ is $CH_2CH_2C(O)NH_2$, $R_1$ is H, Z is $CH_3$, and $Z_1$ is $CO_2CH_2CH_3$, or $R_2$ is $CH_2CH_2C(O)NH_2$, $R_1$ is H, and Z and $Z_1$ together form

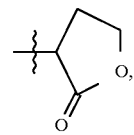

or $R_2$ is $CH_2CH_2C(O)NH_2$, $R_1$ is H, Z is H, and $Z_1$ is —CHO or —CH=NOCH_3;

or a pharmaceutically acceptable prodrug, salt, or solvate thereof.

25. A compound according to claim 1, wherein the compound has the formula XIV:

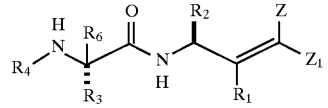

(XIV)

wherein $R_6$ is H, $R_1$ is H, $R_2$ is $CH_2CH_2C(O)NH_2$, Z is H, $Z_1$ is $CO_2CH_2CH_3$, and $R_3$ is $CH_2Ph$ and $R_4$ is

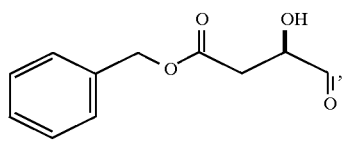

121
R₃ is
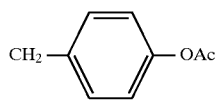
and R₄ is
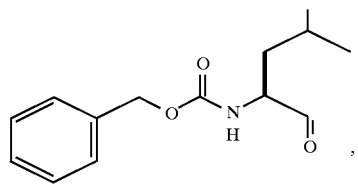,
R₃ is CH₂Ph and R₄ is
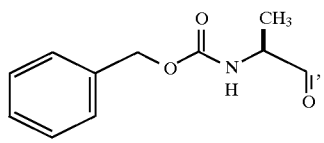,
R₃ is CH₂Ph and R₄ is
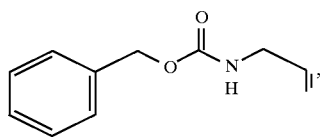,
R₃ is
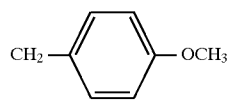
and R₄ is
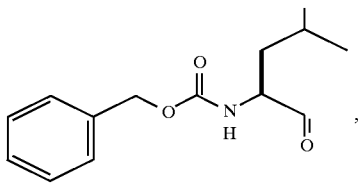,
122
R₃ is CH₂Ph and R₄ is
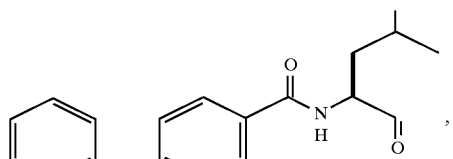,
R₃ is
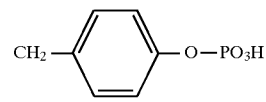
and R₄ is
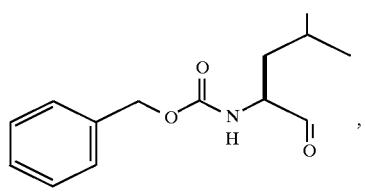,
R₃ is CH₂Ph and R₄ is
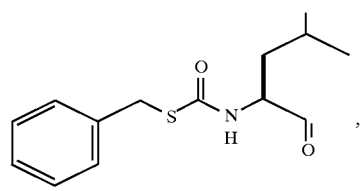,
R₃ is CH₂Ph and R₄ is
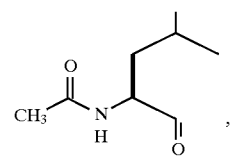, R₃ is CH₂CH₃ and R₄ is

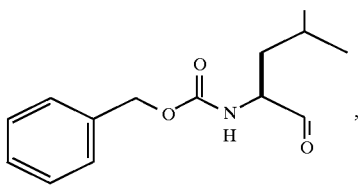

R₃ is CH₃ and R₄ is

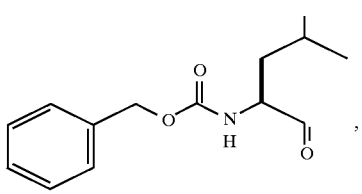

R₃ is CH₂Ph and R₄ is

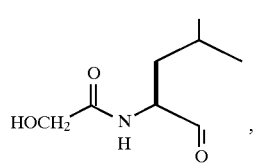

R₃ is

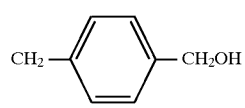

and R₄ is

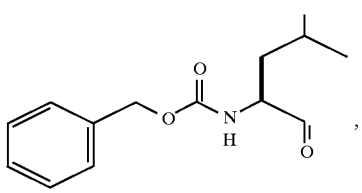

R₃ is CH₂Ph and R₄ is

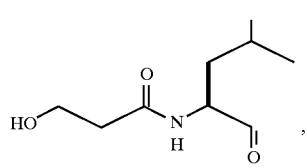

R₃ is CH₂Ph and R₄ is

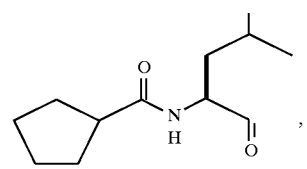

R₃ is CH₂Ph and R₄ is

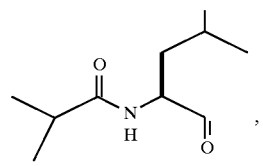

R₃ is CH₂Ph and R₄ is

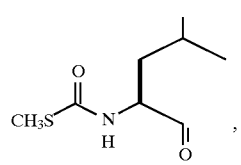

or R₃ is CH₂Ph and R₄ is

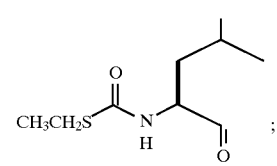

or a pharmaceutically acceptable prodrug, salt, or solvate thereof.

26. A compound according to claim 1, wherein the compound has the formula XIV:

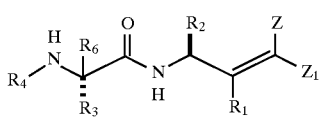 (XIV)

wherein R₆ is H, R₁ is H, R₃ is CH₂Ph, R₂ is CH₂CH₂C(O)NH₂, Z and Z₁ together form

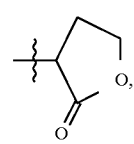

and R₄ is

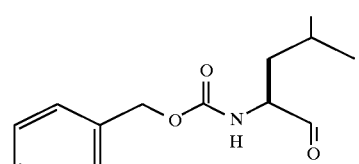

or a pharmaceutically acceptable prodrug, salt, or solvate thereof.

27. A compound according to claim 1, wherein the compound has the formula XIV:

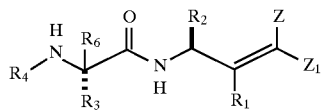

wherein R$_6$ H, R$_1$ is H, R$_2$ is CH$_2$CH$_2$C(O)NH$_2$, R$_4$ is

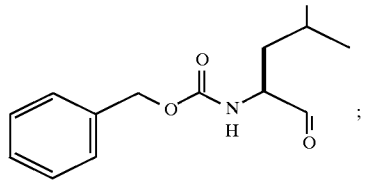

;

R$_3$ is CH(OH)CH$_3$, Z is H and Z$_1$ is CO$_2$CH$_2$CH$_3$,

R$_3$ is

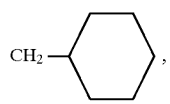

,

Z is H and Z$_1$ is CO$_2$CH$_2$CH$_3$,

R$_3$ is

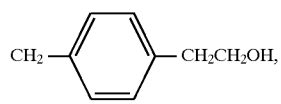

Z is H and Z$_1$ is CO$_2$CH$_2$CH$_3$,

R$_3$ is

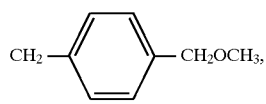

Z is H and Z$_1$ is CO$_2$CH$_2$CH$_3$,

R$_3$ is CH$_2$CH(CH$_3$)$_2$, Z is H and Z$_1$ is CO$_2$CH$_2$CH$_3$,
R$_3$ is CH$_2$SCH$_3$, Z is H and Z$_1$ is CO$_2$CH$_2$CH$_3$,
or R$_3$ is CH$_2$SCH$_2$CH$_3$, Z is H and Z$_1$ is CO$_2$CH$_2$CH$_3$;
or a phanraceutically acceptable prodrug, salt, or solvate thereof.

28. A compound according to claim 1, wherein the compound has the formula IX:

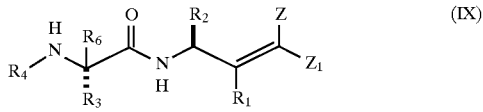

wherein R$_6$ is H, R$_3$ is CH$_2$Ph, R$_2$ is CH$_2$CH$_2$C(O)NH$_2$, and

R$_1$ is OH, Z is H, Z$_1$ is CO$_2$CH$_2$CH$_3$, and R$_4$ is

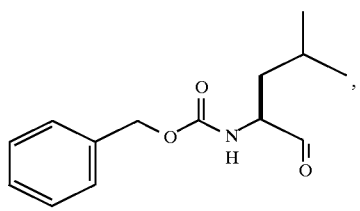

,

R$_1$ is H, Z is H, Z$_1$ is CO$_2$CH$_2$CH$_3$, and R$_4$ is

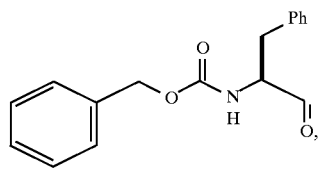

,

R$_1$ is H, Z is H, Z$_1$ is CO$_2$CH$_2$CH$_3$, and R$_4$ is

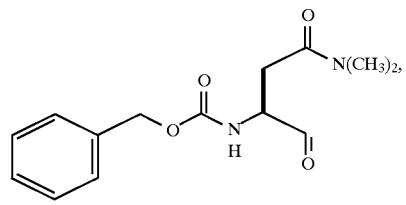

,

R$_1$ is H, Z is H, Z$_1$ is CO$_2$CH$_2$CH$_3$, and R$_4$ is

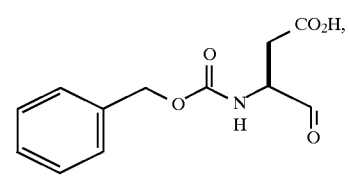

,

R$_1$ is H, Z is H, Z$_1$ is CO$_2$CH$_2$CH$_3$, and R$_4$ is

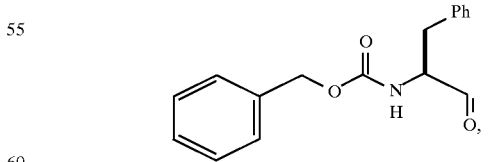

,

127

R₁ is H, Z is H, Z₁ is $CO_2CH_2CH_3$, and R₄ is

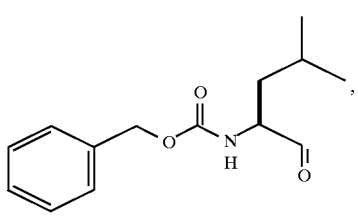,

R₁ is H, Z is H, Z₁ is $CO_2CH_2C(CH_3)_3$, and R₄

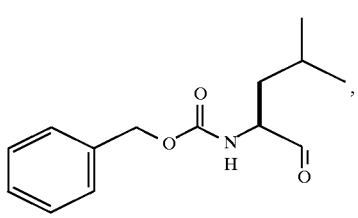,

R₁ is H, Z is H, Z₁ is $CO_2CH_2CH_3$, and R₄ is

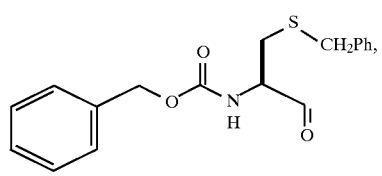,

R₁ is H, Z is H, Z₁ is $CO_2CH_2CH_3$, and R₄ is

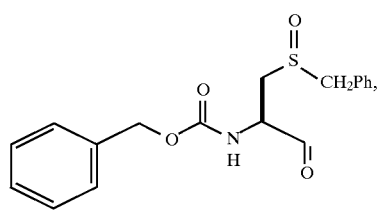

R₁ is H, Z is H, Z₁ is $CO_2CH_2CH_3$, and R₄ is

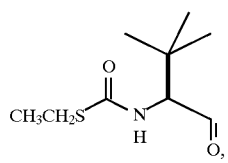,

R₁ is H, Z is $CH_3$, Z₁ is $CO_2CH_2CH_3$, and R₄ is

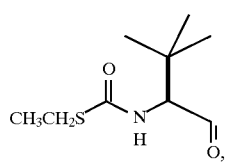

128

R₁ is H, Z is H, Z₁ is $CO_2CH_2CH_3$, and R₄ is

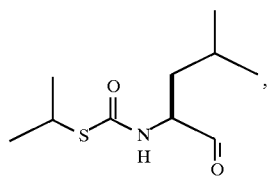,

R₁ is H, Z is $CH_3$, Z₁ is $CO_2CH_2CH_3$, and R₄ is

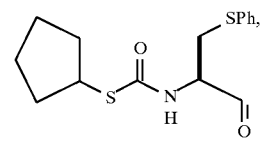,

R₁ is H, Z is H, Z₁ is $CO_2CH_2CH_3$, and R₄ is

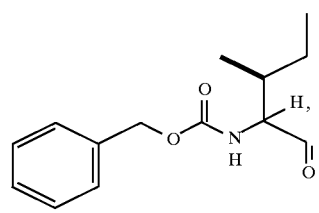

or R₁ is H, Z is H, Z₁ is $CO_2CH_2CH_3$, and R₄ is

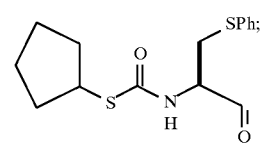

or a pharmaceutically acceptable prodrug, salt, or solvate thereof.

29. A compound according to claim 1, wherein the compound has the formula IX:

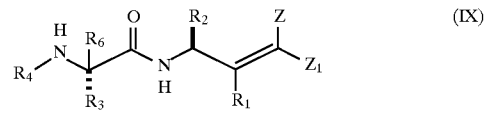 (IX)

wherein R₆ is H, R₂ is $CH_2CH_2C(O)NH_2$, R₁ is H, and Z is H, Z₁ is $CO_2CH_2CH_3$, R₃ is

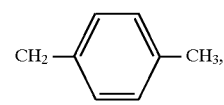

and R₄ is

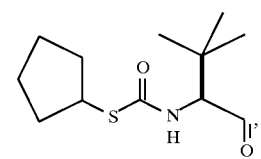

Z is Ch₃ Z₁ is CO₂CH₂CH₃, R₃ is

[structure: CH₂-C₆H₄-CH₃ (para)]

and R₄ is

[structure: cyclopentyl-S-C(=O)-NH-CH(C(CH₃)₃)-CHO]

Z is H, Z₁ is CO₂CH₂CH₃, R₃ is

[structure: CH₂-C₆H₄-F (para)]

and R₄ is

[structure: cyclopentyl-S-C(=O)-NH-CH(C(CH₃)₃)-CHO]

Z is CH₃, Z₁ is CO₂CH₂CH₃, R₃ is

[structure: CH₂-C₆H₄-F (para)]

and R₄ is

[structure: cyclopentyl-S-C(=O)-NH-CH(C(CH₃)₃)-CHO]

Z is H, Z₁ is CO₂CH₂CH₃, R₃ is CH₂Ph, and R₄ is

[structure: cyclopentyl-S-C(=O)-NH-CH(C(CH₃)₂SCH₃)-CHO],

Z is H, Z₁ is CO₂CH₂CH₃, R₃ is CH₂Ph, and R₄ is

[structure: cyclopentyl-S-C(=O)-NH-CH(C(CH₃)₂S(O)CH₃)-CHO],

Z is H, Z₁ is CO₂CH₂CH₃, R₃ is CH₂Ph, and R₄ is

[structure: CH₃CH₂S-C(=O)-NH-CH(CH(CH₃)₂)-CHO],

Z is H, Z₁ is CO₂CH₂CH₃, R₃ is CH₂Ph, and R₄ is

[structure: cyclopentyl-S-C(=O)-NH-CH(CH₂CH(CH₃)₂)-CHO],

Z is H, Z₁ is CO₂CH₂CH₃, R₃ is

[structure: CH₂-C₆H₄-CH₃ (para)]

and R₄ is

[structure: cyclopentyl-S-C(=O)-NH-CH(CH(CH₃)₂)-CHO],

Z is H, Z₁ is CO₂CH₂CH₃, R₃ is

[structure: CH₂-C₆H₄-F (para)]

and R₄ is

[structure: cyclopentyl-S-C(=O)-NH-CH(CH(CH₃)₂)-CHO], or Z is H, Z₁ is CO₂CH₂CH₃, R₃ is

[structure: CH₂-C₆H₄-F (para)]

and R₄ is
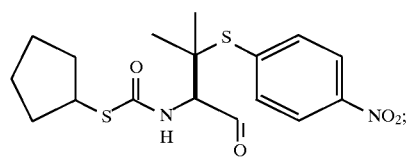
or a pharmaceutically acceptable prodrug, salt, or solvate thereof.
* * * * *

UNITED STATES PATENT AND TRADEMARK OFFICE
CERTIFICATE OF CORRECTION

PATENT NO.: 5,856,530

DATED: January 5, 1999

INVENTOR(S): WEBBER et al.

It is certified that an error appears in the above-identified patent and that said Letters Patent is hereby corrected as shown below:

Claim 5, column 116, line 30, before "$Z_1$", insert --or--.

Claim 15, column 117, line 47, before "comprising", delete "(" (parenthesis);

line 57, before "solvate", insert --or--.

Claim 25, column 121, line 35, the formula:

" 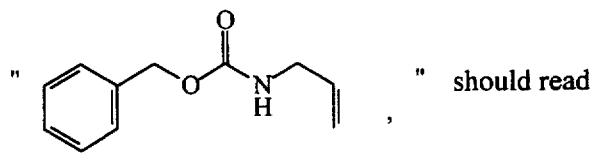 " should read

-- 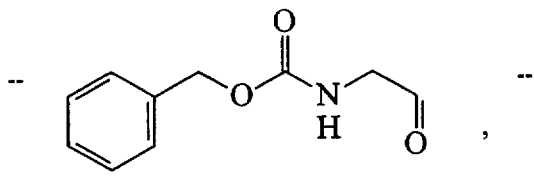 --

Claim 27, column 125, line 7, "$R_6H$" should read --$R_6$ is H--.

Claim 28, column 126, lines 55-60, the formula:

" 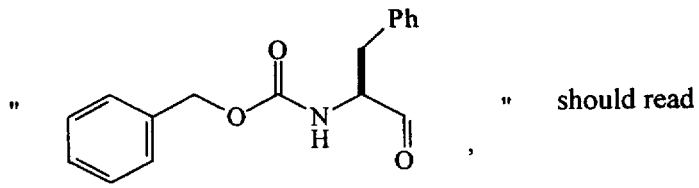 " should read

UNITED STATES PATENT AND TRADEMARK OFFICE
CERTIFICATE OF CORRECTION

PATENT NO. : 5,856,530
DATED : January 5, 1999
INVENTOR(S) : WEBBER, ET AL.

It is certified that error appears in the above-identified patent and that said Letters Patent is hereby corrected as shown below:

column 127, lines 5-10, the formula:

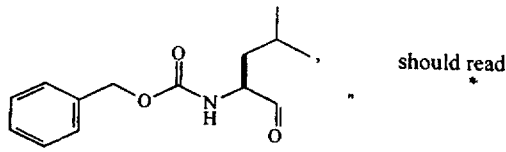, should read

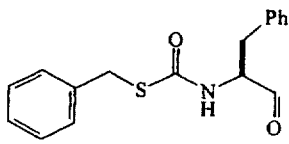

Column 128, lines 25-30, the formula:

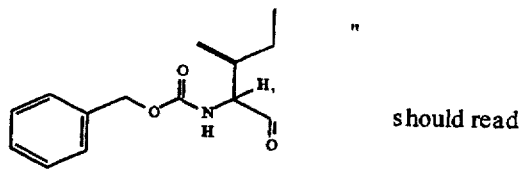  should read

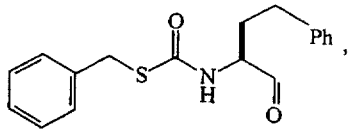

UNITED STATES PATENT AND TRADEMARK OFFICE
CERTIFICATE OF CORRECTION

Page 3 of 4

PATENT NO. : 5,856,530
DATED : January 5, 1999
INVENTOR(S) : WEBBER, ET AL.

It is certified that error appears in the above-identified patent and that said Letters Patent is hereby corrected as shown below:

-- 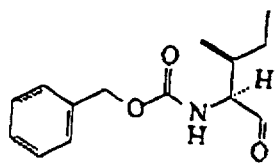 --

Claim 29, column 129, line 1, "Z is $Ch_3Z_1$," should read -- Z is $CH_3$, $Z_1$ --.

Title page, column 1, below "[22] Filed: May 2, 1997", insert -- Related U.S. Application Da [63] Continuation-in-part of Ser. No. 645,687, filed May 14, 1996, now abandoned.

Column 15, lines 25-35, the formula

" 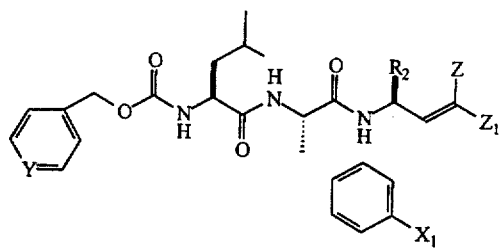 "

should read

UNITED STATES PATENT AND TRADEMARK OFFICE
CERTIFICATE OF CORRECTION

Page 4 of 4

PATENT NO. : 5,856,530
DATED : January 5, 1999
INVENTOR(S) : WEBBER, ET AL.

It is certified that error appears in the above-identified patent and that said Letters Patent is hereby corrected as shown below:

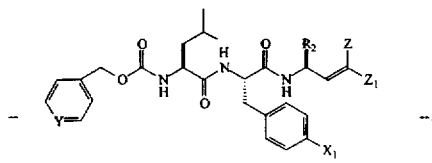

Claim 21, column 118, lines 50-62, the formula

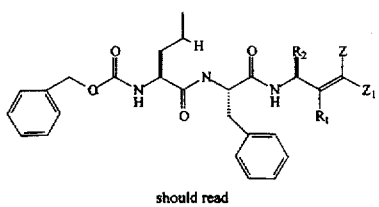

should read

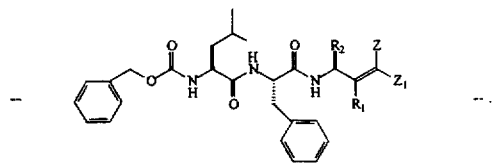

Signed and Sealed this

Tenth Day of August, 1999

*Attest:*

Q. TODD DICKINSON

*Attesting Officer*   Acting Commissioner of Patents and Trademarks